United States Patent
Uchida

(10) Patent No.: US 11,187,886 B2
(45) Date of Patent: Nov. 30, 2021

(54) OPTICAL SYSTEM FOR STEREOSCOPIC VISION AND IMAGE PICKUP APPARATUS USING THE SAME

(71) Applicant: OLYMPUS CORPORATION, Hachioji (JP)

(72) Inventor: Yoshihiro Uchida, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 133 days.

(21) Appl. No.: 16/745,733

(22) Filed: Jan. 17, 2020

(65) Prior Publication Data

US 2020/0150415 A1    May 14, 2020

Related U.S. Application Data

(63) Continuation of application No. PCT/JP2017/035567, filed on Sep. 29, 2017.

(51) Int. Cl.
   *G02B 23/24*    (2006.01)
   *G02B 30/24*    (2020.01)
   *H04N 13/207*   (2018.01)

(52) U.S. Cl.
   CPC ....... *G02B 23/2415* (2013.01); *G02B 23/243* (2013.01); *H04N 13/207* (2018.05); *G02B 30/24* (2020.01)

(58) Field of Classification Search
   CPC ... G02B 23/2415; G02B 30/24; G02B 23/243
   USPC .......................................................... 348/45
   See application file for complete search history.

(56) References Cited

U.S. PATENT DOCUMENTS

| | | |
|---|---|---|
| 5,557,454 A | 9/1996 | Takahashi |
| 5,743,846 A | 4/1998 | Takahashi et al. |
| 5,971,915 A | 10/1999 | Yamamoto et al. |
| 5,976,071 A | 11/1999 | Sekiya |
| 6,306,082 B1 | 10/2001 | Takahashi et al. |
| 6,338,711 B1 | 1/2002 | Sekiya et al. |
| 6,364,888 B1 | 4/2002 | Niemeyer et al. |

(Continued)

FOREIGN PATENT DOCUMENTS

| | | |
|---|---|---|
| JP | H735989 A | 2/1995 |
| JP | H07261094 A | 10/1995 |

(Continued)

OTHER PUBLICATIONS

Office Action (Non-Final Rejection) dated Sep. 2, 2020 issued in related U.S. Appl. No. 16/706,324.

(Continued)

*Primary Examiner* — Jeffery A Williams
(74) *Attorney, Agent, or Firm* — Holtz, Holtz & Volek PC

(57) ABSTRACT

An optical system for stereoscopic vision includes in order from an object side, a front unit and a rear unit. Each of the front unit and the rear unit includes a lens component consisting of a single lens or a cemented lens. The front unit includes a first front unit and a second front unit, and an optical axis of the first front unit, an optical axis of the second front unit, and an optical axis of the rear unit are positioned in a same plane. The optical axis of the rear unit is positioned between the optical axis of the first front unit and the optical axis of the second front unit, and the following conditional expression (1) is satisfied:

$$0.15 < De/\Phi < 0.85 \qquad (1).$$

50 Claims, 73 Drawing Sheets

(56) References Cited

U.S. PATENT DOCUMENTS

| | | |
|---|---|---|
| 6,383,131 B1 | 5/2002 | Yamamoto et al. |
| 6,396,627 B1 | 5/2002 | Tachihara et al. |
| 6,414,791 B1 | 7/2002 | Sugawara |
| 6,517,479 B1 | 2/2003 | Sekiya |
| 6,720,988 B1 | 4/2004 | Gere et al. |
| 6,976,956 B2 | 12/2005 | Takahashi et al. |
| 7,564,619 B2 | 7/2009 | Uzawa et al. |
| 8,221,304 B2 | 7/2012 | Shioda et al. |
| 8,345,084 B2 | 1/2013 | Namii et al. |
| 8,648,896 B2 | 2/2014 | Takahashi |
| 8,743,185 B2 | 6/2014 | Yamaguchi et al. |
| 8,934,169 B2 | 1/2015 | Mirlay |
| 10,274,717 B2 | 4/2019 | Togino |
| 10,488,634 B2 | 11/2019 | Uchida et al. |
| 10,634,883 B2 | 4/2020 | Uchida et al. |
| 10,634,884 B2 | 4/2020 | Takada et al. |
| 10,642,005 B2 | 5/2020 | Uchida et al. |
| 2001/0055062 A1 | 12/2001 | Shioda et al. |
| 2002/0055795 A1 | 5/2002 | Niemeyer et al. |
| 2002/0082476 A1 | 6/2002 | Takahashi et al. |
| 2003/0029463 A1 | 2/2003 | Niemeyer |
| 2005/0020876 A1 | 1/2005 | Shioda et al. |
| 2005/0027397 A1 | 2/2005 | Niemeyer |
| 2006/0092273 A1 | 5/2006 | Gere et al. |
| 2006/0146009 A1 | 7/2006 | Syrbe et al. |
| 2006/0274433 A1 | 12/2006 | Kamo |
| 2007/0285508 A1 | 12/2007 | Gere et al. |
| 2008/0174861 A1 | 7/2008 | Uzawa et al. |
| 2010/0208046 A1 | 8/2010 | Takahashi |
| 2012/0008194 A1 | 1/2012 | Mizuta et al. |
| 2012/0075448 A1 | 3/2012 | Namii et al. |
| 2012/0113233 A1 | 5/2012 | Yamaguchi et al. |
| 2013/0044369 A1 | 2/2013 | Mirlay |
| 2013/0070123 A1 | 3/2013 | Imoka |
| 2013/0113891 A1 | 5/2013 | Mayhew et al. |
| 2013/0242412 A1 | 9/2013 | Uchida et al. |
| 2014/0300711 A1 | 10/2014 | Kroon et al. |
| 2015/0036146 A1 | 2/2015 | Staloff |
| 2015/0168710 A1 * | 6/2015 | Zobel ............... A61B 1/00193 348/45 |
| 2016/0131869 A1 | 5/2016 | Liao et al. |
| 2016/0266370 A1 | 9/2016 | Uchida et al. |
| 2016/0320606 A1 | 11/2016 | Togino |
| 2017/0168264 A1 | 6/2017 | Chen et al. |
| 2017/0235123 A1 | 8/2017 | Kamo |
| 2018/0120554 A1 | 5/2018 | Fukushima |
| 2018/0224635 A1 | 8/2018 | Takada et al. |
| 2018/0224637 A1 | 8/2018 | Uchida et al. |
| 2018/0224639 A1 | 8/2018 | Takada et al. |
| 2018/0231748 A1 | 8/2018 | Chang et al. |
| 2020/0008660 A1 | 1/2020 | Uchida et al. |
| 2020/0018935 A1 | 1/2020 | Uchida |
| 2020/0107707 A1 | 4/2020 | Uchida |

FOREIGN PATENT DOCUMENTS

| | | |
|---|---|---|
| JP | H07261099 A | 10/1995 |
| JP | H08304714 A | 11/1996 |
| JP | H116967 A | 1/1999 |
| JP | 2001075011 A | 3/2001 |
| JP | 2002011022 A | 1/2002 |
| JP | 3283084 B2 | 3/2002 |
| JP | 2008170803 A | 7/2008 |
| JP | 4750175 B2 | 8/2011 |
| JP | 2012113281 A | 6/2012 |
| JP | 2013524285 A | 6/2013 |
| JP | 2014110910 A | 6/2014 |
| JP | 2014160240 A | 9/2014 |
| JP | 2014174390 A | 9/2014 |
| WO | 2011049195 A1 | 4/2011 |
| WO | 2017033234 A1 | 3/2017 |

OTHER PUBLICATIONS

U.S. Appl. No. 16/703,324, filed Dec. 6, 2019 and published as US 2020/0107707 on Apr. 9, 2020.

U.S. Appl. No. 16/574,651, filed Sep. 18, 2019 and published as US 2020/008660 on Jan. 9, 2020; and.

U.S. Appl. No. 16/583,057, filed Sep. 25, 2019 and published as US 2020/0018935 on Jan. 16, 2020.

International Search Report (ISR) (and English translation thereof) dated Dec. 26, 2017 issued in International Application No. PCT/JP2017/035567.

Written Opinion dated Dec. 26, 2017 issued in International Application No. PCT/JP2017/035567.

Related U.S. Appl. No. 16/574,651; First Named Inventor: Yoshihiro Uchida; Title:"Stereoscopic-Vision Endoscope Optical System and Endoscope Using the Same"; Filed: Sep. 18, 2019.

Related U.S. Appl. No. 16/583,057; First Named Inventor: Yoshihiro Uchida; Title:"Optical System for Stereoscopic Vision and Endoscope Using the Same"; Filed: Sep. 25, 2019.

Related U.S. Appl. No. 16/706,324; First Named Inventor: Yoshihiro Uchida; Title:"Optical System for Stereoscopic Vision and Image Pickup Apparatus Using the Same"; Filed: Dec. 6, 2019.

* cited by examiner

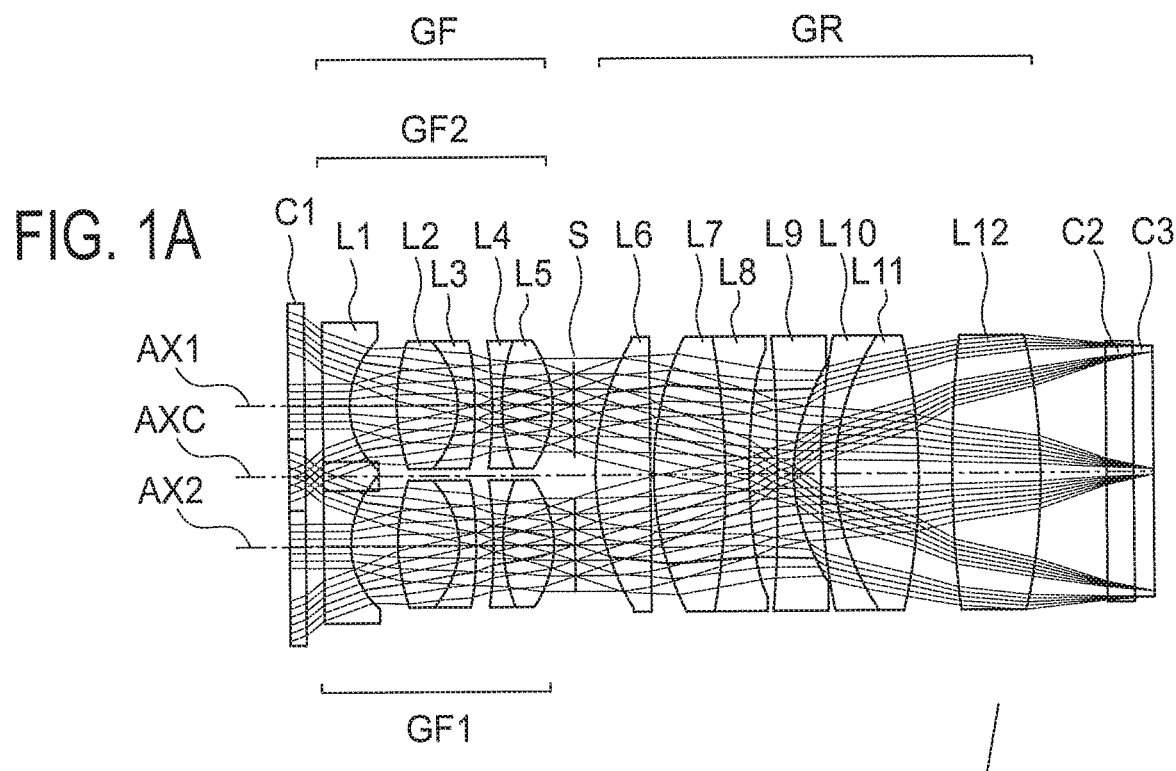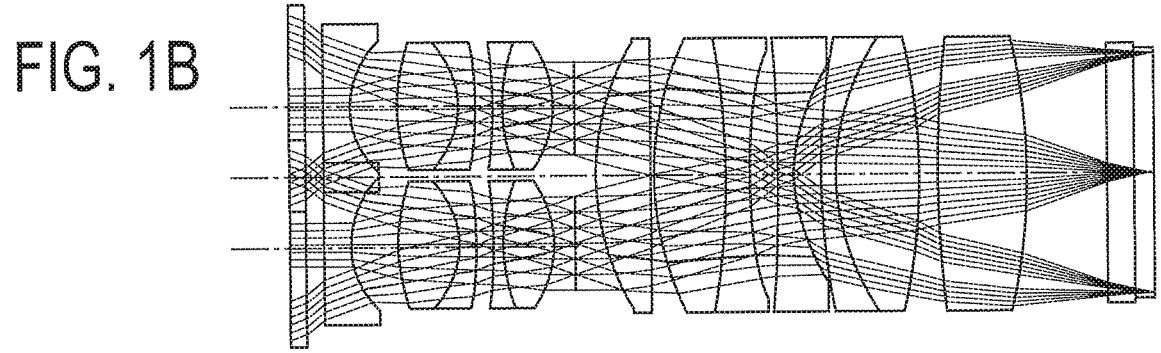

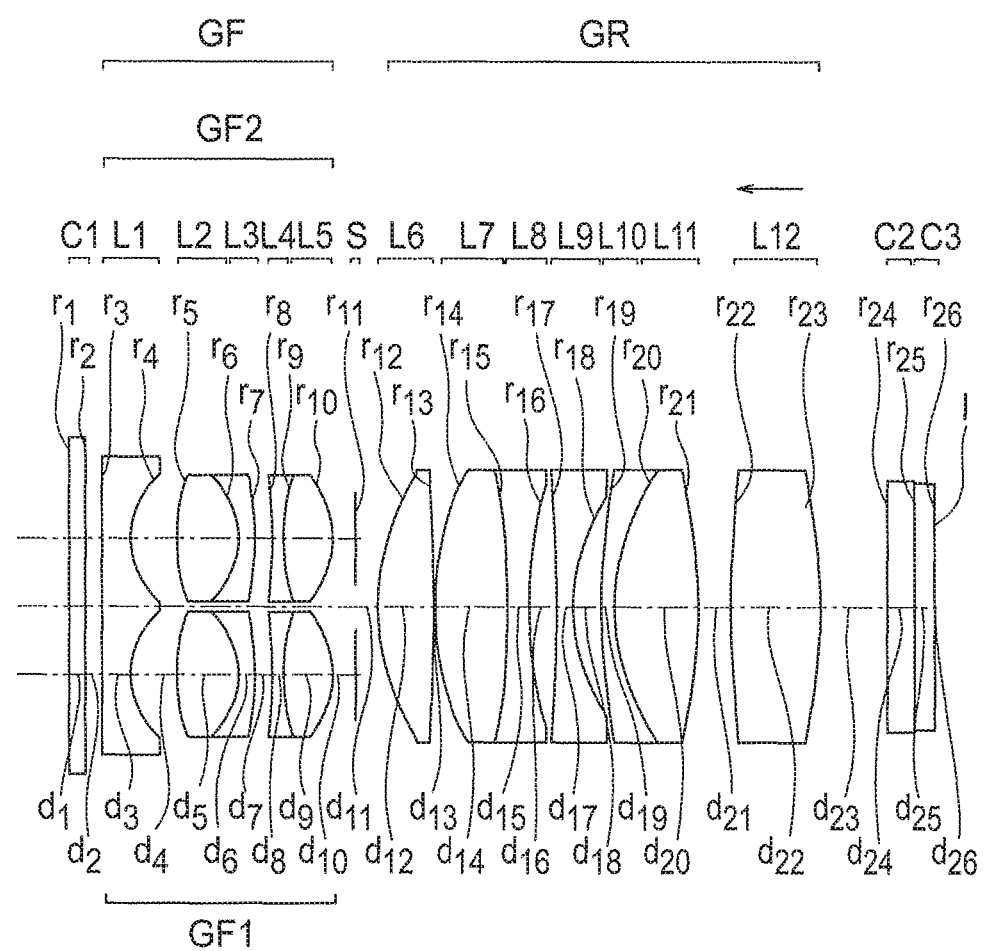

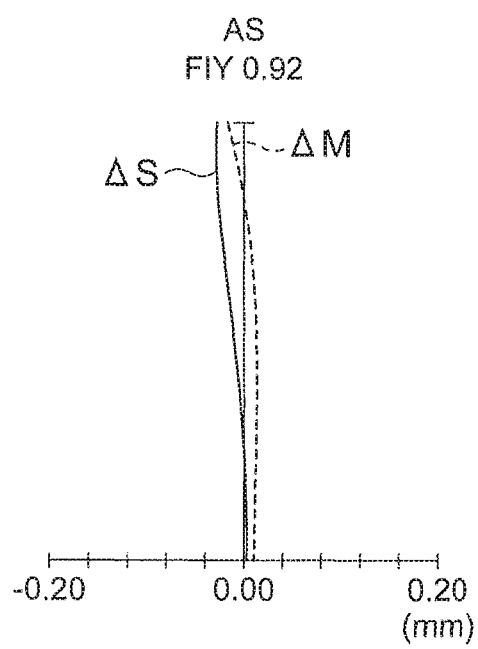
FIG. 17A
AS
FIY 0.92
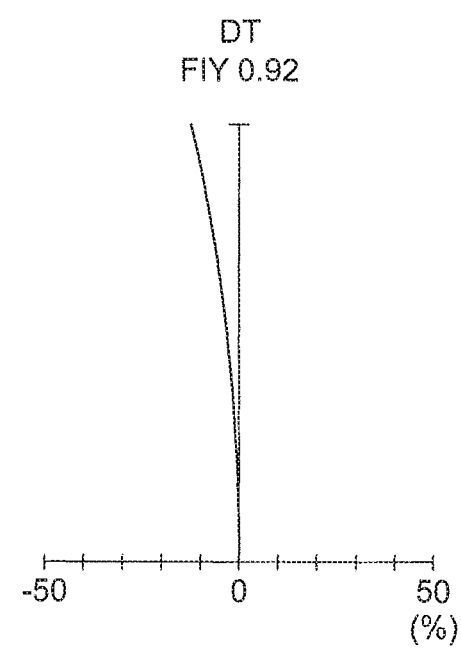
FIG. 17B
DT
FIY 0.92
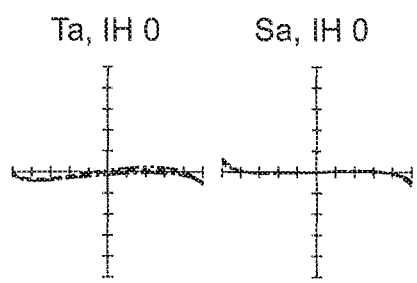
FIG. 17C   FIG. 17D
Ta, IH 0    Sa, IH 0
FIG. 17E   FIG. 17F
Ta, IH 0.5  Sa, IH 0.5
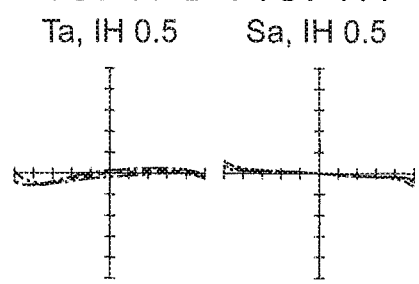
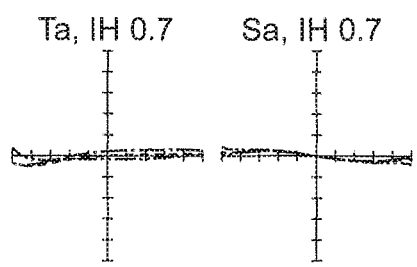
FIG. 17G   FIG. 17H
Ta, IH 0.7  Sa, IH 0.7
FIG. 17I   FIG. 17J
Ta, IH 1.0  Sa, IH 1.0
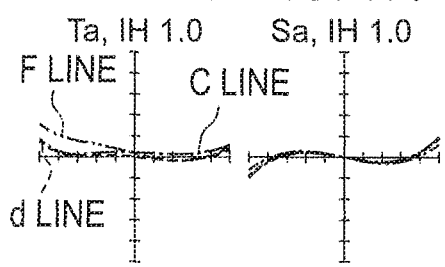
—·—·— 0.486
———— 0.588
-------- 0.656

AS
FIY 0.92

DT
FIY 0.92

Ta, IH 0   Sa, IH 0

Ta, IH 0.5  Sa, IH 0.5

Ta, IH 0.7  Sa, IH 0.7

Ta, IH 1.0  Sa, IH 1.0

AS
FIY 0.92

DT
FIY 0.92

Ta, IH 0  Sa, IH 0

Ta, IH 0.5  Sa, IH 0.5

Ta, IH 0.7  Sa, IH 0.7

Ta, IH 1.0  Sa, IH 1.0

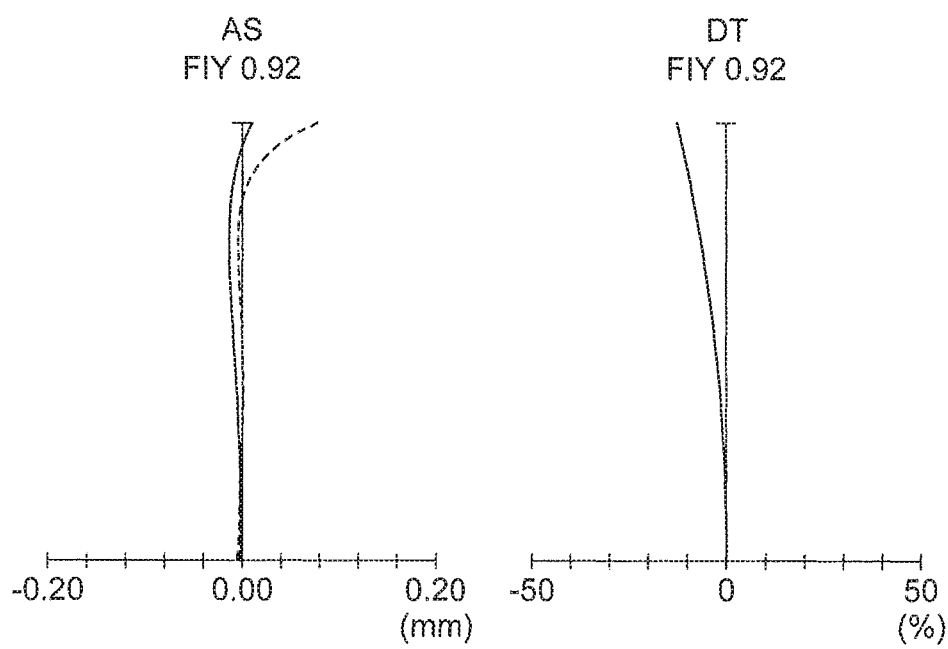
FIG. 20A
AS
FIY 0.92
FIG. 20B
DT
FIY 0.92
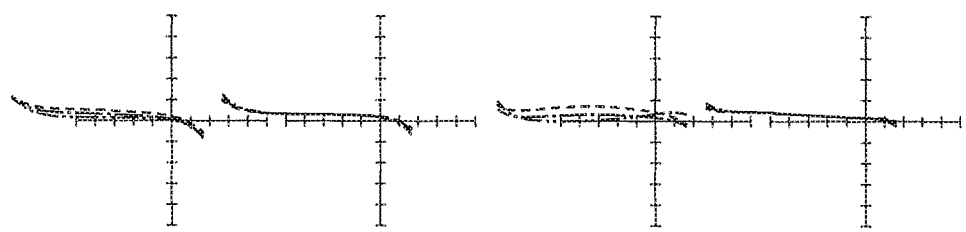
FIG. 20C  FIG. 20D
Ta, IH 0    Sa, IH 0
FIG. 20E  FIG. 20F
Ta, IH 0.5  Sa, IH 0.5
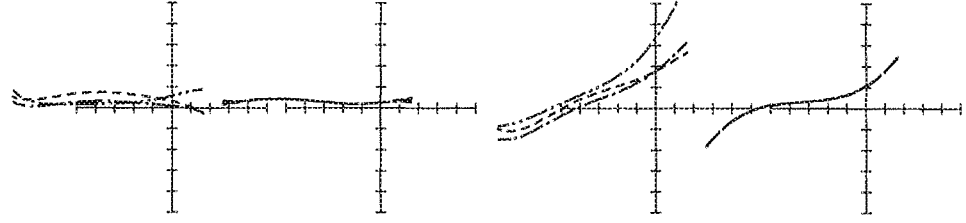
FIG. 20G  FIG. 20H
Ta, IH 0.7  Sa, IH 0.7
FIG. 20I  FIG. 20J
Ta, IH 1.0  Sa, IH 1.0

AS
FIY 0.92

DT
FIY 0.92

Ta, IH 0     Sa, IH 0

Ta, IH 0.5   Sa, IH 0.5

Ta, IH 0.7   Sa, IH 0.7

Ta, IH 1.0   Sa, IH 1.0

AS
FIY 0.92

DT
FIY 0.92

Ta, IH 0     Sa, IH 0

Ta, IH 0.5   Sa, IH 0.5

Ta, IH 0.7   Sa, IH 0.7

Ta, IH 1.0   Sa, IH 1.0

AS
FIY 0.92

DT
FIY 0.92

Ta, IH 0   Sa, IH 0

Ta, IH 0.5  Sa, IH 0.5

Ta, IH 0.7  Sa, IH 0.7

Ta, IH 1.0  Sa, IH 1.0

AS
FIY 0.92

DT
FIY 0.92

Ta, IH 0      Sa, IH 0

Ta, IH 0.5    Sa, IH 0.5

Ta, IH 0.7    Sa, IH 0.7

Ta, IH 1.0    Sa, IH 1.0

AS
FIY 0.92

DT
FIY 0.92

Ta, IH 0    Sa, IH 0

Ta, IH 0.5  Sa, IH 0.5

Ta, IH 0.7  Sa, IH 0.7

Ta, IH 1.0  Sa, IH 1.0

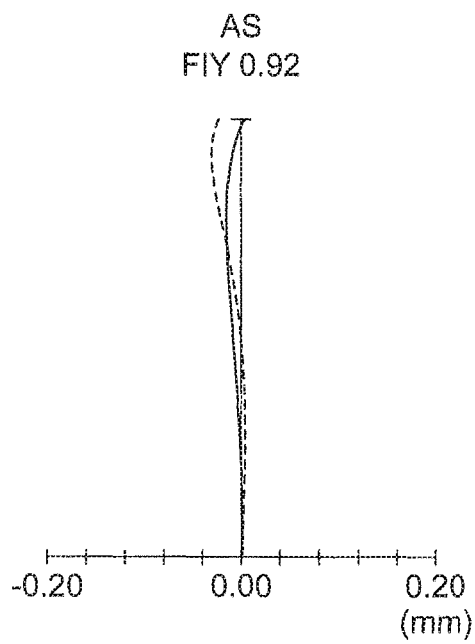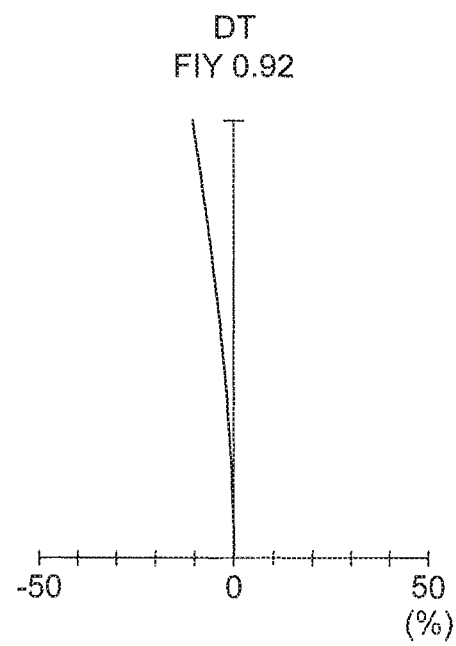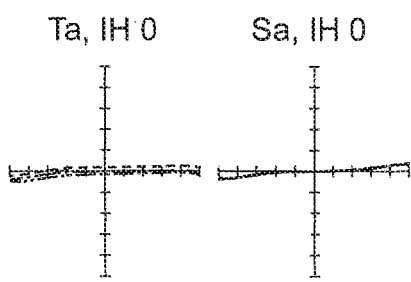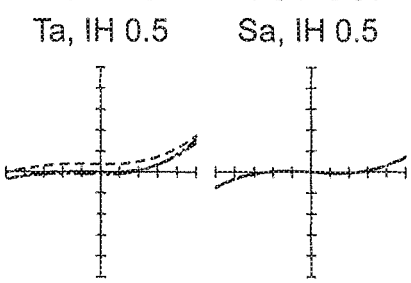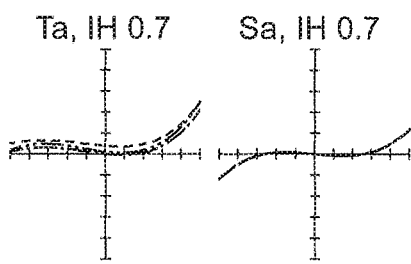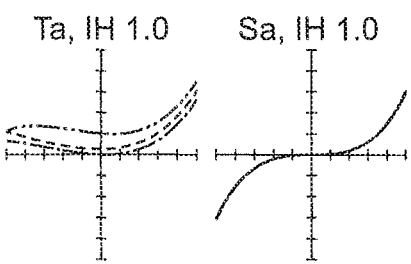

AS
FIY 0.92

DT
FIY 0.92

Ta, IH 0    Sa, IH 0

Ta, IH 0.5  Sa, IH 0.5

Ta, IH 0.7  Sa, IH 0.7

Ta, IH 1.0  Sa, IH 1.0

AS
FIY 0.92

DT
FIY 0.92

Ta, IH 0    Sa, IH 0

Ta, IH 0.5  Sa, IH 0.5

Ta, IH 0.7  Sa, IH 0.7

Ta, IH 1.0  Sa, IH 1.0

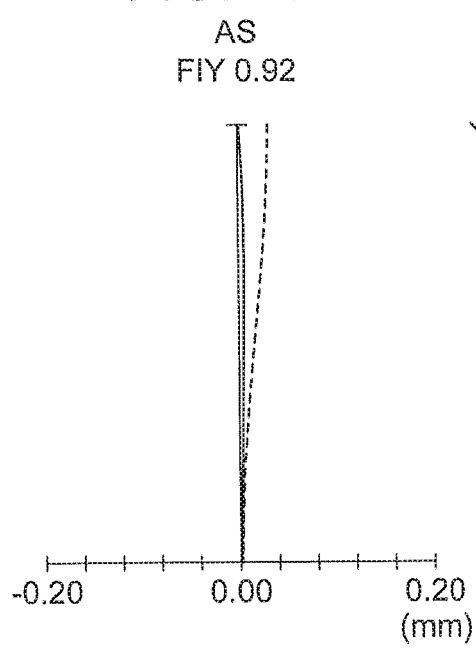
FIG. 29A
AS
FIY 0.92
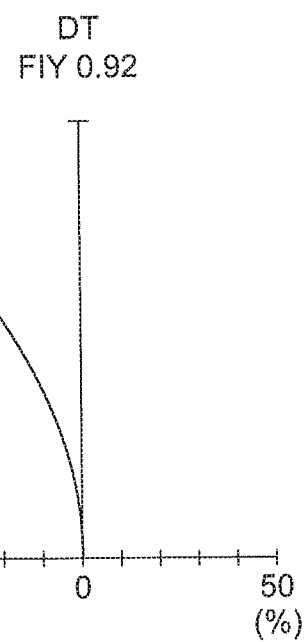
FIG. 29B
DT
FIY 0.92
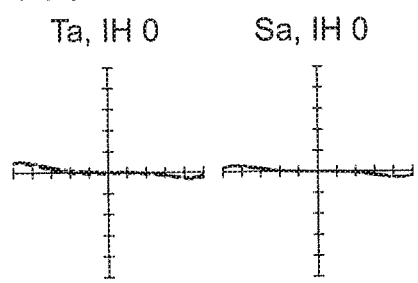
FIG. 29C    FIG. 29D
Ta, IH 0     Sa, IH 0
FIG. 29E    FIG. 29F
Ta, IH 0.5   Sa, IH 0.5
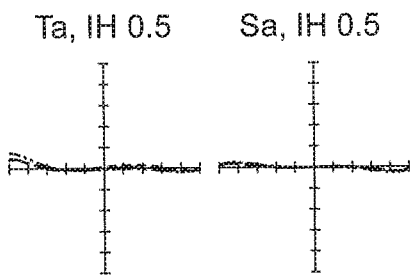
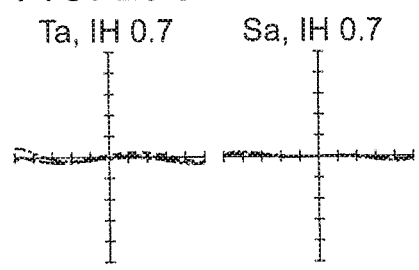
FIG. 29G    FIG. 29H
Ta, IH 0.7   Sa, IH 0.7
FIG. 29I    FIG. 29J
Ta, IH 1.0   Sa, IH 1.0
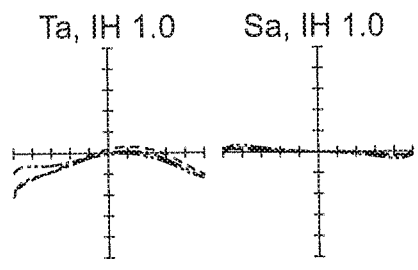

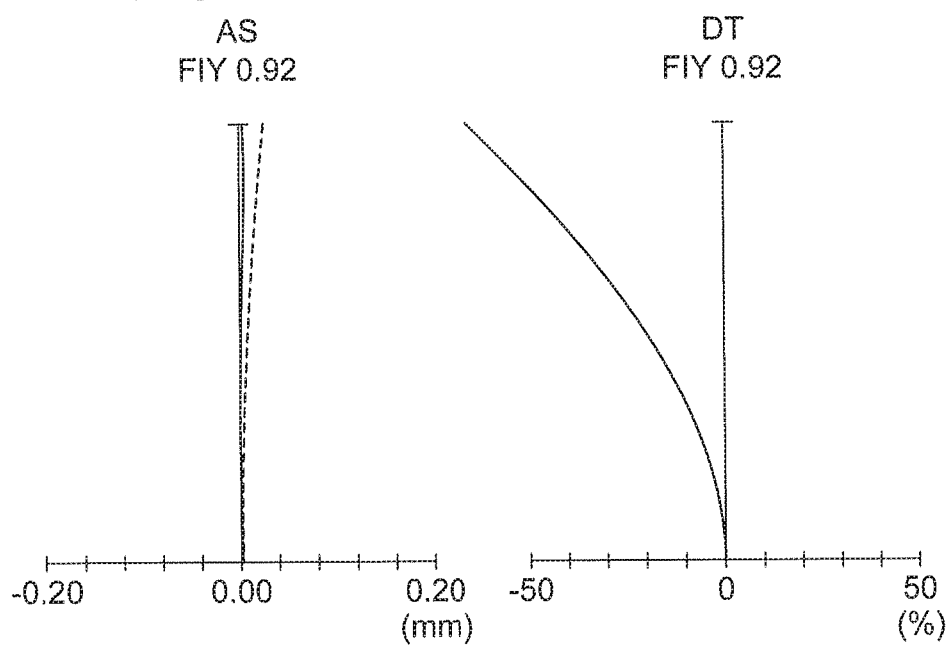
FIG. 30A
AS
FIY 0.92
FIG. 30B
DT
FIY 0.92
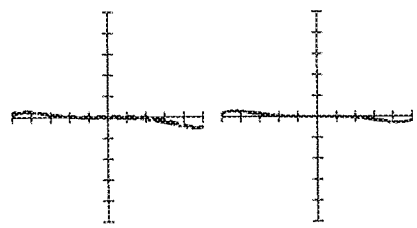
FIG. 30C  FIG. 30D
Ta, IH 0   Sa, IH 0
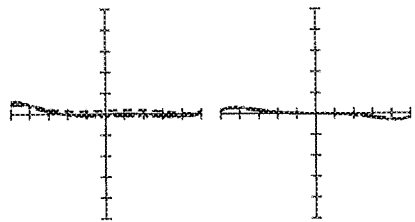
FIG. 30E  FIG. 30F
Ta, IH 0.5  Sa, IH 0.5
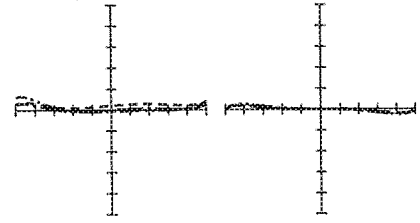
FIG. 30G  FIG. 30H
Ta, IH 0.7  Sa, IH 0.7
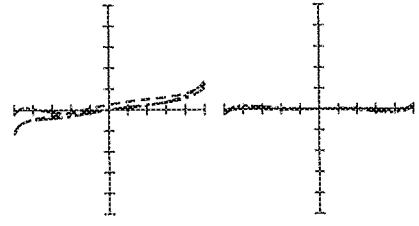
FIG. 30I  FIG. 30J
Ta, IH 1.0  Sa, IH 1.0

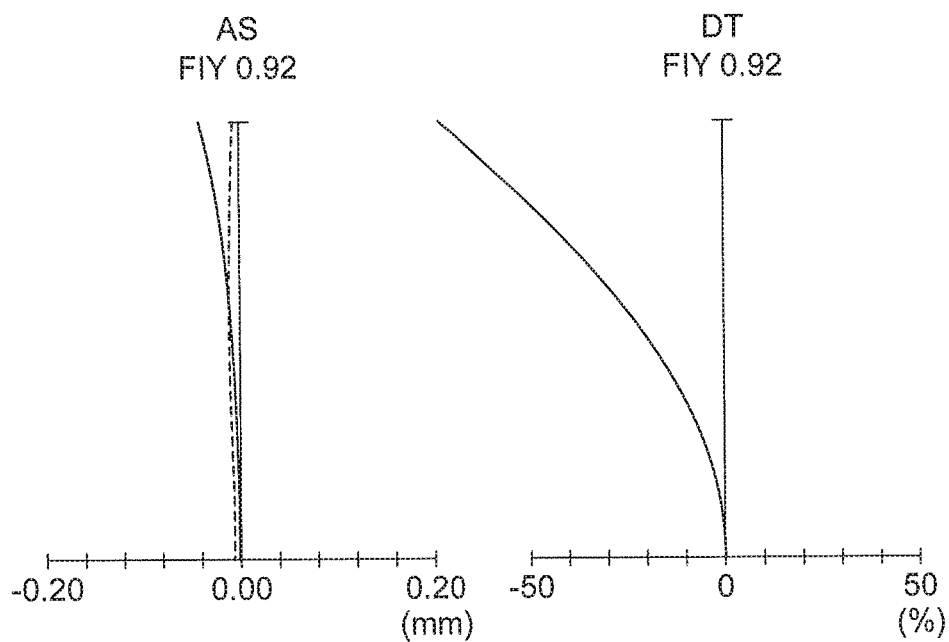
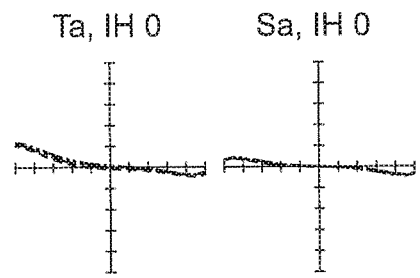
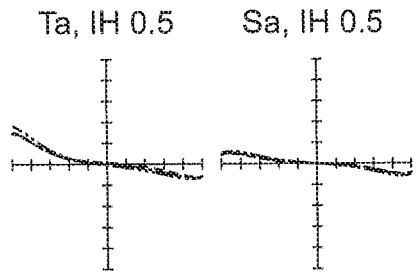
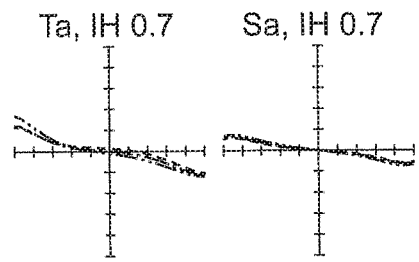
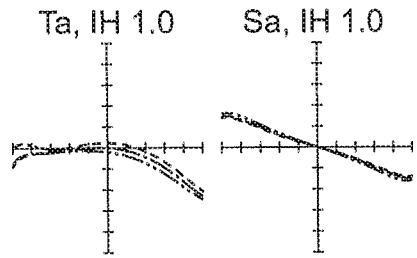

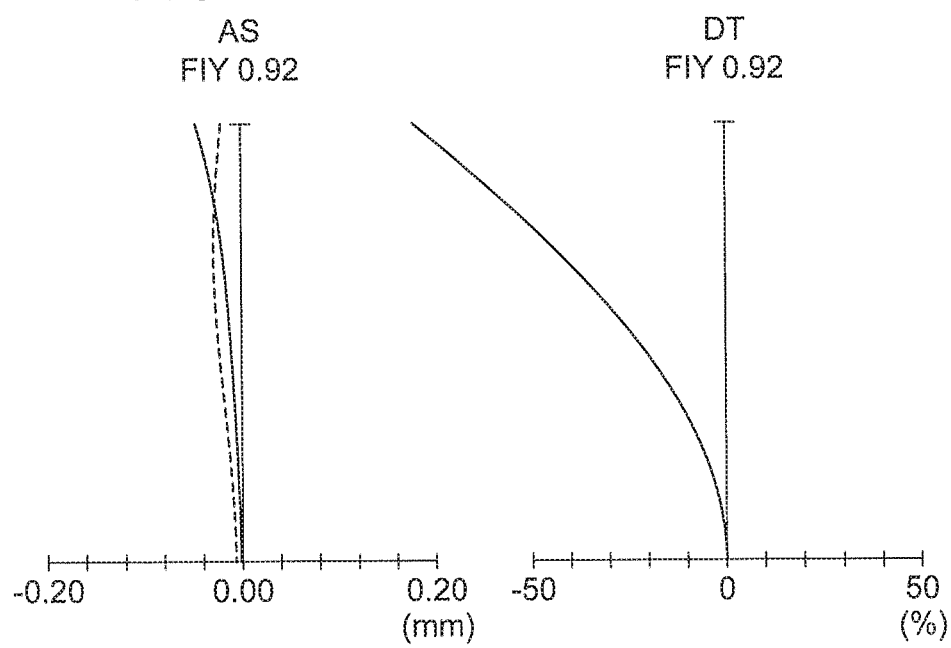
FIG. 32A
AS
FIY 0.92
FIG. 32B
DT
FIY 0.92
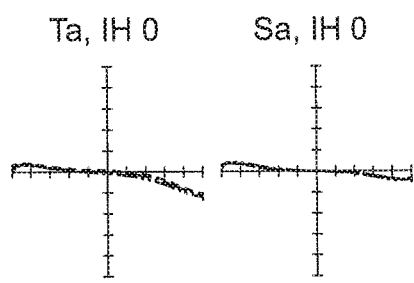
FIG. 32C
Ta, IH 0
FIG. 32D
Sa, IH 0
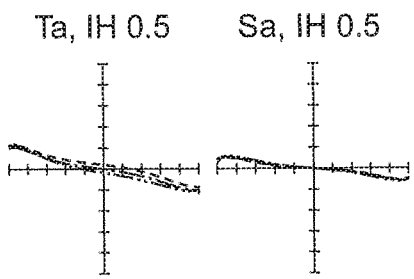
FIG. 32E
Ta, IH 0.5
FIG. 32F
Sa, IH 0.5
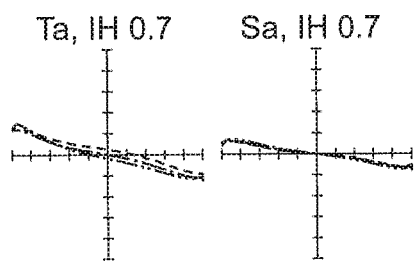
FIG. 32G
Ta, IH 0.7
FIG. 32H
Sa, IH 0.7
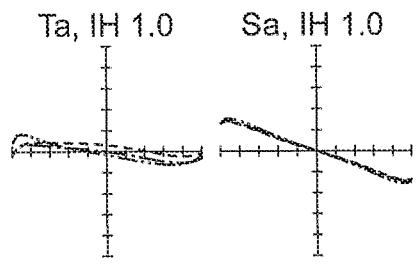
FIG. 32I
Ta, IH 1.0
FIG. 32J
Sa, IH 1.0

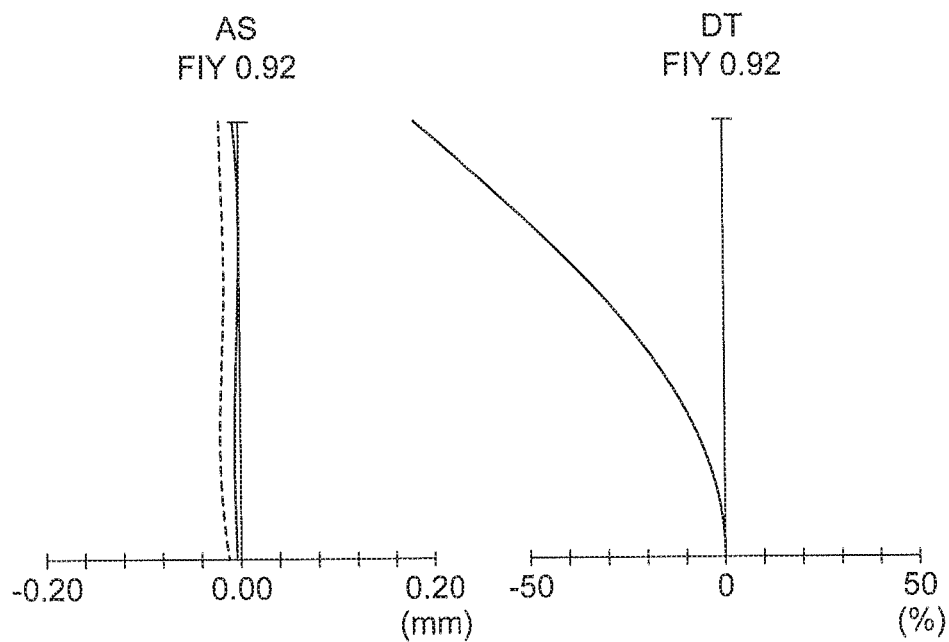
FIG. 33A
AS
FIY 0.92
FIG. 33B
DT
FIY 0.92
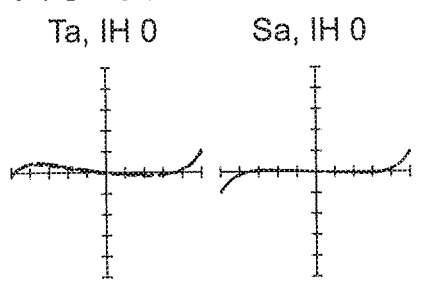
FIG. 33C
Ta, IH 0
FIG. 33D
Sa, IH 0
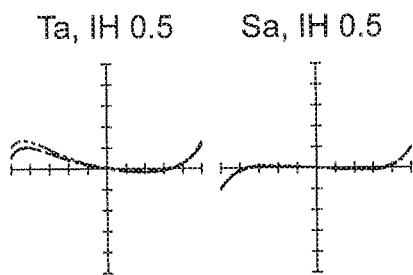
FIG. 33E
Ta, IH 0.5
FIG. 33F
Sa, IH 0.5
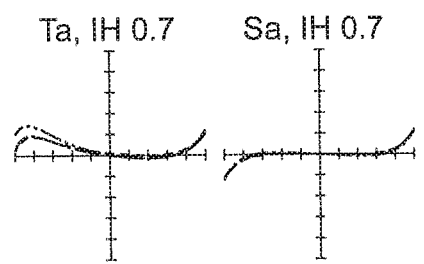
FIG. 33G
Ta, IH 0.7
FIG. 33H
Sa, IH 0.7
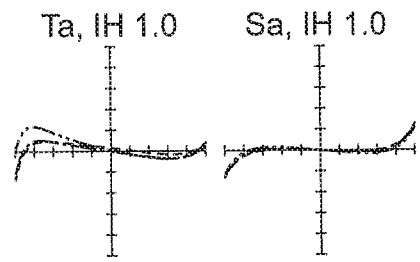
FIG. 33I
Ta, IH 1.0
FIG. 33J
Sa, IH 1.0

AS
FIY 0.92

DT
FIY 0.92

Ta, IH 0        Sa, IH 0

Ta, IH 0.5      Sa, IH 0.5

Ta, IH 0.7      Sa, IH 0.7

Ta, IH 1.0      Sa, IH 1.0

AS
FIY 0.92

DT
FIY 0.92

Ta, IH 0   Sa, IH 0

Ta, IH 0.5  Sa, IH 0.5

Ta, IH 0.7  Sa, IH 0.7

Ta, IH 1.0  Sa, IH 1.0

AS
FIY 0.92

DT
FIY 0.92

Ta, IH 0    Sa, IH 0

Ta, IH 0.5  Sa, IH 0.5

Ta, IH 0.7  Sa, IH 0.7

Ta, IH 1.0  Sa, IH 1.0

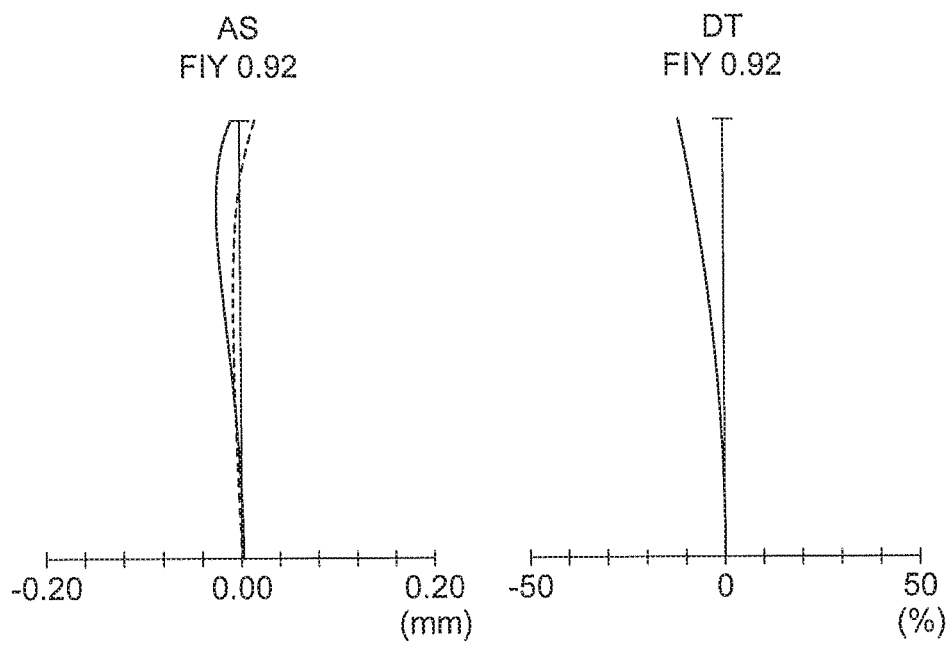
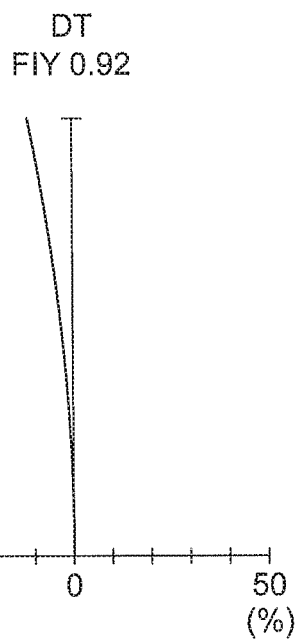
FIG. 37A AS FIY 0.92
FIG. 37B DT FIY 0.92
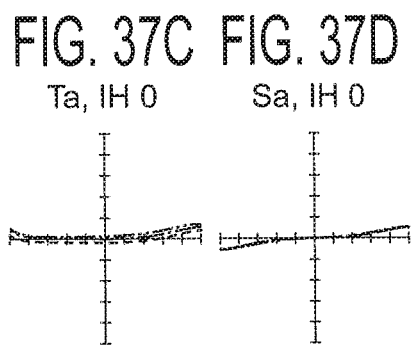
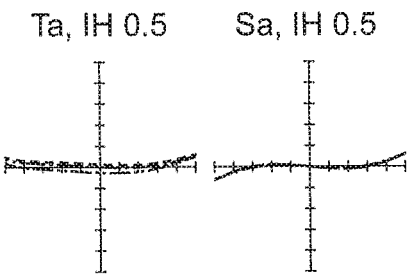
FIG. 37C Ta, IH 0   FIG. 37D Sa, IH 0   FIG. 37E Ta, IH 0.5   FIG. 37F Sa, IH 0.5
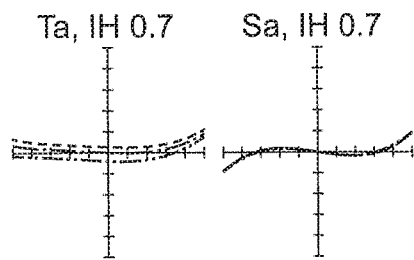
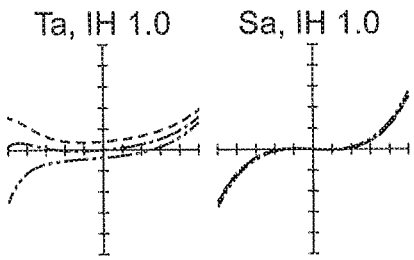
FIG. 37G Ta, IH 0.7   FIG. 37H Sa, IH 0.7   FIG. 37I Ta, IH 1.0   FIG. 37J Sa, IH 1.0

AS
FIY 0.92

DT
FIY 0.92

Ta, IH 0   Sa, IH 0

Ta, IH 0.5  Sa, IH 0.5

Ta, IH 0.7  Sa, IH 0.7

Ta, IH 1.0  Sa, IH 1.0

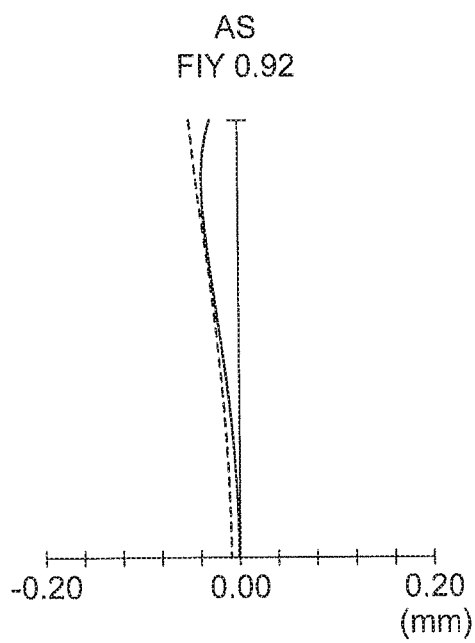
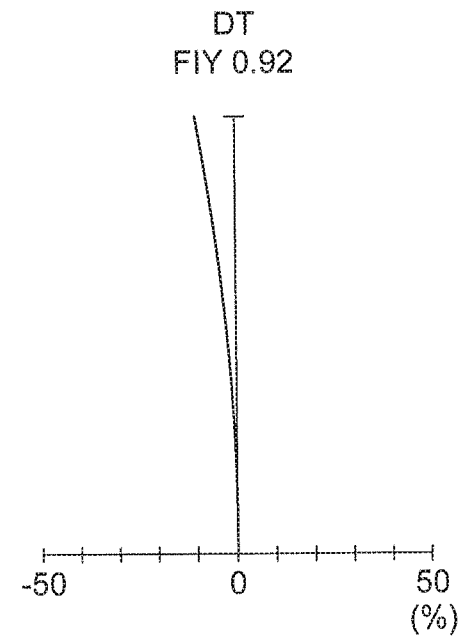
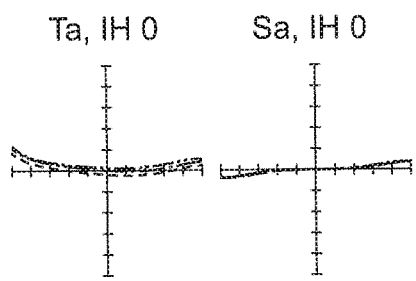
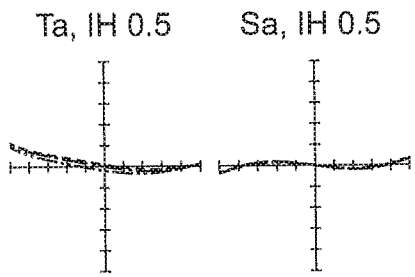
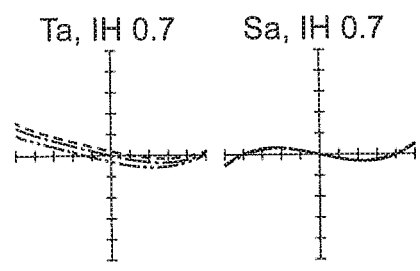
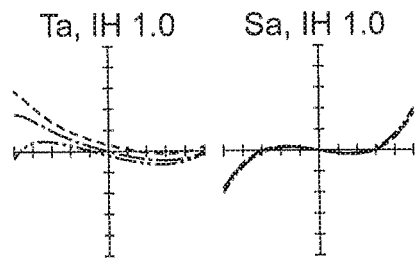

AS
FIY 0.92

DT
FIY 0.92

Ta, IH 0     Sa, IH 0

Ta, IH 0.5   Sa, IH 0.5

Ta, IH 0.7   Sa, IH 0.7

Ta, IH 1.0   Sa, IH 1.0

FIG. 41A
AS
FIY 0.92
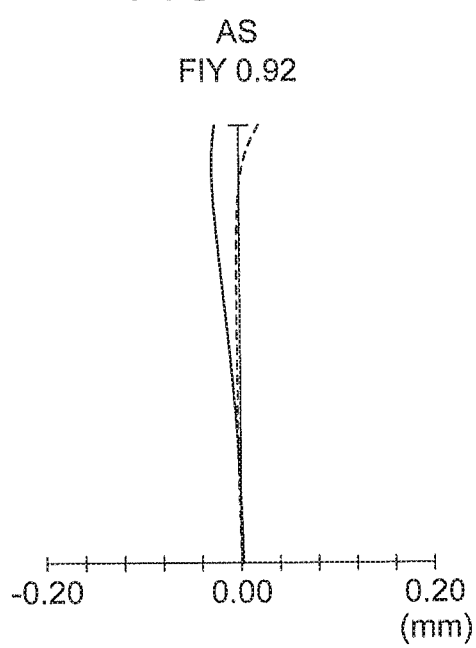
FIG. 41B
DT
FIY 0.92
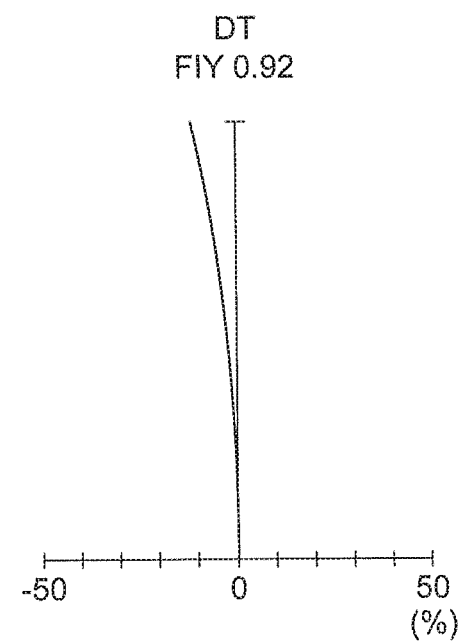
FIG. 41C        FIG. 41D
Ta, IH 0         Sa, IH 0
FIG. 41E        FIG. 41F
Ta, IH 0.5       Sa, IH 0.5
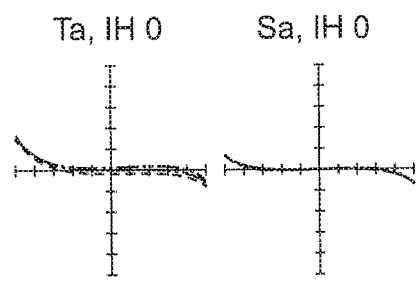
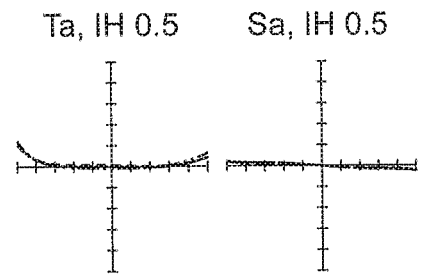
FIG. 41G        FIG. 41H
Ta, IH 0.7       Sa, IH 0.7
FIG. 41I         FIG. 41J
Ta, IH 1.0       Sa, IH 1.0
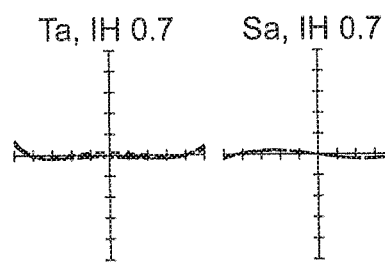
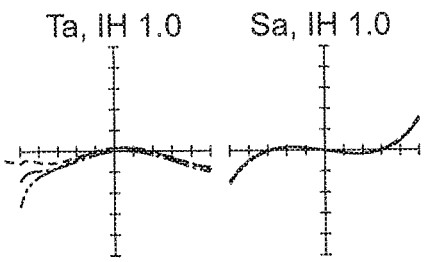

AS
FIY 0.92

DT
FIY 0.92

Ta, IH 0   Sa, IH 0

Ta, IH 0.5  Sa, IH 0.5

Ta, IH 0.7  Sa, IH 0.7

Ta, IH 1.0  Sa, IH 1.0

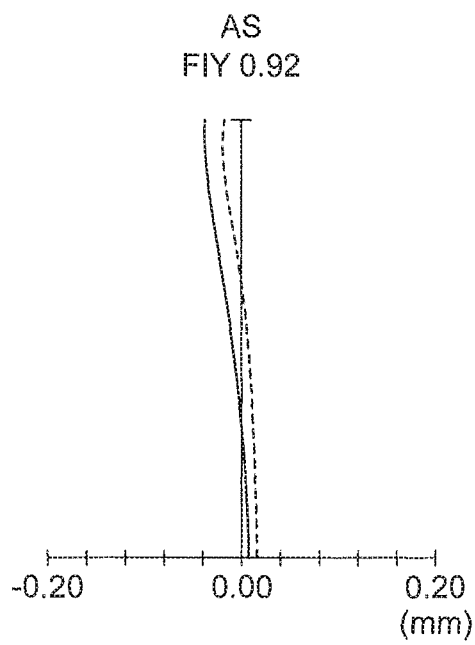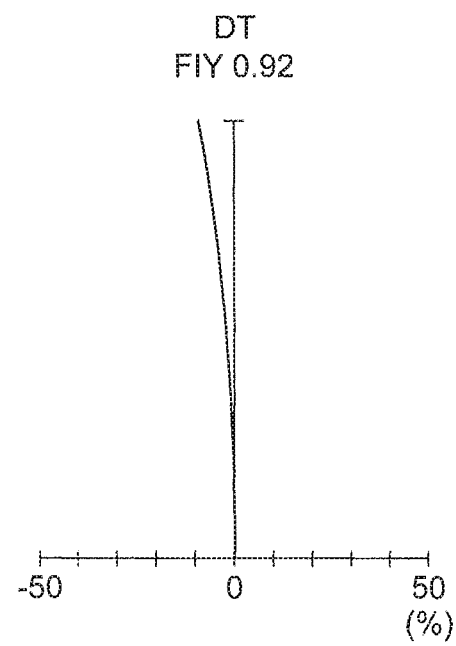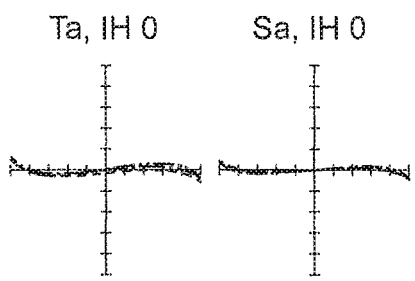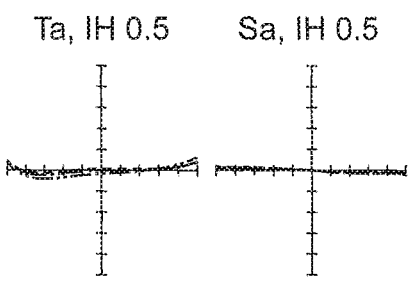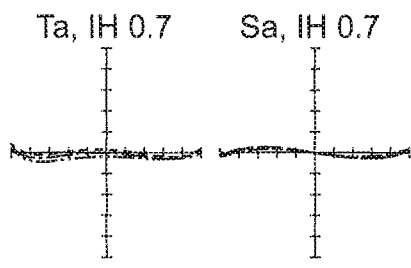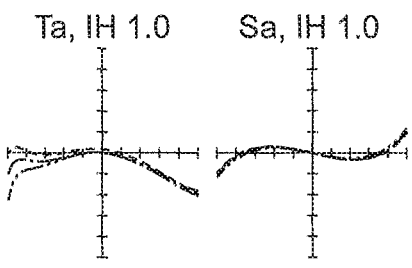

AS
FIY 0.92

DT
FIY 0.92

Ta, IH 0    Sa, IH 0

Ta, IH 0.5  Sa, IH 0.5

Ta, IH 0.7  Sa, IH 0.7

Ta, IH 1.0  Sa, IH 1.0

AS
FIY 0.92

DT
FIY 0.92

Ta, IH 0    Sa, IH 0

Ta, IH 0.5   Sa, IH 0.5

Ta, IH 0.7   Sa, IH 0.7

Ta, IH 1.0   Sa, IH 1.0

AS
FIY 0.92

DT
FIY 0.92

Ta, IH 0    Sa, IH 0

Ta, IH 0.5  Sa, IH 0.5

Ta, IH 0.7  Sa, IH 0.7

Ta, IH 1.0  Sa, IH 1.0

FIG. 47A
AS
FIY 0.92
FIG. 47B
DT
FIY 0.92
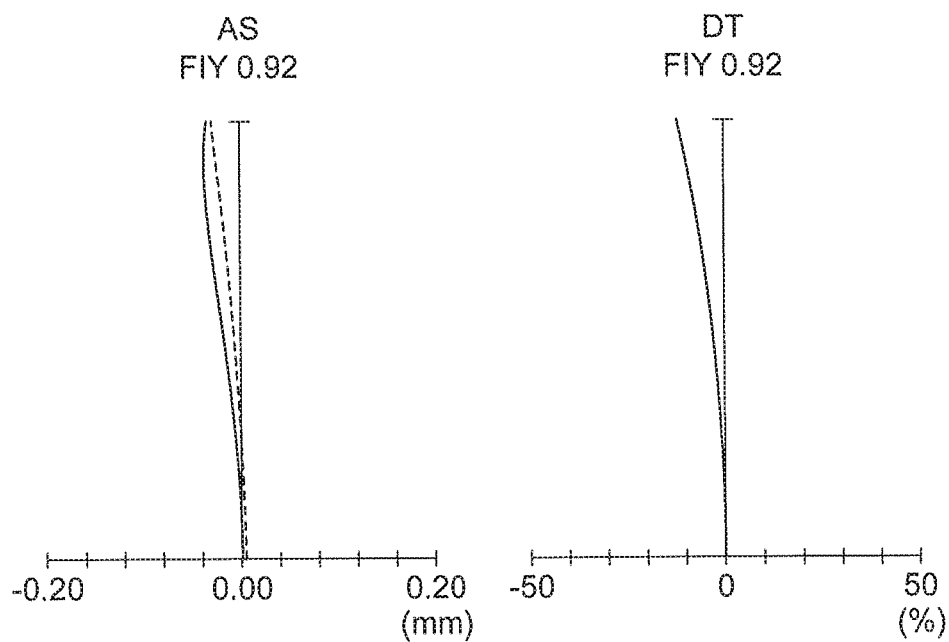
FIG. 47C    FIG. 47D
Ta, IH 0      Sa, IH 0
FIG. 47E    FIG. 47F
Ta, IH 0.5    Sa, IH 0.5
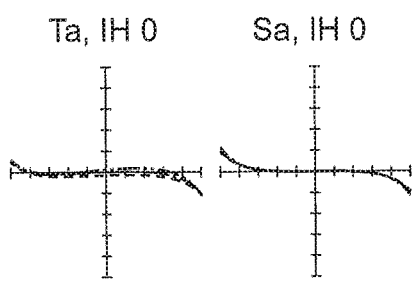 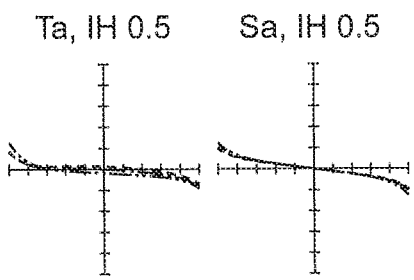
FIG. 47G    FIG. 47H
Ta, IH 0.7    Sa, IH 0.7
FIG. 47I    FIG. 47J
Ta, IH 1.0    Sa, IH 1.0
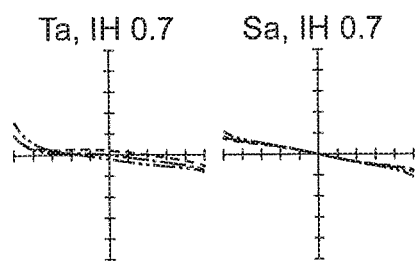 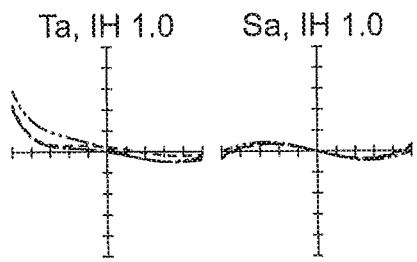

AS
FIY 0.92

-0.20　0.00　0.20
(mm)

DT
FIY 0.92

-50　0　50
(%)

Ta, IH 0   Sa, IH 0

Ta, IH 0.5   Sa, IH 0.5

Ta, IH 0.7   Sa, IH 0.7

Ta, IH 1.0   Sa, IH 1.0

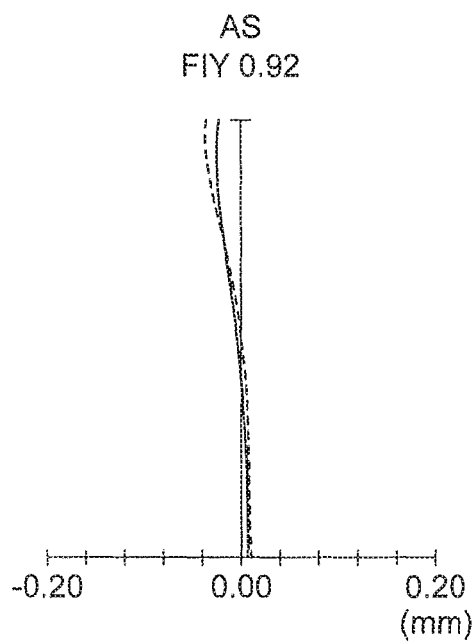
FIG. 49A
AS
FIY 0.92
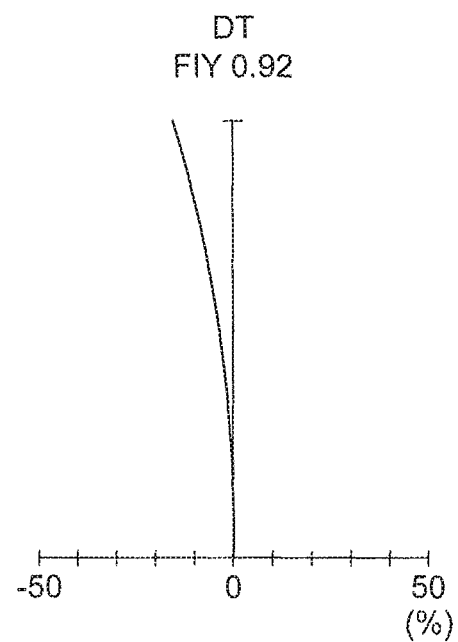
FIG. 49B
DT
FIY 0.92
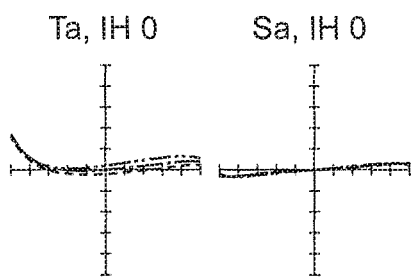
FIG. 49C Ta, IH 0    FIG. 49D Sa, IH 0
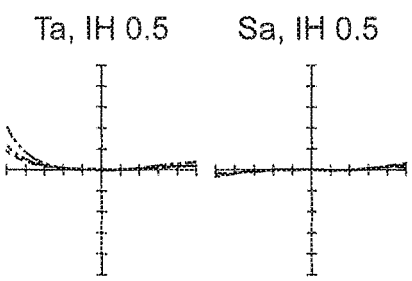
FIG. 49E Ta, IH 0.5    FIG. 49F Sa, IH 0.5
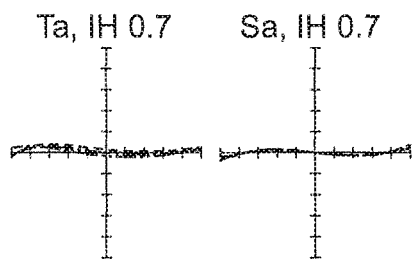
FIG. 49G Ta, IH 0.7    FIG. 49H Sa, IH 0.7
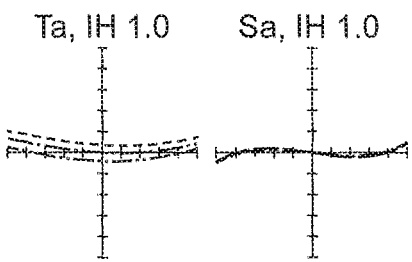
FIG. 49I Ta, IH 1.0    FIG. 49J Sa, IH 1.0

FIG. 50A
AS
FIY 0.92
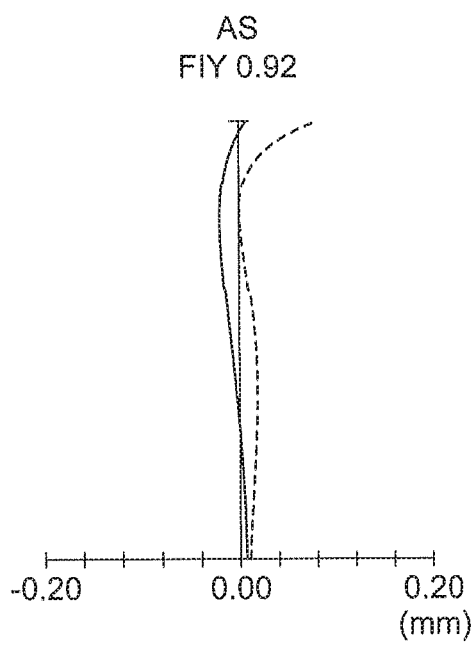
FIG. 50B
DT
FIY 0.92
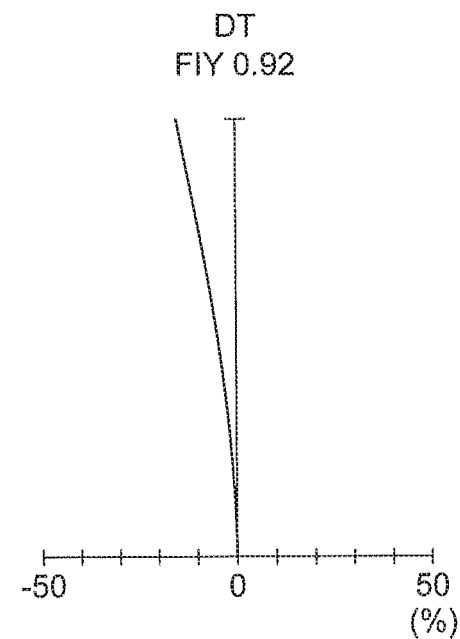
FIG. 50C Ta, IH 0    FIG. 50D Sa, IH 0    FIG. 50E Ta, IH 0.5    FIG. 50F Sa, IH 0.5
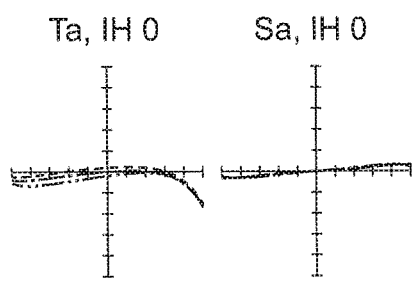 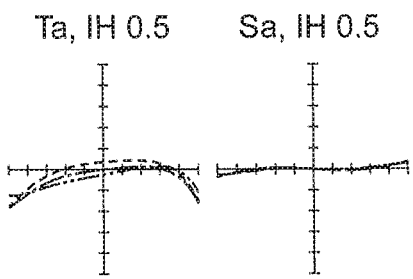
FIG. 50G Ta, IH 0.7    FIG. 50H Sa, IH 0.7    FIG. 50I Ta, IH 1.0    FIG. 50J Sa, IH 1.0
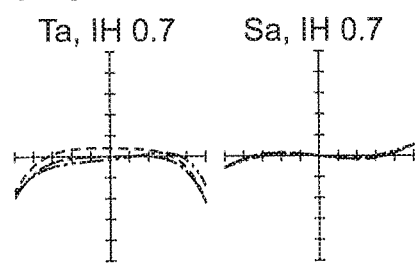 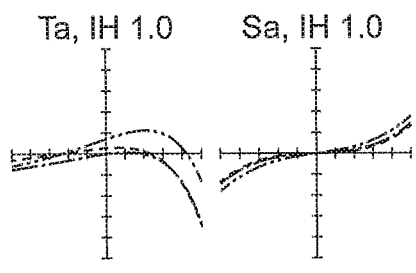

AS
FIY 0.92

DT
FIY 0.92

Ta, IH 0   Sa, IH 0

Ta, IH 0.5   Sa, IH 0.5

Ta, IH 0.7   Sa, IH 0.7

Ta, IH 1.0   Sa, IH 1.0

AS
FIY 0.92

DT
FIY 0.92

Ta, IH 0      Sa, IH 0

Ta, IH 0.5    Sa, IH 0.5

Ta, IH 0.7    Sa, IH 0.7

Ta, IH 1.0    Sa, IH 1.0

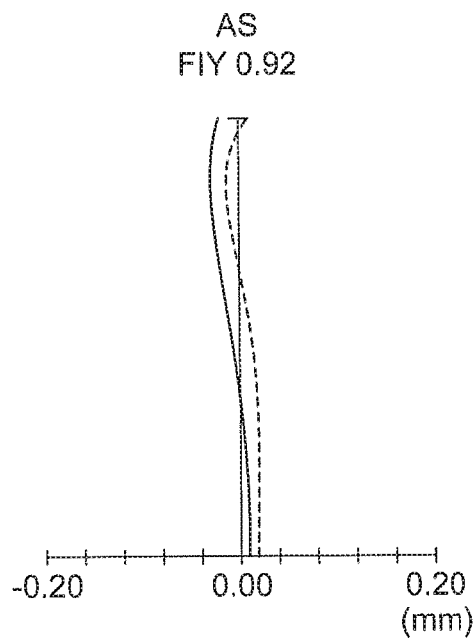
FIG. 53A
AS
FIY 0.92
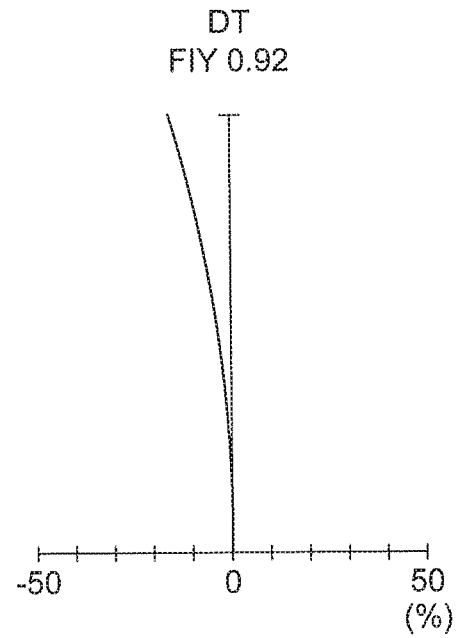
FIG. 53B
DT
FIY 0.92
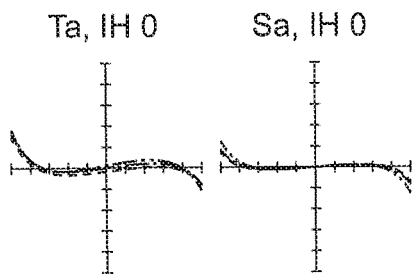
FIG. 53C Ta, IH 0
FIG. 53D Sa, IH 0
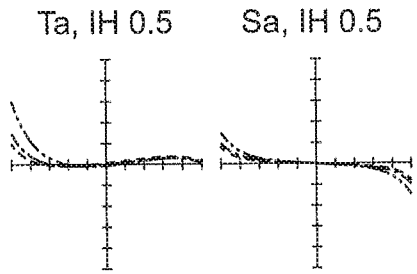
FIG. 53E Ta, IH 0.5
FIG. 53F Sa, IH 0.5
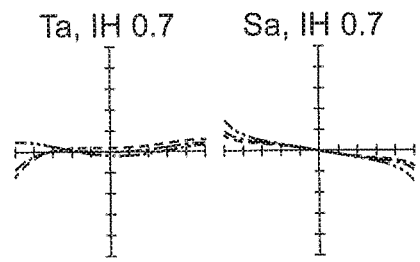
FIG. 53G Ta, IH 0.7
FIG. 53H Sa, IH 0.7
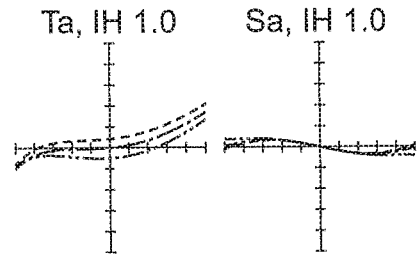
FIG. 53I Ta, IH 1.0
FIG. 53J Sa, IH 1.0

AS
FIY 0.92

DT
FIY 0.92

Ta, IH 0    Sa, IH 0

Ta, IH 0.5  Sa, IH 0.5

Ta, IH 0.7  Sa, IH 0.7

Ta, IH 1.0  Sa, IH 1.0

FIG. 55A
AS
FIY 0.92
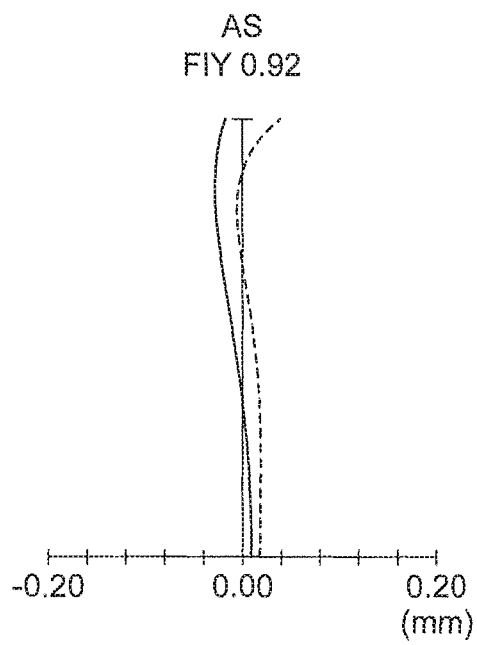
-0.20   0.00   0.20
(mm)
FIG. 55B
DT
FIY 0.92
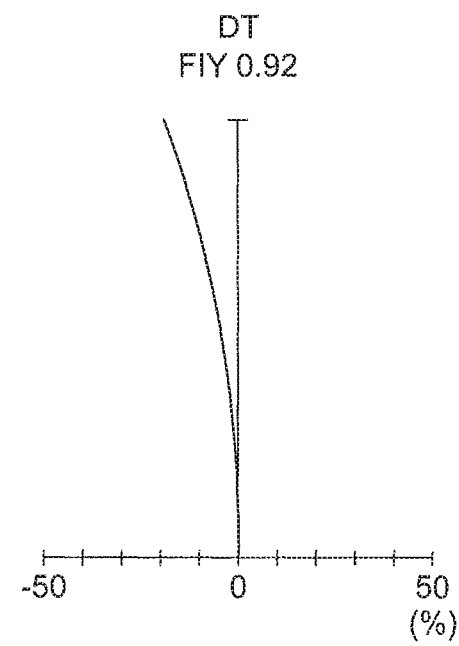
-50   0   50
(%)
FIG. 55C
Ta, IH 0
FIG. 55D
Sa, IH 0
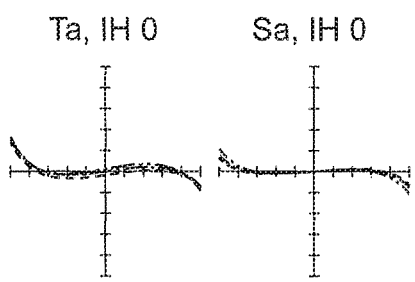
FIG. 55E
Ta, IH 0.5
FIG. 55F
Sa, IH 0.5
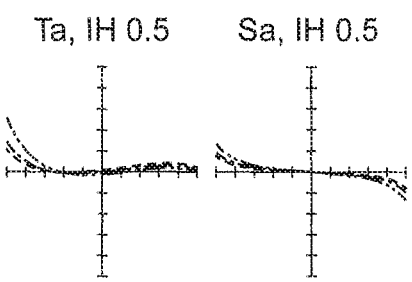
FIG. 55G
Ta, IH 0.7
FIG. 55H
Sa, IH 0.7
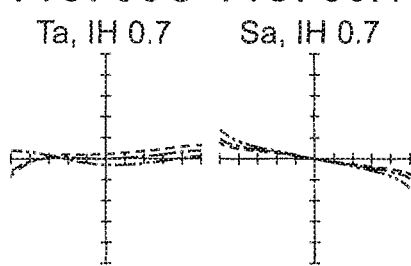
FIG. 55I
Ta, IH 1.0
FIG. 55J
Sa, IH 1.0
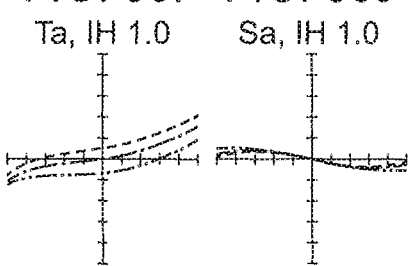

AS
FIY 0.92

DT
FIY 0.92

Ta, IH 0   Sa, IH 0

Ta, IH 0.5  Sa, IH 0.5

Ta, IH 0.7  Sa, IH 0.7

Ta, IH 1.0  Sa, IH 1.0

AS
FIY 0.92

DT
FIY 0.92

Ta, IH 0   Sa, IH 0

Ta, IH 0.5  Sa, IH 0.5

Ta, IH 0.7  Sa, IH 0.7

Ta, IH 1.0  Sa, IH 1.0

AS
FIY 0.92

DT
FIY 0.92

Ta, IH 0     Sa, IH 0

Ta, IH 0.5   Sa, IH 0.5

Ta, IH 0.7   Sa, IH 0.7

Ta, IH 1.0   Sa, IH 1.0

AS
FIY 0.92

DT
FIY 0.92

Ta, IH 0   Sa, IH 0

Ta, IH 0.5  Sa, IH 0.5

Ta, IH 0.7  Sa, IH 0.7

Ta, IH 1.0  Sa, IH 1.0

FIG. 60A
AS
FIY 0.92
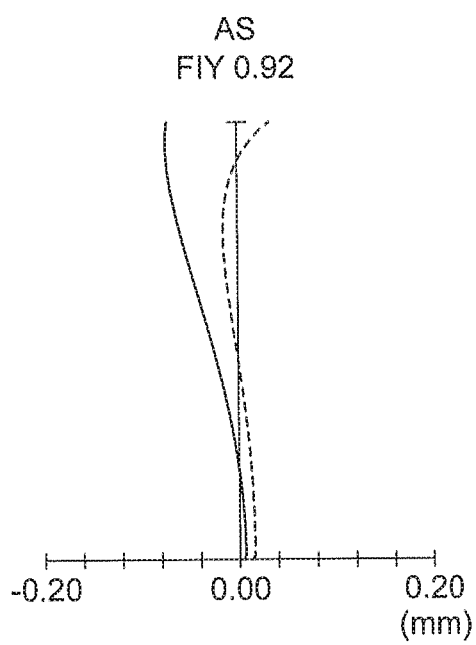
-0.20  0.00  0.20
(mm)
FIG. 60B
DT
FIY 0.92
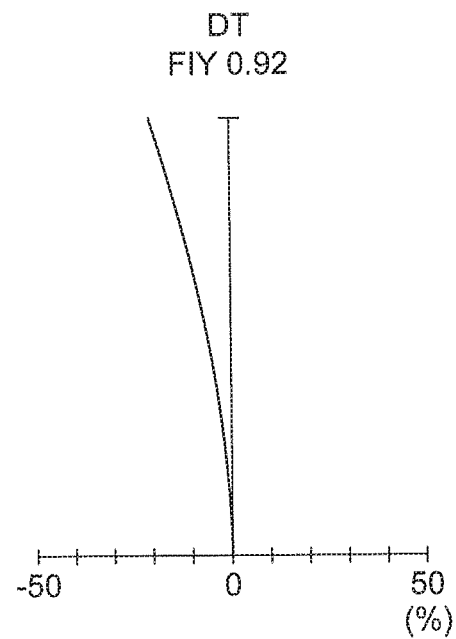
-50  0  50
(%)
FIG. 60C  FIG. 60D
Ta, IH 0    Sa, IH 0
FIG. 60E  FIG. 60F
Ta, IH 0.5  Sa, IH 0.5
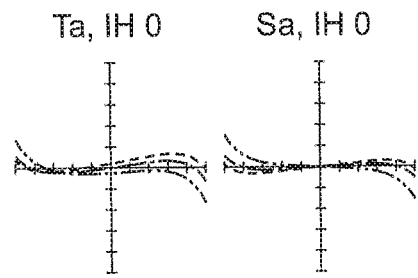 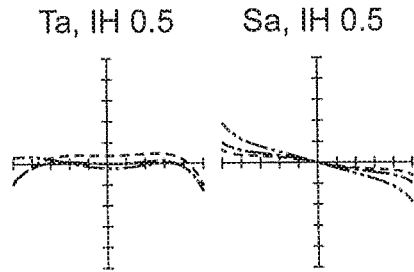
FIG. 60G  FIG. 60H
Ta, IH 0.7  Sa, IH 0.7
FIG. 60I  FIG. 60J
Ta, IH 1.0  Sa, IH 1.0
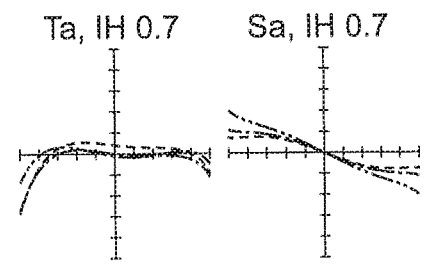 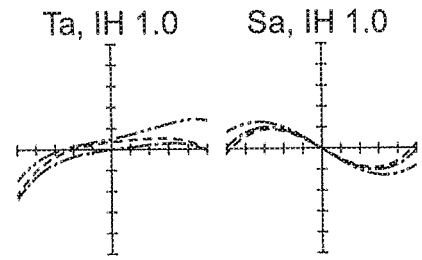

AS
FIY 0.92

DT
FIY 0.92

Ta, IH 0    Sa, IH 0

Ta, IH 0.5  Sa, IH 0.5

Ta, IH 0.7  Sa, IH 0.7

Ta, IH 1.0  Sa, IH 1.0

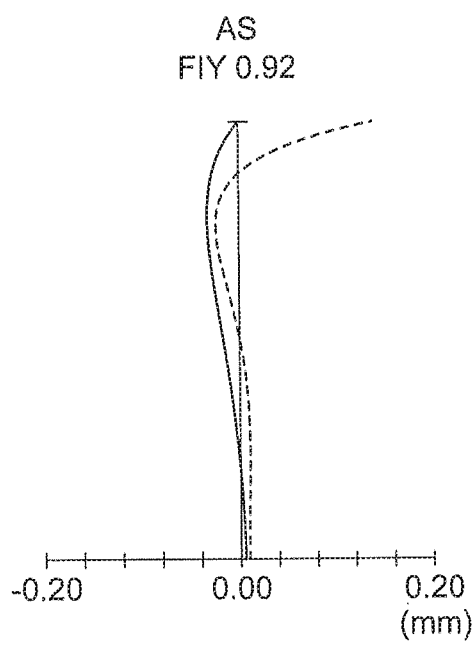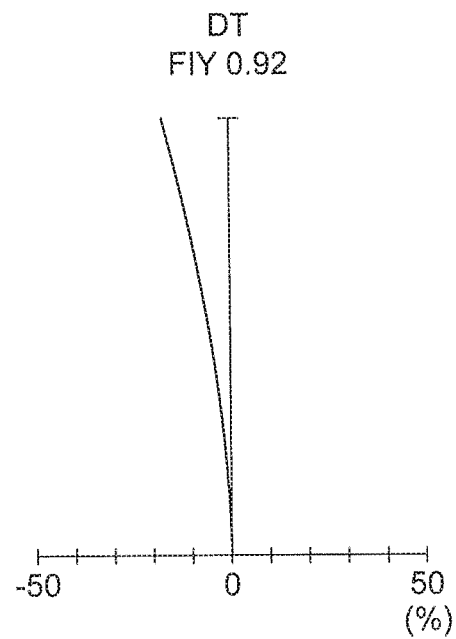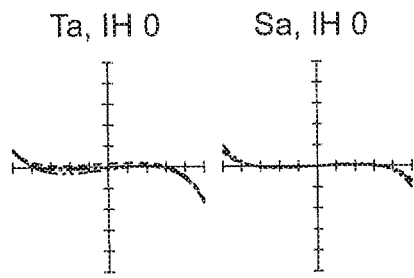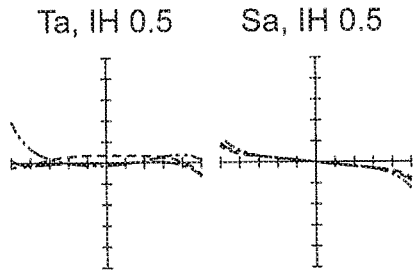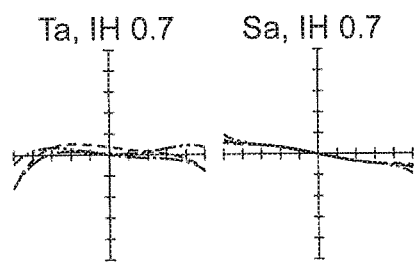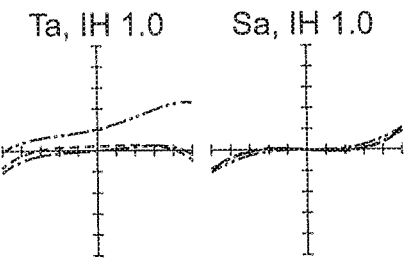

AS
FIY 0.92

DT
FIY 0.92

Ta, IH 0   Sa, IH 0

Ta, IH 0.5  Sa, IH 0.5

Ta, IH 0.7  Sa, IH 0.7

Ta, IH 1.0  Sa, IH 1.0

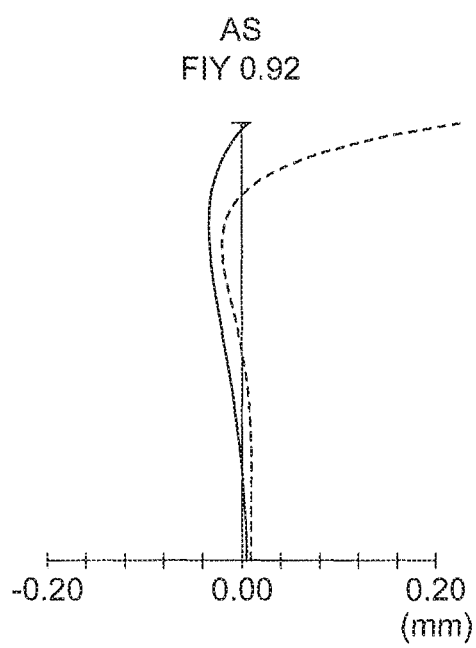
FIG. 64A
AS
FIY 0.92
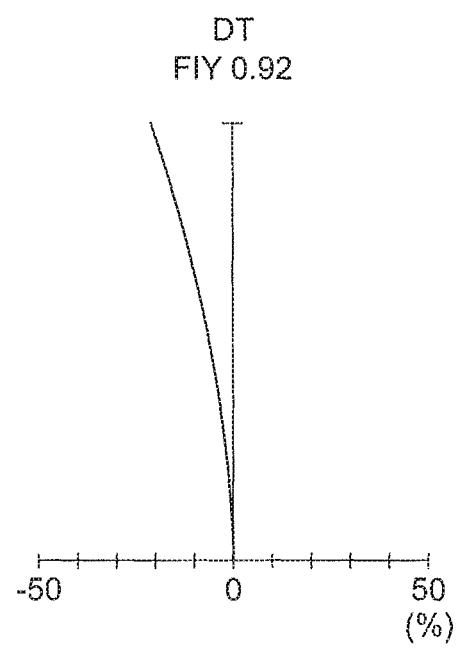
FIG. 64B
DT
FIY 0.92
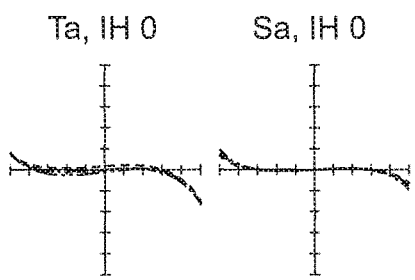
FIG. 64C Ta, IH 0    FIG. 64D Sa, IH 0
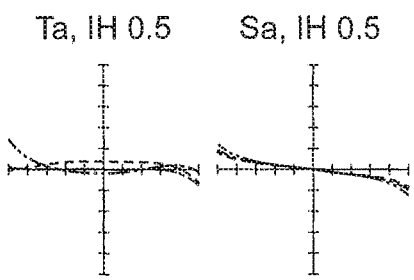
FIG. 64E Ta, IH 0.5    FIG. 64F Sa, IH 0.5
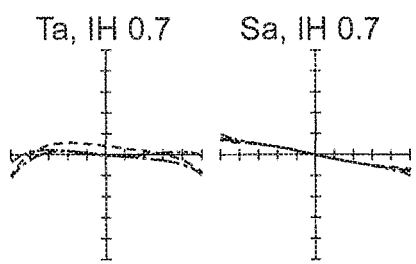
FIG. 64G Ta, IH 0.7    FIG. 64H Sa, IH 0.7
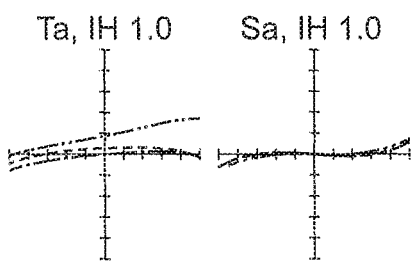
FIG. 64I Ta, IH 1.0    FIG. 64J Sa, IH 1.0

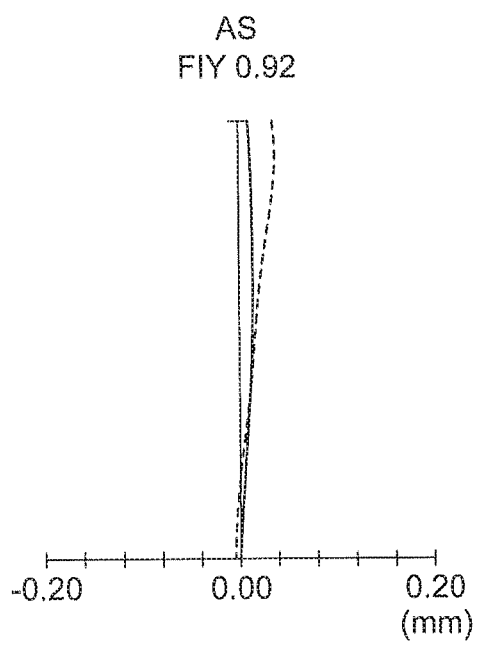
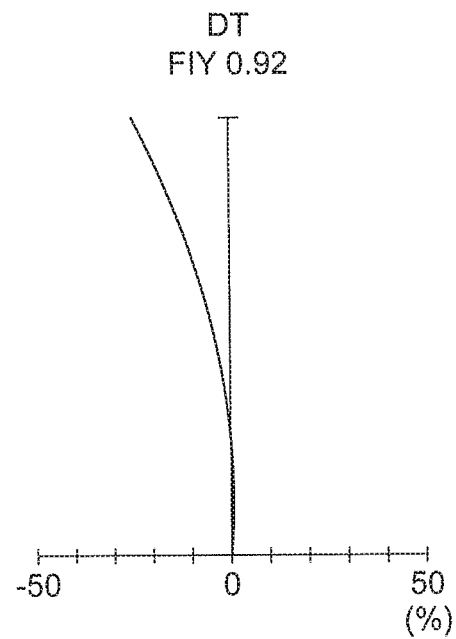
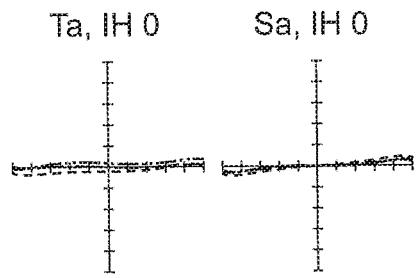
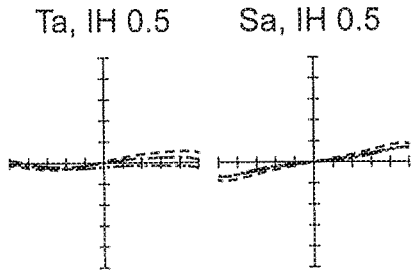
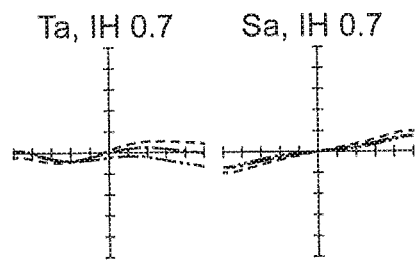
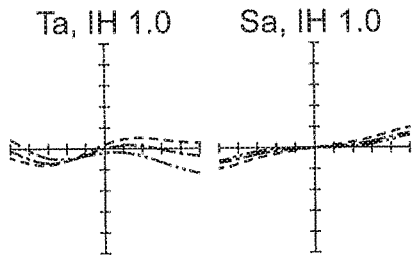

AS
FIY 0.92

DT
FIY 0.92

Ta, IH 0    Sa, IH 0

Ta, IH 0.5  Sa, IH 0.5

Ta, IH 0.7  Sa, IH 0.7

Ta, IH 1.0  Sa, IH 1.0

AS
FIY 0.92

DT
FIY 0.92

Ta, IH 0     Sa, IH 0

Ta, IH 0.5   Sa, IH 0.5

Ta, IH 0.7   Sa, IH 0.7

Ta, IH 1.0   Sa, IH 1.0

AS
FIY 0.92

DT
FIY 0.92

Ta, IH 0   Sa, IH 0

Ta, IH 0.5  Sa, IH 0.5

Ta, IH 0.7  Sa, IH 0.7

Ta, IH 1.0  Sa, IH 1.0

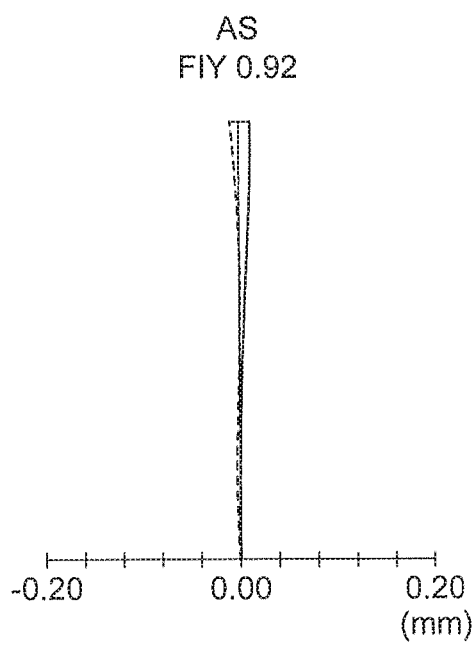
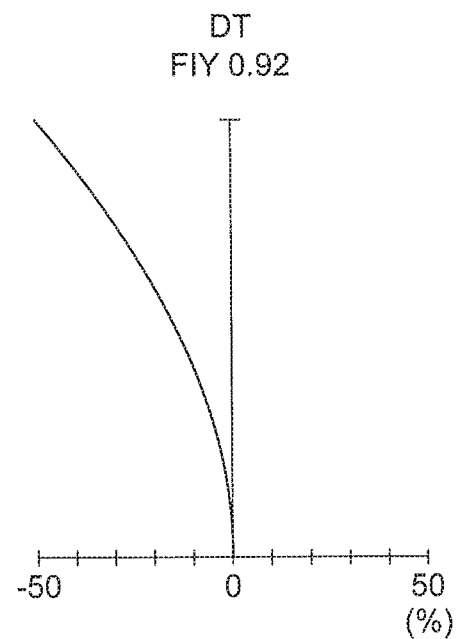
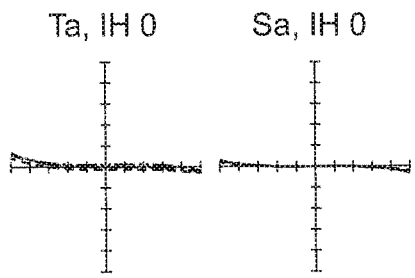
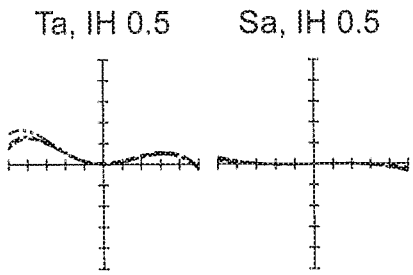
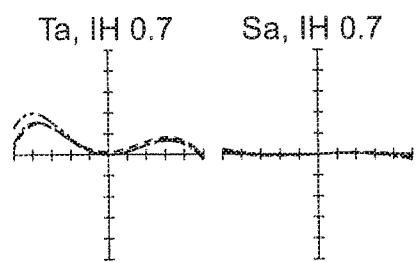
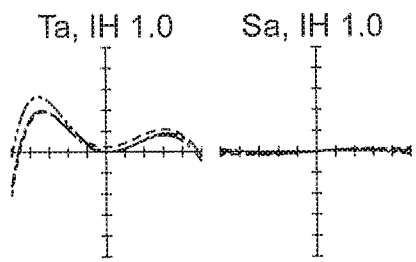

AS
FIY 0.92

DT
FIY 0.92

Ta, IH 0    Sa, IH 0

Ta, IH 0.5  Sa, IH 0.5

Ta, IH 0.7  Sa, IH 0.7

Ta, IH 1.0  Sa, IH 1.0

AS
FIY 0.92

DT
FIY 0.92

Ta, IH 0     Sa, IH 0

Ta, IH 0.5   Sa, IH 0.5

Ta, IH 0.7   Sa, IH 0.7

Ta, IH 1.0   Sa, IH 1.0

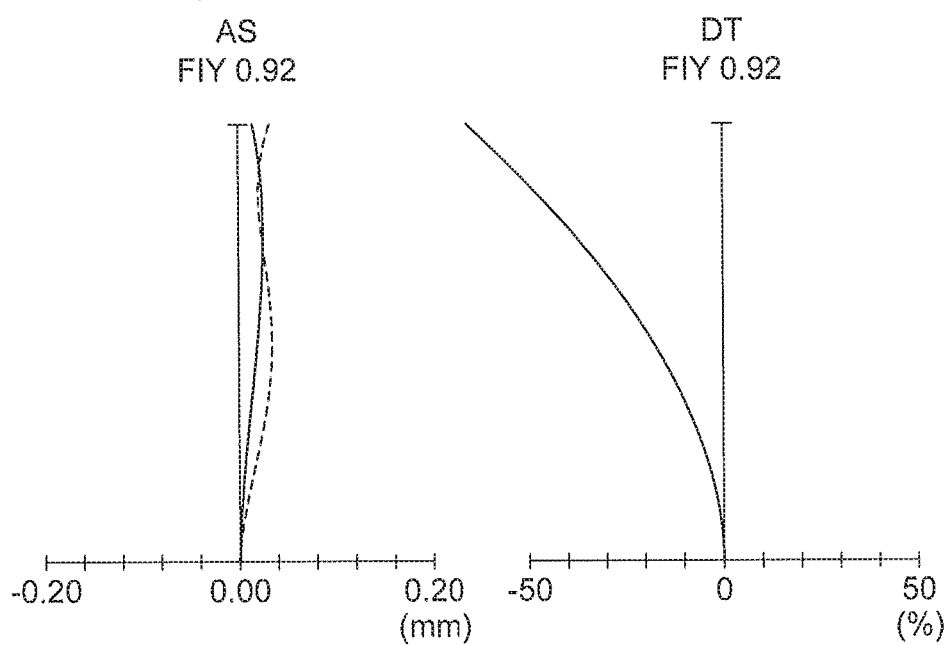
FIG. 72A
AS
FIY 0.92
FIG. 72B
DT
FIY 0.92
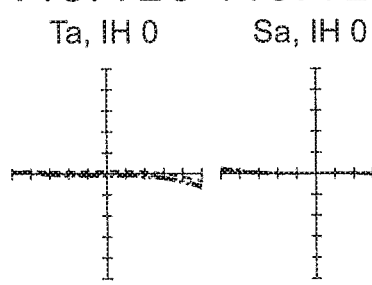
FIG. 72C
Ta, IH 0
FIG. 72D
Sa, IH 0
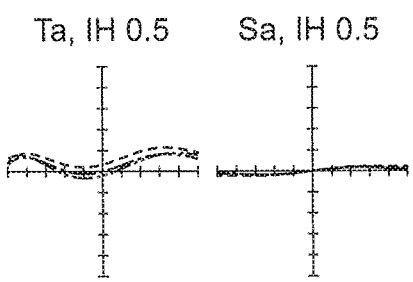
FIG. 72E
Ta, IH 0.5
FIG. 72F
Sa, IH 0.5
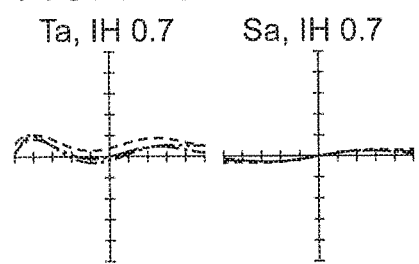
FIG. 72G
Ta, IH 0.7
FIG. 72H
Sa, IH 0.7
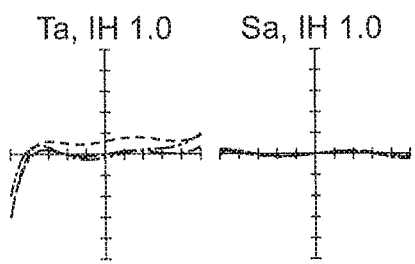
FIG. 72I
Ta, IH 1.0
FIG. 72J
Sa, IH 1.0

OPTICAL SYSTEM FOR STEREOSCOPIC VISION AND IMAGE PICKUP APPARATUS USING THE SAME

CROSS-REFERENCE TO RELATED APPLICATION

The present application is a continuation application of International Application No. PCT/JP2017/035567 filed on Sep. 29, 2017, the entire contents of which are incorporated herein by reference.

BACKGROUND

Technical Field

The present disclosure relates to an optical system for stereoscopic vision and an image pickup apparatus using the same, and particularly to an optical system for stereoscopic vision to be used mainly in a field of endoscopes, and an image pickup apparatus using the same.

Description of the Related Art

An optical system in which two optical images are formed in the same area of an image formation surface has been disclosed in Japanese Patent No. 4750175 Publication and Japanese Patent Application Laid-open Publication No. 2014-174390.

In Japanese Patent No. 4750175 Publication, a stereoscopic optical system is disclosed. The stereoscopic optical system includes an optical system in which two optical paths are formed, an image forming optical system, and a time-division optical path switching unit. The optical system in which two optical paths are formed includes two afocal optical systems. An optical image is formed by one of the afocal optical systems and the image forming optical system, and an optical image is formed by the other afocal optical system and the image forming optical system. By the time-division optical path switching unit, only light from the one afocal optical system is incident on the image forming optical system.

In Japanese Patent No. 4750175, two optical images are formed in a same area of the image formation surface. Consequently, it is possible to make a size of the image larger as compared to a case in which two optical images are formed in parallel.

In Japanese Patent Application Laid-open Publication No. 2014-174390, an optical system in which two optical images are formed in a same area is specifically disclosed. An imaging optical system includes a front unit and a rear unit. The front unit includes a first front unit and a second front unit. The first front unit and the second front unit consist of at least a negative front first unit, a front second unit of a cemented lens, a front third unit of a cemented lens, and an aperture.

SUMMARY

An optical system for stereoscopic vision according to at least some embodiments of the present disclosure includes in order from an object side:

a front unit, and
a rear unit, wherein
each of the front unit and the rear unit includes a lens component consisting of a single lens or a cemented lens, the front unit includes a first front unit and a second front unit,
an optical axis of the first front unit, an optical axis of the second front unit, and an optical axis of the rear unit are positioned in a same plane,
the optical axis of the rear unit is positioned between the optical axis of the first front unit and the optical axis of the second front unit, and
the following conditional expression (1) is satisfied:

$$0.15 < De/\Phi < 0.85 \qquad (1)$$

where,
$\Phi$ denotes an image-circle diameter at an image forming position, and
De denotes a distance between a center of an entrance pupil in the first front unit and a center of an entrance pupil in the second front unit.

Moreover, an image pickup apparatus according to at least some embodiments of the present disclosure includes:

an optical system, and
an imager which has an imager which converts an image formed on an image pickup surface by the optical system to an electric signal, wherein
the optical system is the abovementioned optical system for stereoscopic vision.

BRIEF DESCRIPTION OF THE DRAWINGS

FIG. 1A and FIG. 1B are lens cross-sectional views of a first common optical system;

FIG. 3 is a lens cross-sectional view of an optical system for stereoscopic vision of an example 1;

FIG. 17A, FIG. 17B, FIG. 17C, FIG. 17D, FIG. 17E, FIG. 17F, FIG. 17G, FIG. 17H, FIG. 17I, and FIG. 17J are aberration diagrams of the optical system for stereoscopic vision of the example 1;

FIG. 20A, FIG. 20B, FIG. 20C, FIG. 20D, FIG. 20E, FIG. 20F, FIG. 20G, FIG. 20H, FIG. 20I, and FIG. 20J are aberration diagrams of the optical system for stereoscopic vision of the example 1;

FIG. 26A, FIG. 26B, FIG. 26C, FIG. 26D, FIG. 26E, FIG. 26F, FIG. 26G, FIG. 26H, FIG. 26I, and FIG. 26J are aberration diagrams of the optical system for stereoscopic vision of the example 3;

FIG. 29A, FIG. 29B, FIG. 29C, FIG. 29D, FIG. 29E, FIG. 29F, FIG. 29G, FIG. 29H, FIG. 29I, and FIG. 29J are aberration diagrams of the optical system for stereoscopic vision of the example 4;

FIG. 30A, FIG. 30B, FIG. 30C, FIG. 30D, FIG. 30E, FIG. 30F, FIG. 30G, FIG. 30H, FIG. 30I, and FIG. 30J are aberration diagrams of the optical system for stereoscopic vision of the example 4;

FIG. 31A, FIG. 31B, FIG. 31C, FIG. 31D, FIG. 31E, FIG. 31F, FIG. 31G, FIG. 31H, FIG. 31I, and FIG. 31J are aberration diagrams of the optical system for stereoscopic vision of the example 4;

FIG. 32A, FIG. 32B, FIG. 32C, FIG. 32D, FIG. 32E, FIG. 32F, FIG. 32G, FIG. 32H, FIG. 32I, and FIG. 32J are aberration diagrams of the optical system for stereoscopic vision of the example 4;

FIG. 33A, FIG. 33B, FIG. 33C, FIG. 33D, FIG. 33E, FIG. 33F, FIG. 33G, FIG. 33H, FIG. 33I, and FIG. 33J are aberration diagrams of the optical system for stereoscopic vision of the example 5;

FIG. 37A, FIG. 37B, FIG. 37C, FIG. 37D, FIG. 37E, FIG. 37F, FIG. 37G, FIG. 37H, FIG. 37I, and FIG. 37J are aberration diagrams of the optical system for stereoscopic vision of the example 6;

FIG. 39A, FIG. 39B, FIG. 39C, FIG. 39D, FIG. 39E, FIG. 39F, FIG. 39G, FIG. 39H, FIG. 39I, and FIG. 39J are aberration diagrams of the optical system for stereoscopic vision of the example 6;

FIG. 41A, FIG. 41B, FIG. 41C, FIG. 41D, FIG. 41E, FIG. 41F, FIG. 41G, FIG. 41H, FIG. 41I, and FIG. 41J are aberration diagrams of the optical system for stereoscopic vision of the example 7;

FIG. 43A, FIG. 43B, FIG. 43C, FIG. 43D, FIG. 43E, FIG. 43F, FIG. 43G, FIG. 43H, FIG. 43I, and FIG. 43J are aberration diagrams of the optical system for stereoscopic vision of the example 7;

FIG. 47A, FIG. 47B, FIG. 47C, FIG. 47D, FIG. 47E, FIG. 47F, FIG. 47G, FIG. 47H, FIG. 47I, and FIG. 47J are aberration diagrams of the optical system for stereoscopic vision of the example 8;

FIG. 49A, FIG. 49B, FIG. 49C, FIG. 49D, FIG. 49E, FIG. 49F, FIG. 49G, FIG. 49H, FIG. 49I, and FIG. 49J are aberration diagrams of the optical system for stereoscopic vision of the example 9;

FIG. 50A, FIG. 50B, FIG. 50C, FIG. 50D, FIG. 50E, FIG. 50F, FIG. 50G, FIG. 50H, FIG. 50I, and FIG. 50J are aberration diagrams of the optical system for stereoscopic vision of the example 9;

FIG. 53A, FIG. 53B, FIG. 53C, FIG. 53D, FIG. 53E, FIG. 53F, FIG. 53G, FIG. 53H, FIG. 53I, and FIG. 53J are aberration diagrams of the optical system for stereoscopic vision of the example 10;

FIG. 55A, FIG. 55B, FIG. 55C, FIG. 55D, FIG. 55E, FIG. 55F, FIG. 55G, FIG. 55H, FIG. 55I, and FIG. 55J are aberration diagrams of the optical system for stereoscopic vision of the example 10;

FIG. 60A, FIG. 60B, FIG. 60C, FIG. 60D, FIG. 60E, FIG. 60F, FIG. 60G, FIG. 60H, FIG. 60I, and FIG. 60J are aberration diagrams of the optical system for stereoscopic vision of the example 11;

FIG. 62A, FIG. 62B, FIG. 62C, FIG. 62D, FIG. 62E, FIG. 62F, FIG. 62G, FIG. 62H, FIG. 62I, and FIG. 62J are aberration diagrams of the optical system for stereoscopic vision of the example 12;

FIG. 64A, FIG. 64B, FIG. 64C, FIG. 64D, FIG. 64E, FIG. 64F, FIG. 64G, FIG. 64H, FIG. 64I, and FIG. 64J are aberration diagrams of the optical system for stereoscopic vision of the example 12;

FIG. 65A, FIG. 65B, FIG. 65C, FIG. 65D, FIG. 65E, FIG. 65F, FIG. 65G, FIG. 65H, FIG. 65I, and FIG. 65J are aberration diagrams of the optical system for stereoscopic vision of the example 13;

FIG. 69A, FIG. 69B, FIG. 69C, FIG. 69D, FIG. 69E, FIG. 69F, FIG. 69G, FIG. 69H, FIG. 69I, and FIG. 69J are aberration diagrams of the optical system for stereoscopic vision of the example 14;

FIG. 72A, FIG. 72B, FIG. 72C, FIG. 72D, FIG. 72E, FIG. 72F, FIG. 72G, FIG. 72H, FIG. 72I, and FIG. 72J are aberration diagrams of the optical system for stereoscopic vision of the example 14.

DETAILED DESCRIPTION

Figure 2A:
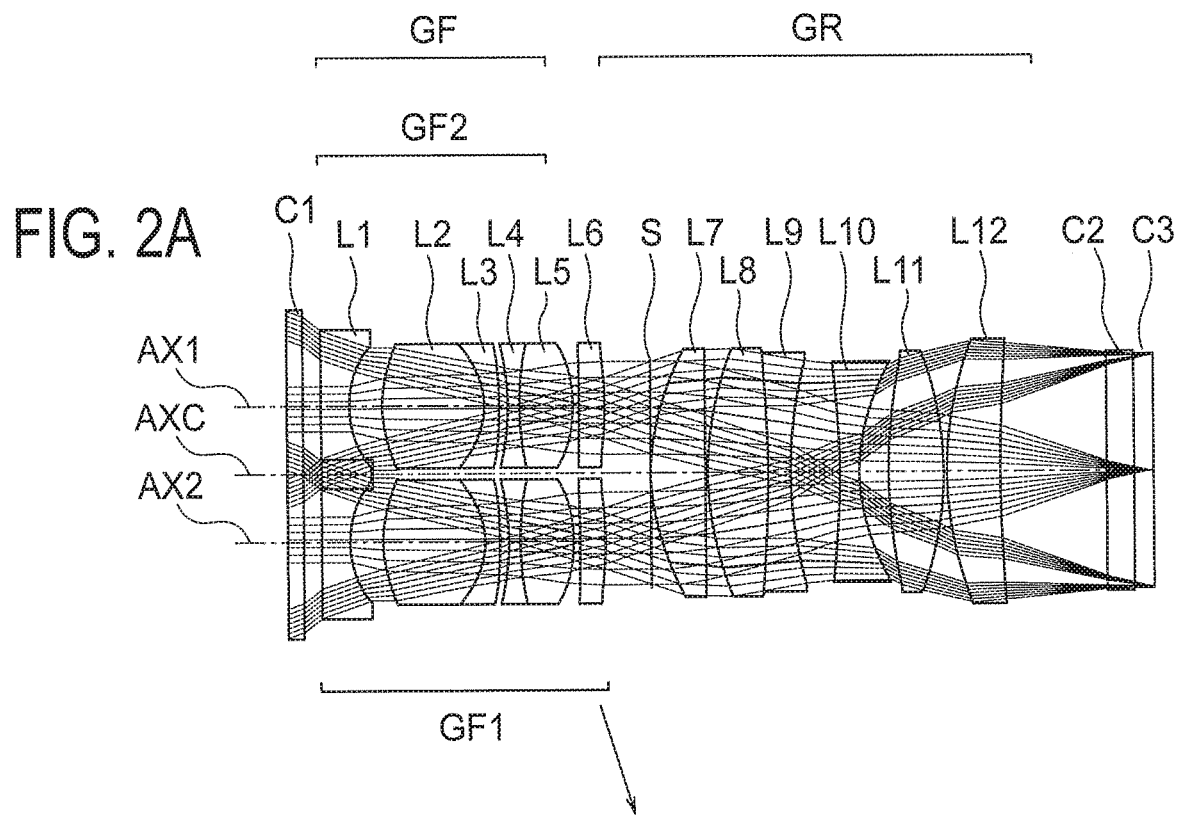
FIG. 2A and FIG. 2B are lens cross-sectional views of a second common optical system.

Action and effect of embodiments according to certain aspects of the present disclosure will be described below. In the explanation of the action and effect of the embodiments concretely, the explanation will be made by citing concrete examples. However, similar to a case of the examples to be described later, aspects exemplified thereof are only some of the aspects included in the present disclosure, and there exists a large number of variations in these aspects. Consequently, the present disclosure is not restricted to the aspects that will be exemplified.

Optical systems for stereoscopic vision of embodiments from a first embodiment to a fourth embodiment will be described below. Prior to the description, an optical system common to the optical system for stereoscopic vision of the four embodiments (hereinafter, referred to as 'common optical system') will be described below.

The common optical system includes in order from an object side, a front unit and a rear unit, wherein each of the front unit and the rear unit includes a lens component consisting of a single lens or a cemented lens, the front unit includes a first front unit and a second front unit, an optical axis of the first front unit, an optical axis of the second front unit, and an optical axis of the rear unit are positioned in a same plane, the optical axis of the rear unit is positioned between the optical axis of the first front unit and the optical axis of the second front unit, and the following conditional expression (1) is satisfied:

$$0.15 < De/\Phi < 0.85 \qquad (1)$$

where,

Φ denotes an image-circle diameter at an image forming position, and

De denotes a distance between a center of an entrance pupil in the first front unit and a center of an entrance pupil in the second front unit.

The common optical system includes in order from the object side, the front unit and the rear unit. Each of the front unit and the rear unit includes a lens component consisting of a single lens or a cemented lens.

The front unit includes the first front unit and the second front unit. The optical axis of the first front unit, the optical axis of the second front unit, and the optical axis of the rear unit are positioned in the same plane, and the optical axis of the rear unit is positioned between the optical axis of the first front unit and the optical axis of the second front unit. The first front unit and the second front unit are disposed parallel across the optical axis of the rear unit.

In the common optical system, a first optical system is formed by the first front unit and the rear unit, and a second optical system is formed by the second front unit and the rear unit. A first optical image is formed by the first optical system and a second optical image is formed by the second optical system.

In the common optical system, the first optical image and the second optical image are formed in a same area. Therefore, when compared to a case in which two optical images are formed in parallel, it is possible to make a size of an optical image larger. In such manner, in the common optical system, it is possible to secure a high image height even while being a small-size optical system.

Conditional expression (1) is a conditional expression related to the image-circle diameter and the distance between the two entrance pupils. An image forming position is a position of an image plane and the image-circle diameter is a diameter in which the maximum image height is doubled.

In a case of exceeding an upper limit value of conditional expression (1), a lens diameter of the rear unit becomes large. Consequently, an aberration correction becomes difficult. Particularly, a spherical aberration and a coma are deteriorated. Therefore, exceeding the upper limit value of conditional expression (1) is not preferable.

In a case of falling below a lower limit value of conditional expression (1), the distance between the first front unit and the second front unit becomes excessively narrow. In this case, both an effective aperture of the first front unit and an effective aperture of the second front unit have to be restricted so that the first front unit and the second front unit do not come in contact. However, when the effective apertures are restricted, it becomes difficult to secure brightness. Moreover, it becomes difficult to secure a high resolution in a peripheral portion of the optical image. Therefore, falling below the lower limit value of conditional expression (1) is not preferable.

As mentioned above, the first front unit and the second front unit are disposed in parallel. Consequently, there is a shift between the first optical image and the second optical image. Therefore, by using these two optical images, it is possible to carry out stereoscopic vision.

The first optical image and the second optical image are captured by an imager of an image pickup apparatus. In the image pickup apparatus, an image of two optical images acquired by capturing are displayed on a 3D (3-dimensional) monitor. Accordingly, it is possible to view an image of an object stereoscopically.

In the common optical system, by shielding light which passes through the second front unit, only the first optical image is formed, and by shielding light which passes through the first front unit, only the second optical image is formed. By making such arrangement, it is possible to form each of the first optical image and the second optical image separately.

In a case of carrying out stereoscopic vision, it is preferable that the first front unit and the second front unit be disposed such that a distance from the optical axis of the rear unit up to the optical axis of the first front unit and a distance from the optical axis of the rear unit and the optical axis of the second front unit are equal.

It is preferable that each of the first front unit and the second front unit include a stop. The stop is provided with an opening. When the first front unit and the second front unit are deemed as two eyes of a human being, a distance between the two openings, or in other words, a distance between the two stops, corresponds to a pupillary distance.

An angle of convergence is an angle made by a line of sight of a right eye and a line of sight of a left eye, when the same object point is viewed. In the common optical system, light emerged from the same object point is incident on the first front unit and the second front unit. Of the incident light, a light ray passing through a center of the opening corresponds to the line of sight. A light ray passing through a center of the opening of the first front unit and a light ray passing through a center of the opening of the second front unit intersect at a position of the same object point. When an angle of intersection of these two lines of intersection is an inward angle, the inward angle corresponds to the angle of convergence.

As the pupillary distance varies with respect to the same object point, the angle of convergence varies. As the angle of convergence varies, visibility at a time of viewing stereoscopically (hereinafter, referred to as 'stereoscopic effect') varies. In a case of carrying out stereoscopic vision, it is necessary to dispose the first front unit and the second front unit such that an appropriate stereoscopic effect is achieved. By satisfying conditional expression (1), it is possible to achieve an appropriate stereoscopic effect.

In a case of exceeding the upper limit value of conditional expression (1), the inward angle becomes excessively large with respect to the image height of the optical image. In this case, the stereoscopic image is extended in a direction of depth. Particularly, when an image of an object positioned near the optical system is projected in the entire stereoscopic image, only the image of this object is extended largely in the direction of depth. Consequently, it causes fatigue to an observer. Therefore, exceeding the upper limit value of conditional expression (1) is not preferable.

In a case of falling below the lower limit value of conditional expression (1), the inward angle becomes excessively small with respect to the image height of the optical image. In this case, in the stereoscopic image, it becomes difficult to secure a high resolution in the direction of depth. In a case in which the resolution in the direction of depth is low, it becomes difficult to capture a minute change in the variation on a surface of an object to be observed for example. In such manner, since cognition in the direction of depth is deteriorated, falling below the lower limit value of conditional expression (1) is not preferable.

A specific arrangement of the common optical system will be described. By imparting a focusing function to the common optical system, it is possible to form a sharp optical image in a wide range in an optical axial direction. A first common optical system and a second common optical system will be described below as a common optical system which is provided with the focusing function. The common optical system provided with the focusing function is an example of a more preferable common optical system. Therefore, the common optical system may not be provided with the focusing function.

FIG. 1A and FIG. 1B are lens cross-sectional views of a first common optical system. FIG. 1A shows a lens cross-sectional view at a time of focusing to a far point. FIG. 1B shows a lens cross-sectional view at a time of focusing to a near point.

The near point is a point which is positioned nearest to an optical system in a focusing range. The far point is a point which is positioned farthest from the optical system in the focusing range. The focusing range is a range in an object space, and is a range in which an optical image of an object is obtained sharply when a lens in the optical system is moved along an optical axis.

The first common optical system includes in order from an object side, a front unit GF and a rear unit GR. Each of the front unit GF and the rear unit GR includes a lens component. The lens component is either a single lens or a cemented lens.

The front unit GF includes a first front unit GF1 and a second front unit GF2. An optical axis AXC of the rear unit GR is positioned between an optical axis AX1 of the first front unit GF1 and an optical axis AX2 of the second front unit GF2. The first front unit GF1 and the second front unit GF2 are disposed symmetrically across the optical axis AXC. In FIG. 1A and FIG. 1B, an optical element C1, an optical element C2, and an optical element C3 are also shown. These optical elements are not components of the first common optical system but will be described below collectively for the sake of expediency.

In the first common optical system, the first front unit GF1 and the second front unit GF2 are the same optical systems. Therefore, the first front unit GF1 will be described below.

The first front unit GF1 includes a planoconcave negative lens L1, a biconvex positive lens L2, a negative meniscus lens L3 having a convex surface directed toward an image side, a biconcave negative lens L4, and a biconvex positive lens L5.

The biconvex positive lens L2 and the negative meniscus lens L3 are cemented. The biconcave negative lens L4 and the biconvex positive lens L5 are cemented.

The rear unit GR includes a biconvex positive lens L6, a biconvex positive lens L7, a biconcave negative lens L8, a biconcave negative lens L9, a negative meniscus lens L10 having a convex surface directed toward the object side, a biconvex positive lens L11, and the biconvex positive lens L12.

The biconvex positive lens L7 and the biconcave negative lens L8 are cemented. The negative meniscus lens L10 and the biconvex positive lens L11 are cemented.

A stop S is disposed between the front unit GF and the rear unit GR. The optical element C1 is disposed on the object side of the planoconcave negative lens L1. The optical element C2 and the optical element C3 are disposed on the image side of the biconvex positive lens L12.

The optical element C1 is one plane parallel plate. The optical element C1 is positioned to intersect both the optical axis AX1 and the optical axis AX2. The optical element C1 is not required necessarily.

In the first common optical system, the biconvex positive lens L12 moves at a time of focusing. More elaborately, at a time of focusing from a far point to a near point, the biconvex positive lens L12 moves toward the object side.

Figure 2B:
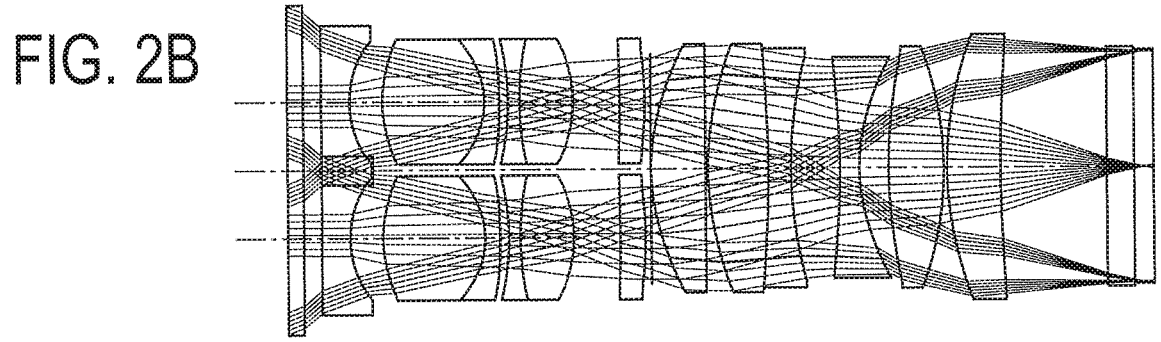
Figure 4:
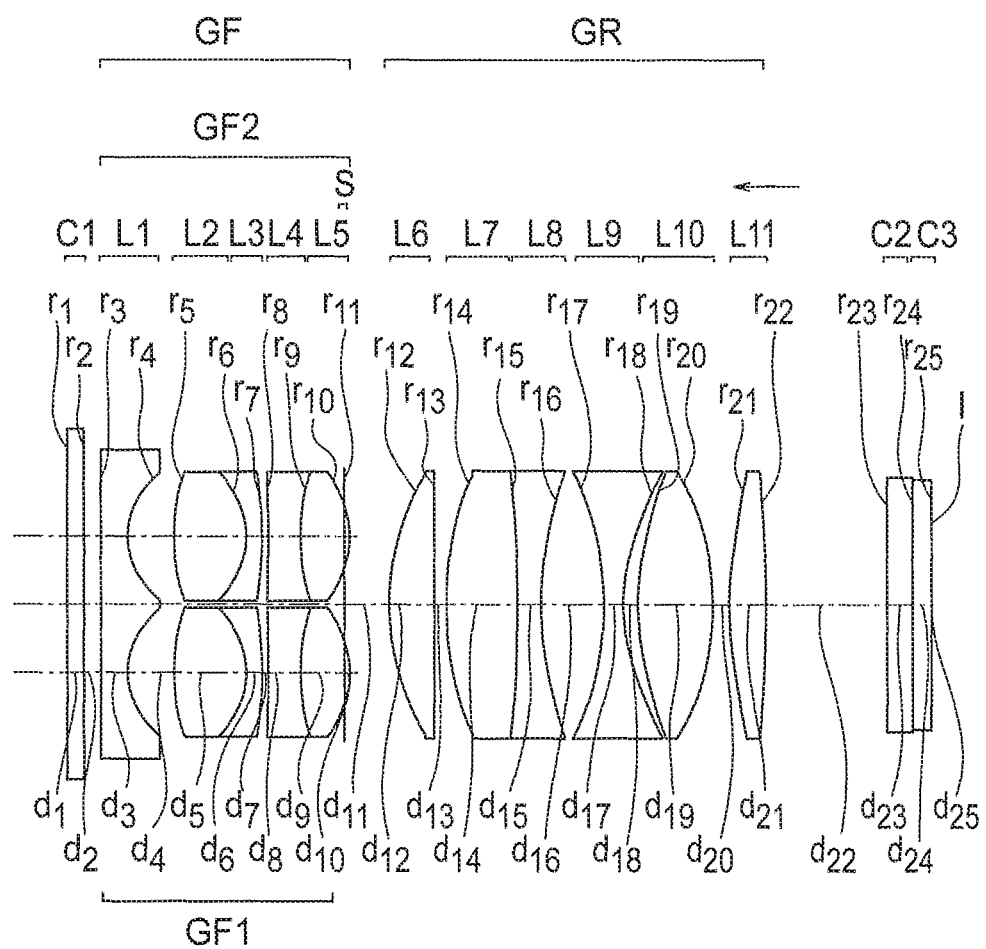
FIG. 4 is a lens cross-sectional view of an optical system for stereoscopic vision of an example 2.
Figure 5:
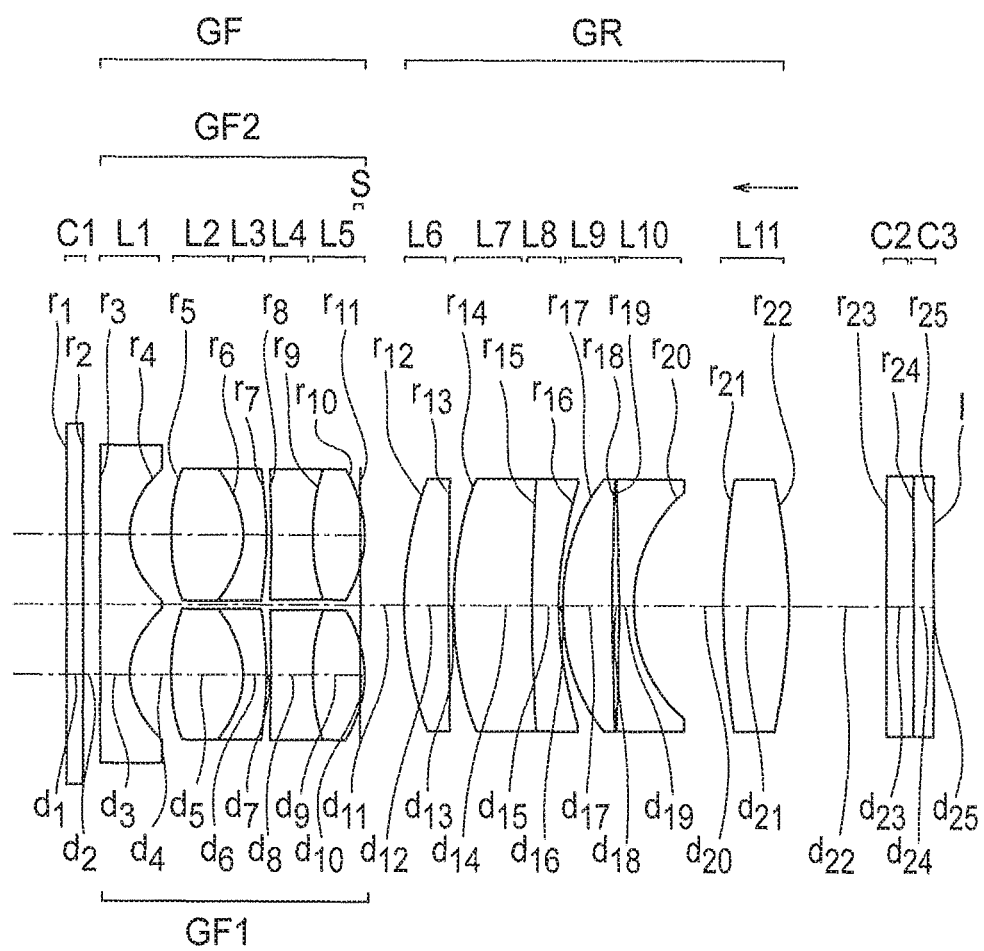
FIG. 5 is a lens cross-sectional view of an optical system for stereoscopic vision of an example 3.
Figure 6:
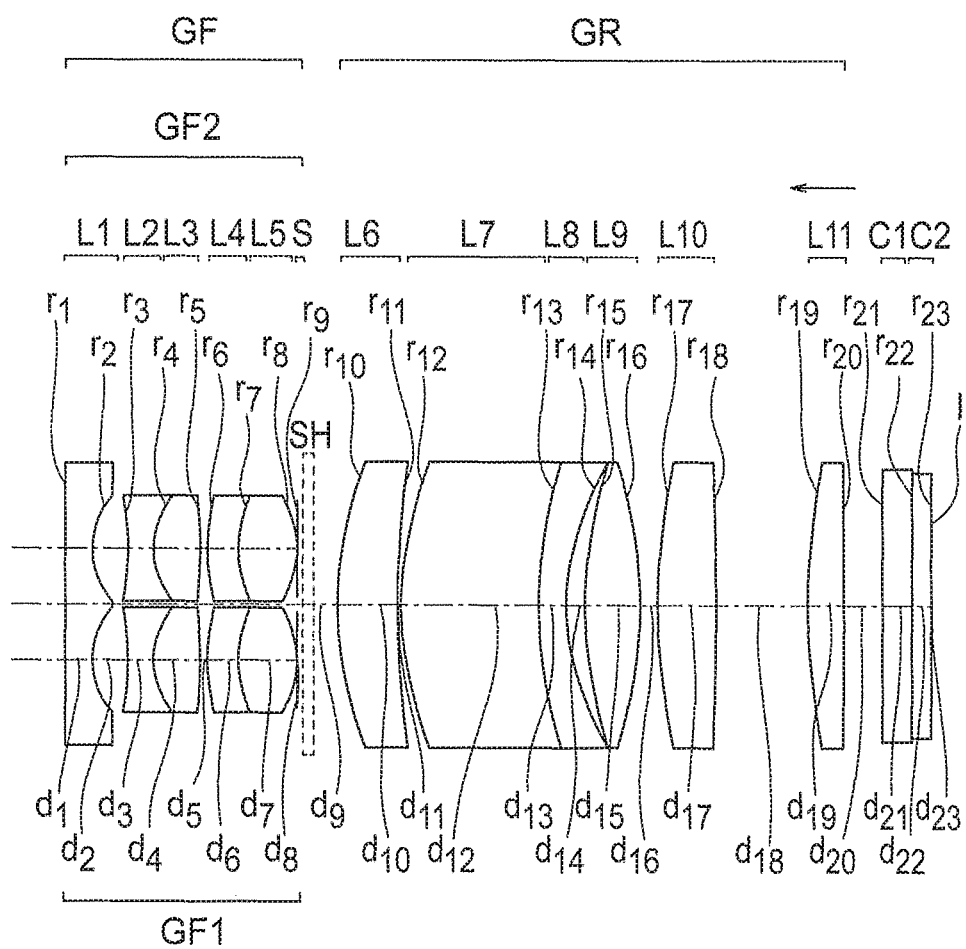
FIG. 6 is a lens cross-sectional view of an optical system for stereoscopic vision of an example 4.
Figure 7:
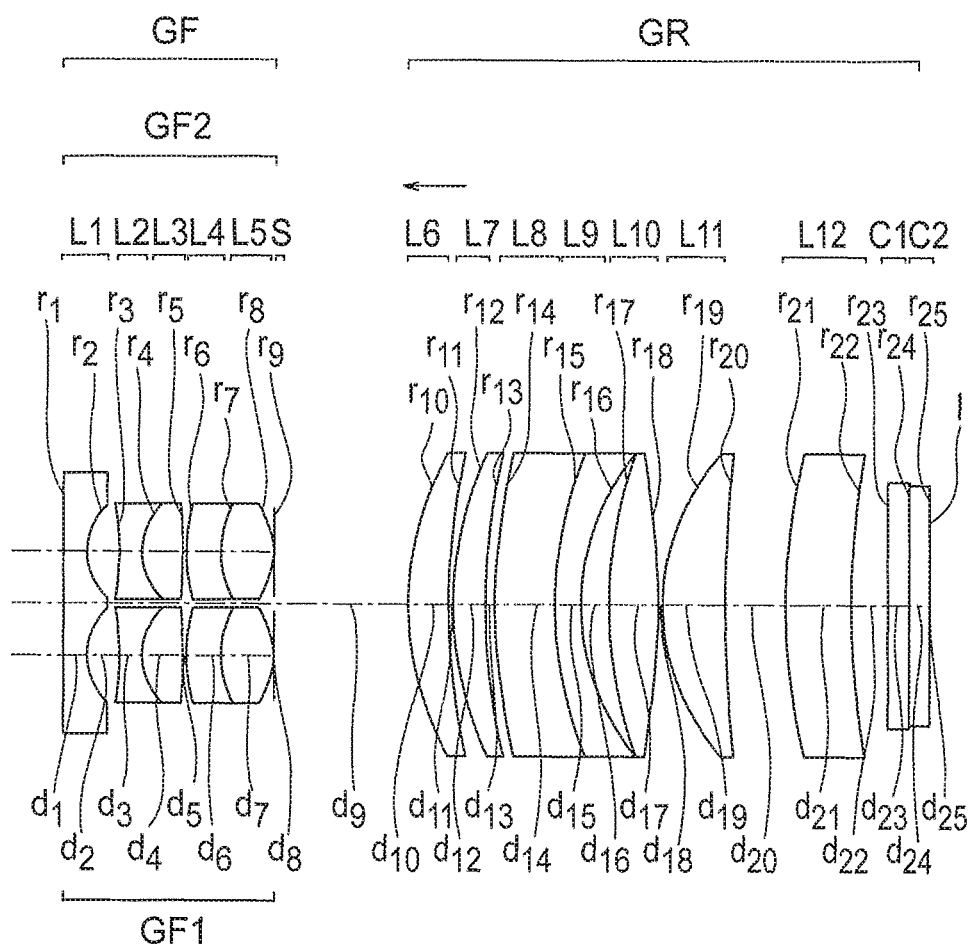
FIG. 7 is a lens cross-sectional view of an optical system for stereoscopic vision of an example 5.
Figure 8:
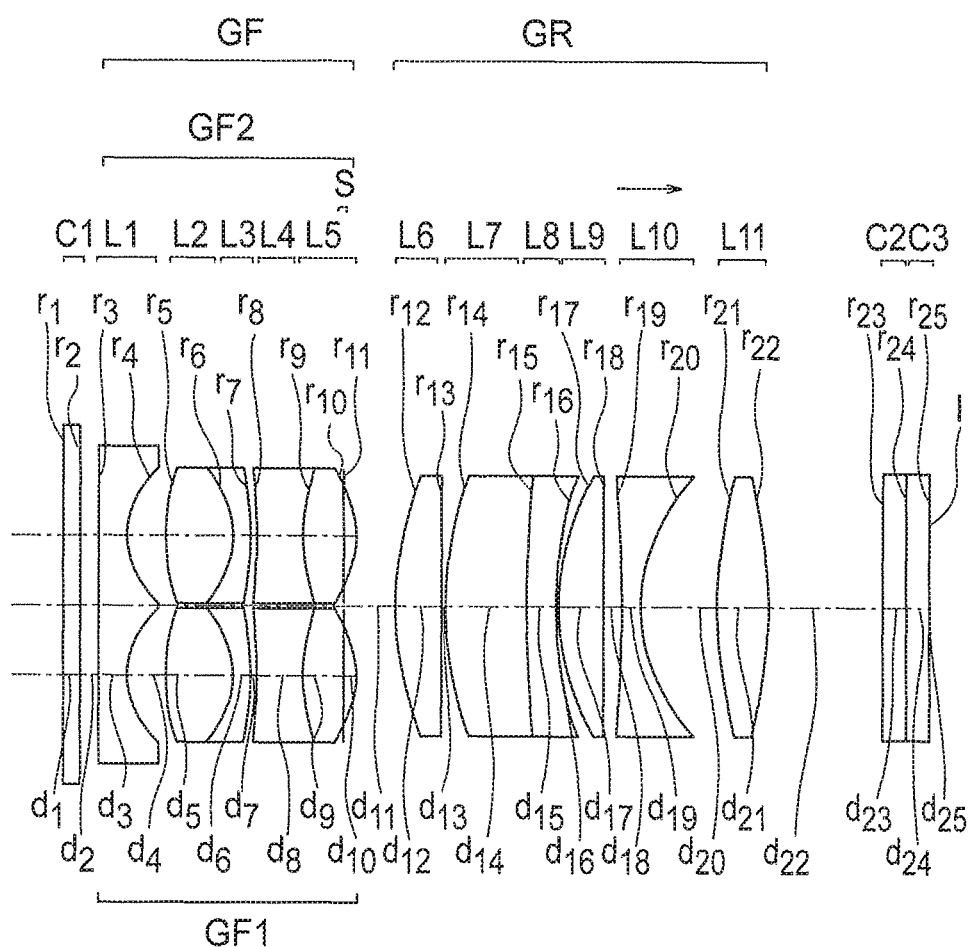
FIG. 8 is a lens cross-sectional view of an optical system for stereoscopic vision of an example 6.
Figure 9:
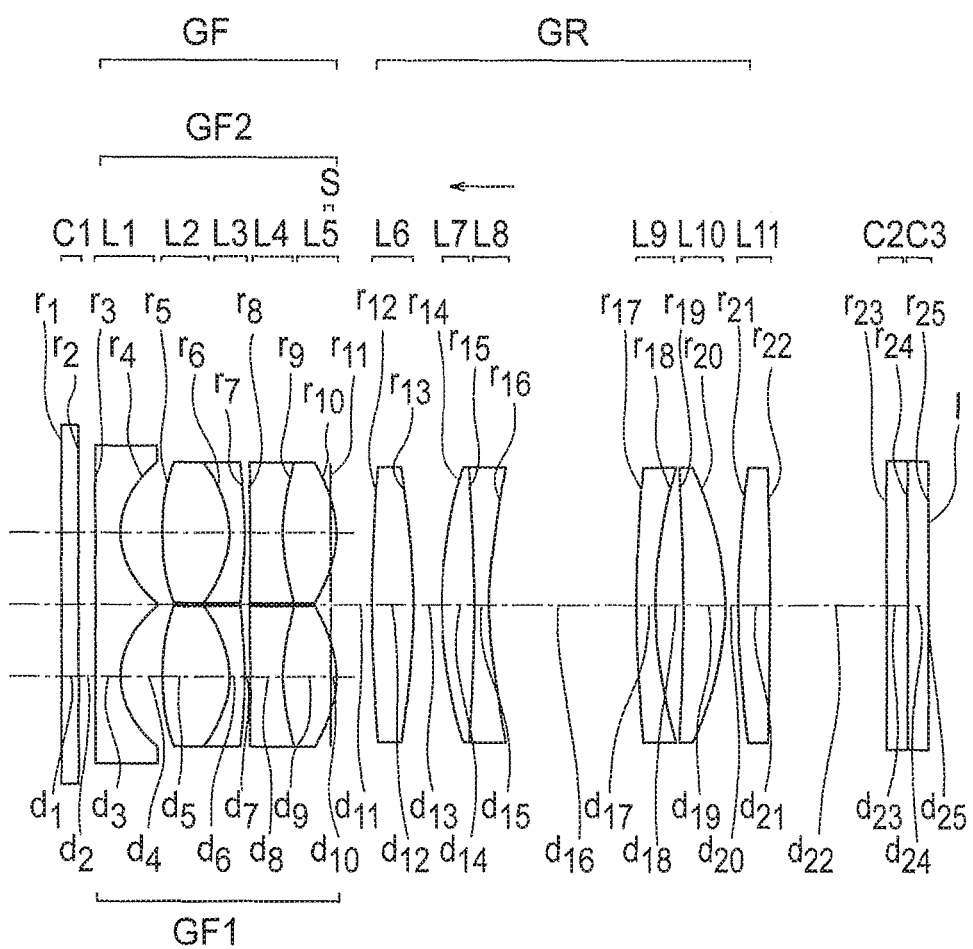
FIG. 9 is a lens cross-sectional view of an optical system for stereoscopic vision of an example 7.
Figure 10:
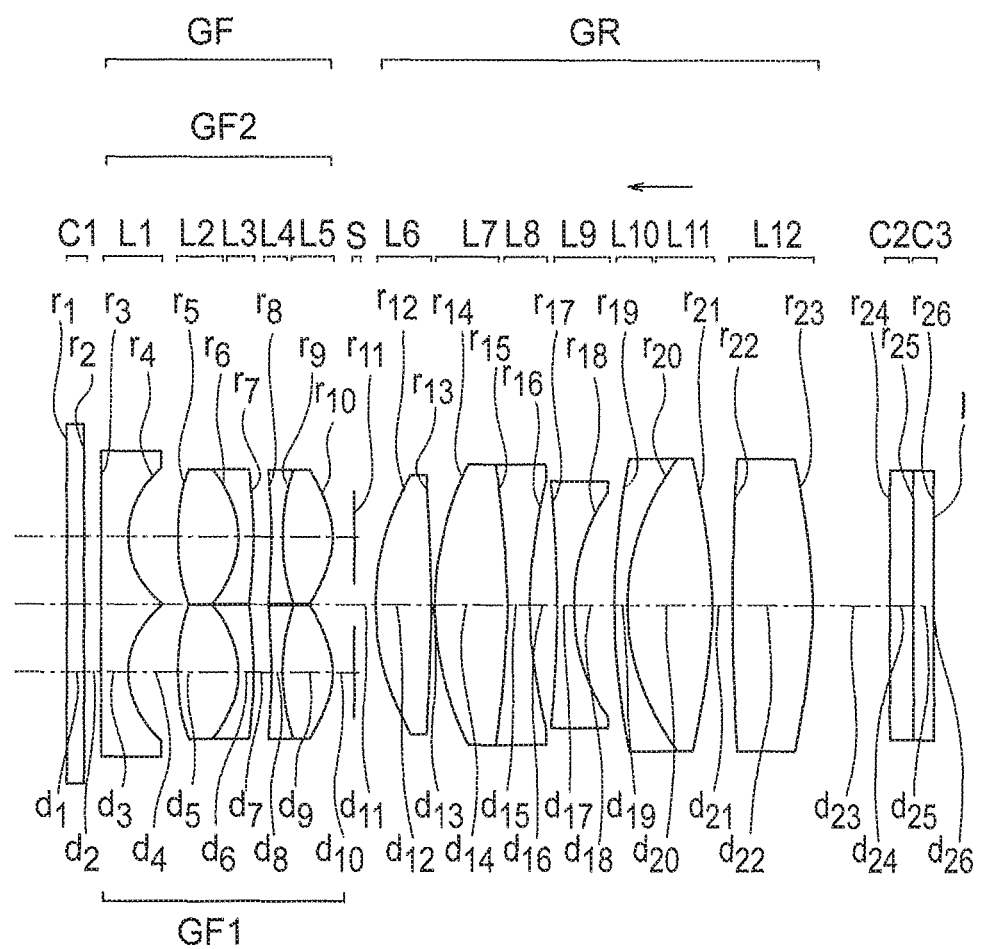
FIG. 10 is a lens cross-sectional view of an optical system for stereoscopic vision of an example 8.
Figure 11:
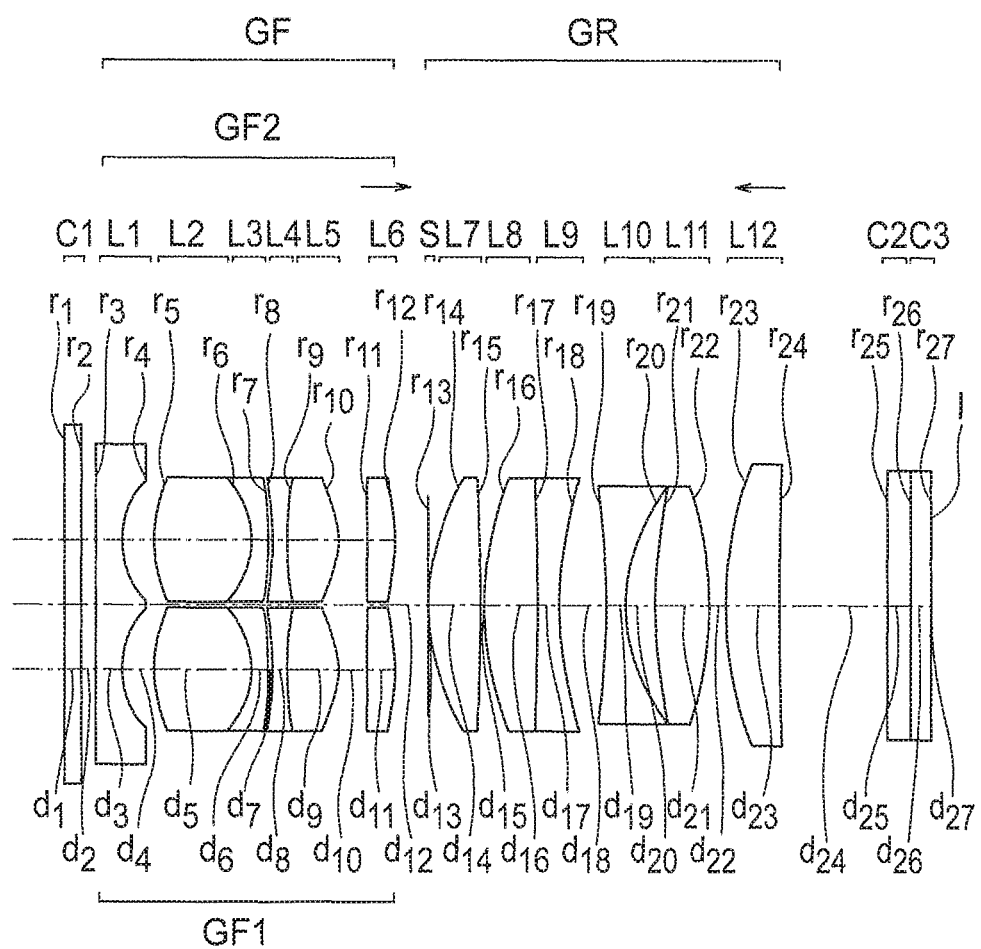
FIG. 11 is a lens cross-sectional view of an optical system for stereoscopic vision of an example 9.
Figure 12:
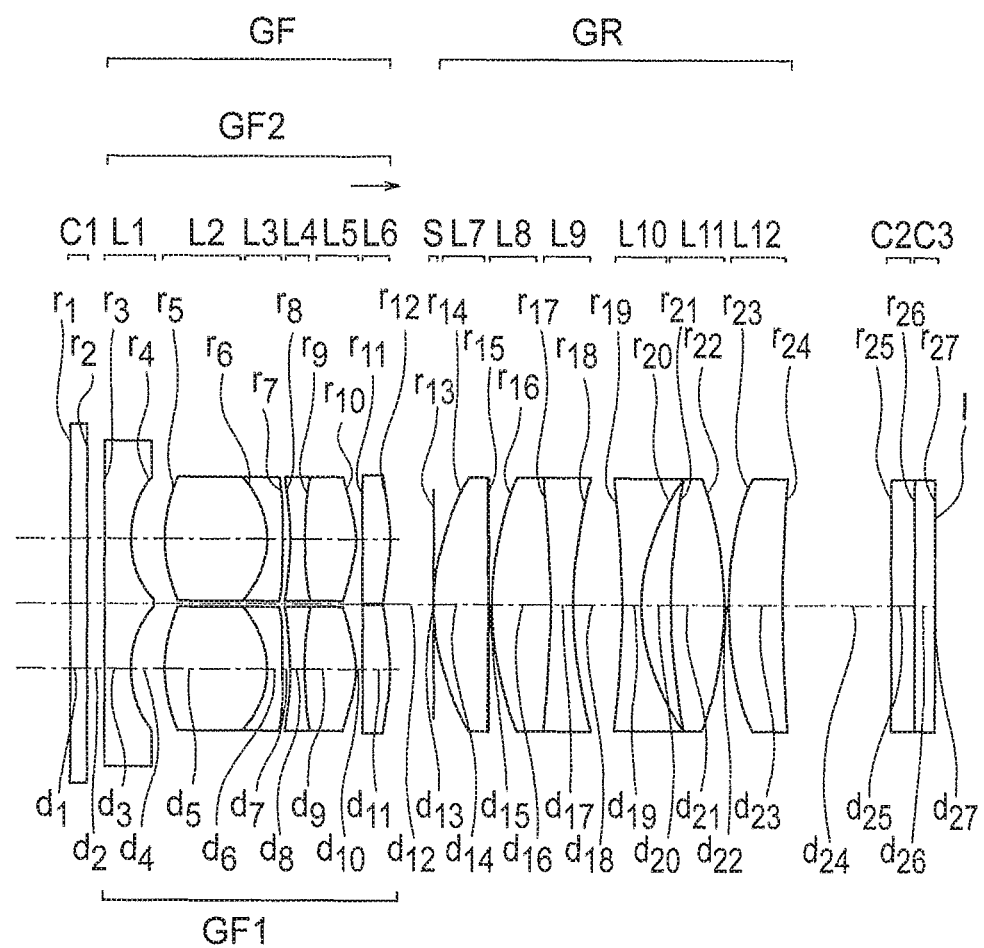
FIG. 12 is a lens cross-sectional view of an optical system for stereoscopic vision of an example 10.
Figure 13:
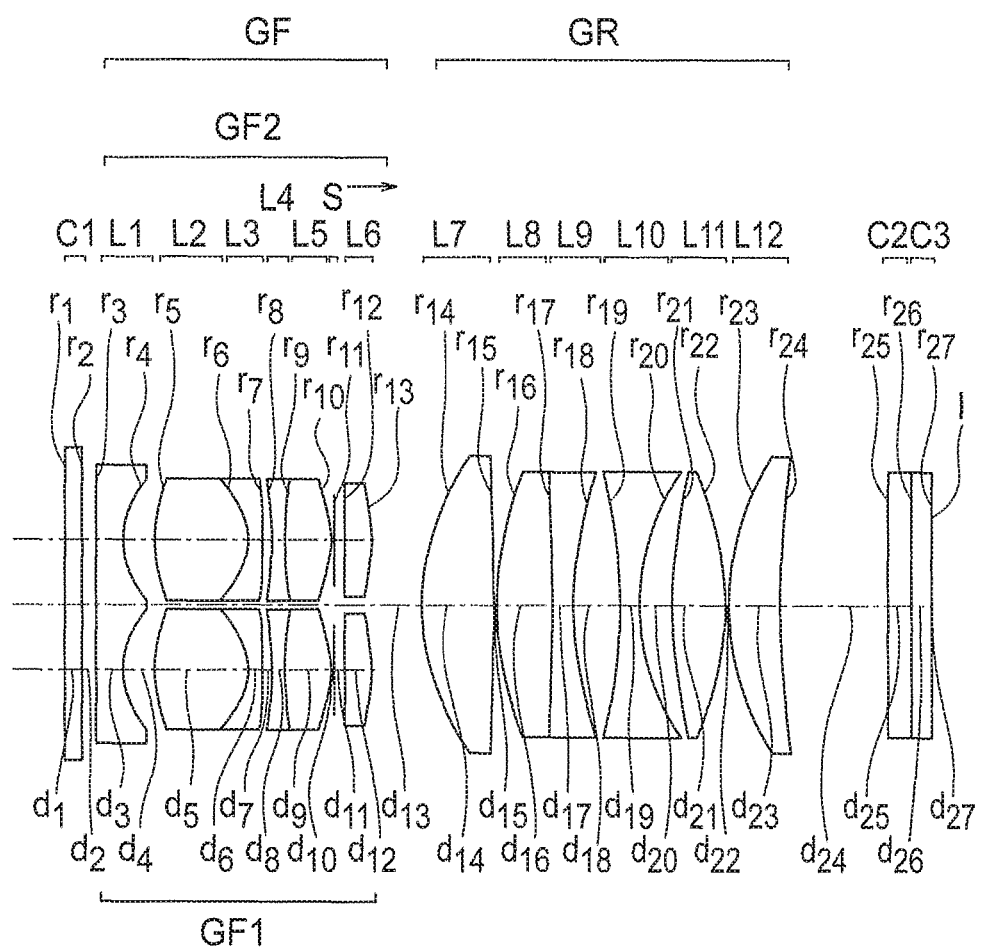
FIG. 13 is a lens cross-sectional view of an optical system for stereoscopic vision of an example 11.
Figure 14:
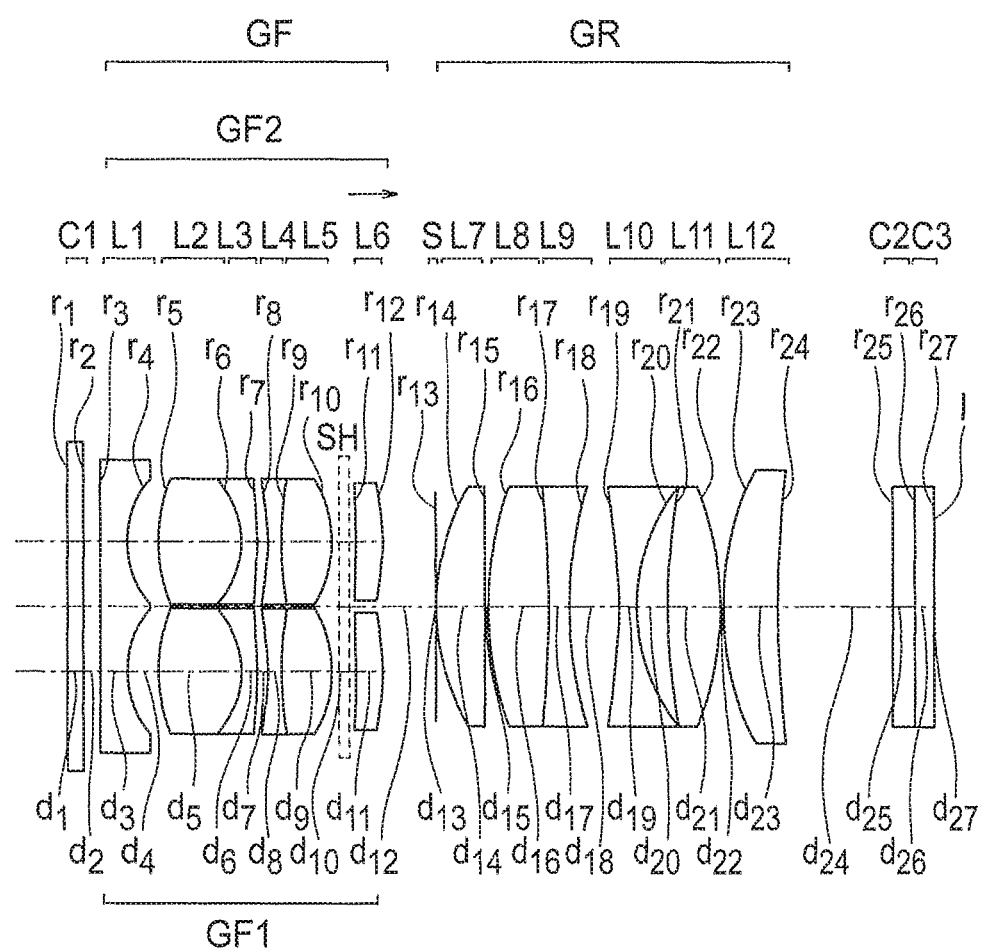
FIG. 14 is a lens cross-sectional view of an optical system for stereoscopic vision of an example 12.
Figure 15:
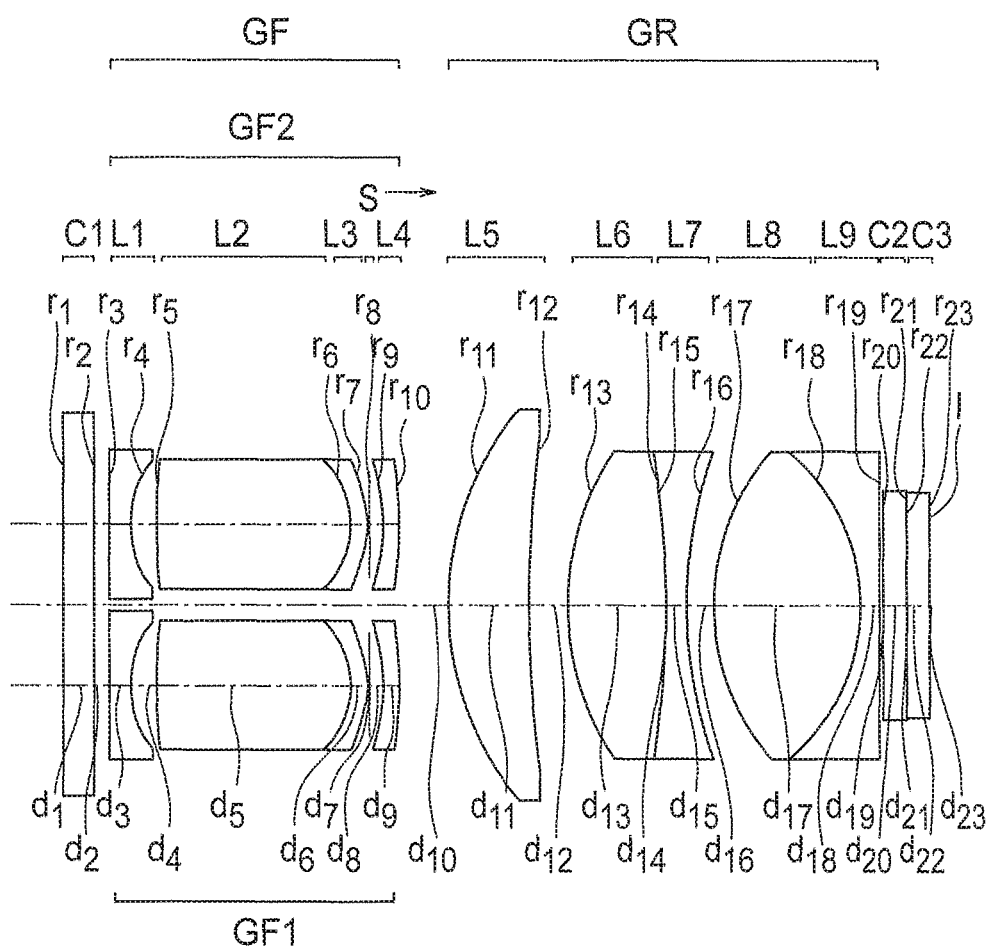
FIG. 15 is a lens cross-sectional view of an optical system for stereoscopic vision of an example 13.
Figure 16:
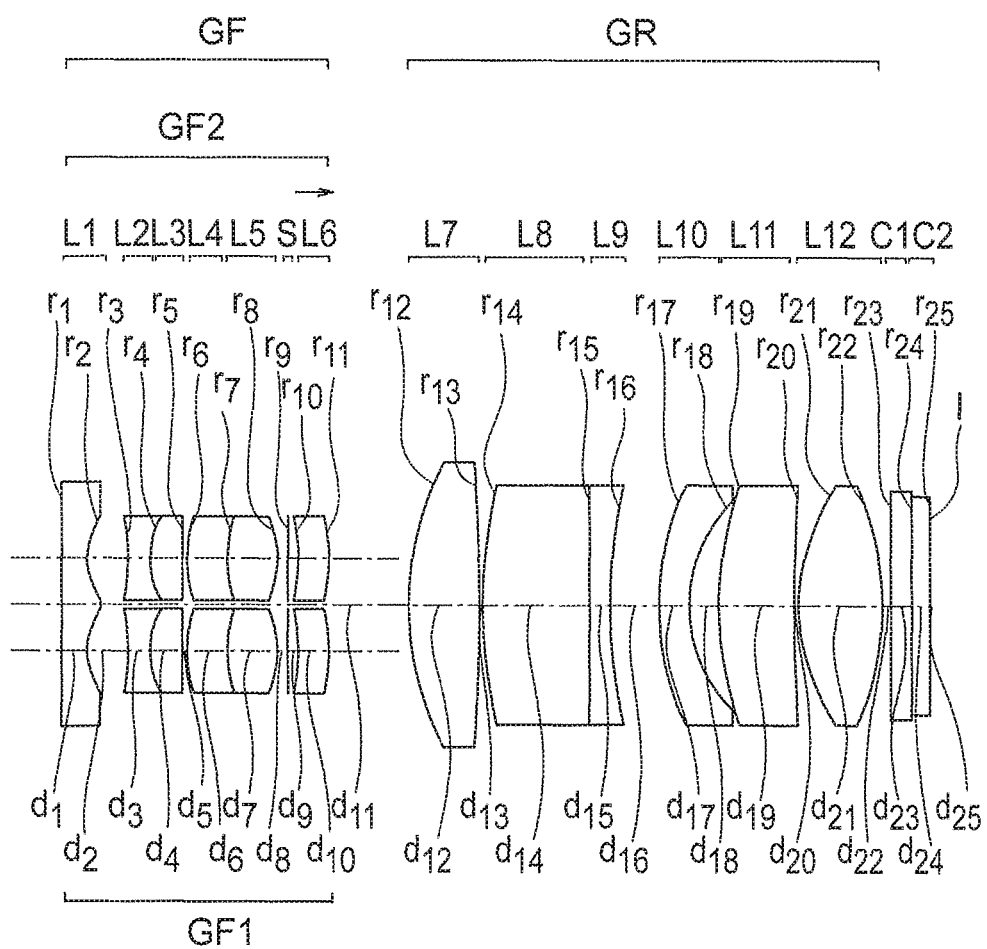
FIG. 16 is a lens cross-sectional view of an optical system for stereoscopic vision of an example 14.
Figure 18A:
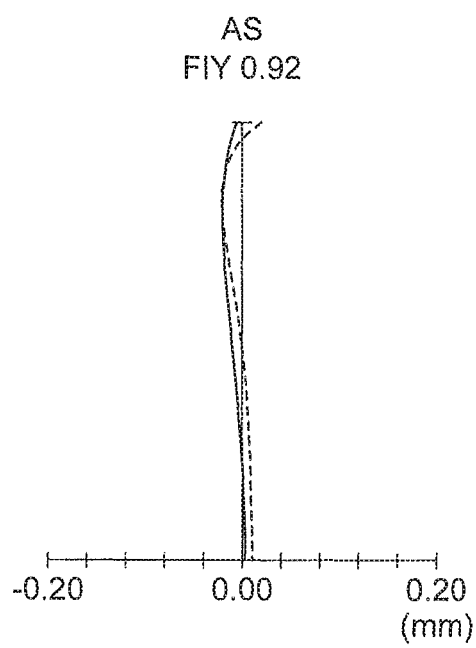
FIG. 18A, FIG. 18B, FIG. 18C, FIG. 18D, FIG. 18E, FIG. 18F, FIG. 18G, FIG. 18H, FIG. 18I, and FIG. 18J are aberration diagrams of the optical system for stereoscopic vision of the example 1.
Figure 18B:
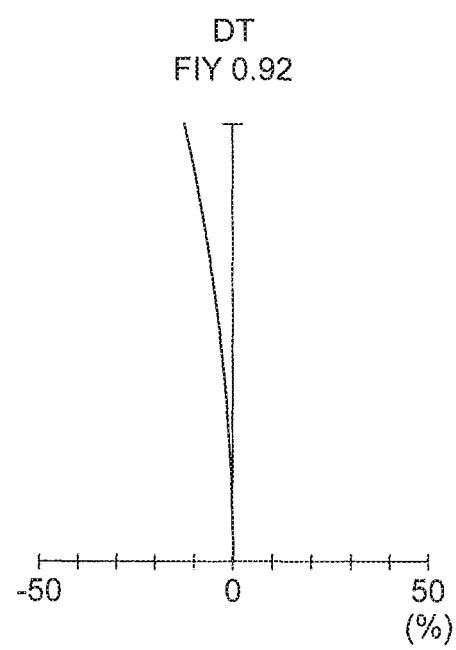
Figures 18C, 18D:
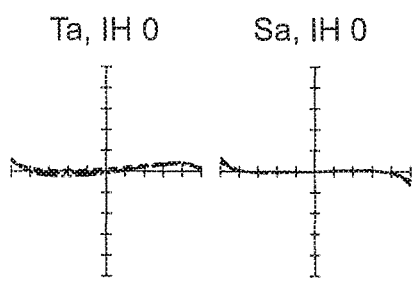
Figures 18E, 18F:
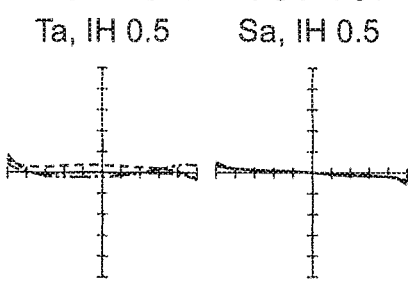
Figures 18G, 18H:
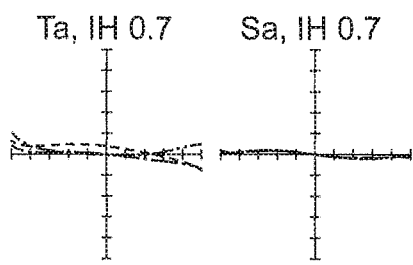
Figures 18I, 18J:
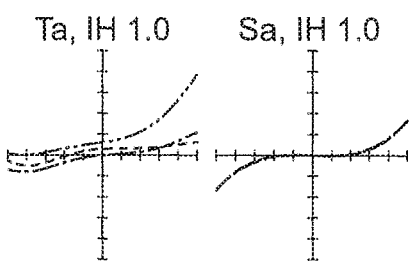
Figure 19A:
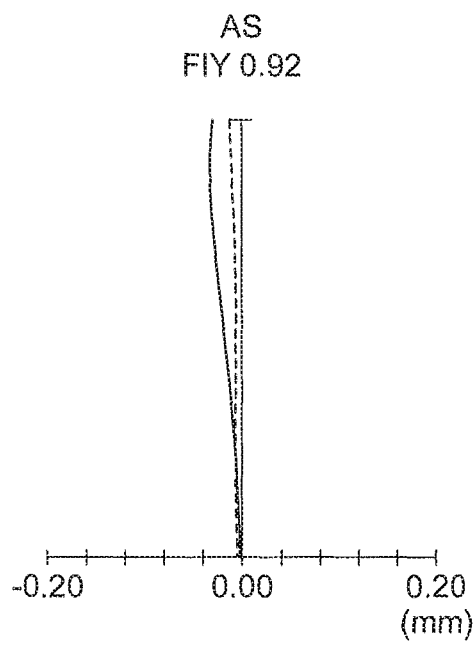
FIG. 19A, FIG. 19B, FIG. 19C, FIG. 19D, FIG. 19E, FIG. 19F, FIG. 19G, FIG. 19H, FIG. 19I, and FIG. 19J are aberration diagrams of the optical system for stereoscopic vision of the example 1.
Figure 19B:
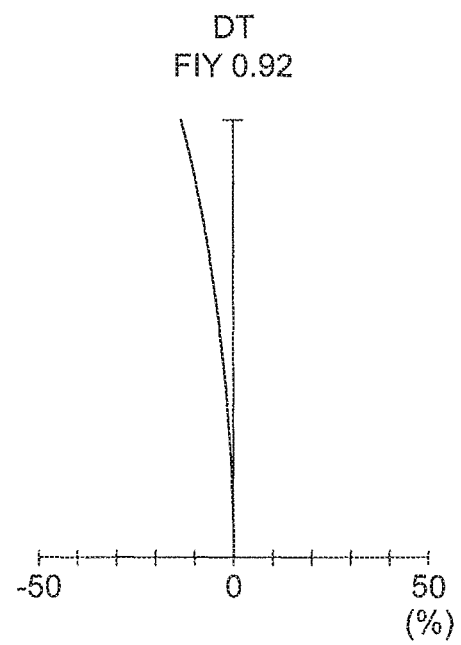
Figures 19C, 19D:
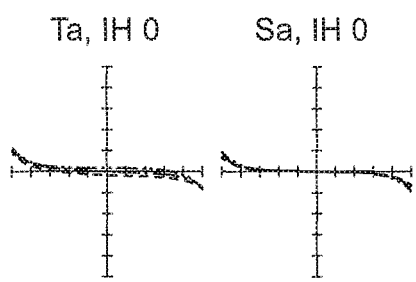
Figures 19E, 19F:
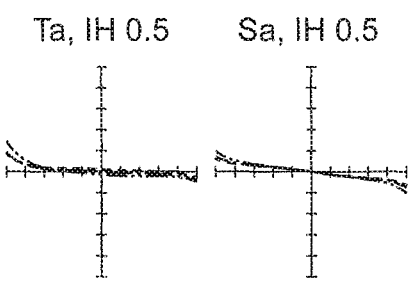
Figures 19G, 19H:
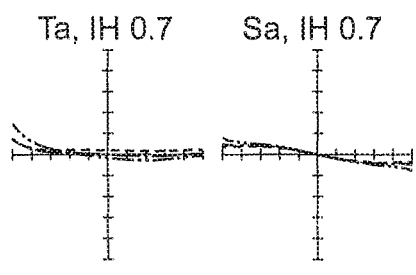
Figures 19I, 19J:
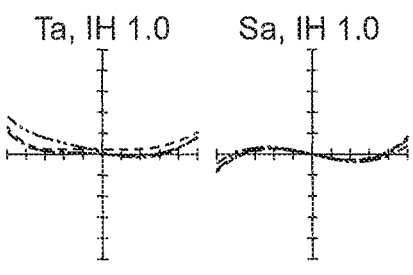
Figure 21A:
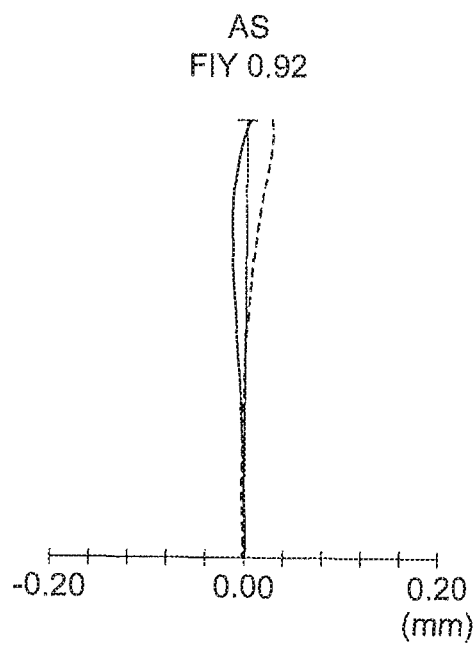
FIG. 21A, FIG. 21B, FIG. 21C, FIG. 21D, FIG. 21E, FIG. 21F, FIG. 21G, FIG. 21H, FIG. 21I, and FIG. 21J are aberration diagrams of the optical system for stereoscopic vision of the example 2.
Figure 21B:
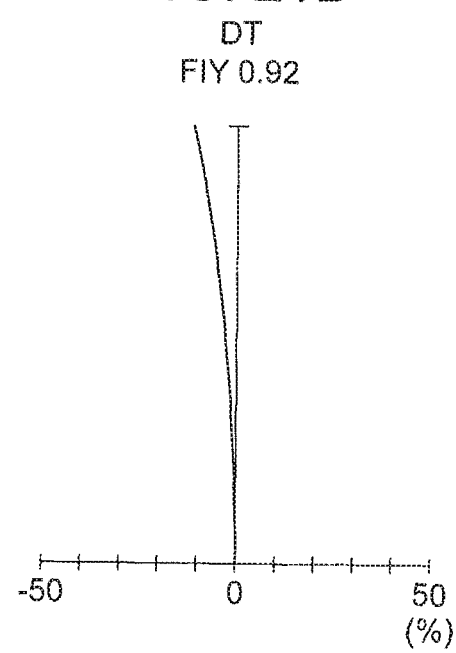
Figures 21C, 21D:
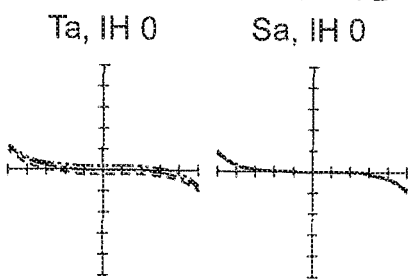
Figures 21E, 21F:
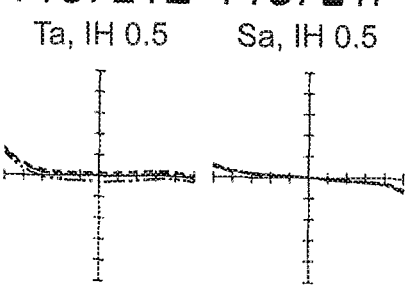
Figures 21G, 21H:
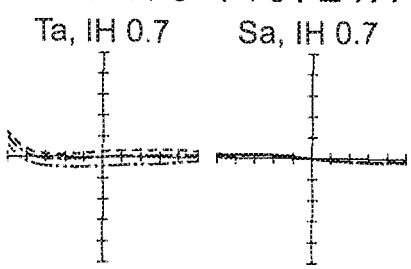
Figures 21I, 21J:
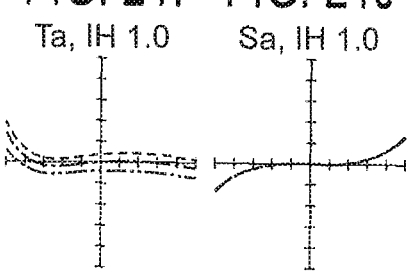
Figure 22A:
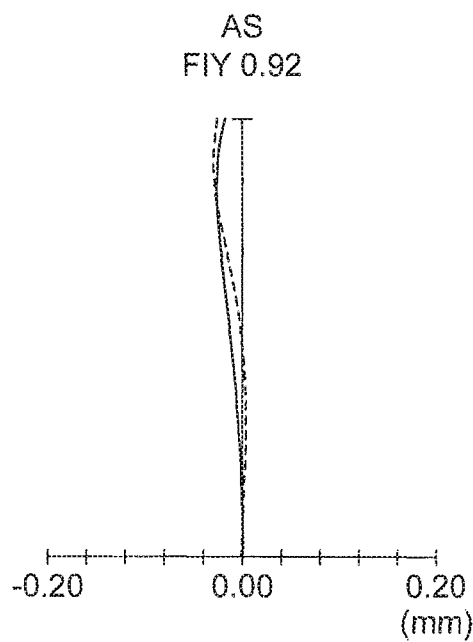
FIG. 22A, FIG. 22B, FIG. 22C, FIG. 22D, FIG. 22E, FIG. 22F, FIG. 22G, FIG. 22H, FIG. 22I, and FIG. 22J are aberration diagrams of the optical system for stereoscopic vision of the example 2.
Figure 22B:
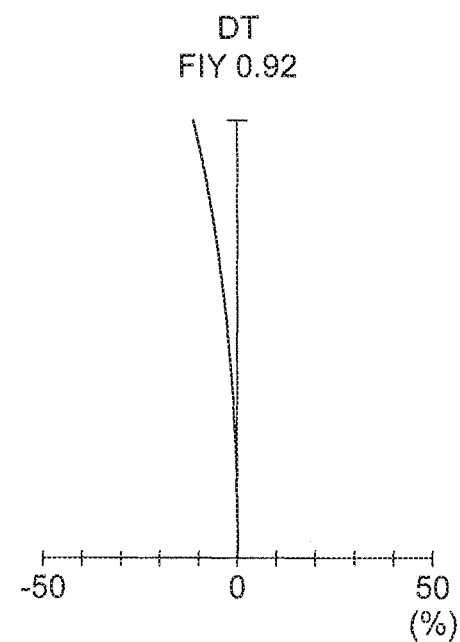
Figures 22C, 22D:
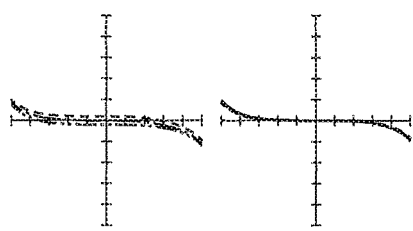
Figures 22E, 22F:
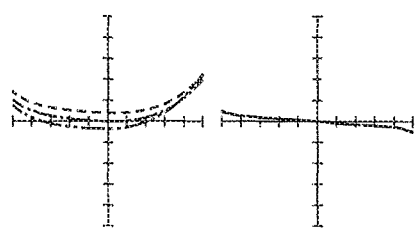
Figures 22G, 22H:
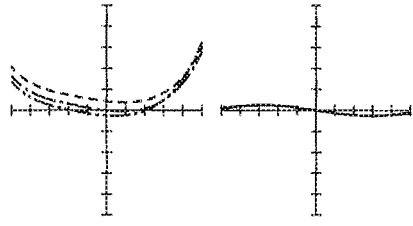
Figures 22I, 22J:
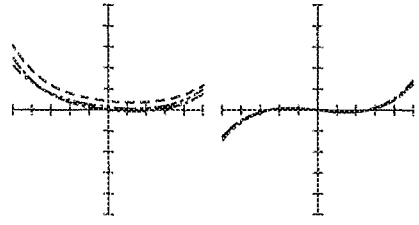
Figure 23A:
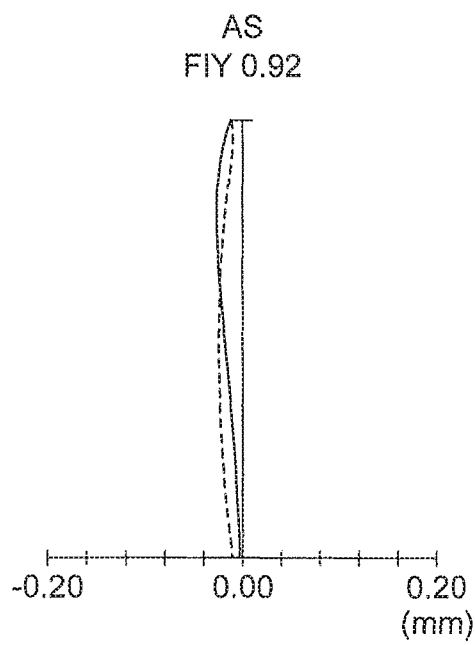
FIG. 23A, FIG. 23B, FIG. 23C, FIG. 23D, FIG. 23E, FIG. 23F, FIG. 23G, FIG. 23H, FIG. 23I, and FIG. 23J are aberration diagrams of the optical system for stereoscopic vision of the example 2.
Figure 23B:
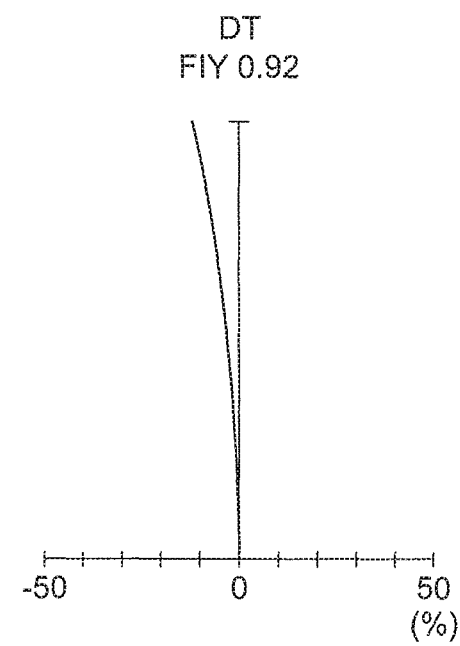
Figures 23C, 23D:
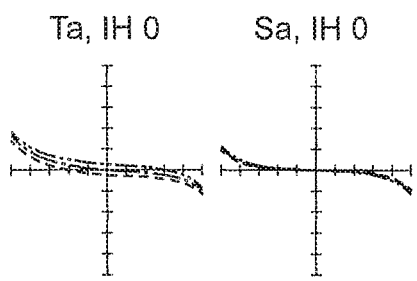
Figures 23E, 23F:
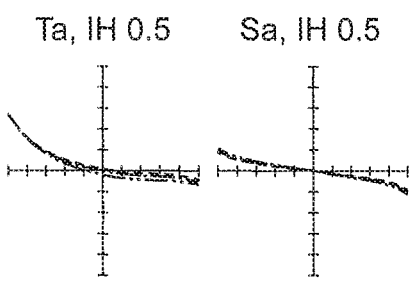
Figures 23G, 23H:
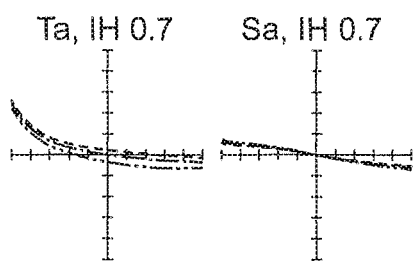
Figures 23I, 23J:
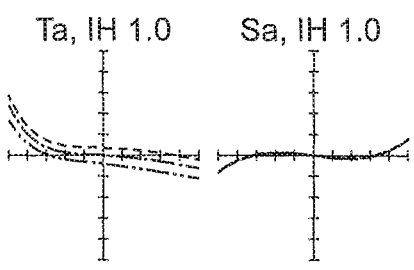
Figure 24A:
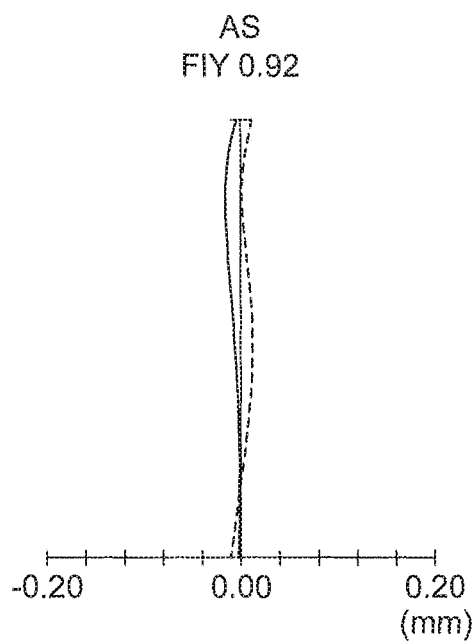
FIG. 24A, FIG. 24B, FIG. 24C, FIG. 24D, FIG. 24E, FIG. 24F, FIG. 24G, FIG. 24H, FIG. 24I, and FIG. 24J are aberration diagrams of the optical system for stereoscopic vision of the example 2.
Figure 24B:
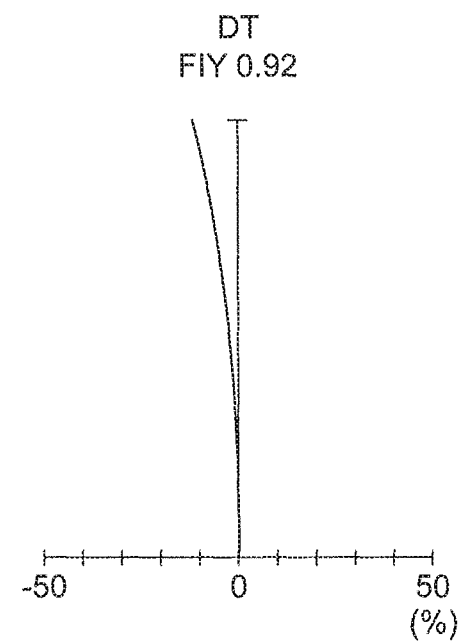
Figures 24C, 24D:
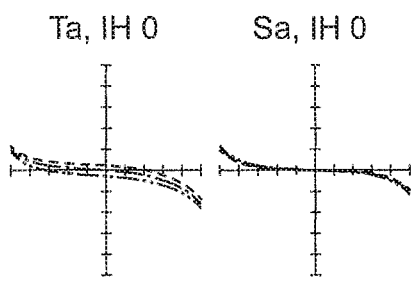
Figures 24E, 24F:
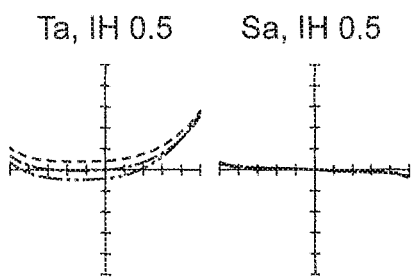
Figures 24G, 24H:
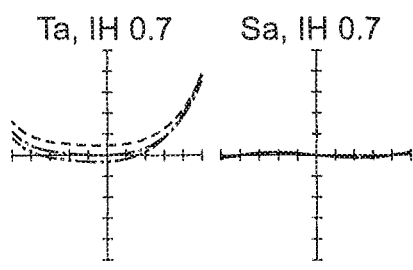
Figures 24I, 24J:
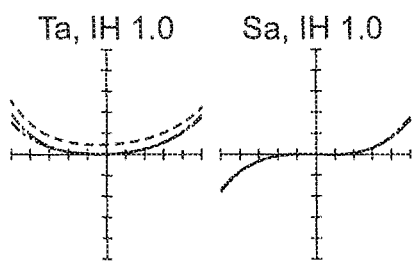
Figure 25A:
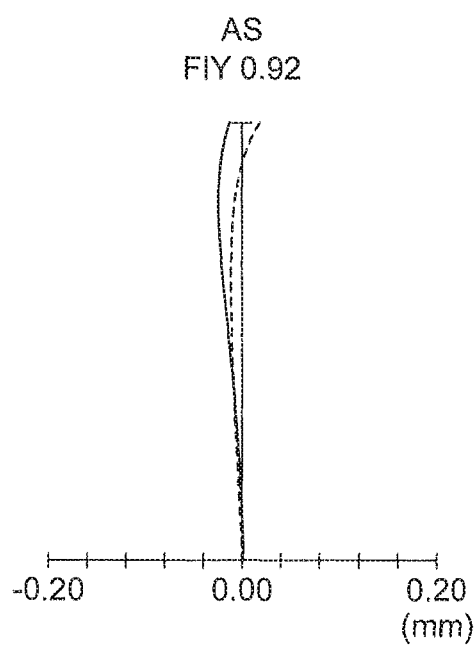
FIG. 25A, FIG. 25B, FIG. 25C, FIG. 25D, FIG. 25E, FIG. 25F, FIG. 25G, FIG. 25H, FIG. 25I, and FIG. 25J are aberration diagrams of the optical system for stereoscopic vision of the example 3.
Figure 25B:
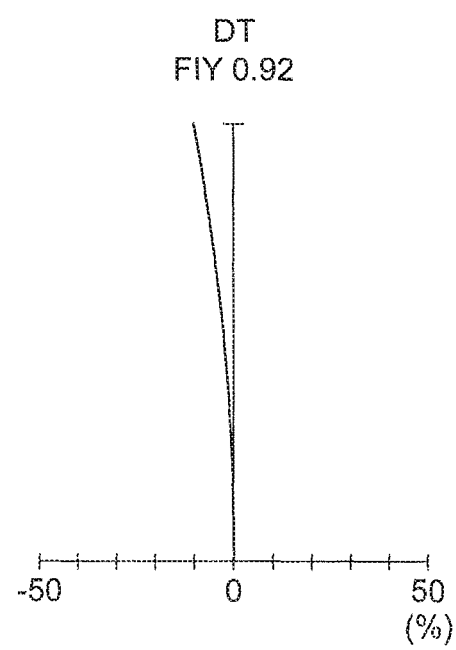
Figures 25C, 25D:
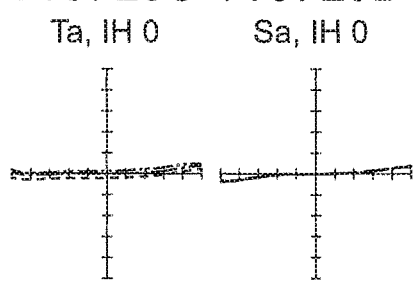
Figures 25E, 25F:
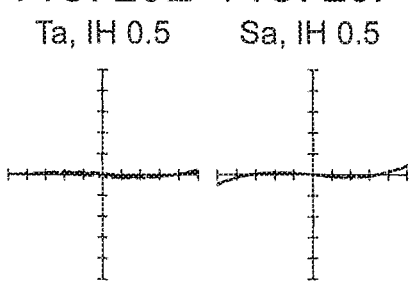
Figures 25G, 25H:
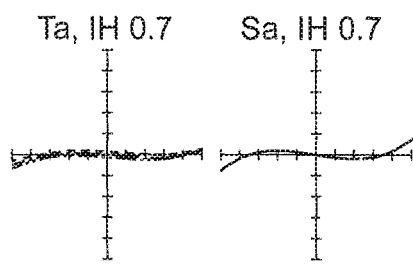
Figures 25I, 25J:
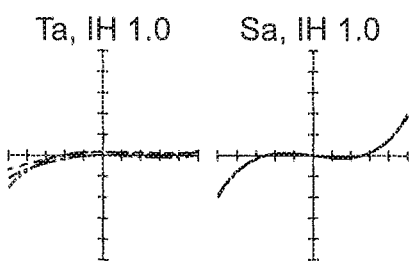
Figure 27A:
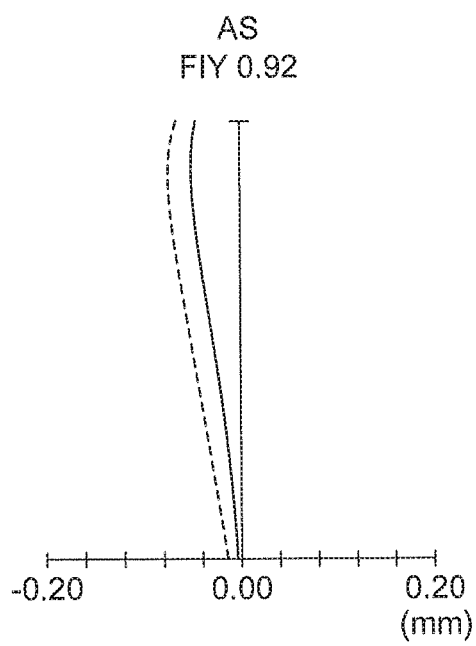
FIG. 27A, FIG. 27B, FIG. 27C, FIG. 27D, FIG. 27E, FIG. 27F, FIG. 27G, FIG. 27H, FIG. 27I, and FIG. 27J are aberration diagrams of the optical system for stereoscopic vision of the example 3.
Figure 27B:
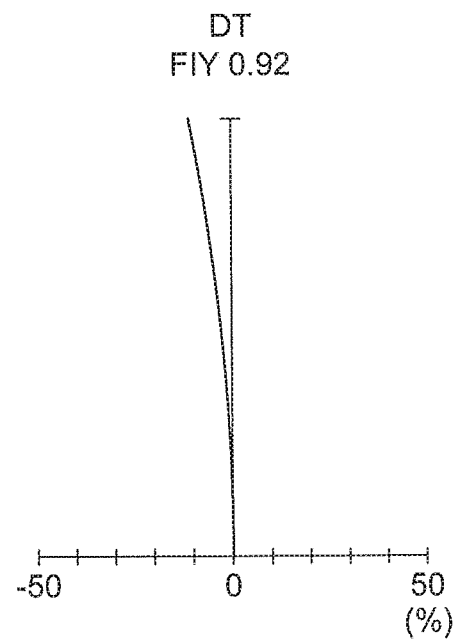
Figures 27C, 27D:
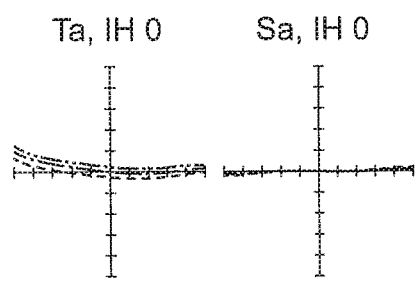
Figures 27E, 27F:
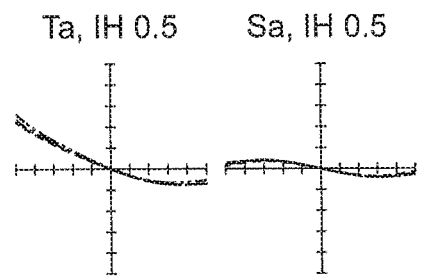
Figures 27G, 27H:
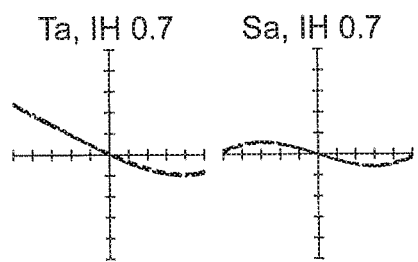
Figures 27I, 27J:
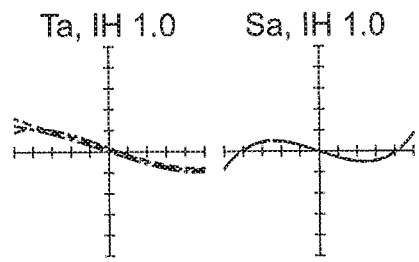
Figure 28A:
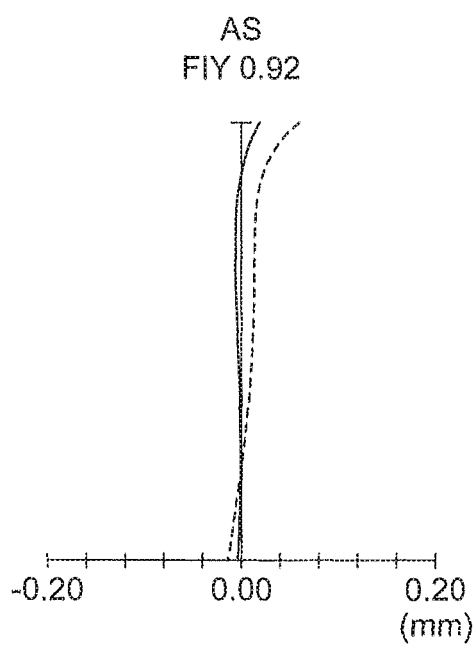
FIG. 28A, FIG. 28B, FIG. 28C, FIG. 28D, FIG. 28E, FIG. 28F, FIG. 28G, FIG. 28H, FIG. 28I, and FIG. 28J are aberration diagrams of the optical system for stereoscopic vision of the example 3.
Figure 28B:
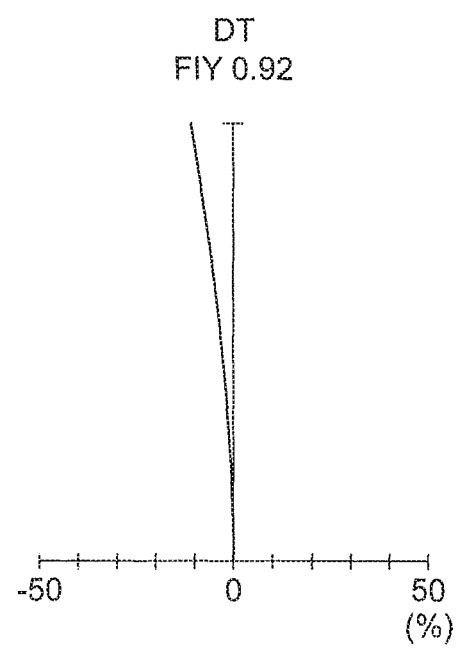
Figures 28C, 28D:
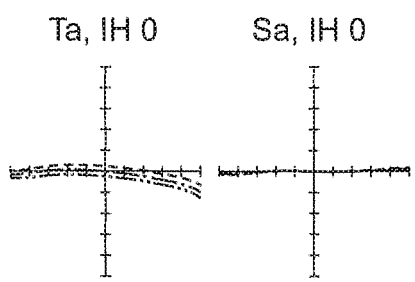
Figures 28E, 28F:
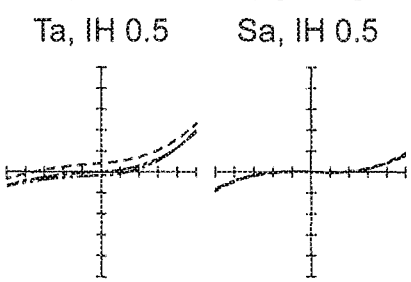
Figures 28G, 28H:
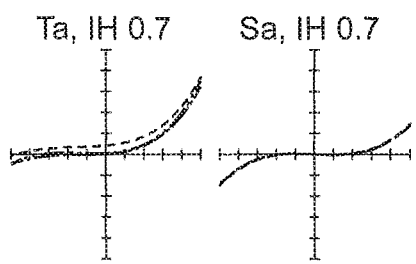
Figures 28I, 28J:
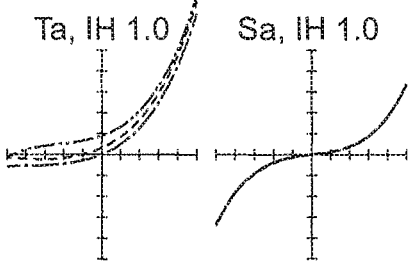
Figure 34A:
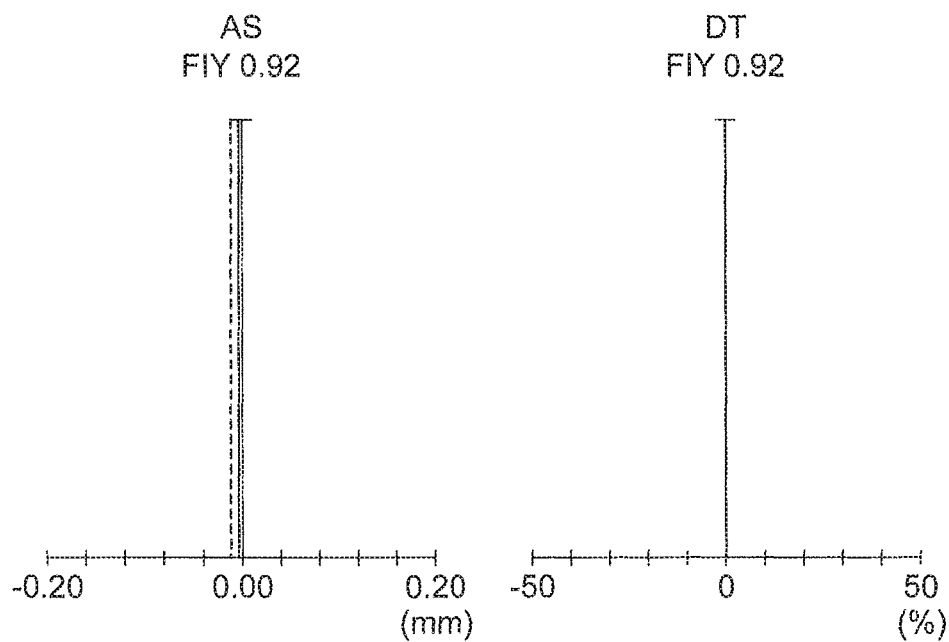
FIG. 34A, FIG. 34B, FIG. 34C, FIG. 34D, FIG. 34E, FIG. 34F, FIG. 34G, FIG. 34H, FIG. 34I, and FIG. 34J are aberration diagrams of the optical system for stereoscopic vision of the example 5.
Figure 34B:
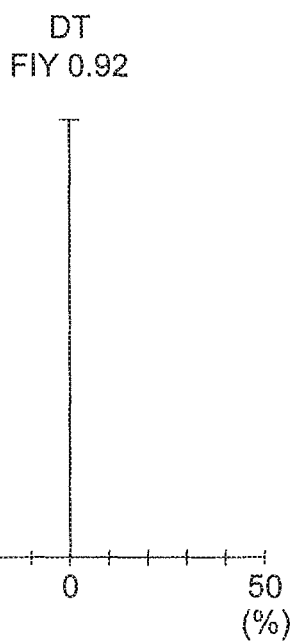
Figures 34C, 34D:
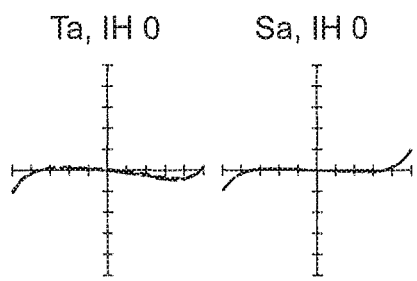
Figures 34E, 34F:
Figures 34G, 34H:
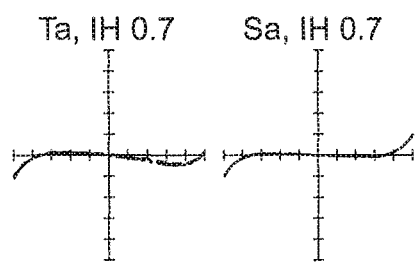
Figures 34I, 34J:
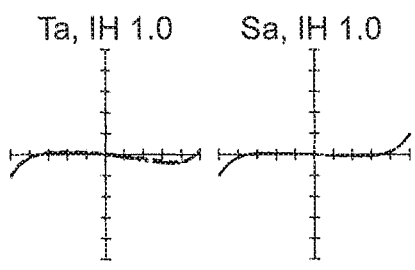
Figure 35A:
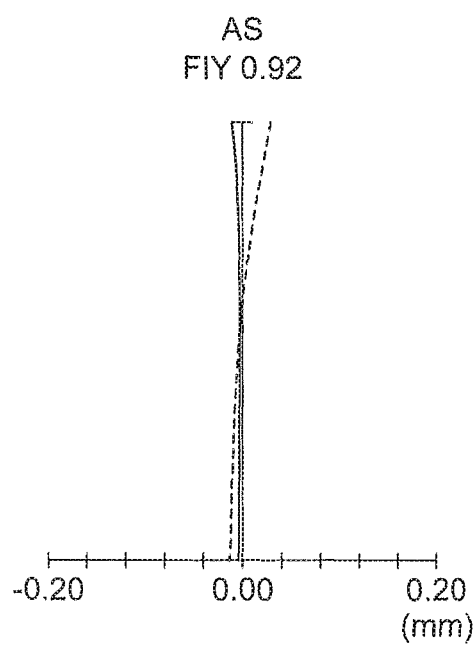
FIG. 35A, FIG. 35B, FIG. 35C, FIG. 35D, FIG. 35E, FIG. 35F, FIG. 35G, FIG. 35H, FIG. 35I, and FIG. 35J are aberration diagrams of the optical system for stereoscopic vision of the example 5.
Figure 35B:
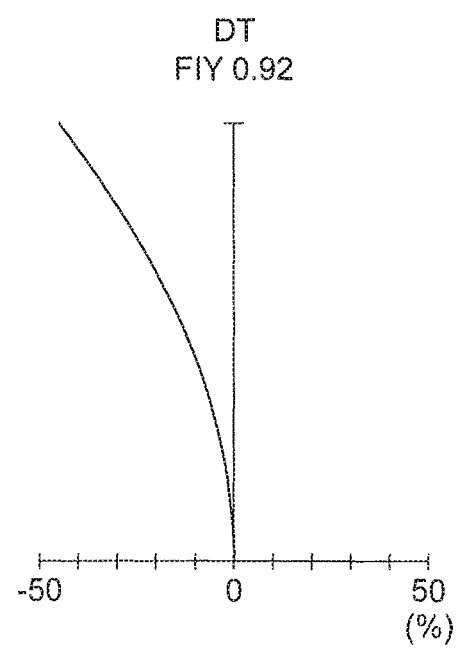
Figures 35C, 35D:
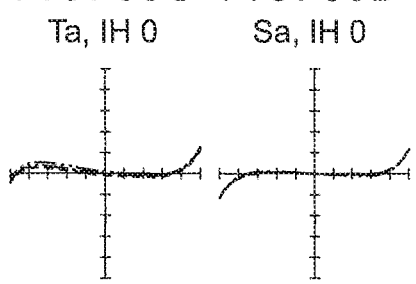
Figures 35E, 35F:
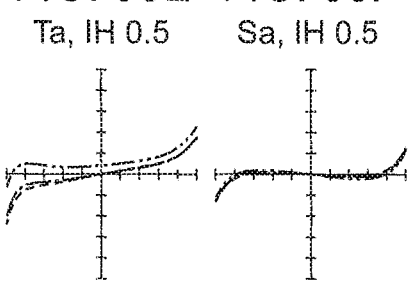
Figures 35G, 35H:
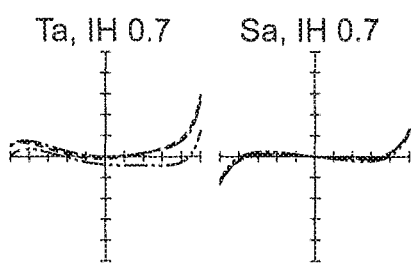
Figures 35I, 35J:
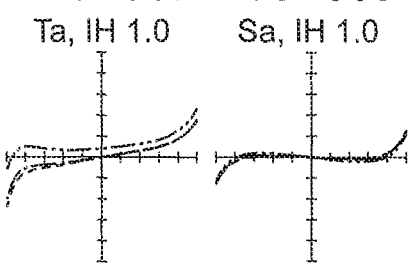
Figure 36A:
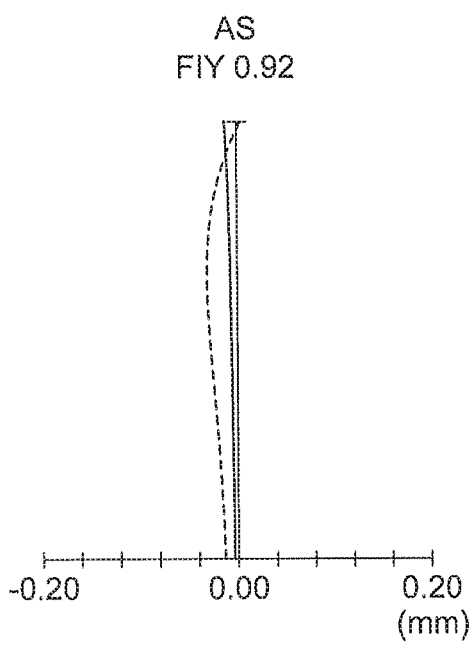
FIG. 36A, FIG. 36B, FIG. 36C, FIG. 36D, FIG. 36E, FIG. 36F, FIG. 36G, FIG. 36H, FIG. 36I, and FIG. 36J are aberration diagrams of the optical system for stereoscopic vision of the example 5.
Figure 36B:
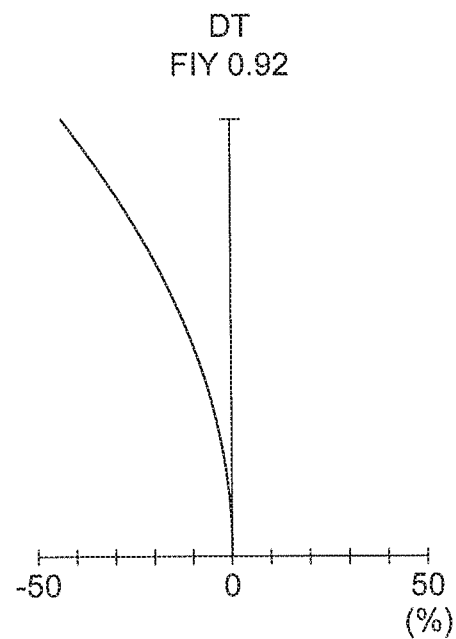
Figures 36C, 36D:
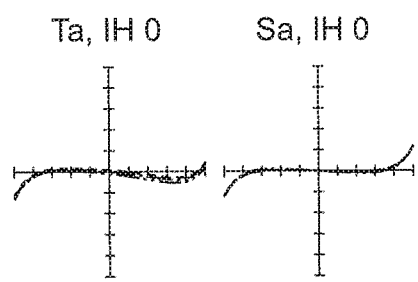
Figures 36E, 36F:
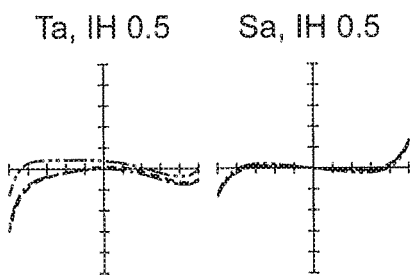
Figures 36G, 36H:
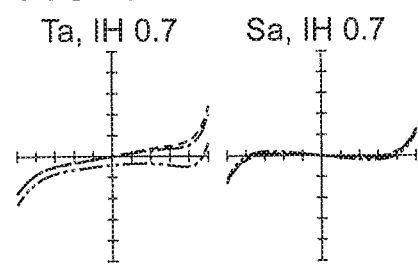
Figures 36I, 36J:
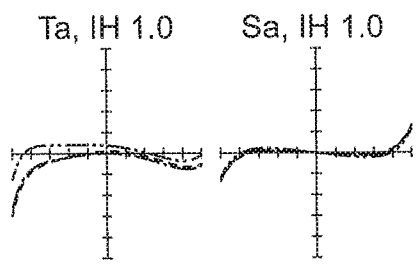
Figure 38A:
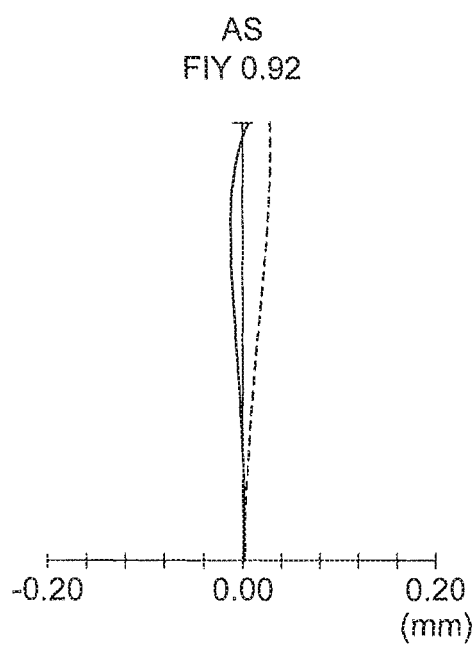
FIG. 38A, FIG. 38B, FIG. 38C, FIG. 38D, FIG. 38E, FIG. 38F, FIG. 38G, FIG. 38H, FIG. 38I, and FIG. 38J are aberration diagrams of the optical system for stereoscopic vision of the example 6.
Figure 38B:
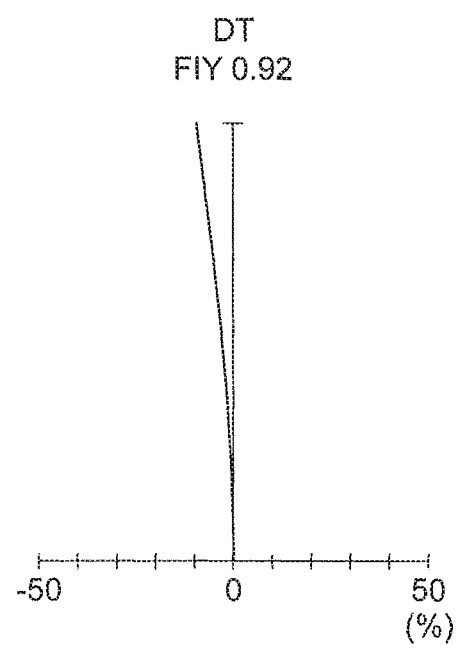
Figures 38C, 38D:
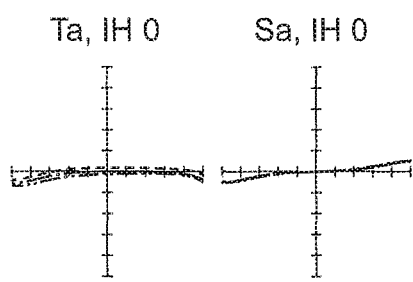
Figures 38E, 38F:
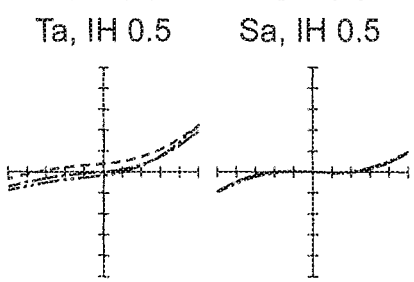
Figures 38G, 38H:
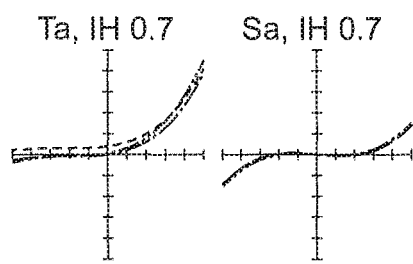
Figures 38I, 38J:
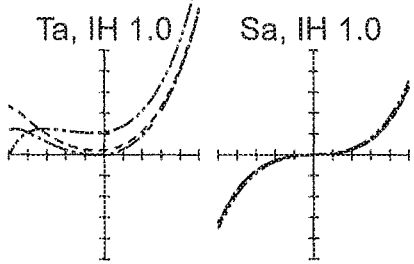
Figure 40A:
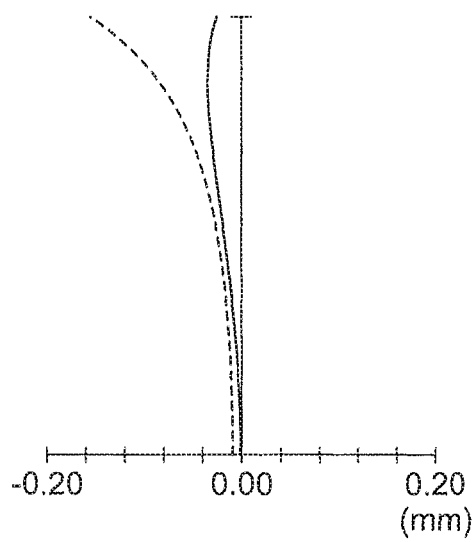
FIG. 40A, FIG. 40B, FIG. 40C, FIG. 40D, FIG. 40E, FIG. 40F, FIG. 40G, FIG. 40H, FIG. 40I, and FIG. 40J are aberration diagrams of the optical system for stereoscopic vision of the example 6.
Figure 40B:
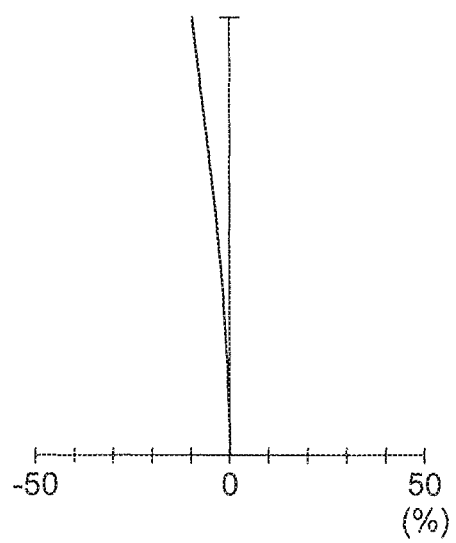
Figures 40C, 40D:
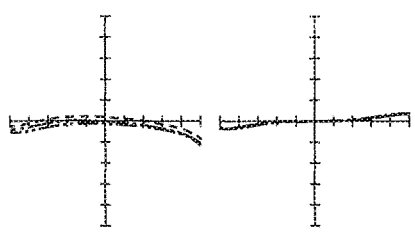
Figures 40E, 40F:
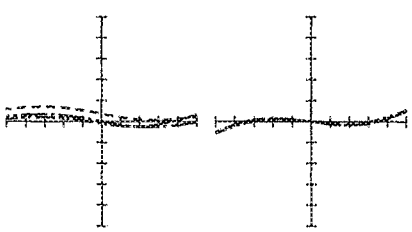
Figures 40G, 40H:
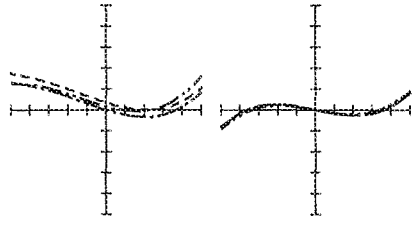
Figures 40I, 40J:
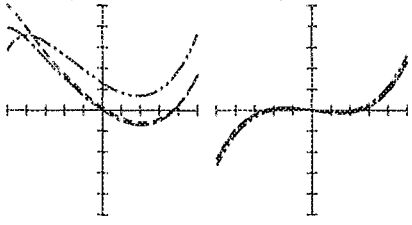
Figure 42A:
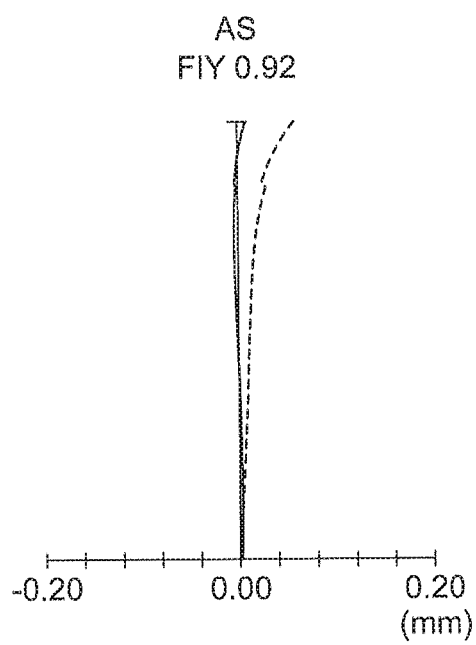
FIG. 42A, FIG. 42B, FIG. 42C, FIG. 42D, FIG. 42E, FIG. 42F, FIG. 42G, FIG. 42H, FIG. 42I, and FIG. 42J are aberration diagrams of the optical system for stereoscopic vision of the example 7.
Figure 42B:
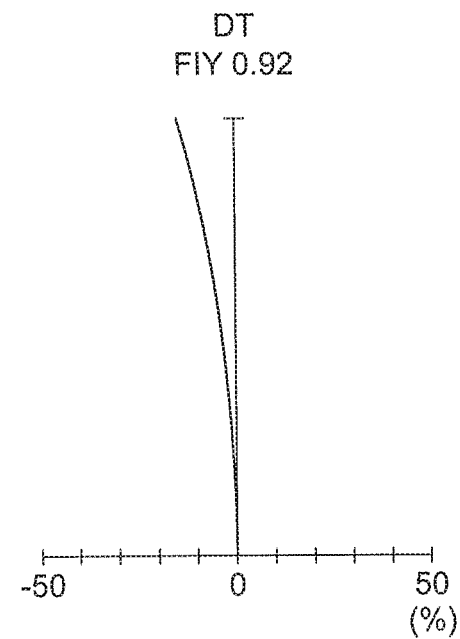
Figures 42C, 42D:
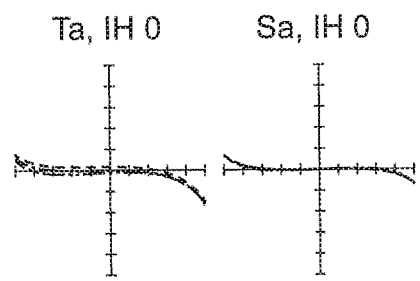
Figures 42E, 42F:
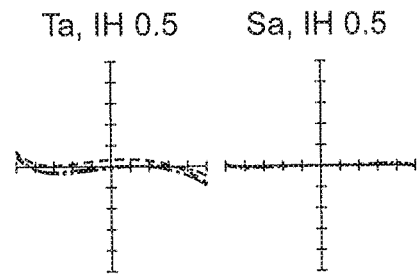
Figures 42G, 42H:
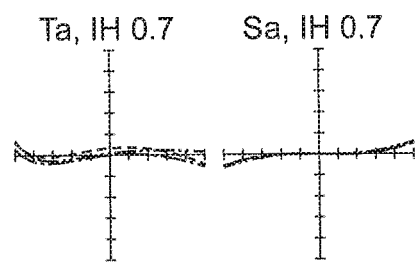
Figures 42I, 42J:
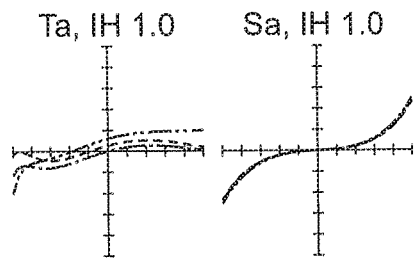
Figure 44A:
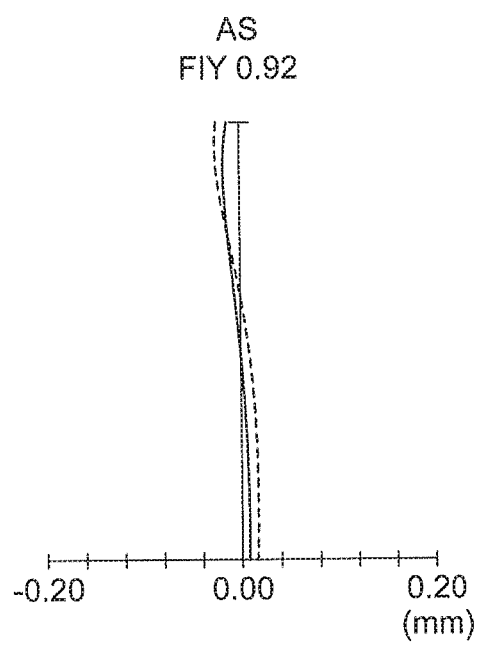
FIG. 44A, FIG. 44B, FIG. 44C, FIG. 44D, FIG. 44E, FIG. 44F, FIG. 44G, FIG. 44H, FIG. 44I, and FIG. 44J are aberration diagrams of the optical system for stereoscopic vision of the example 7.
Figure 44B:
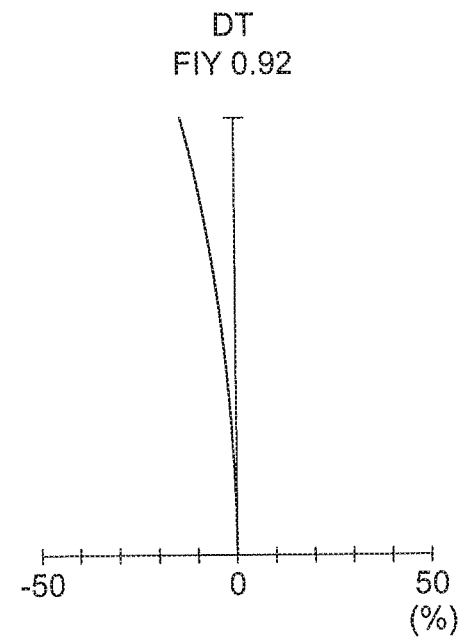
Figures 44C, 44D:
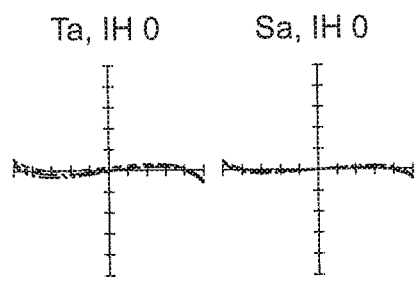
Figures 44E, 44F:
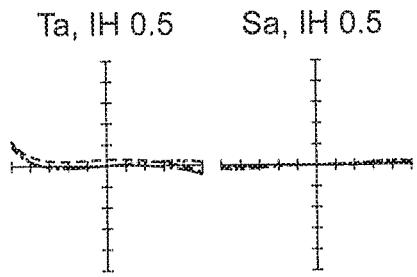
Figures 44G, 44H:
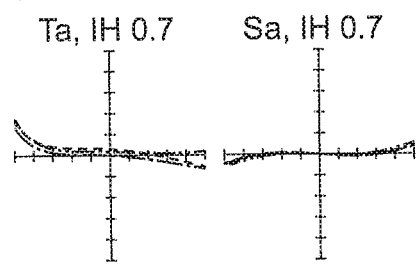
Figures 44I, 44J:
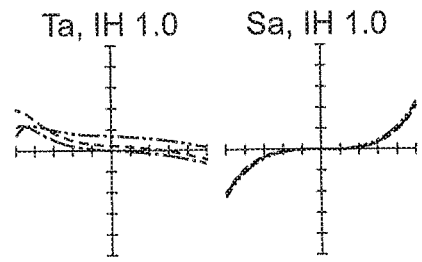
Figure 45A:
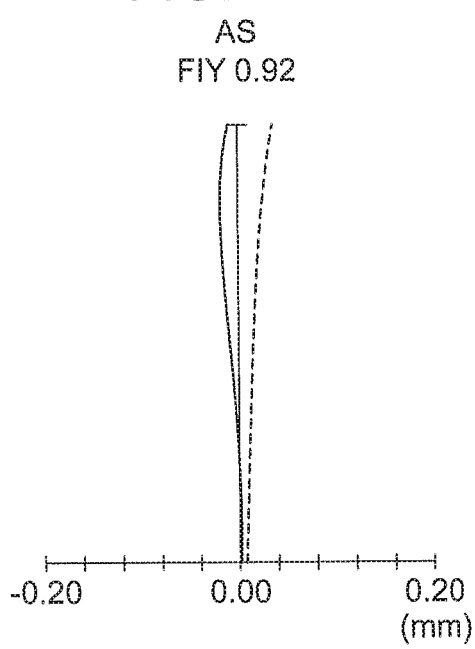
FIG. 45A, FIG. 45B, FIG. 45C, FIG. 45D, FIG. 45E, FIG. 45F, FIG. 45G, FIG. 45H, FIG. 45I, and FIG. 45J are aberration diagrams of the optical system for stereoscopic vision of the example 8.
Figure 45B:
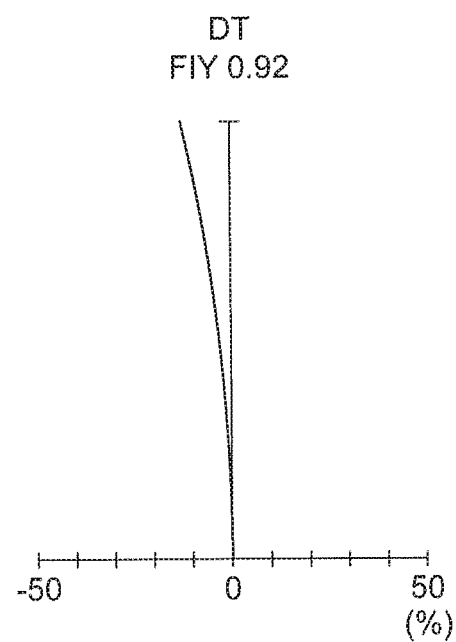
Figures 45C, 45D:
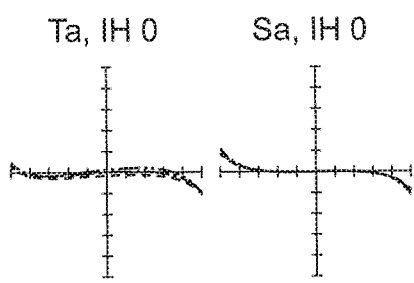
Figures 45E, 45F:
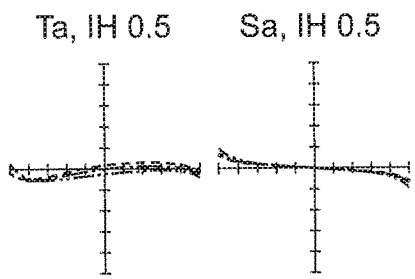
Figures 45G, 45H:
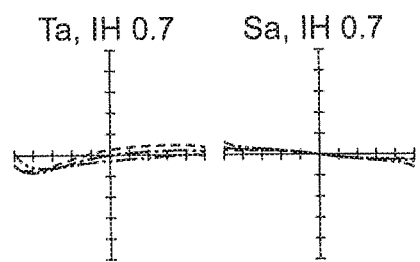
Figures 45I, 45J:
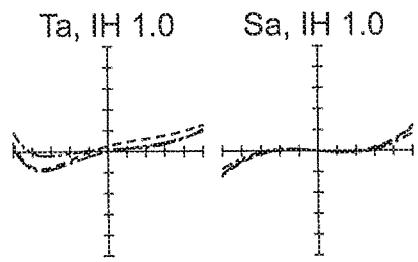
Figure 46A:
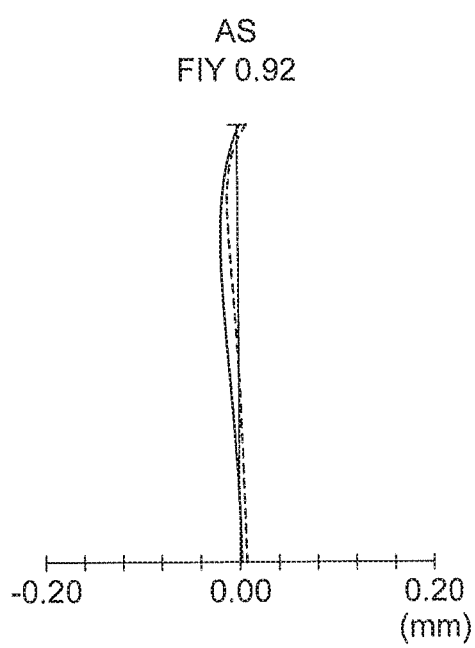
FIG. 46A, FIG. 46B, FIG. 46C, FIG. 46D, FIG. 46E, FIG. 46F, FIG. 46G, FIG. 46H, FIG. 46I, and FIG. 46J are aberration diagrams of the optical system for stereoscopic vision of the example 8.
Figure 46B:
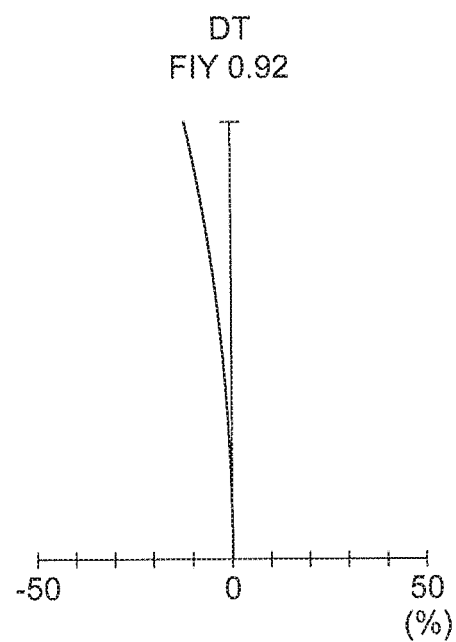
Figures 46C, 46D:
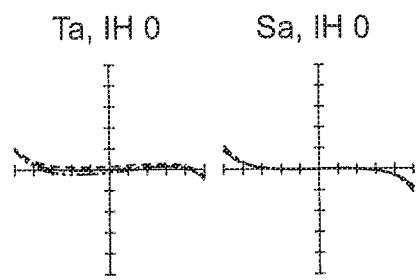
Figures 46E, 46F:
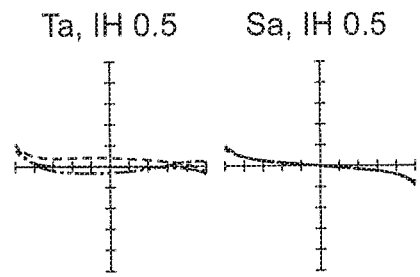
Figures 46G, 46H:
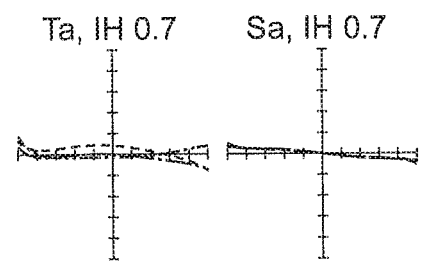
Figures 46I, 46J:
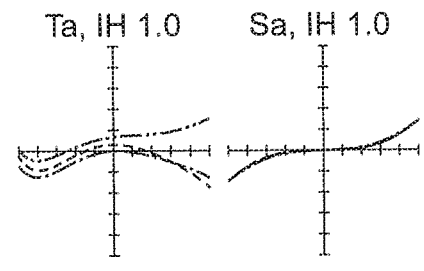
Figure 48A:
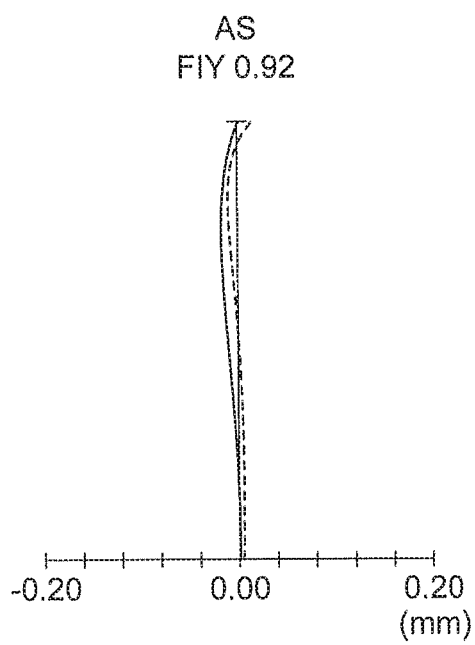
FIG. 48A, FIG. 48B, FIG. 48C, FIG. 48D, FIG. 48E, FIG. 48F, FIG. 48G, FIG. 48H, FIG. 48I, and FIG. 48J are aberration diagrams of the optical system for stereoscopic vision of the example 8.
Figure 48B:
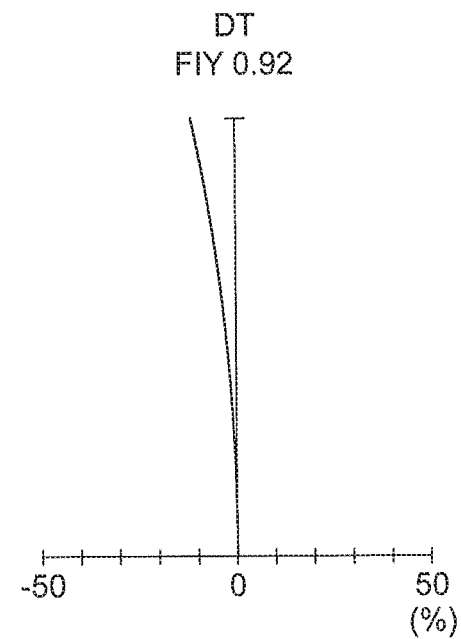
Figures 48C, 48D:
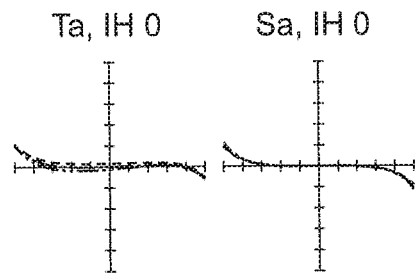
Figures 48E, 48F:
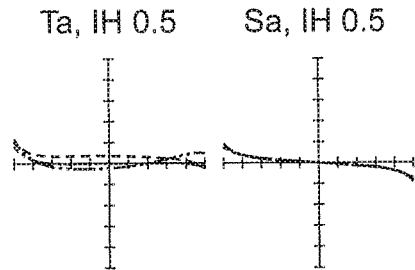
Figures 48G, 48H:
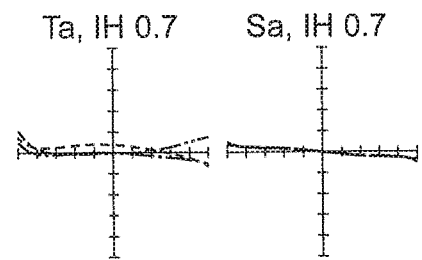
Figures 48I, 48J:
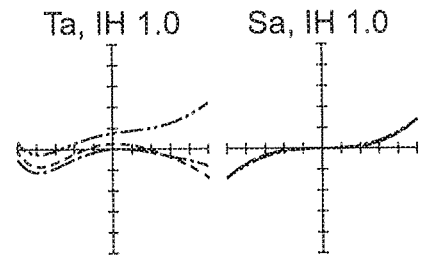
Figure 51A:
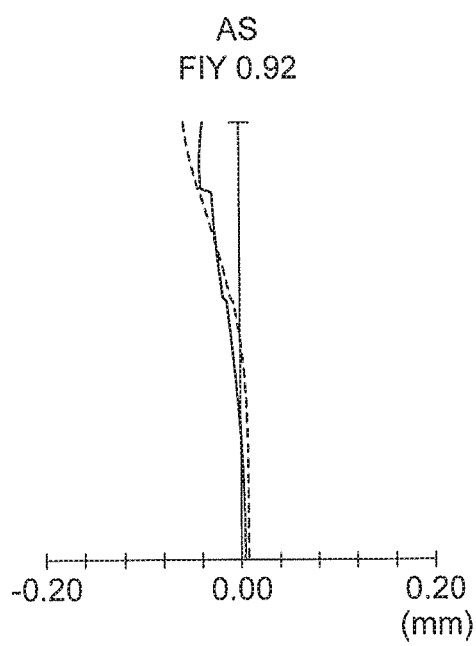
FIG. 51A, FIG. 51B, FIG. 51C, FIG. 51D, FIG. 51E, FIG. 51F, FIG. 51G, FIG. 51H, FIG. 51I, and FIG. 51J are aberration diagrams of the optical system for stereoscopic vision of the example 9.
Figure 51B:
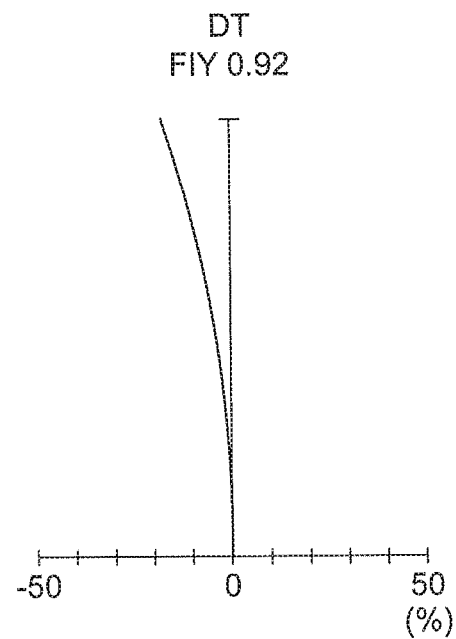
Figures 51C, 51D:
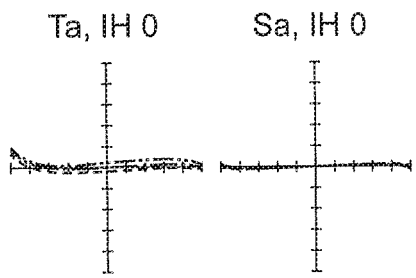
Figures 51E, 51F:
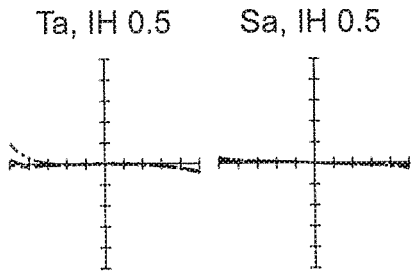
Figures 51G, 51H:
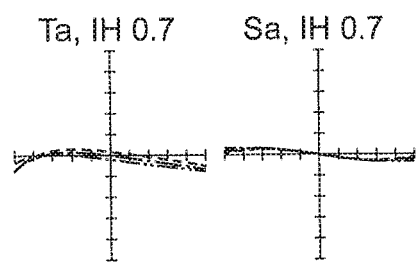
Figures 51I, 51J:
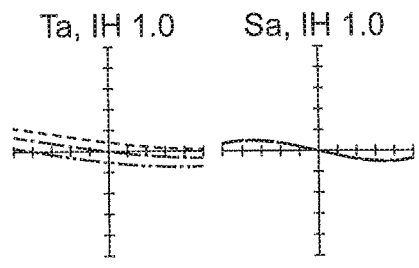
Figure 52A:
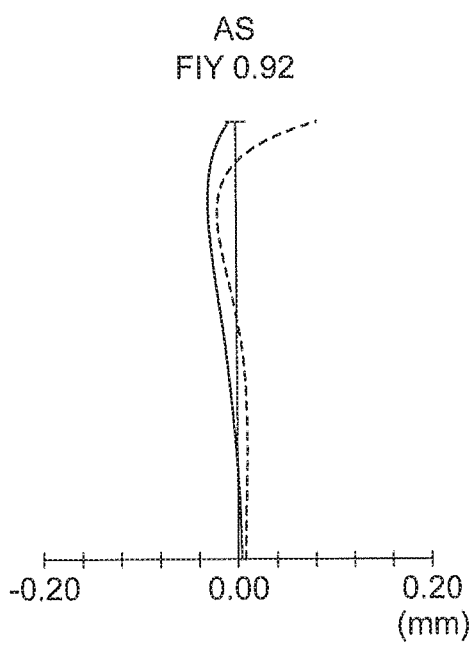
FIG. 52A, FIG. 52B, FIG. 52C, FIG. 52D, FIG. 52E, FIG. 52F, FIG. 52G, FIG. 52H, FIG. 52I, and FIG. 52J are aberration diagrams of the optical system for stereoscopic vision of the example 9.
Figure 52B:
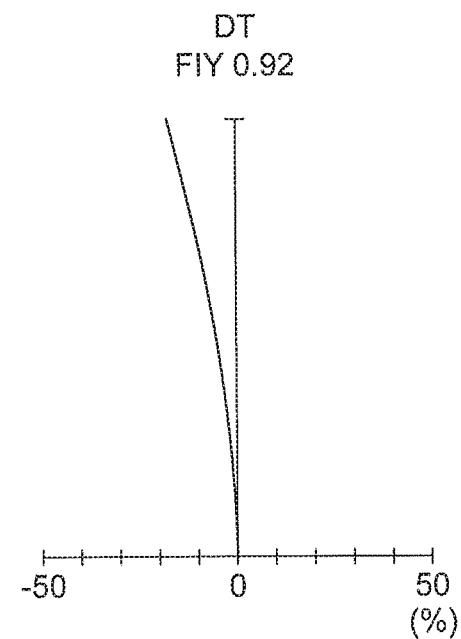
Figures 52C, 52D:
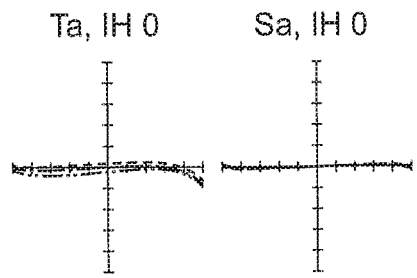
Figures 52E, 52F:
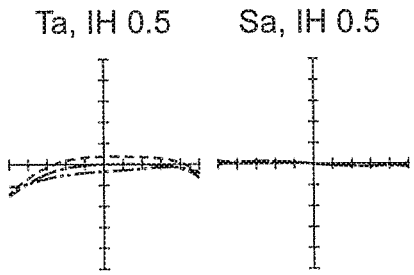
Figures 52G, 52H:
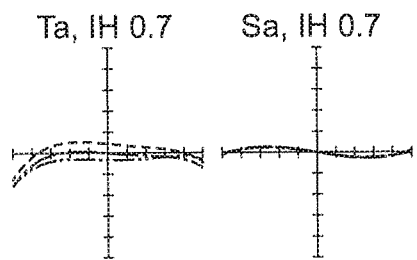
Figures 52I, 52J:
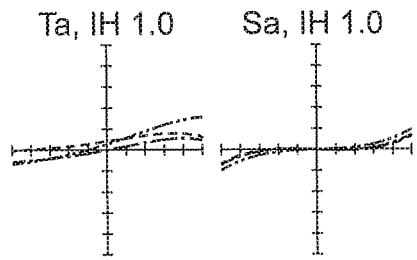
Figure 54A:
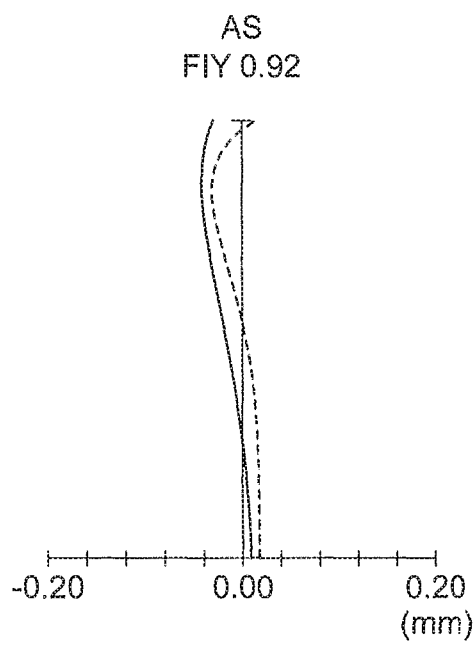
FIG. 54A, FIG. 54B, FIG. 54C, FIG. 54D, FIG. 54E, FIG. 54F, FIG. 54G, FIG. 54H, FIG. 54I, and FIG. 54J are aberration diagrams of the optical system for stereoscopic vision of the example 10.
Figure 54B:
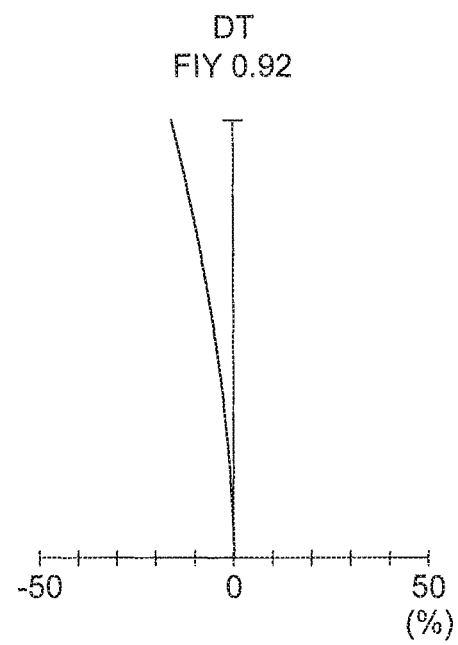
Figures 54C, 54D:
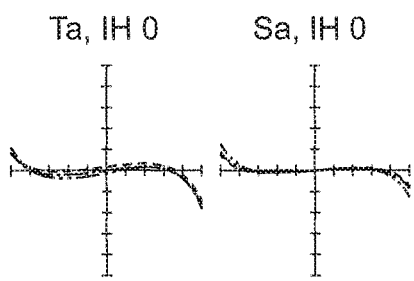
Figures 54E, 54F:
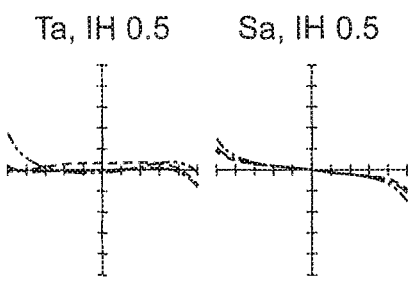
Figures 54G, 54H:
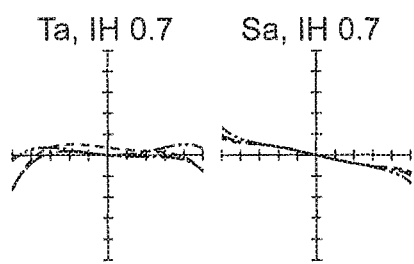
Figures 54I, 54J:
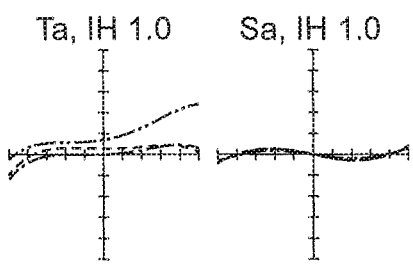
Figure 56A:
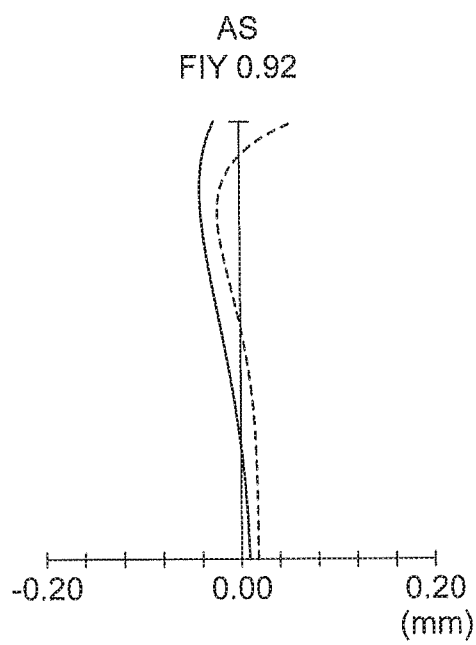
FIG. 56A, FIG. 56B, FIG. 56C, FIG. 56D, FIG. 56E, FIG. 56F, FIG. 56G, FIG. 56H, FIG. 56I, and FIG. 56J are aberration diagrams of the optical system for stereoscopic vision of the example 10.
Figure 56B:
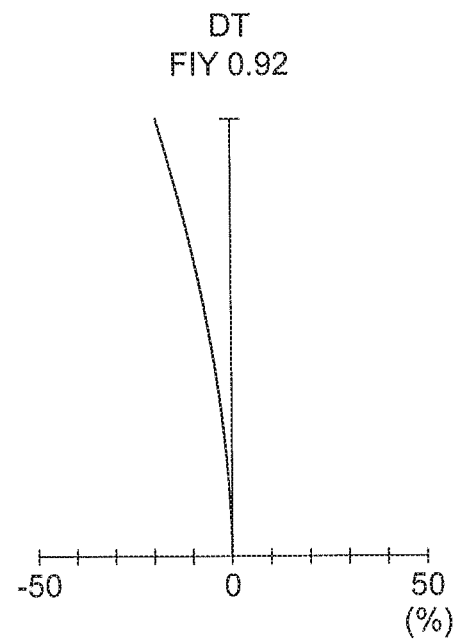
Figures 56C, 56D:
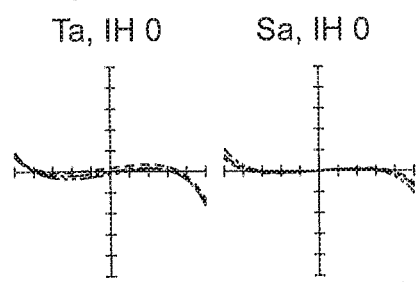
Figures 56E, 56F:
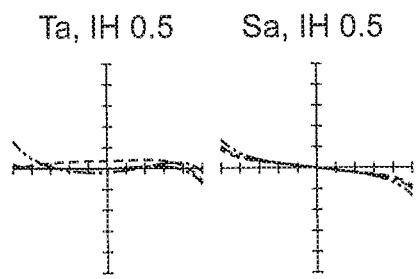
Figures 56G, 56H:
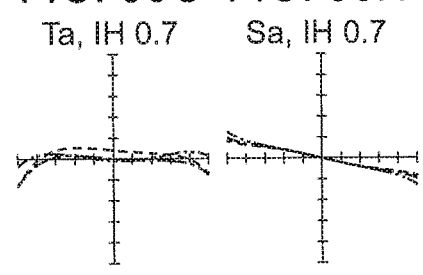
Figures 56I, 56J:
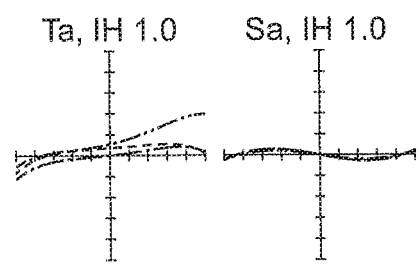
Figure 57A:
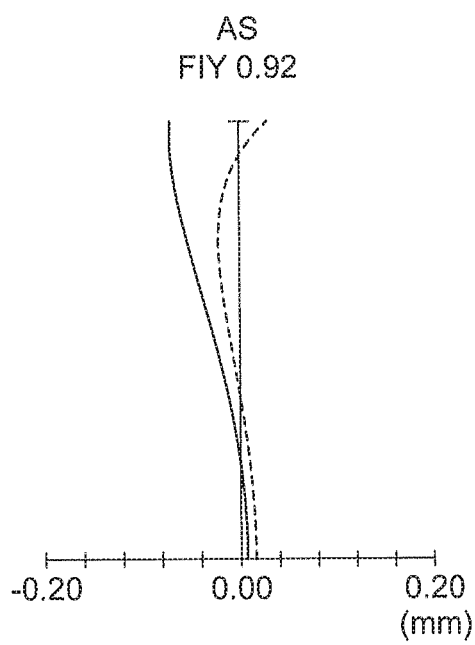
FIG. 57A, FIG. 57B, FIG. 57C, FIG. 57D, FIG. 57E, FIG. 57F, FIG. 57G, FIG. 57H, FIG. 57I, and FIG. 57J are aberration diagrams of the optical system for stereoscopic vision of the example 11.
Figure 57B:
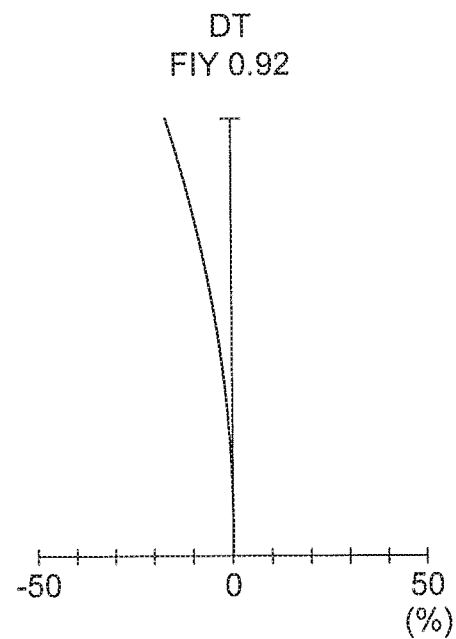
Figures 57C, 57D:
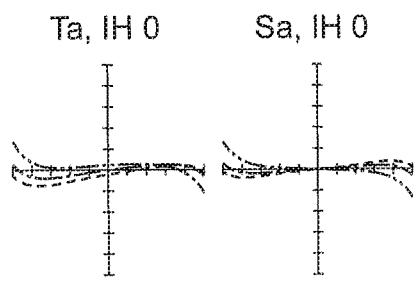
Figures 57E, 57F:
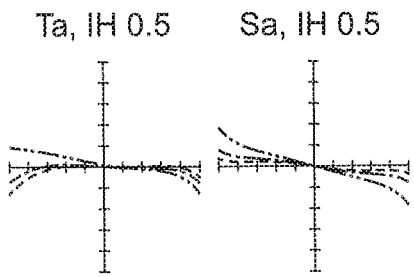
Figures 57G, 57H:
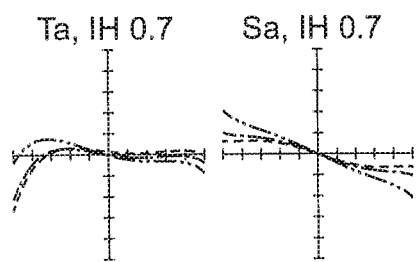
Figures 57I, 57J:
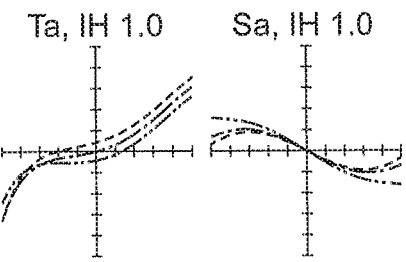
Figure 58A:
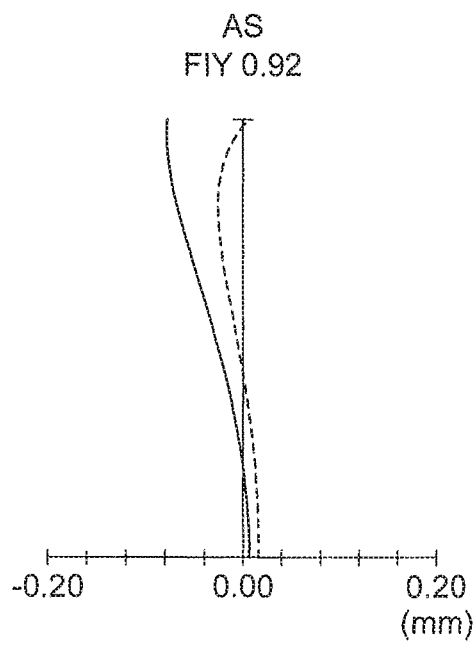
FIG. 58A, FIG. 58B, FIG. 58C, FIG. 58D, FIG. 58E, FIG. 58F, FIG. 58G, FIG. 58H, FIG. 58I, and FIG. 58J are aberration diagrams of the optical system for stereoscopic vision of the example 11.
Figure 58B:
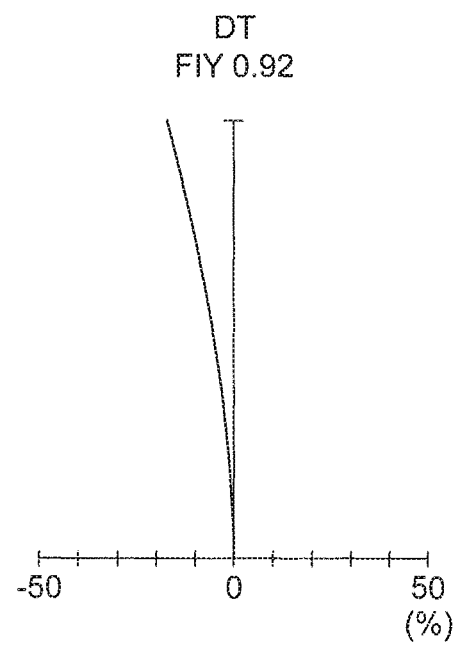
Figures 58C, 58D:
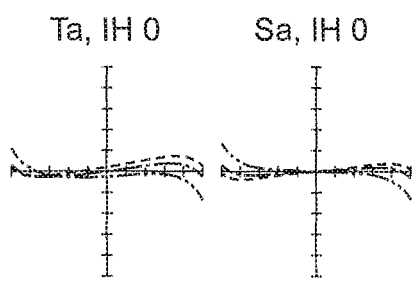
Figures 58E, 58F:
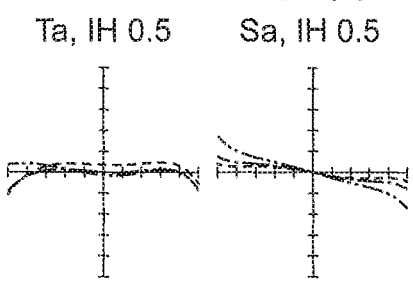
Figures 58G, 58H:
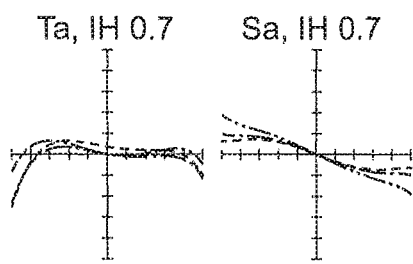
Figures 58I, 58J:
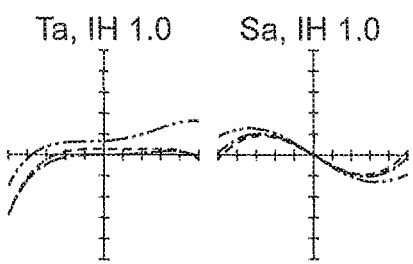
Figure 59A:
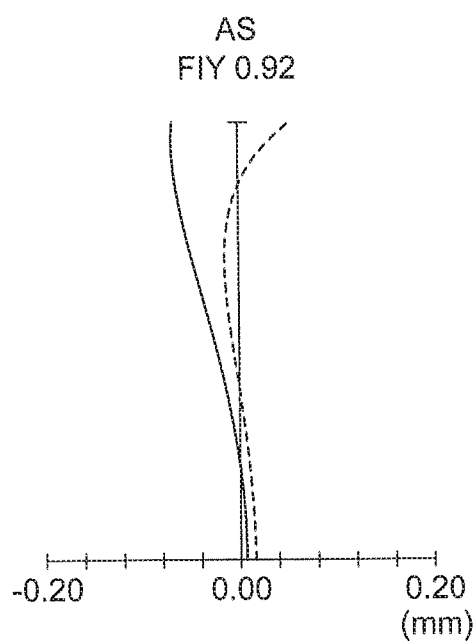
FIG. 59A, FIG. 59B, FIG. 59C, FIG. 59D, FIG. 59E, FIG. 59F, FIG. 59G, FIG. 59H, FIG. 59I, and FIG. 59J are aberration diagrams of the optical system for stereoscopic vision of the example 11.
Figure 59B:
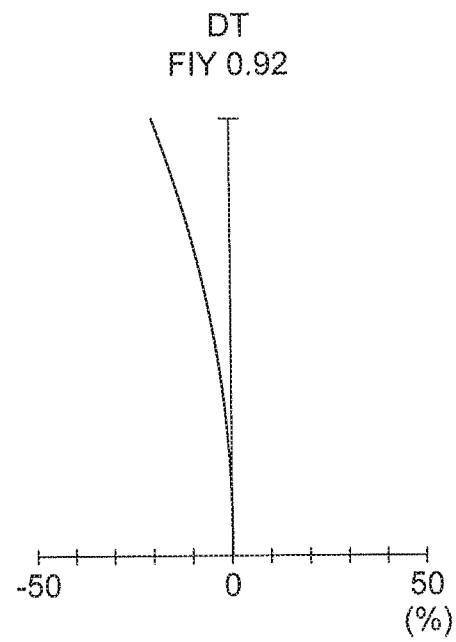
Figures 59C, 59D:
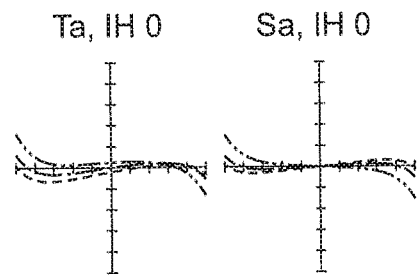
Figures 59E, 59F:
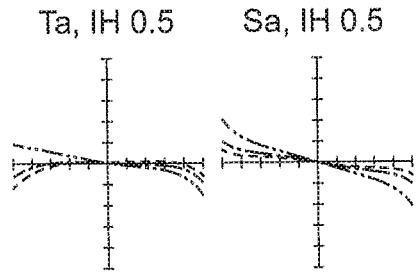
Figures 59G, 59H:
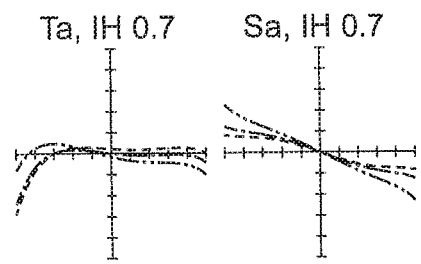
Figures 59I, 59J:
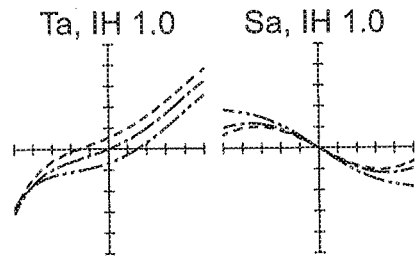
Figure 61A:
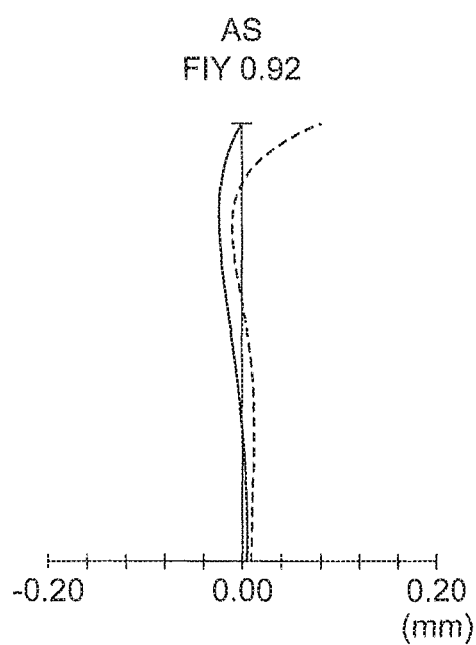
FIG. 61A, FIG. 61B, FIG. 61C, FIG. 61D, FIG. 61E, FIG. 61F, FIG. 61G, FIG. 61H, FIG. 61I, and FIG. 61J are aberration diagrams of the optical system for stereoscopic vision of the example 12.
Figure 61B:
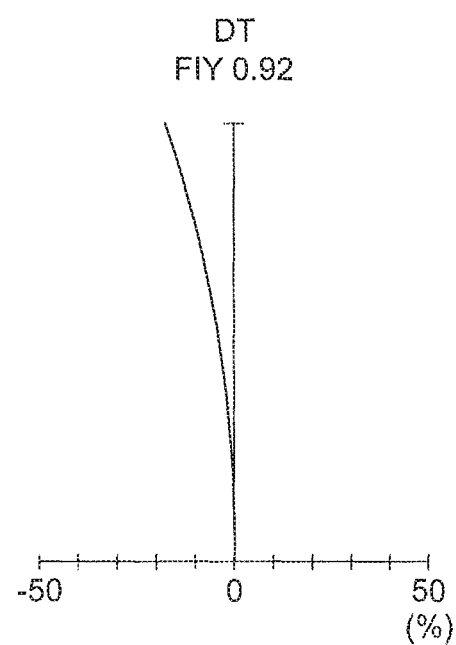
Figures 61C, 61D:
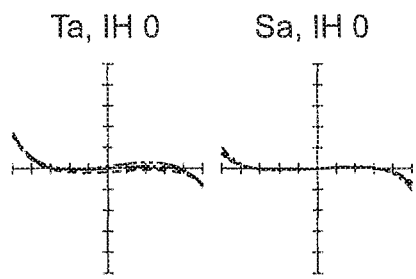
Figures 61E, 61F:
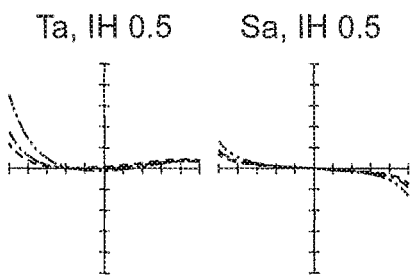
Figures 61G, 61H:
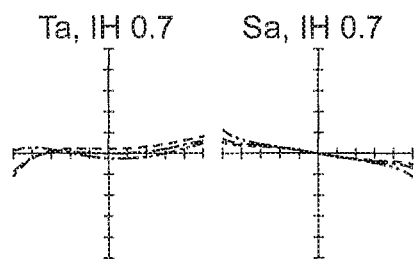
Figures 61I, 61J:
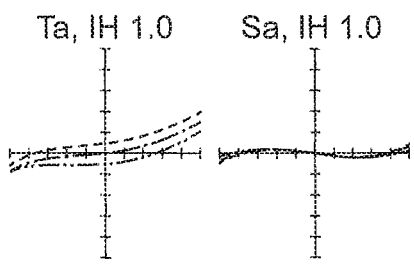
Figure 63A:
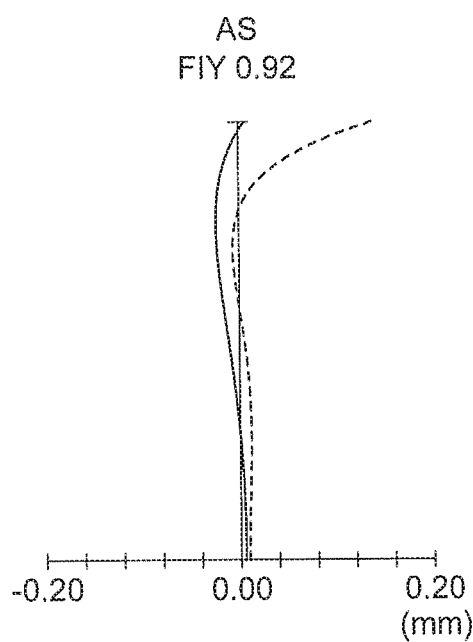
FIG. 63A, FIG. 63B, FIG. 63C, FIG. 63D, FIG. 63E, FIG. 63F, FIG. 63G, FIG. 63H, FIG. 63I, and FIG. 63J are aberration diagrams of the optical system for stereoscopic vision of the example 12.
Figure 63B:
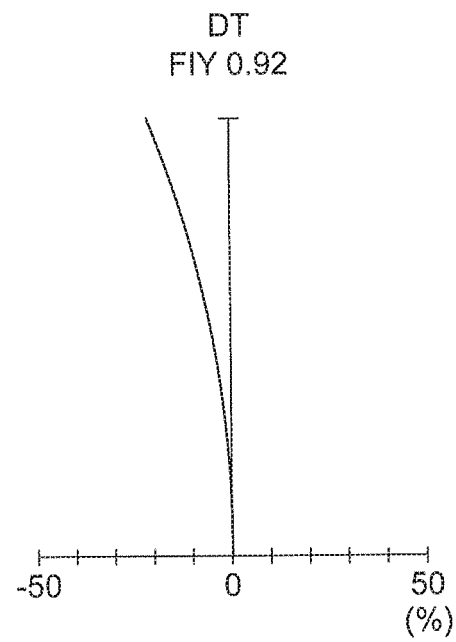
Figures 63C, 63D:
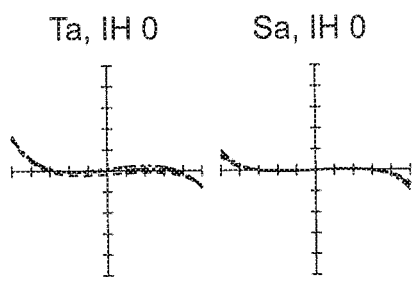
Figures 63E, 63F:
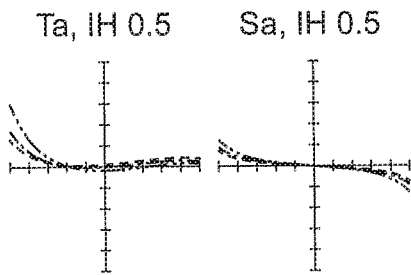
Figures 63G, 63H:
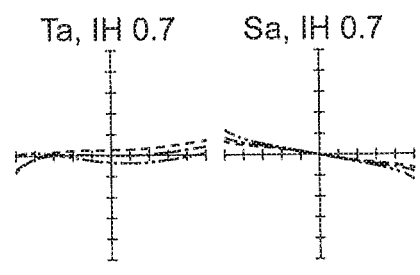
Figures 63I, 63J:
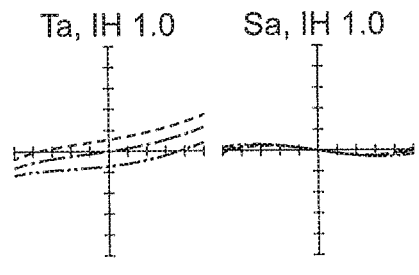
Figure 66A:
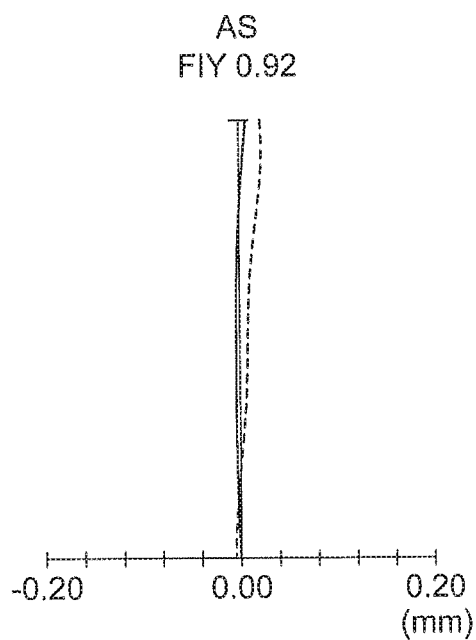
FIG. 66A, FIG. 66B, FIG. 66C, FIG. 66D, FIG. 66E, FIG. 66F, FIG. 66G, FIG. 66H, FIG. 66I, and FIG. 66J are aberration diagrams of the optical system for stereoscopic vision of the example 13.
Figure 66B:
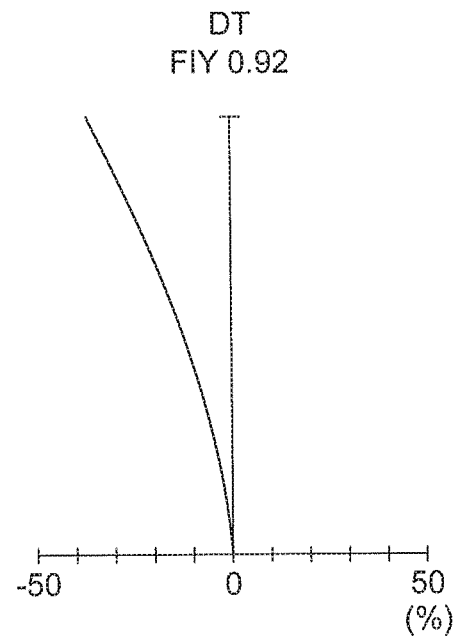
Figures 66C, 66D:
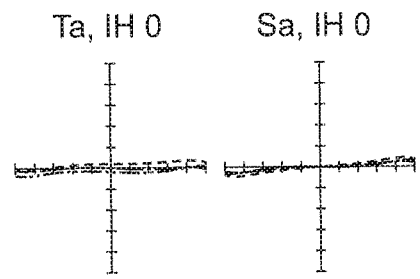
Figures 66E, 66F:
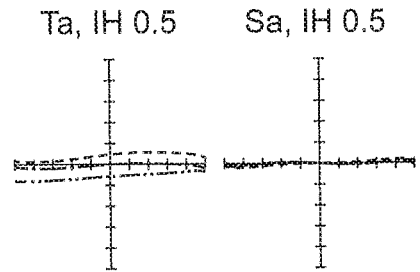
Figures 66G, 66H:
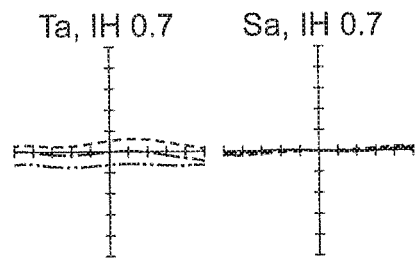
Figures 66I, 66J:
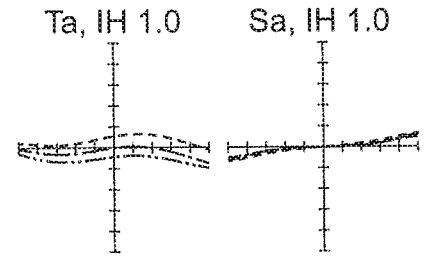
Figure 67A:
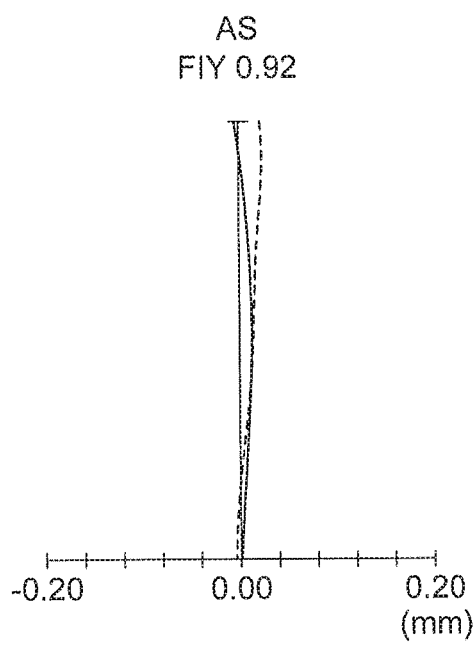
FIG. 67A, FIG. 67B, FIG. 67C, FIG. 67D, FIG. 67E, FIG. 67F, FIG. 67G, FIG. 67H, FIG. 67I, and FIG. 67J are aberration diagrams of the optical system for stereoscopic vision of the example 13.
Figure 67B:
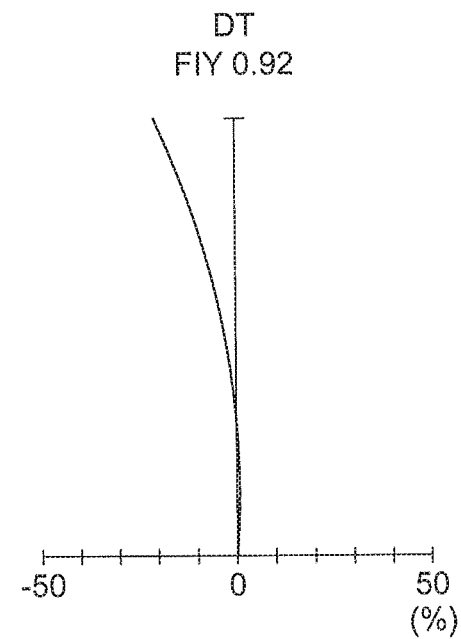
Figures 67C, 67D:
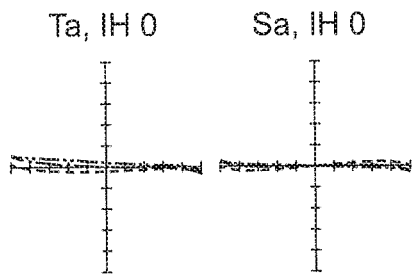
Figures 67E, 67F:
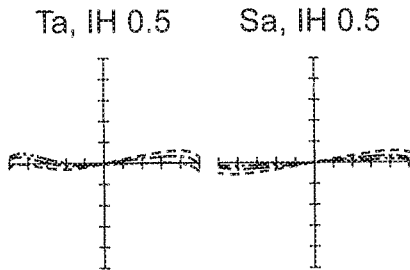
Figures 67G, 67H:
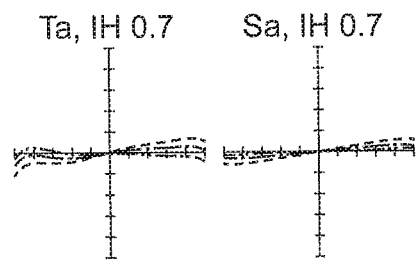
Figures 67I, 67J:
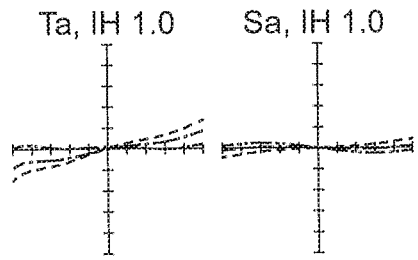
Figure 68A:
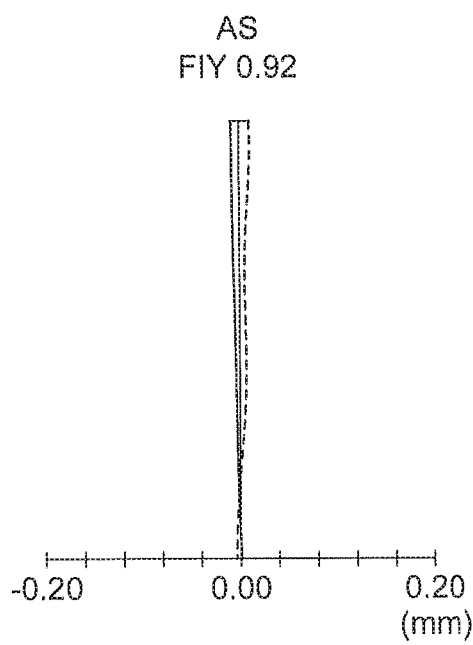
FIG. 68A, FIG. 68B, FIG. 68C, FIG. 68D, FIG. 68E, FIG. 68F, FIG. 68G, FIG. 68H, FIG. 68I, and FIG. 68J are aberration diagrams of the optical system for stereoscopic vision of the example 13.
Figure 68B:
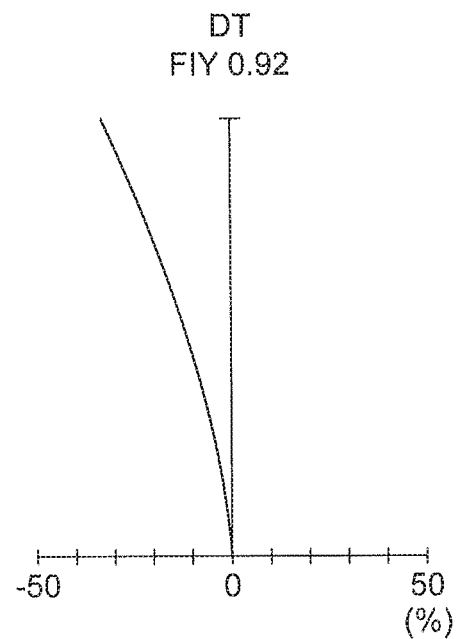
Figures 68C, 68D:
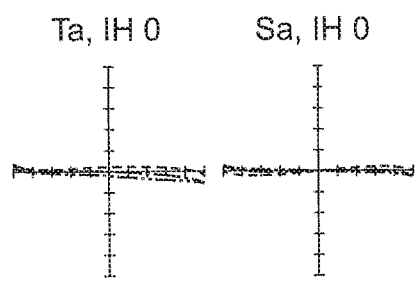
Figures 68E, 68F:
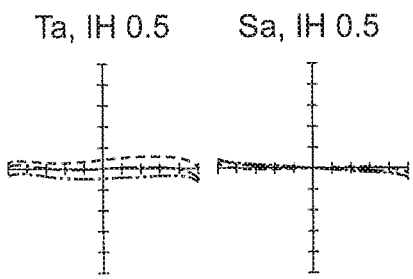
Figures 68G, 68H:
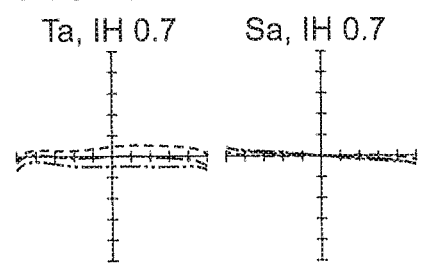
Figures 68I, 68J:
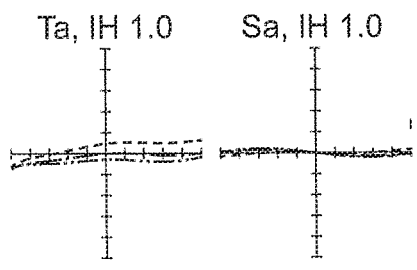
Figure 70A:
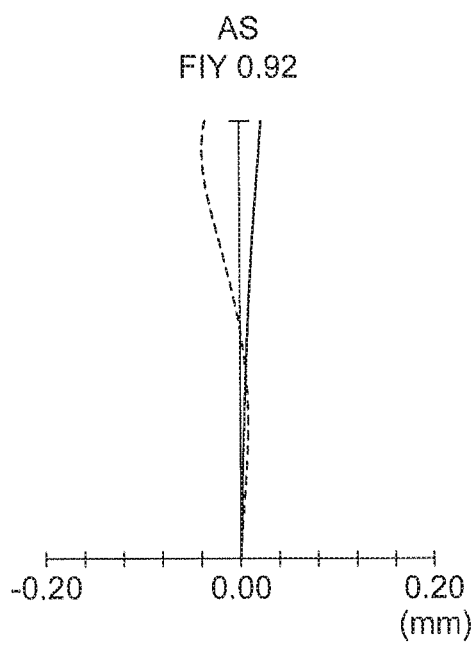
FIG. 70A, FIG. 70B, FIG. 70C, FIG. 70D, FIG. 70E, FIG. 70F, FIG. 70G, FIG. 70H, FIG. 70I, and FIG. 70J are aberration diagrams of the optical system for stereoscopic vision of the example 14.
Figure 70B:
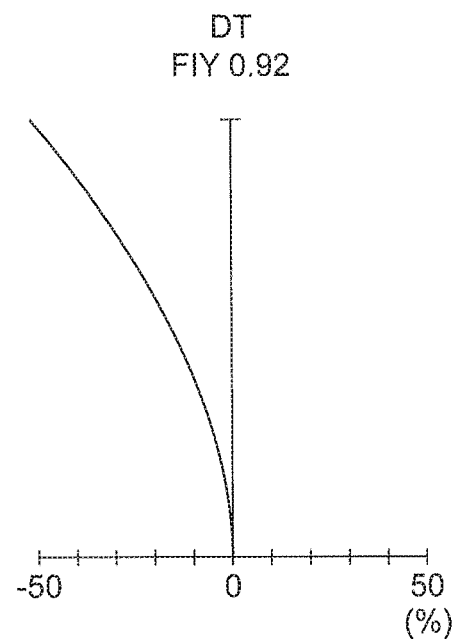
Figures 70C, 70D:
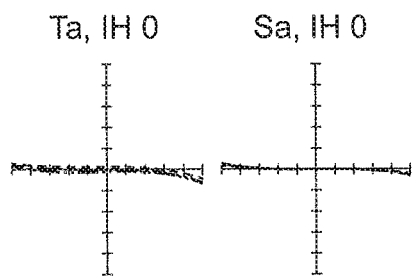
Figures 70E, 70F:
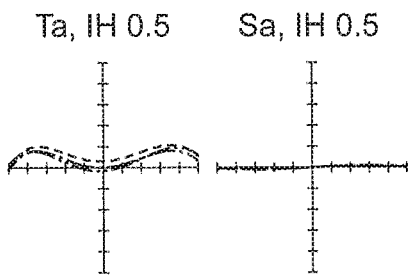
Figures 70G, 70H:
Figures 70I, 70J:
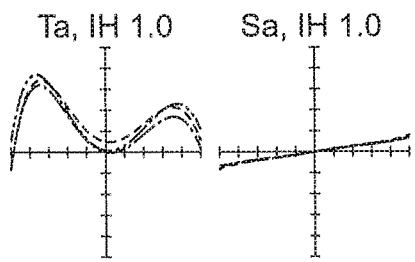
Figure 71A:
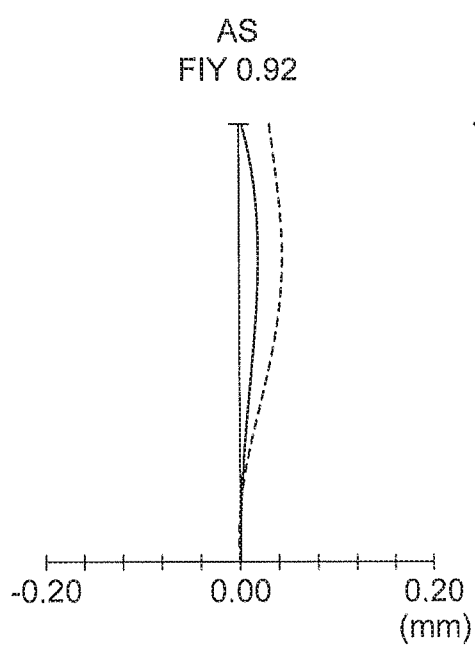
FIG. 71A, FIG. 71B, FIG. 71C, FIG. 71D, FIG. 71E, FIG. 71F, FIG. 71G, FIG. 71H, FIG. 71I, and FIG. 71J are aberration diagrams of the optical system for stereoscopic vision of the example 14.
Figure 71B:
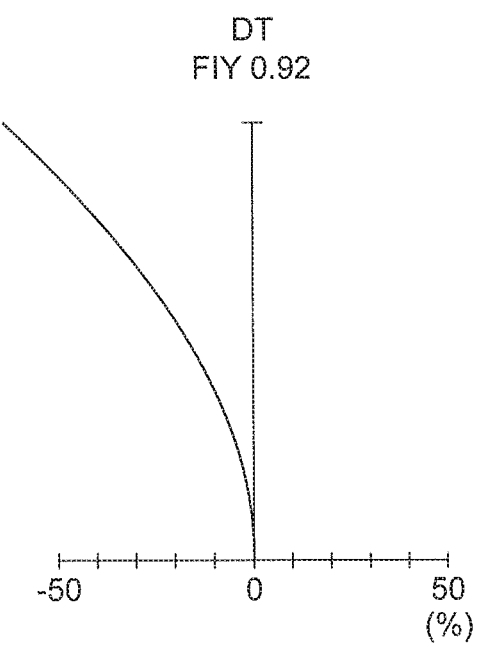
Figures 71C, 71D:
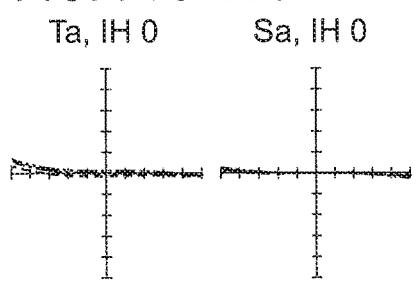
Figures 71E, 71F:
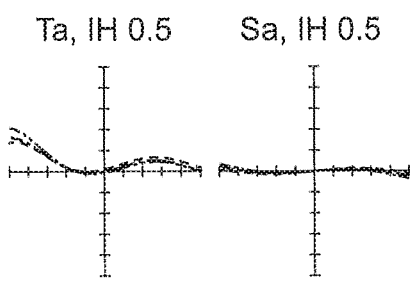
Figures 71G, 71H:
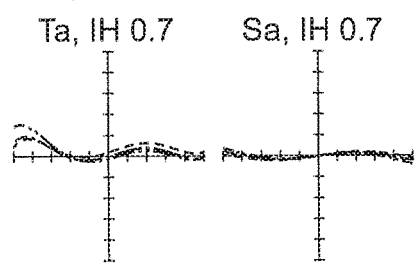
Figures 71I, 71J:
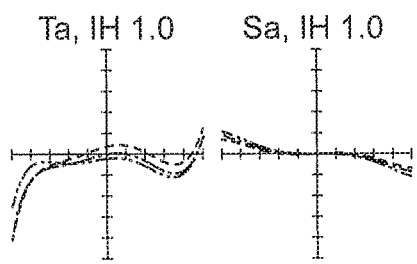

FIG. 2A and FIG. 2B are lens cross-sectional views of a second common optical system. FIG. 2A shows a lens cross-sectional view at a time of focusing to a far point. FIG. 2B shows a lens cross-sectional view at a time of focusing to a near point.

The second common optical system includes in order from an object side, a front unit GF and a rear unit GR. Each of the front unit GF and the rear unit GR includes a lens component. The lens component is either a single lens or a cemented lens.

The front unit GF includes a first front unit GF1 and a second front unit GF2. An optical axis AXC of the rear unit GR is disposed between an optical axis AX1 of the first front unit GF1 and an optical axis AX2 of the second front unit GF2. The first front unit GF1 and the second front unit GF2 are disposed symmetrically across the optical axis AXC. In FIG. 2A and FIG. 2B, an optical element C1, an optical element C2, and an optical element C3 are also shown. These optical elements are not components of the second common optical system but will be described below collectively for the sake of expediency.

In the second optical system, the first front unit GF1 and the second front unit GF2 are the same optical systems. Therefore, the first front unit GF1 will be described below.

The first front unit GF1 includes a planoconcave negative lens L1, a biconvex positive lens L2, a negative meniscus lens L3 having a convex surface directed toward an image side, a biconcave negative lens L4, a biconvex positive lens L5, and a positive meniscus lens L6 having a convex surface directed toward the image side.

The biconvex positive lens L2 and the negative meniscus lens L3 are cemented. The biconcave negative lens L4 and the biconvex positive lens L5 are cemented.

The rear unit GR includes a biconvex positive lens L7, a biconvex positive lens L8, a biconcave negative lens L9, a biconcave negative lens L10, a biconvex positive lens L11, and a positive meniscus lens L12 having a convex surface directed toward the object side.

The biconvex positive lens L8 and the biconcave negative lens L9 are cemented.

A stop S is disposed between the front unit GF and the rear unit GR. The optical element C1 is disposed on the object side of the planoconcave negative lens L1. The optical element C2 and the optical element C3 are disposed on the image side of the positive meniscus lens L12.

The optical element C1 is one plane parallel plate. The optical element C1 is positioned to intersect both the optical axis AX1 and the optical axis AX2. The optical element C1 is not required necessarily.

In the second common optical system, the positive meniscus lens L6 moves at a time of focusing. More elaborately, at a time of focusing from a far point to a near point, the positive meniscus lens L6 moves toward the image side.

In the common optical system, it is preferable that the first front unit include a front unit object-side negative lens, and the front unit object-side negative lens be disposed nearest to an object.

By making such arrangement, it is possible to secure a wide angle of view while maintaining the overall length of the optical system short.

In the common optical system, it is preferable that an object-side surface of the front unit object-side negative lens be a flat surface.

By making such arrangement, it is possible to make a lens diameter small while securing a wide angle of view.

In the common optical system, it is preferable that a positive lens component be disposed on an image side of the front unit object-side negative lens.

By making such arrangement, it is possible to correct the coma which occurs at the front unit object-side negative lens.

In the common optical system, it is preferable that the first front unit include the front unit object-side negative lens, an object-side cemented lens, and an image-side cemented lens, the front unit object-side negative lens be disposed nearest to the object, the object-side cemented lens be disposed on an image side of the front unit object-side negative lens, the image-side cemented lens be disposed on the image side of the object-side cemented lens, the object-side cemented lens include in order from the object side, a positive lens and a negative lens, and the image-side cemented lens include in order from the object side, a negative lens and a positive lens.

In the object-side cemented lens, the positive lens is disposed on the object side. By making such arrangement, it is possible to correct the coma which occurs at the front unit object-side negative lens. Moreover, in the image-side cemented lens, the positive lens is disposed on the image side. By making such arrangement, it is possible to suppress the spherical aberration.

In the common optical system, it is preferable that the first front unit include a front unit image-side lens component, and the front unit image-side lens component be disposed nearest to an image, and an image-side surface thereof have a shape which is convex toward the image side.

By making such arrangement, it is possible to suppress a height of a light ray incident on the rear unit.

Particularly, in a case of satisfying conditional expression (3) which will be described later, it is preferable that the abovementioned front unit image-side lens component be disposed in the first front unit.

When such arrangement is made, since it is possible to make small an angle made by an off-axis light ray emerged from the front unit image-side lens component and the optical axis, it is possible to suppress the height of a light ray incident on the rear unit. As a result, an aberration correction, particularly correction of the coma, in the rear unit becomes easy.

In a case in which the front unit object-side negative lens is disposed in the first front unit, by disposing the abovementioned front unit image-side lens component in the first front unit, it is possible to make the first front unit small-sized.

In the common optical system, it is preferable that the first front unit include the front unit image-side lens component, and the front unit image-side lens component be disposed nearest to the image, and have a positive refractive power.

By making such arrangement, it is possible to suppress the height of a light ray incident on the rear unit.

Particularly, in a case of satisfying conditional expression (3) which will be described later, it is preferable that the abovementioned front unit image-side lens component be disposed in the first front unit.

When such arrangement is made, since it is possible to make small an angle made by an off-axis light ray emerged from the front unit image-side lens component and the optical axis, it is possible to suppress the height of a light ray incident on the rear unit. As a result, an aberration correction, particularly correction of the coma, in the rear unit becomes easy.

Moreover, in a case in which the front unit object-side negative lens is disposed in the first front unit, by disposing the abovementioned front unit image-side lens component in the first front unit, it is possible to make the first front unit small-sized.

It is preferable that the image-side surface of the front unit image-side lens component have a shape which is convex toward the image side. Moreover, it is desirable to satisfy conditional expression (6) which will be described later.

In the common optical system, it is preferable that the first front unit include the front unit image-side lens component and a first predetermined lens component, the front unit image-side lens component be disposed nearest to the image, and the first predetermined lens component be disposed on the object side of the front unit image-side lens component, and an image-side surface thereof have a shape which is convex toward the image side.

By making such arrangement, it is possible to suppress a diameter of a light beam emerged from the first front unit and a diameter of a light beam emerged from the second front unit. Both the light beam emerged from the first front unit and the light beam emerged from the second front unit are incident on the rear unit. Accordingly, it is possible to suppress a diameter of a light beam incident on the rear unit.

It is preferable either to satisfy conditional expression (6) which will be described later or to satisfy conditional expression (7) which will be described later. By making such arrangement, it is possible to suppress an occurrence of the spherical aberration and an occurrence of the coma.

In the common optical system, it is preferable that the rear unit include a rear unit object-side lens component, and the rear unit object-side lens component be disposed nearest to the object, and have a positive refractive power.

By making such arrangement, it is possible to suppress the height of a light ray incident on the rear unit. Furthermore, it is possible to bring a position of a principal point closer to the object. Therefore, making such arrangement is advantageous not only for small-sizing of the optical system but also for shortening the overall length of the optical system.

In the common optical system, it is preferable that an object-side surface of the rear unit object-side lens component have a shape which is convex toward the object side.

By making such arrangement, it is possible to suppress the occurrence of the spherical aberration and the occurrence of the coma.

In the common optical system, it is preferable that the rear unit include the rear unit object-side lens component and a second predetermined lens component, the rear unit object-side lens component be disposed nearest to the object, and have a positive refractive power, and the second predetermined lens component be disposed on image side of the rear unit object-side lens component.

By making such arrangement, it is possible to suppress the height of a light ray incident on the rear unit. Furthermore, it is possible to bring a position of a principal point closer to the object. Consequently, making such arrangement becomes useful not only for small-sizing the optical system but also for shortening the overall length of the optical system.

It is preferable that the common optical system satisfy conditional expression (9) which will be described later. By making such arrangement, it is possible to distribute the positive refractive power. As a result, particularly, it is possible to suppress the occurrence of the spherical aberration and the occurrence of the coma.

In the common optical system, it is preferable that the rear unit include at least two positive lenses and at least one negative lens component, and the one negative lens component be disposed between the two positive lenses.

By making such arrangement, it is possible to correct a curvature of field in particular.

In the common optical system, it is preferable that the rear unit include a rear unit image-side lens component, and the rear unit image-side lens component be disposed nearest to the image, and have a positive refractive power.

By making such arrangement, it is possible to make small both an angle of incidence of an off-axis light ray incident on an image plane from the first optical system and an angle of incidence of an off-axis light ray incident on the image plane from the second optical system.

In the common optical system, it is preferable that the rear unit include the rear unit image-side lens component, and the rear unit image-side lens component be disposed nearest to the image, and have a positive refractive power, and an object-side surface thereof have a shape which is convex toward the object side.

By making such arrangement, it is possible to correct a distortion. Moreover, it is possible to suppress an occurrence of the curvature of field.

In the optical system for stereoscopic vision of the first embodiment, it is preferable that the optical system for stereoscopic vision include the abovementioned common optical system, the rear unit include a focusing lens component, and the focusing lens component move along an optical axis at a time of focusing.

When such arrangement is made, when the focusing lens component has been moved, both an amount of movement of the focusing lens component with respect to the first front unit and an amount of movement of the focusing lens component with respect to the second front unit become same. Consequently, a difference in a magnification of the first optical system and a magnification of second optical system, and a difference in a focal position of the first optical system and a focal position of the second optical system do not vary largely due to the movement of the focusing lens component.

In a case in which the focusing lens component is disposed in the front unit, according to a lateral magnification of the rear unit, an aberration extends due to the movement of the focusing lens component in some cases. When the focusing lens component is disposed in the rear unit, it is possible to suppress the increase in aberration due to the movement of the focusing lens component.

In the optical system for stereoscopic vision of the first embodiment, it is preferable that the following conditional expression (2) be satisfied:

$$0.3 < LOfarf1/FLf1 < 2.0 \quad (2)$$

where,

LOfarf1 denotes a distance from a far point to a position of an object-side principal point of the first front unit, FLf1 denotes a focal length of the first front unit, and the far point is a point in a focusing range, which is positioned farthest from the optical system for stereoscopic vision.

With the movement of the focusing lens component, a height of a marginal light ray passing through the rear unit varies. As the height of the marginal light ray varies, a decentration aberration also varies accordingly. By satisfying conditional expression (2), it is possible to make a light beam incident on the rear unit a parallel light beam or a substantially parallel light beam. Consequently, even when the focusing lens component moves, it is possible to make an amount of variation of the decentration aberration small.

In a case of exceeding an upper limit value of conditional expression (2), a light ray incident on the rear unit becomes divergent light. In a case of falling below a lower limit value of conditional expression (2), a light ray incident on the rear unit becomes convergent light. In both cases, when the focusing lens component is moved, an amount of decentration aberration which occurs in the rear unit becomes large. Therefore, exceeding the upper limit value of conditional expression (2) and falling below the lower limit value of conditional expression (2) are not preferable.

In the optical system for stereoscopic vision of the first embodiment, it is preferable that the following conditional expression (3) be satisfied:

$$5.0 < FLf1/TTLf1 < 100 \quad (3)$$

where,

FLf1 denotes the focal length of the first front unit, and

TTLf1 denotes a distance on the optical axis from an object-side surface of a lens disposed nearest to the object in the first front unit up to an image-side surface of a lens disposed nearest to the image in the first front unit.

In a case of exceeding an upper limit value of conditional expression (3), the focal length of the first front unit becomes excessively long with respect to an overall length of the first front unit. Consequently, it becomes difficult to achieve both of small-sizing the optical system and securing a wide angle of view.

In a case of falling below a lower limit value of conditional expression (3), the focal length of the first front unit becomes excessively short with respect to the overall length of the first front unit. Consequently, it becomes difficult to suppress the occurrence of the spherical aberration and the occurrence of the coma.

When conditional expression (2) and conditional expression (3) are satisfied, it is possible to secure a necessary working distance.

In an optical system of an endoscope, a wide angle of view is sought. In the optical system for stereoscopic vision of the first embodiment, by satisfying conditional expression (3), it is possible to secure a wide angle of view. Therefore, in a case of using the optical system for stereoscopic vision of the first embodiment for an optical system of an endoscope, it is desirable to satisfy conditional expression (3).

In the optical system for stereoscopic vision of the first embodiment, it is preferable that the first front unit include the front unit object-side negative lens, and the front unit object-side negative lens be disposed nearest to the object, and the following conditional expression (4) be satisfied:

$$-0.7 < FLf1a/TTLf1 < -0.2 \quad (4)$$

where,

FLf1a denotes a focal length of the front unit object-side negative lens, and

TTLf1 denotes the distance on the optical axis from the object-side surface of the lens disposed nearest to the object in the first front unit up to the image-side surface of the lens disposed nearest to the image in the first front unit.

In a case of exceeding an upper limit value of conditional expression (4), it becomes difficult to secure a wide angle of view while shortening the overall length of the optical system. Moreover, it becomes difficult to make small a lens diameter of the front unit object-side negative lens while securing a wide angle of view.

In a case of falling below a lower limit value of conditional expression (4), the distortion and the coma are susceptible to occur. Therefore, falling below the lower limit value of conditional expression (4) is not preferable.

In the optical system for stereoscopic vision of the first embodiment, it is preferable that the first front unit include the front unit object-side negative lens and the positive lens component, the front unit object-side negative lens be disposed nearest to the object, the positive lens component be disposed on an image side of the front unit object-side negative lens, and the following conditional expression (5) be satisfied:

$$0.3 < FLf1b/TTLf1 < 1.2 \quad (5)$$

where,

FLf1b denotes a focal length of the positive lens component in the first front unit, and TTLf1 denotes the distance on the optical axis from the object-side surface of the lens disposed nearest to the object in the first front unit up to the image-side surface of the lens disposed nearest to the image in the first front unit.

In a case of exceeding an upper limit value of conditional expression (5), it is not possible to achieve sufficiently large positive refractive power by the positive lens component. Consequently, it is not possible to correct the coma which occurs at the front unit object-side negative lens. Moreover, a height of an axial light ray becomes high. Therefore, exceeding the upper limit value of conditional expression (5) becomes disadvantageous for small-sizing of the optical system.

In a case of falling below a lower limit value of conditional expression (5), the positive refractive power of the positive lens component becomes excessively large. In this case, the coma of high order is susceptible to occur. Therefore, falling below a lower limit value of conditional expression (5) is not preferable.

In the optical system for stereoscopic vision of the first embodiment, it is preferable that the conditional expression (5) be satisfied, and the positive lens component be disposed on the image side of the front unit object-side negative lens.

It is preferable that the positive lens component in the first front unit be disposed adjacent to the front unit object-side negative lens, on the image side thereof. In such manner, it is preferable that the positive lens component of the first front unit be a positive lens component adjacent to the front unit object-side negative lens, on the image side thereof. Or, in a case in which the first front unit includes a plurality of positive lens components, it is preferable that the positive lens component which is closer to the front unit object-side negative lens satisfy conditional expression (5).

In the optical system for stereoscopic vision of the first embodiment, it is preferable that the first front unit include the front unit image-side lens component, the front unit image-side lens component be disposed nearest to the image, and the image-side surface thereof have a shape which is convex toward the image side, and the following conditional expression (6) be satisfied:

$$-0.55 < Rrf1c/FLf1 < -0.25 \quad (6)$$

where,

Rrf1c denotes a radius of curvature of the image-side surface of the front unit image-side lens component, and FLf1 denotes the focal length of the first front unit.

In a case of exceeding an upper limit value of conditional expression (6), it is not possible to make the positive refractive power of the front unit image-side lens component adequately large. In this case, it is not possible to make an angle made by an off-axis light ray emerged from the front unit image-side lens component and the optical axis adequately small. Consequently, small-sizing of the rear unit becomes difficult. Moreover, an off-axis aberration such as the coma is susceptible to occur.

In a case of falling below a lower limit value of conditional expression (6), at the image-side surface of the front unit image-side lens component, the spherical aberration and the coma occur substantially. Therefore, falling below the lower limit value of conditional expression (6) is not preferable.

In the optical system for stereoscopic vision of the first embodiment, it is preferable that the first front unit include the front unit image-side lens component, the front unit image-side lens component be disposed nearest to the image, and have a positive refractive power, and the following conditional expression (7) be satisfied:

$$0.5 < FLf1c/FLf1 < 10.0 \quad (7)$$

where,

FLf1c denotes a focal length of the front unit image-side lens component, and

FLf1 denotes the focal length of the first front unit.

In a case of exceeding an upper limit value of conditional expression (7), it is not possible to make the positive refractive power of the front unit image-side lens component adequately large. In this case, it is not possible to make the angle made by the off-axis light ray emerged from the front unit image-side lens component and the optical axis adequately small. Consequently, small-sizing of the rear unit become difficult. Moreover, an off-axis aberration such as the coma is susceptible to occur.

In a case of falling below a lower limit value of conditional expression (7), the spherical aberration and the coma occur substantially at the image-side surface of the front unit image-side lens component. Therefore, falling below the lower limit value of conditional expression (7) is not preferable.

In the optical system for stereoscopic vision of the first embodiment, it is desirable that conditional expression (7) be satisfied as well as conditional expression (6) be satisfied.

In the optical system for stereoscopic vision of the first embodiment, it is preferable that the following conditional expression (8) be satisfied:

$$0.2 < FLr/TTL < 0.7 \quad (8)$$

where,

FLr denotes a focal length of the rear unit at the time of focusing to a far point, TTL denotes a distance on the optical axis from an object-side surface of a lens disposed nearest to the object in the front unit up to an image plane, and the far point is a point in a focusing range, which is positioned farthest from the optical system for stereoscopic vision.

In a case of exceeding an upper limit value of conditional expression (8), the focal length of the rear unit becomes excessively long with respect to the overall length of the rear unit. Consequently, it becomes difficult to achieve both of small-sizing of the optical system and securing a wide angle of view.

In a case of falling below a lower limit value of conditional expression (8), the focal length of the rear unit becomes excessively short with respect to the overall length of the rear unit. Consequently, it becomes difficult to achieve both of correction of an off-axis aberration and correction of a longitudinal aberration.

In the optical system for stereoscopic vision of the first embodiment, it is preferable that the rear unit include the rear unit object-side lens component, the rear unit object-side lens component be disposed nearest to the object, and have a positive refractive power, and the following conditional expression (9) be satisfied:

$$-3.5 < (Rfra + Rrra)/(Rfra - Rrra) < 0.5 \quad (9)$$

where,

Rfra denotes a radius of curvature of an object-side surface of the rear unit object-side lens component, and Rrra denotes a radius of curvature of an image-side surface of the rear unit object-side lens component.

In a case of exceeding an upper limit value of conditional expression (9), it becomes difficult to secure adequately a positive refractive power which is necessary for the rear unit object-side lens component. For securing the positive refractive power adequately, the radius of curvature of the object-side surface has to be made small. However, when the radius of curvature of the object-side surface is made small, the coma and the spherical aberration of high order are susceptible to occur.

In a case of falling below a lower limit value of conditional expression (9), the positive refractive power of the image-side surface becomes excessively large with respect to that of the object-side surface. In this case, correction of the spherical aberration and correction of the coma become difficult. Therefore, falling below the lower limit value of conditional expression (9) is not preferable.

In the optical system for stereoscopic vision of the first embodiment, it is preferable that the rear unit include the rear unit object-side lens component and the second predetermined lens component, the rear unit object-side lens component be disposed nearest to the object, and have a positive refractive power, the second predetermined lens component be disposed on an image side of the rear unit object-side lens component, and the following conditional expression (10) be satisfied:

$$0.02 < Lr1/TTL < 0.2 \quad (10)$$

where,

Lr1 denotes a distance on the optical axis from an object-side surface of the rear unit object-side lens component up to an object-side surface of the second predetermined lens component, and TTL denotes the distance on the optical axis from the object-side surface of the lens disposed nearest to the object in the front unit up to the image plane.

In a case of exceeding an upper limit value of conditional expression (10), a distance between the object-side surface of the rear unit object-side lens component and the object-side surface of the second predetermined lens component becomes excessively long. In this case, when the positive refractive power of the rear unit object-side lens component is not made large, since a height of off-axis light ray becomes high, small-sizing of the optical system becomes difficult. However, when the refractive power of the rear unit object-side lens component is made large, the spherical aberration and the coma are susceptible to occur. Therefore, exceeding the upper limit value of conditional expression (10) is not preferable.

In a case of falling below a lower limit value of conditional expression (10), it is not possible to achieve adequately a thickness of the rear unit object-side lens component. Consequently, in the rear unit object-side lens component, it becomes difficult to secure the positive refractive power adequately. For small-sizing the optical system by making the height of the off-axis light ray small in such state, the refractive power of the second predetermined lens component has to be made large accordingly. However, when the refractive power of the second predetermined lens component is made large, the spherical aberration and the coma are susceptible to occur. Therefore, falling below the lower limit value of conditional expression (10) is not preferable.

It is preferable that the second predetermined lens component be disposed adjacent to the rear unit object-side lens component, on the image side thereof. In such manner, it is preferable that the second predetermined lens component be a lens component disposed adjacent to the rear unit object-side lens component, on the image side thereof. Or, it is preferable that the second predetermined lens component be a lens component positioned nearest to the rear unit object-side lens component.

In the optical system for stereoscopic vision of the second embodiment, it is preferable that the focusing lens component be disposed nearest to the image in the rear unit.

By making such arrangement, it is possible to suppress a fluctuation in aberration due to the movement of the focusing lens component, such as a fluctuation in the spherical aberration, a fluctuation in the coma, and a fluctuation in a chromatic aberration.

In the optical system for stereoscopic vision of the second embodiment, it is preferable that the following conditional expression (11) be satisfied:

$$0.1 < 1-(\beta focus)^2 < 0.9 \quad (11)$$

where,

βfocus denotes a lateral magnification of the focusing lens component at the time of focusing to a far point, and the far point is a point in the focusing range, which is positioned farthest from the optical system for stereoscopic vision.

Conditional expression (11) is a conditional expression for making appropriate an amount of movement of the focusing lens unit and achieving a favorable imaging performance. At the time of focusing, the focusing lens component stops at a position determined in advance. It is preferable that an error in a stopping position of the focusing lens component and the position determined in advance (hereinafter, referred to as 'positional error') be small.

In a case of exceeding an upper limit value of conditional expression (11), a fluctuation in the focal length due to the positional error becomes excessively large. Particularly, at the time of near-point observation, since a depth of field becomes shallow, there is a large effect due to the positional error and the imaging performance is degraded. Therefore, exceeding the upper limit value of conditional expression (11) is not preferable.

In a case of falling below a lower limit value of conditional expression (11), for securing the necessary focusing range, the amount of movement of the focusing lens component has to be made large. In this case, the rear unit becomes large in size. Therefore, falling below a lower limit value of conditional expression (11) is not preferable.

In the optical system for stereoscopic vision of the third embodiment, it is preferable that the rear unit include the rear unit image-side lens component, the rear unit image-side lens component be disposed nearest to the image, and the focusing lens component be disposed on the object side of the rear unit image-side lens component.

By making such arrangement, it is possible to suppress a fluctuation in aberration due to the movement of the focusing lens component, such as a fluctuation in the curvature of field and a fluctuation in the distortion.

In the optical system for stereoscopic vision of the third embodiment, it is preferable that the following conditional expression (12) be satisfied:

$$0.7 < 1-(\beta focus)^2 \times \beta r^2 < 1.0 \quad (12)$$

where,

βfocus denotes the lateral magnification of the focusing lens component at the time of focusing to the far point, βr denotes a lateral magnification of a predetermined lens unit at the time of focusing to the farthest point, the predetermined lens unit includes all lenses positioned on the image side of the focusing lens component, and the far point is a point in the focusing range, which is positioned farthest from the optical system for stereoscopic vision.

Conditional expression (12) is a conditional expression for making appropriate the amount of movement of the focusing lens component and achieving a favorable imaging performance.

In a case of exceeding an upper limit value of conditional expression (12), the fluctuation in the focal length due to the positional error becomes excessively large. Particularly, at the time of near-point observation, since the depth of field becomes shallow, there is a large effect due to the positional error and the imaging performance is degraded. Therefore, exceeding the upper limit value of conditional expression (12) is not preferable.

In a case of falling below a lower limit value of conditional expression (12), for securing the necessary focusing range, the amount of movement of the focusing lens component has to be made large. In this case, the rear unit becomes large in size. Therefore, falling below the lower limit value of conditional expression (12) is not preferable.

In the optical system for stereoscopic vision of the second embodiment and the optical system for stereoscopic vision of the third embodiment, it is preferable that the following conditional expression (13) be satisfied:

$$0.2 < FLfocus/TTL < 4.0 \qquad (13)$$

where,

FLfocus denotes a focal length of the focusing lens component, and

TTL denotes the distance on the optical axis from the object-side surface of the lens disposed nearest to the object in the front unit up to the image plane.

When conditional expression (13) is not satisfied, the fluctuation in the curvature of field due to the movement of the focusing lens component becomes large. Therefore, exceeding the upper limit value of conditional expression (13) and falling below the lower limit value of conditional expression (13) are not preferable.

In the optical system for stereoscopic vision of the first embodiment, the optical system for stereoscopic vision of the second embodiment, and the optical system for stereoscopic vision of the third embodiment, the focusing lens component may have been disposed in the first front unit as well. In this case, LOfarf1 and TTLf1 denote distances at the time of focusing to a near point and FLf1 denotes a focal length at the time of focusing to a near point.

In the optical system for stereoscopic vision of the fourth embodiment, it is preferable that the first front unit include the focusing lens component, and the focusing lens component move along an optical axis at the time of focusing.

By making such arrangement, it is possible to suppress an occurrence of the decentration aberration.

In the optical system for stereoscopic vision of the fourth embodiment, it is preferable that the following conditional expressions (14) and (15) be satisfied:

$$0.1 < LOfarf1/FLfarf1 < 5.0 \qquad (14)$$

$$0.1 < LOnearf1/FLnearf1 < 4.0 \qquad (15)$$

where,

LOfarf1 denotes the distance from the far point up to the position of the object-side principal point of the first front unit, LOnearf1 denotes a distance from a near point up to the position of the object-side principal point of the first front unit, FLfarf1 denotes a focal length of the first front unit at the time of focusing to the far point, FLnearf1 denotes a focal length of the first front unit at the time of focusing to the near point, the far point is a point in the focusing range, which is positioned farthest from the optical system for stereoscopic vision, and the near point is a point in the focusing range, which is positioned nearest to the optical system for stereoscopic vision.

With the movement of the focusing lens component, a height of a marginal light ray passing through the rear unit varies. As the height of the marginal light ray varies, the decentration aberration also varies accordingly. By satisfying conditional expressions (14) and (15), it is possible to make a light beam incident on the rear unit a parallel light beam or a substantially parallel light beam. Consequently, even when the focusing lens component moves, it is possible to make the amount of variation in the decentration aberration small.

In a case of exceeding an upper limit value of conditional expression (14) and in a case of exceeding an upper limit value of conditional expression (15), a light ray incident on the rear unit becomes divergent light. In a case of falling below a lower limit value of conditional expression (14) and in a case of falling below a lower limit value of conditional expression (15), the light ray incident on the rear unit becomes a convergent light. In both the cases, at the rear unit, the decentration aberration occurs in accordance with the variation in the height of the marginal light ray. Therefore, exceeding the upper limit value of conditional expression (14) and exceeding the upper limit value of conditional expression (15) are not preferable. Moreover, falling below the lower limit value of conditional expression (14) and falling below the lower limit value of conditional expression (15) are not preferable.

In the optical system for stereoscopic vision of the fourth embodiment, it is preferable that the first front unit include the front unit object-side negative lens, the front unit object-side negative lens be disposed nearest to the object, the rear unit include the rear unit object-side lens component, the rear unit object-side lens component be disposed nearest to the object, and the following conditional expression (16) be satisfied:

$$3.0 < FLfarf1/TTLf1' < 70.0 \qquad (16)$$

where,

FLfarf1 denotes the focal length of the first front unit at the time of focusing to the far point, TTLf1' denotes a distance on the optical axis from an object-side surface of the front unit object-side negative lens up to an object-side surface of the rear unit object-side lens component, and the far point is a point in the focusing range, which is positioned farthest from the optical system for stereoscopic vision.

In a case of exceeding an upper limit value of conditional expression (16), the focal length of the first front unit becomes excessively long. Consequently, it becomes difficult to achieve both of small-sizing of the front unit and securing a wide angle of view.

In a case of falling below a lower limit value of conditional expression (16), the focal length of the first front unit becomes excessively short. Consequently, it becomes difficult to suppress the occurrence of the spherical aberration and the occurrence of the coma.

When conditional expression (2) and conditional expression (16) are satisfied, it is possible to secure the required working distance.

In an optical system of an endoscope, a wide angle of view is sought. In the optical system for stereoscopic vision of the fourth embodiment, by satisfying conditional expression (16), it is possible to secure a wide angle of view. Therefore, in a case of using the optical system for stereoscopic vision of the fourth embodiment for an optical system of an endoscope, it is desirable that conditional expression (16) be satisfied.

In the optical system for stereoscopic vision of the fourth embodiment, it is preferable that the first front unit include the front unit object-side negative lens, the front unit object-side negative lens be disposed nearest to the object, and the following conditional expression (17) be satisfied:

$$-0.3 < FLf1a/TTL < -0.04 \quad (17)$$

where,

FLf1a denotes the focal length of the front unit object-side negative lens, and

TTL denotes the distance on the optical axis from the object-side surface of the lens disposed nearest to the object in the front unit up to the image plane.

In a case of exceeding an upper limit value of conditional expression (17), it becomes difficult to secure a wide angle of view while shortening the overall length of the optical system. Moreover, it becomes difficult to make small a lens diameter of the front unit object-side negative lens while securing a wide field of view.

In a case of falling below a lower limit value of conditional expression (17), the distortion and the coma are susceptible to occur. Therefore, falling below the lower limit value of conditional expression (17) is not preferable.

In the optical system for stereoscopic vision of the fourth embodiment, it is preferable that the first front unit include the front unit object-side negative lens and the positive lens component, the front unit object-side negative lens be disposed nearest to the object, the positive lens component be disposed on the image side of the front unit object-side negative lens, and the following conditional expression (18) be satisfied:

$$0.1 < FLf1b/TTL < 0.4 \quad (18)$$

where,

FLf1b denotes the focal length of the positive lens component in the first front unit, and TTL denotes the distance on the optical axis from the object-side surface of the lens disposed nearest to the object in the front unit up to the image plane.

In a case of exceeding an upper limit value of conditional expression (18), it is not possible to achieve sufficiently large positive refractive power by the positive lens component. Consequently, it is not possible to correct the coma which occurs at the front unit object-side negative lens. Moreover, a height of an axial light ray becomes high. Therefore, exceeding the upper limit value of conditional expression (18) becomes disadvantageous for small-sizing of the optical system.

In a case of falling below a lower limit value of conditional expression (18), the positive refractive power of the positive lens component becomes excessively large. In this case, the coma of high order is susceptible to occur. Therefore, falling below the lower limit value of conditional expression (18) is not preferable.

In the optical system for stereoscopic vision of the fourth embodiment, it is desirable that conditional expression (18) be satisfied as well as condition expression (5) be satisfied.

It is preferable that the positive lens component in the first front unit be disposed adjacent to the front unit object-side negative lens, on the image side thereof. In such manner, it is preferable that the positive lens component of the first front unit be a positive lens component adjacent to the front unit object-side negative lens, on the image side thereof. Or, in a case in which the first front unit includes a plurality of positive lens components, it is preferable that the positive lens component which is closer to the front unit object-side negative lens satisfy conditional expression (18).

In the optical system for stereoscopic vision of the fourth embodiment, it is preferable that the first front unit include the front unit object-side negative lens, the object-side cemented lens, and the image-side cemented lens, the front unit object-side negative lens be disposed nearest to the object, the object-side cemented lens be disposed on an image side of the object-side negative lens, the image-side cemented lens be disposed on the image side of the object-side cemented lens, the object-side cemented lens include in order from the object side, a positive lens and a negative lens, the image-side cemented lens include in order from the object side, a negative lens and a positive lens, and the focusing lens component be disposed on the image side of the image-side cemented lens.

By making such arrangement, at the time of focusing, it is possible to suppress the variation in the height of a light ray incident on the focusing lens component to be small. Therefore, making such arrangement is advantageous for favorable aberration correction and small-sizing of the optical system.

In the optical system for stereoscopic vision of the fourth embodiment, it is preferable that the first front unit include the front unit image-side lens component, the front unit image-side lens component be disposed nearest to the image, and the image-side surface thereof have a shape which is convex toward the image side, and the following conditional expression (19) be satisfied:

$$-0.5 < Rrf1c/TTL < -0.1 \quad (19)$$

where,

Rrf1c denotes the radius of curvature of the image-side surface of the front unit image-side lens component, and TTL denotes the distance on the optical axis from the object-side surface of the lens disposed nearest to the object in the front unit up to the image plane.

In a case of exceeding an upper limit value of conditional expression (19), it is not possible to make the positive refractive power of the front unit image-side lens component adequately large. In this case, it is not possible to make an angle made by an off-axis light ray emerged from the front unit image-side lens component and the optical axis adequately small. Consequently, small-sizing of the rear unit becomes difficult. Moreover, an off-axis aberration such as the coma is susceptible to occur.

In a case of falling below a lower limit value of conditional expression (19), at the image-side surface of the front unit image-side lens component, the spherical aberration and the coma occur substantially. Therefore, falling below the lower limit value of conditional expression (19) is not preferable.

In the optical system for stereoscopic vision of the fourth embodiment, it is preferable that the first front unit include the front unit image-side lens component, the front unit image-side lens component be disposed nearest to the image, and the image-side surface thereof have a shape which is convex toward the image side, and the following conditional expression (20) be satisfied:

$$-2.0 < FLf1c/TTL < 2.0 \qquad (20)$$

where,

FLf1c denotes the focal length of the front unit image-side lens component, and

TTL denotes the distance on the optical axis from the object-side surface of the lens disposed nearest to the object in the front unit up to the image plane.

By making such arrangement, it is possible to suppress the height of a light ray incident on the rear unit.

In a case in which the front unit object-side negative lens is disposed in the first front unit, by disposing the front unit image-side lens component nearest to the image and making the image-side surface a surface which is convex toward the image side, it is possible to small-size the first front unit.

In the optical system for stereoscopic vision of the fourth embodiment, it is preferable that the first front unit include the front unit object-side negative lens, the front unit image-side lens component, and the first predetermined lens component, the front unit object-side negative lens be disposed nearest to the object, the front unit image-side lens component be disposed nearest to the image, the first predetermined lens component be disposed on an object side of the front unit image-side lens component, and the following conditional expression (21) be satisfied:

$$0.5 < Rrf1d/FLf1a < 2.0 \qquad (21)$$

where,

Rrf1d denotes a radius of curvature of an image-side surface of the first predetermined lens component, and FLf1a denotes the focal length of the front unit object-side negative lens.

In a case of exceeding an upper limit value of conditional expression (21), it is not possible to make the positive refractive power of the first predetermined lens component adequately large. In this case, it is not possible to converge adequately a light ray emerged from the first predetermined lens component. Moreover, it is not possible to make an angle made by an off-axis light ray emerged from the front unit image-side lens component and the optical axis adequately small.

Even when the positive refractive power is imparted to the front unit image-side lens component, it becomes difficult to make a diameter of a light beam incident on the rear unit small when the refractive power is not large. Moreover, various aberrations occur. In other words, small-sizing of the rear unit becomes difficult and an off-axis aberration such as the coma is susceptible to occur.

In a case of falling below a lower limit value of conditional expression (21), at the image-side surface of the front unit image-side lens component, the spherical aberration and the coma occur substantially. Therefore, falling below the lower limit value of conditional expression (21) is not preferable.

It is preferable that the first predetermined lens component be disposed adjacent to the front unit image-side lens component, on the object side thereof. In such manner, it is preferable that the first predetermined lens component be a lens component adjacent to the front unit image-side lens component, on the object side thereof. Or, it is preferable that the first predetermined lens component be a lens component positioned nearest to the front unit image-side lens component.

In the optical system for stereoscopic vision of the fourth embodiment, it is preferable that the following conditional expression (22) be satisfied:

$$0.3 < FLr'/TTLr < 2.0 \qquad (22)$$

where,

FLr' denotes a focal length of the rear unit, and

TTLr denotes a distance on the optical axis from an object-side surface of a lens disposed nearest to the object in the rear unit up to an image-side surface of a lens disposed nearest to the image in the rear unit.

In a case of exceeding an upper limit value of conditional expression (22), the focal length of the rear unit becomes excessively long with respect to the overall length of the rear unit. Consequently, it becomes difficult to achieve both of small-sizing of the optical system and securing a wide angle of view.

In a case of falling below a lower limit value of conditional expression (22), the focal length of the rear unit becomes excessively short with respect to the overall length of the rear unit. Consequently, it becomes difficult to achieve both of correction of an off-axis aberration and correction of a longitudinal aberration.

In the optical system for stereoscopic vision of the fourth embodiment, it is preferable that the rear unit include the rear unit object-side lens component, the rear unit object-side lens component be disposed nearest to the object, and the object-side surface thereof be a convex surface, and the following conditional expression (9') be satisfied:

$$-2.5 < (Rfra + Rrra)/(Rfra - Rrra) < -0.2 \qquad (9')$$

where,

Rfra denotes the radius of curvature of the object-side surface of the rear unit object-side lens component, and Rrra denotes the radius of curvature of the image-side surface of the rear unit object-side lens component.

In a case of exceeding an upper limit value of conditional expression (9'), it becomes difficult to secure adequately the positive refractive power which is necessary for the rear unit object-side lens component. For securing the positive refractive power adequately, the radius of curvature of the object-side surface has to be made small. However, when the radius of curvature of the object-side surface is made small, the coma and the spherical aberration of high order are susceptible to occur.

In a case of falling below a lower limit value of conditional expression (9'), the positive refractive power of the image-side surface becomes excessively large with respect to that of the object-side surface. In this case, correction of the spherical aberration and correction of the coma become difficult. Therefore, falling below the lower limit value of conditional expression (9') is not preferable.

In the optical system for stereoscopic vision of the fourth embodiment, it is preferable that the rear unit include the rear unit object-side lens component and the second predetermined lens component, the rear unit object-side lens component be disposed nearest to the object, and have a positive refractive power, the second predetermined lens component be disposed on the image side of the rear unit object-side lens component, and the following conditional expression (10') be satisfied:

$$0.02 < Lr1/TTL < 0.3 \qquad (10')$$

where,

Lr1 denotes the distance on the optical axis from the object-side surface of the rear unit object-side lens component up to the object-side surface of the second predetermined lens component, and TTL denotes the distance on the optical axis from the object-side surface of the lens disposed nearest to the object in the front unit up to the image plane.

In a case of exceeding an upper limit value of conditional expression (10'), the distance between the object-side surface of the rear unit object-side lens component and the object-side surface of the second predetermined lens component becomes excessively long. In this case, when the positive refractive power of the rear unit object-side lens component is not made large, since the height of the off-axis light ray becomes high, small-sizing of the optical system becomes difficult. However, when the positive refractive power of the rear unit object-side lens component is made large, the spherical aberration and the coma are susceptible to occur. Therefore, exceeding the upper limit value of conditional expression (10') is not preferable.

In a case of falling below a lower limit value of conditional expression (10'), it is not possible to secure adequately the thickness of the rear unit object-side lens component. Consequently, in the rear unit object-side lens component, it becomes difficult to secure the positive refractive power adequately. For small-sizing the optical system by making the height of the off-axis light ray small in such state, the refractive power of the second predetermined lens component has to be made large accordingly. However, when the refractive power of the second predetermined lens component is made large, the spherical aberration and the coma are susceptible to occur. Therefore, falling below the lower limit value of conditional expression (10') is not preferable.

It is preferable that the second predetermined lens component be disposed adjacent to the rear unit object-side lens component, on the image side thereof. In such manner, it is preferable that the second predetermined lens component be a lens component disposed adjacent to the rear unit object-side lens component, on the image side thereof. Or, it is preferable that the second predetermined lens component be a lens component positioned nearest to the rear unit object-side lens component.

In the optical system for stereoscopic vision of the present embodiment, it is preferable that the rear unit include the rear unit image-side lens component, the rear unit image-side lens component be disposed nearest to the image, and the following conditional expression (23) be satisfied:

$$-2.5<(Rfrb+Rrrb)/(Rfrb-Rrrb)<-0.1 \quad (23)$$

where,

Rfrb denotes a radius of curvature of an object-side surface of the rear unit image-side lens component, and Rrrb denotes a radius of curvature of an image-side surface of the rear unit image-side lens component.

In a case of exceeding an upper limit value of conditional expression (23), it becomes difficult to secure adequately a positive refractive power which is necessary for the rear unit image-side lens component. For securing the positive refractive power adequately, the radius of curvature of the object-side surface has to be made small. However, when the radius of curvature of the object-side surface is made small, the coma of high order is susceptible to occur.

In a case of falling below a lower limit value of conditional expression (23), the positive refractive power of the image-side surface become excessively large with respect to that of the object-side surface. In this case, correction of the coma becomes difficult. Therefore, falling below the lower limit value of conditional expression (23) is not preferable.

In the optical system for stereoscopic vision of the fourth embodiment, it is preferable that the focusing lens component be disposed nearest to the image in the front unit.

By making such arrangement, it is possible to suppress an occurrence of an off-axis aberration such as the curvature of field, the astigmatism, and the distortion.

In the optical system for stereoscopic vision of the fourth embodiment, it is preferable that the following conditional expression (13') be satisfied:

$$-2.0<FLfocus/TTL<2.0 \quad (13')$$

where,

FLfocus denotes the focal length of the focusing lens component, and

TTL denotes the distance on the optical axis from the object-side surface of the lens disposed nearest to the object in the front unit up to the image plane.

In a case of exceeding an upper limit value of conditional expression (13'), a fluctuation in the spherical aberration and a fluctuation in the coma become large according to the focusing position. Therefore, exceeding the upper limit value of conditional expression (13') is not preferable.

In a case of falling below a lower limit value of conditional expression (13'), a height of a light ray of an off-axis light beam incident on the rear unit becomes excessively high. Consequently, small-sizing of the optical system becomes difficult.

In the optical system for stereoscopic vision of the fourth embodiment, it is preferable that the second front unit include a focusing lens component, and the focusing lens component in the first front unit and the focusing lens component in the second front unit move together.

By making such arrangement, it is possible to carry out focusing expeditiously.

In the optical system for stereoscopic vision of the fourth embodiment, it is preferable that the second front unit includes the focusing lens component, and the focusing lens component in the first front unit and the focusing lens component in the second front unit are integrated.

When such arrangement is made, in a case in which the two focusing lens components are moved, both an amount of movement of the focusing lens component in the first front unit with respect to the rear unit and an amount of movement of the focusing lens component in the second front unit with respect to the rear unit become same. Consequently, it is possible to suppress an occurrence of a focal shift due to a positional error of the focusing lens component of the first front unit and a positional error of the focusing lens component of the second front unit.

Moreover, it is possible to hold the focusing lens component of the first front unit and the focusing lens component of the second front unit by one frame. Consequently, it is possible to simplify a moving mechanism.

Preferable arrangements and conditional expressions to be satisfied for the optical system for stereoscopic vision of the present embodiment have been described heretofore. Since the description for the first front unit is also applicable to the second front unit, in the description made above, description of the second front unit has been omitted. By substituting the first front unit with the second front unit in the description made by using the first front unit, it is possible to understand preferable arrangements, conditional expressions to be satisfied, and technical significance for the second front unit.

Regarding conditional expressions for the first front unit, it is preferable that the second front unit also satisfy the conditional expressions. For each conditional expression, numerical values for the first front unit and numerical values for the second front unit are achieved. Both the numerical values have to be within a range from a lower limit value up to an upper limit value. Accordingly, the two numerical values may not be same.

In the optical system for stereoscopic vision of the first embodiment to the optical system for stereoscopic vision for the fourth embodiment (hereinafter, referred to as 'optical system for stereoscopic vision of the present embodiment'), it is preferable that the first front unit and the second front unit be same optical systems.

By making such arrangement, it is possible to make small a difference in a magnification of the first optical system and a magnification of the second optical system and a difference in a focal position of the first optical system and a focal position of the second optical system. As a result, it is possible to make small a difference in a size of the first optical image and a size of the second optical image.

By capturing the first optical image and the second optical image by an imager, two images are acquired. In stereoscopic vision, one of the two images is used as an image for a right eye and the other image is used as an image for a left eye.

When the difference between the size of the first optical image and the size of the second optical image is small, a difference in a size of the image for the right eye and a size of the image for the left eye also becomes small. Consequently, even when the two images are overlapped, it is possible to carry out stereoscopic vision without an uncomfortable feeling.

In the optical system for stereoscopic vision of the present embodiment, it is preferable that a light-beam selector be disposed on the object side of the rear unit, and the light beam selector shield one of a light beam that passes through the first front unit and a light beam that passes through the second front unit.

By making such arrangement, it is possible to capture the first optical image and the second optical image separately.

In the optical system for stereoscopic vision of the present embodiment, it is preferable that each of the first front unit and the second front unit include an aperture stop, the light-beam selector includes a light shielding portion, at a first position, the light shielding portion is positioned in an optical path of the first front unit, and at a second position, the light shielding portion is positioned in an optical path of the second front unit.

By making such arrangement, it is possible to capture the first optical image and the second optical image separately.

In movement of the light shielding portion to the first position or movement of the light shielding portion the second position, the light shielding portion may be rotated around an optical axis of the rear unit. Or, the light shielding portion may be moved in a plane orthogonal to the optical axis of the rear unit.

In the optical system for stereoscopic vision of the present embodiment, it is preferable that the light beam selector include the light shielding portion and an opening, at the first position, the light shielding portion be positioned in the optical path of the first front unit and the opening be positioned in the optical path of the second front unit, and at the second position, the light shielding portion be positioned in the optical path of the second front unit, and the opening be positioned in the optical path of the first front unit.

By making such arrangement, it is possible to capture the first optical image and the second optical image separately.

In movement of the light shielding portion to the first position or movement of the light shielding portion to the second position, the light shielding portion may be rotated around the optical axis of the rear unit. The opening is disposed such that the opening faces the light shielding portion across the optical axis of the rear unit, in a plane orthogonal to the optical axis of the rear unit. Therefore, it is possible to position the light shielding portion in one of the optical paths of the first front unit and the optical path of the second front unit, and to position the opening in the other optical path.

In the optical system for stereoscopic vision of the present embodiment, it is preferable that the light beam selector include a first polarizing element, a second polarizing element, and a third polarizing element, the first polarizing element be disposed in the optical path of the first front unit and be positioned on the object side of the third polarizing element, the second polarizing element be disposed in the optical path of the second front unit and be positioned on the object side of the third polarizing element, a direction of polarization of the first polarizing element and a direction of polarization of the second polarizing element be orthogonal, and a direction of polarization of the third polarizing element coincide with the direction of polarization of the first polarizing element or coincide with the direction of polarization of the second polarizing element.

By making such arrangement, it is possible to capture the first optical image and the second optical image separately.

In change of the direction of polarization of the third polarizing element, the third polarizing element may be rotated around the optical axis of the rear unit.

In the optical system for stereoscopic vision of the present embodiment, it is preferable that the light beam selector include a liquid crystal panel.

In this case, as the third polarizing element, it is possible to use a liquid-crystal polarization rotator, for example. In the liquid-crystal polarization rotator, it is possible to change a direction of polarization of light which passes through the liquid-crystal polarization rotator electrically by 90°. As a result, it is possible to switch between a state of light from the first polarizing element being transmitted and a state of light from the second polarizing element being transmitted. In such manner, it becomes unnecessary to rotate the third polarizing element mechanically.

By making such arrangement, it is possible to capture the first optical image and the second optical image separately.

It is possible to dispose one liquid crystal panel in each of the optical path of the first front unit and the optical path of the second front unit. In this case, it is possible to let a position of the liquid crystal panel to be different in each of the first front unit and the second front unit. In a case in which an arrangement of the optical system of the first front unit and an arrangement of the optical system of the second front unit are different, it is possible to dispose the liquid crystal panel easily.

Moreover, one liquid crystal panel may be disposed in the optical path of the first front unit and the optical path of the second front unit. In this case, it is possible to let the position of the liquid crystal panel to be same in each of the first front unit and the second front unit. In a case in which an arrangement of the optical system of the first front unit and an arrangement of the optical system of the second front unit are same, it is possible to dispose the liquid crystal panel easily.

In the optical system for stereoscopic vision of the present embodiment, it is preferable that movement of the focusing lens component of the first front unit and movement of the focusing lens component of the second front unit be achieved separately.

It is preferable that the optical system for stereoscopic vision of the present embodiment include an optical filter, and the optical filter has a characteristic which transmits ultraviolet light, infrared light, or visible light.

By making such arrangement, it is possible to capture an optical image formed by various wavelengths.

From an optical image formed by the ultraviolet light, it is possible to acquire an ultraviolet light image. From an optical image formed by the infrared light, it is possible to acquire an infrared light image. From an optical image formed by the visible light, it is possible to acquire a visible light image.

As a result, it is possible to carry out stereoscopic vision using the ultraviolet light image, stereoscopic vision using the infrared light image, or stereoscopic vision using the visible light image. Moreover, images may be combined by using at least two of the ultraviolet light image, the infrared light image, and the visible light image. By making such arrangement, it is possible to carry out stereoscopic vision in a wide wavelength region.

An image pickup apparatus of the present embodiment includes an optical system, and an imager which has an image pickup surface, and which converts an image formed on the image pickup surface by the optical system to an electric signal, wherein the optical system is the abovementioned optical system for stereoscopic vision.

According to the image pickup apparatus of the present embodiment, it is possible to acquire an image in which an appropriate stereoscopic effect can be achieved when an object is viewed stereoscopically, while the image pickup apparatus being small-sized. As a result, it is possible to carry out stereoscopic vision with less fatigue.

For each conditional expression, the upper limit value or the lower limit value may be changed as shown below. By doing so, since it is possible to have an effect of each conditional expression more assuredly, it is preferable to change the values as shown below.

For conditional expression (1), it is preferable to make the lower limit value 0.20 or 0.25, and it is preferable to make the upper limit value 0.80 or 0.70.

For conditional expression (2), it is preferable to make the lower limit value 0.40 or 0.45, and it is preferable to make the upper limit value 1.50 or 1.00.

For conditional expression (3), it is preferable to make the lower limit value 8.00 or 10.00, and it is preferable to make the upper limit value 70.00 or 50.00.

For conditional expression (4), it is preferable to make the lower limit value −0.50 or −0.45, and it is preferable to make the upper limit value −0.25 or −0.30.

For conditional expression (5), it is preferable to make the lower limit value 0.4 or 0.5, and it is preferable to make the upper limit value 1.00 or 0.85.

For conditional expression (6), it is preferable to make the lower limit value −0.50 or −0.48, and it is preferable to make the upper limit value −0.30 or −0.35.

For conditional expression (7), it is preferable to make the lower limit value 0.70 or 0.80, and it is preferable to make the upper limit value 8.00 or 6.70.

For conditional expression (8), it is preferable to make the lower limit value 0.25 or 0.30, and it is preferable to make the upper limit value 0.60 or 0.50.

For conditional expression (9), it is preferable to make the lower limit value −3.00 or −2.50, and it is preferable to make the upper limit value 0.35 or 0.30.

For conditional expression (10), it is preferable to make the lower limit value 0.03 or 0.04, and it is preferable to make the upper limit value 0.15 or 0.10.

For conditional expression (11), it is preferable to make the lower limit value 0.15 or 0.20, and it is preferable to make the upper limit value 0.88 or 0.86.

For conditional expression (12), it is preferable to make the lower limit value 0.75 or 0.80, and it is preferable to make the upper limit value 1.00.

For conditional expression (13), it is preferable to make the lower limit value 0.25 or 0.30, and it is preferable to make the upper limit value 3.00 or 1.80.

For conditional expression (14), it is preferable to make the lower limit value 0.20 or 0.30, and it is preferable to make the upper limit value 4.00 or 3.00.

For conditional expression (15), it is preferable to make the lower limit value 0.20 or 0.25, and it is preferable to make the upper limit value 3.00 or 2.00.

For conditional expression (16), it is preferable to make the lower limit value 3.50 or 4.00, and it is preferable to make the upper limit value 50.00 or 35.00.

For conditional expression (17), it is preferable to make the lower limit value −0.25 or −0.20, and it is preferable to make the upper limit value −0.06 or −0.08.

For conditional expression (18), it is preferable to make the lower limit value 0.15 or 0.18, and it is preferable to make the upper limit value 0.35 or 0.30.

For conditional expression (19), it is preferable to make the lower limit value −0.45 or −0.40, and it is preferable to make the upper limit value −0.12 or −0.15.

For conditional expression (20), it is preferable to make the lower limit value −1.50 or −1.40, and it is preferable to make the upper limit value 1.50 or 1.20.

For conditional expression (21), it is preferable to make the lower limit value 0.70 or 1.00, and it is preferable to make the upper limit value 1.50 or 1.30.

For conditional expression (22), it is preferable to make the lower limit value 0.50 or 0.70, and it is preferable to make the upper limit value 1.50 or 1.10.

For conditional expression (9'), it is preferable to make the lower limit value −2.00 or −1.70, and it is preferable to make the upper limit value −0.50 or −0.80.

For conditional expression (10'), it is preferable to make the lower limit value 0.04 or 0.05, and it is preferable to make the upper limit value 0.25 or 0.20.

For conditional expression (23), it is preferable to make the lower limit value −2.00 or −1.80, and it is preferable to make the upper limit value −0.13 or −0.15.

For conditional expression (13'), it is preferable to make the lower limit value −1.50 or −1.30, and it is preferable to make the upper limit value 1.50 or 1.20.

Examples of optical systems for stereoscopic vision will be described below in detail by referring to the accompanying diagrams. However, the present disclosure is not restricted to the examples described below.

Lens cross-sectional diagrams of examples will be described below. FIG. 3, FIG. 4, FIG. 5, FIG. 6, FIG. 7, FIG. 8, FIG. 9, FIG. 10, FIG. 11, FIG. 12, FIG. 13, FIG. 14, FIG. 15, and FIG. 16 are lens cross-sectional diagrams at the time of focusing to a far point. In each example, the first front unit and the second front unit are same.

Aberration diagrams of the examples will be described below.

FIG. 17A, FIG. 18A, FIG. 19A, FIG. 20A, FIG. 21A, FIG. 22A, FIG. 23A, FIG. 24A, FIG. 25A, FIG. 26A, FIG. 27A, FIG. 28A, FIG. 29A, FIG. 30A, FIG. 31A, FIG. 32A, FIG. 33A, FIG. 34A, FIG. 35A, FIG. 36A, FIG. 37A, FIG. 38A, FIG. 39A, FIG. 40A, FIG. 41A, FIG. 42A, FIG. 43A, FIG. 44A, FIG. 45A, FIG. 46A, FIG. 47A, FIG. 48A, FIG. 49A, FIG. 50A, FIG. 51A, FIG. 52A, FIG. 53A, FIG. 54A,

FIG. 55A, FIG. 56A, FIG. 57A, FIG. 58A, FIG. 59A, FIG. 60A, FIG. 61A, FIG. 62A, FIG. 63A, FIG. 64A, FIG. 65A, FIG. 66A, FIG. 67A, FIG. 68A, FIG. 69A, FIG. 70A, FIG. 71A, and FIG. 72A show astigmatism.

FIG. 17B, FIG. 18B, FIG. 19B, FIG. 20B, FIG. 21B, FIG. 22B, FIG. 23B, FIG. 24B, FIG. 25B, FIG. 26B, FIG. 27B, FIG. 28B, FIG. 29B, FIG. 30B, FIG. 31B, FIG. 32B, FIG. 33B, FIG. 34B, FIG. 35B, FIG. 36B, FIG. 37B, FIG. 38B, FIG. 39B, FIG. 40B, FIG. 41B, FIG. 42B, FIG. 43B, FIG. 44B, FIG. 45B, FIG. 46B, FIG. 47B, FIG. 48B, FIG. 49B, FIG. 50B, FIG. 51B, FIG. 52B, FIG. 53B, FIG. 54B, FIG. 55B, FIG. 56B, FIG. 57B, FIG. 58B, FIG. 59B, FIG. 60B, FIG. 61B, FIG. 62B, FIG. 63B, FIG. 64B, FIG. 65B, FIG. 66B, FIG. 67B, FIG. 68B, FIG. 69B, FIG. 70B, FIG. 71B, and FIG. 72B show a distortion.

FIG. 17C, FIG. 17D, FIG. 17E, FIG. 17F, FIG. 17G, FIG. 17H, FIG. 17I, FIG. 17J, FIG. 18C, FIG. 18D, FIG. 18E, FIG. 18F, FIG. 18G, FIG. 18H, FIG. 18I, FIG. 18J, FIG. 19C, FIG. 19D, FIG. 19E, FIG. 19F, FIG. 19G, FIG. 19H, FIG. 19I, and FIG. 19J show a transverse aberration.

FIG. 20C, FIG. 20D, FIG. 20E, FIG. 20F, FIG. 20G, FIG. 20H, FIG. 20I, FIG. 20J, FIG. 21C, FIG. 21D, FIG. 21E, FIG. 21F, FIG. 21G, FIG. 21H, FIG. 21I, FIG. 21J, FIG. 22C, FIG. 22D, FIG. 22E, FIG. 22F, FIG. 22G, FIG. 22H, FIG. 22I, FIG. 22J, FIG. 23C, FIG. 23D, FIG. 23E, FIG. 23F, FIG. 23G, FIG. 23H, FIG. 23I, FIG. 23J, FIG. 24C, FIG. 24D, FIG. 24E, FIG. 24F, FIG. 24G, FIG. 24H, FIG. 24I, FIG. 24J, FIG. 25C, FIG. 25D, FIG. 25E, FIG. 25F, FIG. 25G, FIG. 25H, FIG. 25I, FIG. 25J, FIG. 26C, FIG. 26D, FIG. 26E, FIG. 26F, FIG. 26G, FIG. 26H, FIG. 26I, FIG. 26J, FIG. 27C, FIG. 27D, FIG. 27E, FIG. 27F, FIG. 27G, FIG. 27H, FIG. 27I, FIG. 27J, FIG. 28C, FIG. 28D, FIG. 28E, FIG. 28F, FIG. 28G, FIG. 28H, FIG. 28I, FIG. 28J, FIG. 29C, FIG. 29D, FIG. 29E, FIG. 29F, FIG. 29G, FIG. 29H, FIG. 29I, and FIG. 29J show the transverse aberration.

FIG. 30C, FIG. 30D, FIG. 30E, FIG. 30F, FIG. 30G, FIG. 30H, FIG. 30I, FIG. 30J, FIG. 31C, FIG. 31D, FIG. 31E, FIG. 31F, FIG. 31G, FIG. 31H, FIG. 31I, FIG. 31J, FIG. 32C, FIG. 32D, FIG. 32E, FIG. 32F, FIG. 32G, FIG. 32H, FIG. 32I, FIG. 32J, FIG. 33C, FIG. 33D, FIG. 33E, FIG. 33F, FIG. 33G, FIG. 33H, FIG. 33I, FIG. 33J, FIG. 34C, FIG. 34D, FIG. 34E, FIG. 34F, FIG. 34G, FIG. 34H, FIG. 34I, FIG. 34J, FIG. 35C, FIG. 35D, FIG. 35E, FIG. 35F, FIG. 35G, FIG. 35H, FIG. 35I, FIG. 35J, FIG. 36C, FIG. 36D, FIG. 36E, FIG. 36F, FIG. 36G, FIG. 36H, FIG. 36I, FIG. 36J, FIG. 37C, FIG. 37D, FIG. 37E, FIG. 37F, FIG. 37G, FIG. 37H, FIG. 37I, FIG. 37J, FIG. 38C, FIG. 38D, FIG. 38E, FIG. 38F, FIG. 38G, FIG. 38H, FIG. 38I, FIG. 38J, FIG. 39C, FIG. 39D, FIG. 39E, FIG. 39F, FIG. 39G, FIG. 39H, FIG. 39I, and FIG. 39J show the transverse aberration.

FIG. 40C, FIG. 40D, FIG. 40E, FIG. 40F, FIG. 40G, FIG. 40H, FIG. 40I, FIG. 40J, FIG. 41C, FIG. 41D, FIG. 41E, FIG. 41F, FIG. 41G, FIG. 41H, FIG. 41I, FIG. 41J, FIG. 42C, FIG. 42D, FIG. 42E, FIG. 42F, FIG. 42G, FIG. 42H, FIG. 42I, FIG. 42J, FIG. 43C, FIG. 43D, FIG. 43E, FIG. 43F, FIG. 43G, FIG. 43H, FIG. 43I, FIG. 43J, FIG. 44C, FIG. 44D, FIG. 44E, FIG. 44F, FIG. 44G, FIG. 44H, FIG. 44I, FIG. 44J, FIG. 45C, FIG. 45D, FIG. 45E, FIG. 45F, FIG. 45G, FIG. 45H, FIG. 45I, FIG. 45J, FIG. 46C, FIG. 46D, FIG. 46E, FIG. 46F, FIG. 46G, FIG. 46H, FIG. 46I, FIG. 46J, FIG. 47C, FIG. 47D, FIG. 47E, FIG. 47F, FIG. 47G, FIG. 47H, FIG. 47I, FIG. 47J, FIG. 48C, FIG. 48D, FIG. 48E, FIG. 48F, FIG. 48G, FIG. 48H, FIG. 48I, FIG. 48J, FIG. 49C, FIG. 49D, FIG. 49E, FIG. 49F, FIG. 49G, FIG. 49H, FIG. 49I, and FIG. 49J show the transverse aberration.

FIG. 50C, FIG. 50D, FIG. 50E, FIG. 50F, FIG. 50G, FIG. 50H, FIG. 50I, FIG. 50J, FIG. 51C, FIG. 51D, FIG. 51E, FIG. 51F, FIG. 51G, FIG. 51H, FIG. 51I, FIG. 51J, FIG. 52C, FIG. 52D, FIG. 52E, FIG. 52F, FIG. 52G, FIG. 52H, FIG. 52I, FIG. 52J, FIG. 53C, FIG. 53D, FIG. 53E, FIG. 53F, FIG. 53G, FIG. 53H, FIG. 53I, FIG. 53J, FIG. 54C, FIG. 54D, FIG. 54E, FIG. 54F, FIG. 54G, FIG. 54H, FIG. 54I, FIG. 54J, FIG. 55C, FIG. 55D, FIG. 55E, FIG. 55F, FIG. 55G, FIG. 55H, FIG. 55I, FIG. 55J, FIG. 56C, FIG. 56D, FIG. 56E, FIG. 56F, FIG. 56G, FIG. 56H, FIG. 56I, FIG. 56J, FIG. 57C, FIG. 57D, FIG. 57E, FIG. 57F, FIG. 57G, FIG. 57H, FIG. 57I, FIG. 57J, FIG. 58C, FIG. 58D, FIG. 58E, FIG. 58F, FIG. 58G, FIG. 58H, FIG. 58I, FIG. 58J, FIG. 59C, FIG. 59D, FIG. 59E, FIG. 59F, FIG. 59G, FIG. 59H, FIG. 59I, and FIG. 59J show the transverse aberration.

FIG. 60C, FIG. 60D, FIG. 60E, FIG. 60F, FIG. 60G, FIG. 60H, FIG. 60I, FIG. 60J, FIG. 61C, FIG. 61D, FIG. 61E, FIG. 61F, FIG. 61G, FIG. 61H, FIG. 61I, FIG. 61J, FIG. 62C, FIG. 62D, FIG. 62E, FIG. 62F, FIG. 62G, FIG. 62H, FIG. 62I, FIG. 62J, FIG. 63C, FIG. 63D, FIG. 63E, FIG. 63F, FIG. 63G, FIG. 63H, FIG. 63I, FIG. 63J, FIG. 64C, FIG. 64D, FIG. 64E, FIG. 64F, FIG. 64G, FIG. 64H, FIG. 64I, FIG. 64J, FIG. 65C, FIG. 65D, FIG. 65E, FIG. 65F, FIG. 65G, FIG. 65H, FIG. 65I, FIG. 65J, FIG. 66C, FIG. 66D, FIG. 66E, FIG. 66F, FIG. 66G, FIG. 66H, FIG. 66I, FIG. 66J, FIG. 67C, FIG. 67D, FIG. 67E, FIG. 67F, FIG. 67G, FIG. 67H, FIG. 67I, FIG. 67J, FIG. 68C, FIG. 68D, FIG. 68E, FIG. 68F, FIG. 68G, FIG. 68H, FIG. 68I, FIG. 68J, FIG. 69C, FIG. 69D, FIG. 69E, FIG. 69F, FIG. 69G, FIG. 69H, FIG. 69I, and FIG. 69J show the transverse aberration.

FIG. 70C, FIG. 70D, FIG. 70E, FIG. 70F, FIG. 70G, FIG. 70H, FIG. 70I, FIG. 70J, FIG. 71C, FIG. 71D, FIG. 71E, FIG. 71F, FIG. 71G, FIG. 71H, FIG. 71I, FIG. 71J, FIG. 72C, FIG. 72D, FIG. 72E, FIG. 72F, FIG. 72G, FIG. 72H, FIG. 72I, and FIG. 72J show the transverse aberration.

FIY is an image height.

In examples 1 to 14, for one example, there are two types of aberration diagrams at the time of focusing to a far point and two types of aberration diagrams at the time of focusing to a near point. In the example 1, FIG. 17A to FIG. 17J are aberration diagrams at the time of focusing to a far point of a first optical system, FIG. 18A to FIG. 18J are aberration diagrams at the time of focusing to a far point of a second optical system, FIG. 19A to FIG. 19J are aberration diagrams at the time of focusing to a near point of the first optical system, and FIG. 20A to FIG. 20J are aberration diagrams at the time of focusing to a near point of the second optical system.

In the transverse aberration, the maximum value of the horizontal axis is ±20 μm. A vertical axis is normalized by an entrance-pupil diameter. Ta denotes a tangential direction and Sa denotes a sagittal direction. IH0 denotes an axial, IH0.5 denotes 0.5 times of the maximum image height, IH0.7 denotes 0.7 times of the maximum image height, and IH1.0 denotes 1.0 times of the maximum image height.

An optical system for stereoscopic vision of the example 1 includes in order from an object side, a front unit GF and a rear unit GR. The front unit GF includes a first front unit GF1 and a second front unit GF2. An aperture stop (a stop) S is disposed between the front unit GF and the rear unit GR.

The first front unit GF1 includes a planoconcave negative lens L1, a biconvex positive lens L2, a negative meniscus lens L3 having a convex surface directed toward an image side, a biconcave negative lens L4, and a biconvex positive lens L5. Here, the biconvex positive lens L2 and the negative meniscus lens L3 are cemented. The biconcave negative lens L4 and the biconvex positive lens L5 are cemented.

The rear unit GR includes a biconvex positive lens L6, a biconvex positive lens L7, a biconcave negative lens L8, a biconcave negative lens L9, a negative meniscus lens L10 having a convex surface directed toward the object side, a biconvex positive lens L11, and a biconvex positive lens L12. Here, the biconvex positive lens L7 and the biconcave negative lens L8 are cemented. The negative meniscus lens L10 and the biconvex positive lens L11 are cemented.

A cover glass C1 is disposed on the object side of the planoconcave negative lens L1. A cover glass C2 and a cover glass C3 are disposed on the image side of the biconvex positive lens L12.

At a time of focusing, the biconvex positive lens L12 moves. More elaborately, at the time of focusing from a far point to a near point, the biconvex positive lens L12 moves toward the object side.

An aspheric surface is provided to a total of five surfaces which are an image-side surface of the planoconcave negative lens L1, an object-side surface of the biconvex positive lens L6, an image-side surface of the biconcave negative lens L9, and both surfaces of the biconvex positive lens L12.

An optical system for stereoscopic vision of the example 2 includes in order from an object side, a front unit GF and a rear unit GR. The front unit GF includes a first front unit GF1 and a second front unit GF2. An aperture stop (a stop) S is disposed between the front unit GF and the rear unit GR.

The first front unit GF1 includes a planoconcave negative lens L1, a biconvex positive lens L2, a negative meniscus lens L3 having a convex surface directed toward an image side, a biconcave negative lens L4, and a biconvex positive lens L5. Here, the biconvex positive lens L2 and the negative meniscus lens L3 are cemented. The biconcave negative lens L4 and the biconvex positive lens L5 are cemented.

The rear unit GR includes a biconvex positive lens L6, a biconvex positive lens L7, a biconcave negative lens L8, a biconcave negative lens L9, a biconvex positive lens L10, and a biconvex positive lens L11. Here, the biconvex positive lens L7 and the biconcave negative lens L8 are cemented.

A cover glass C1 is disposed on the object side of the planoconcave negative lens L1. A cover glass C2 and a cover glass C3 are disposed on the image side of the biconvex positive lens L11.

At a time of focusing, the biconvex positive lens L11 moves. More elaborately, at the time of focusing from a far point to a near point, the biconvex positive lens L11 moves toward the object side.

An aspheric surface is provided to a total of four surfaces which are an image-side surface of the planoconcave negative lens L1, an object-side surface of the biconvex positive lens L6, and both surfaces of the biconvex positive lens L11.

An optical system for stereoscopic vision of the example 3 includes in order from an object side, a front unit GF and a rear unit GR. The front unit GF includes a first front unit GF1 and a second front unit GF2. An aperture stop (a stop) S is disposed between the front unit GF and the rear unit GR.

The first front unit GF1 includes a planoconcave negative lens L1, a biconvex positive lens L2, a negative meniscus lens L3 having a convex surface directed toward an image side, a biconcave negative lens L4, and a biconvex positive lens L5. Here, the biconvex positive lens L2 and the negative meniscus lens L3 are cemented. The biconcave negative lens L4 and the biconvex positive lens L5 are cemented.

The rear unit GR includes a positive meniscus lens L6 having a convex surface directed toward the object side, a positive meniscus lens L7 having a convex surface directed toward the object side, a negative meniscus lens L8 having a convex surface directed toward the object side, a positive meniscus lens L9 having a convex surface directed toward the object side, a biconcave negative lens L10, and a biconvex positive lens L11. Here, the positive meniscus lens L7 and the negative meniscus lens L8 are cemented.

A cover glass C1 is disposed on the object side of the planoconcave negative lens L1. A cover glass C2 and a cover glass C3 are disposed on the image side of the biconvex positive lens L11.

At a time of focusing, the biconvex positive lens L11 moves. More elaborately, at the time of focusing from a far point to a near point, the biconvex positive lens L11 moves toward the object side.

An aspheric surface is provided to a total of three surfaces which are an image-side surface of the planoconcave negative lens L1, an object-side surface of the positive meniscus lens L6, and an object-side surface of the biconvex positive lens L11.

An optical system for stereoscopic vision of the example 4 includes in order from an object side, a front unit GF and a rear unit GR. The front unit GF includes a first front unit GF1 and a second front unit GF2. An aperture stop (a stop) S is disposed between the front unit GF and the rear unit GR.

The first front unit GF1 includes a planoconcave negative lens L1, a biconcave negative lens L2, a biconvex positive lens L3, a negative meniscus lens L4 having a convex surface directed toward the object side, and a biconvex positive lens L5. Here, the biconcave negative lens L2 and the biconvex positive lens L3 are cemented. The negative meniscus lens L4 and the biconvex positive lens L5 are cemented.

The rear unit GR includes a positive meniscus lens L6 having a convex surface directed toward the object side, a positive meniscus lens L7 having a convex surface directed toward the object side, a negative meniscus lens L8 having a convex surface directed toward the object side, a biconvex positive lens L9, a biconvex positive lens L10, and a biconvex positive lens L11. Here, the positive meniscus lens L7 and the negative meniscus lens L8 are cemented.

No cover glass is disposed on the object side of the planoconcave negative lens L1. A cover glass C1 and a cover glass C2 are disposed on the image side of the biconvex positive lens L11.

At a time of focusing, the biconvex positive lens L11 moves. More elaborately, at the time of focusing from a far point to a near point, the biconvex positive lens L11 moves toward the object side.

An aspheric surface is provided to a total of two surfaces which are an image-side surface of the planoconcave negative lens L1 and an object-side surface of the positive meniscus lens L6.

An optical system for stereoscopic vision of the example 5 includes in order from an object side, a front unit GF and a rear unit GR. The front unit GF includes a first front unit GF1 and a second front unit GF2. An aperture stop (a stop) S is disposed between the front unit GF and the rear unit GR.

The first front unit GF1 includes a planoconcave negative lens L1, a biconcave negative lens L2, a biconvex positive lens L3, a negative meniscus lens L4 having a convex surface directed toward the object side, and a biconvex positive lens L5. Here, the biconcave negative lens L2 and the biconvex positive lens L3 are cemented. The negative meniscus lens L4 and the biconvex positive lens L5 are cemented.

The rear unit GR includes a positive meniscus lens L6 having a convex surface directed toward the object side, a positive meniscus lens L7 having a convex surface directed toward the object side, a negative meniscus lens L8 having a convex surface directed toward the object side, a negative meniscus lens L9 having a convex surface directed toward the object side, a biconvex positive lens L10, a positive meniscus lens L11 having a convex surface directed toward the object side, and a positive meniscus lens L12 having a convex surface directed toward the object side. Here, the negative meniscus lens L8 and the negative meniscus lens L9 are cemented.

No cover glass is disposed on the object side of the planoconcave negative lens L1. A cover glass C1 and a cover glass C2 are disposed on the image side of the positive meniscus lens L12.

At a time of focusing, the positive meniscus lens L6 moves. More elaborately, at the time of focusing from a far point to a near point, the positive meniscus lens L6 moves toward the object side.

An aspheric surface is provided to a total of three surfaces which are an image-side surface of the planoconcave negative lens L1, an object-side surface of the positive meniscus lens L6, and an object-side surface of the positive meniscus lens L12.

An optical system for stereoscopic vision of the example 6 includes in order from an object side, a front unit GF and a rear unit GR. The front unit GF includes a first front unit GF1 and a second front unit GF2. An aperture stop (a stop) S is disposed between the front unit GF and the rear unit GR.

The first front unit GF1 includes a planoconcave negative lens L1, a biconvex positive lens L2, a negative meniscus lens L3 having a convex surface directed toward an image side, a biconcave negative lens L4, and a biconvex positive lens L5. Here, the biconvex positive lens L2 and the negative meniscus lens L3 are cemented. The biconcave negative lens L4 and the biconvex positive lens L5 are cemented.

The rear unit GR includes a positive meniscus lens L6 having a convex surface directed toward the object side, a positive meniscus lens L7 having a convex surface directed toward the object side, a negative meniscus lens L8 having a convex surface directed toward the object side, a biconvex positive lens L9, a biconcave negative lens L10, and a biconvex positive lens L11. Here, the positive meniscus lens L7 and the negative meniscus lens L8 are cemented.

A cover glass C1 is disposed on the object side of the planoconcave negative lens L1. A cover glass C2 and a cover glass C3 are disposed on the image side of the biconvex positive lens L11.

At a time of focusing, the biconcave negative lens L10 moves. More elaborately, at the time of focusing from a far point to a near point, the biconcave negative lens L10 moves toward the image side.

An aspheric surface is provided to a total of three surfaces which are an image-side surface of the planoconcave negative lens L1, an object-side surface of the positive meniscus lens L6, and an object-side surface of the biconvex positive lens L11.

In the optical system for stereoscopic vision of the example 6, a shutter SH is disposed between a front unit GF and a rear unit GR. The shutter SH is the light beam selector. The shutter SH is disposed near an aperture stop S.

The shutter SH shields one of a light beam passing through a first front unit GF1 and a light beam passing through a second front unit GF2. By making such arrangement, it is possible to capture a first optical image and a second optical image separately.

An optical system for stereoscopic vision of the example 7 includes in order from an object side, a front unit GF and a rear unit GR. The front unit GF includes a first front unit GF1 and a second front unit GF2. An aperture stop (a stop) S is disposed between the front unit GF and the rear unit GR.

The first front unit GF1 includes a planoconcave negative lens L1, a biconvex positive lens L2, a negative meniscus lens L3 having a convex surface directed toward an image side, a negative meniscus lens L4 having a convex surface directed toward the object side, and a biconvex positive lens L5. Here, the biconvex positive lens L2 and the negative meniscus lens L3 are cemented. The negative meniscus lens L4 and the biconvex positive lens L5 are cemented.

The rear unit GR includes a biconvex positive lens L6, a biconvex positive lens L7, a biconcave negative lens L8, a negative meniscus lens L9 having a convex surface directed toward the object side, a positive meniscus lens L10 having a convex surface directed toward the image side, and a biconvex positive lens L11. Here, the biconvex positive lens L7 and the biconcave negative lens L8 are cemented.

A cover glass C1 is disposed on the object side of the planoconcave negative lens L1. A cover glass C2 and a cover glass C3 are disposed on the image side of the biconvex positive lens L11.

At a time of focusing, the biconvex positive lens L7 and the biconcave negative lens L8 move. More elaborately, at the time of focusing from a far point to a near point, the biconvex positive lens L7 and the biconcave negative lens L8 move toward the object side.

An aspheric surface is provided to a total of three surfaces which are an image-side surface of the planoconcave negative lens L1, an object-side surface of the biconvex positive lens L6, and an object-side surface of the biconvex positive lens L11.

An optical system for stereoscopic vision of the example 8 includes in order from an object side, a front unit GF and a rear unit GR. The front unit GF includes a first front unit GF1 and a second front unit GF2. An aperture stop (a stop) S is disposed between the front unit GF and the rear unit GR.

The first front unit GF1 includes a planoconcave negative lens L1, a biconvex positive lens L2, a negative meniscus lens L3 having a convex surface directed toward an image side, a biconcave negative lens L4, and a biconvex positive lens L5. Here, the biconvex positive lens L2 and the negative meniscus lens L3 are cemented. The biconcave negative lens L4 and the biconvex positive lens L5 are cemented.

The rear unit GR includes a biconvex positive lens L6, a biconvex positive lens L7, a biconcave negative lens L8, a biconcave negative lens L9, a negative meniscus lens L10 having a convex surface directed toward the object side, a biconvex positive lens L11, and a biconvex positive lens L12. Here, the biconvex positive lens L7 and the biconcave negative lens L8 are cemented. The negative meniscus lens L10 and the biconvex positive lens L11 are cemented.

A cover glass C1 is disposed on the object-side of the planoconcave negative lens L1. A cover glass C2 and a cover glass C3 are disposed on the image side of the biconvex positive lens L12.

At a time of focusing, the negative meniscus lens L10 and the biconvex positive lens L11 move. More elaborately, at the time of focusing from a far point to a near point, the negative meniscus lens L10 and the biconvex positive lens L11 move toward the object side.

An aspheric surface is provided to a total of five surfaces which are an image-side surface of the planoconcave negative lens L1, an object-side surface of the biconvex positive lens L6, an image-side surface of the biconcave negative lens L9, and both surfaces of the biconvex positive lens L12.

An optical system for stereoscopic vision of the example 9 includes in order from an object side, a front unit GF and a rear unit GR. The front unit GF includes a first front unit GF1 and a second front unit GF2. An aperture stop (a stop) S is disposed between the front unit GF and the rear unit GR.

The first front unit GF1 includes a planoconcave negative lens L1, a biconvex positive lens L2, a negative meniscus lens L3 having a convex surface directed toward an image side, a biconcave negative lens L4, a biconvex positive lens L5, and a positive meniscus lens L6 having a convex surface directed toward the image side. Here, the biconvex positive lens L2 and the negative meniscus lens L3 are cemented. The biconcave negative lens L4 and the biconvex positive lens L5 are cemented.

The rear unit GR includes a biconvex positive lens L7, a biconvex positive lens L8, a biconcave negative lens L9, a biconcave negative lens L10, a biconvex positive lens L11, and a positive meniscus lens L12 having a convex surface directed toward the object side. Here, the biconvex positive lens L8 and the biconcave negative lens L9 are cemented.

A cover glass C1 is disposed on the object side of the planoconcave negative lens L1. A cover glass C2 and a cover glass C3 are disposed on the image side of the positive meniscus lens L12.

At a time of focusing, the positive meniscus lens L6 and the positive meniscus lens L12 move. More elaborately, at the time of focusing from a far point to a near point, the positive meniscus lens L6 moves toward the image side and the positive meniscus lens L12 moves toward the object side.

An aspheric surface is provided to a total of four surfaces which are an image-side surface of the planoconcave negative lens L1, an image-side surface of the positive meniscus lens L6, an object-side surface of the biconvex positive lens L7, and an image-side surface of the positive meniscus lens L12.

An optical system for stereoscopic vision of the example 10 includes in order from an object side, a front unit GF and a rear unit GR. The front unit GF includes a first front unit GF1 and a second front unit GF2. An aperture stop (a stop) S is disposed between the front unit GF and the rear unit GR.

The first front unit GF1 includes a planoconcave negative lens L1, a biconvex positive lens L2, a negative meniscus lens L3 having a convex surface directed toward an image side, a biconcave negative lens L4, a biconvex positive lens L5, and a positive meniscus lens L6 having a convex surface directed toward the image side. Here, the biconvex positive lens L2 and the negative meniscus lens L3 are cemented. The biconcave negative lens L4 and the biconvex positive lens L5 are cemented.

The rear unit GR includes a biconvex positive lens L7, a biconvex positive lens L8, a biconcave negative lens L9, a biconcave negative lens L10, a biconvex positive lens L11, and a positive meniscus lens L12 having a convex surface directed toward the object side. Here, the biconvex positive lens L8 and the biconcave negative lens L9 are cemented.

A cover glass C1 is disposed on the object side of the planoconcave negative lens L1. A cover glass C2 and a cover glass C3 are disposed on the image side of the positive meniscus lens L12.

At a time of focusing, the positive meniscus lens L6 moves. More elaborately, at the time of focusing from a far point to a near point, the positive meniscus lens L6 moves toward the image side.

An aspheric surface is provided to a total of four surfaces which are an image-side surface of the planoconcave negative lens L1, a cemented surface of the biconcave negative lens L4 and the biconvex positive lens L5, an image-side surface of the positive meniscus lens L6, and an object-side surface of the biconvex positive lens L7.

An optical system for stereoscopic vision of the example 11 includes in order from an object side, a front unit GF and a rear unit GR. The front unit GF includes a first front unit GF1 and a second front unit GF2. An aperture stop (a stop) S is disposed in the front unit GF.

The first front unit GF1 includes a planoconcave negative lens L1, a biconvex positive lens L2, a negative meniscus lens L3 having a convex surface directed toward an image side, a biconcave negative lens L4, a biconvex positive lens 15, and a positive meniscus lens L6 having a convex surface directed toward the image side. Here, the biconvex positive lens L2 and the negative meniscus lens L3 are cemented. The biconcave negative lens L4 and the biconvex positive lens L5 are cemented.

The rear unit GR includes a biconvex positive lens L7, a biconvex positive lens L8, a biconcave negative lens L9, a biconcave negative lens L10, a biconvex positive lens L11, and a positive meniscus lens L12 having a convex surface directed toward the object side. Here, the biconvex positive lens L8 and the biconcave negative lens L9 are cemented.

A cover glass C1 is disposed on the object side of the planoconcave negative lens L1. A cover glass C2 and a cover glass C3 are disposed on the image side of the positive meniscus lens L12.

At a time of focusing, the positive meniscus lens L6 moves. More elaborately, at the time of focusing from a far point to a near point, the positive meniscus lens L6 moves toward the image side.

An aspheric surface is provided to a total of four surfaces which are an image-side surface of the planoconcave negative lens L1, a cemented surface of the biconcave negative lens L4 and the biconvex positive lens L5, an image-side surface of the positive meniscus lens L6, and an object-side surface of the biconvex positive lens L7.

An optical system for stereoscopic vision of the example 12 includes in order from an object side, a front unit GF and a rear unit GR. The front unit GF includes a first front unit GF1 and a second front unit GF2. An aperture stop (a stop) S is disposed between the front unit GF and the rear unit GR.

The first front unit GF1 includes a planoconcave negative lens L1, a biconvex positive lens L2, a negative meniscus lens L3 having a convex surface directed toward an image side, a biconcave negative lens L4, a biconvex positive lens L5, and a positive meniscus lens L6 having a convex surface directed toward the image side. Here, the biconvex positive lens L2 and the negative meniscus lens L3 are cemented. The biconcave negative lens L4 and the biconvex positive lens L5 are cemented.

The rear unit GR includes a biconvex positive lens L7, a biconvex positive lens L8, a biconcave negative lens L9, a biconcave negative lens L10, a biconvex positive lens L11, and a positive meniscus lens L12 having a convex surface directed toward the object side. Here, the biconvex positive lens L8 and the biconcave negative lens L9 are cemented.

A cover glass C1 is disposed on the object side of the planoconcave negative lens L1. A cover glass C2 and a cover glass C3 are disposed on the image side of the positive meniscus lens L12.

At a time of focusing, the positive meniscus lens L6 moves. More elaborately, at the time of focusing from a far point to a near point, the positive meniscus lens L6 moves toward the image side.

An aspheric surface is provided to a total of four surfaces which are an image-side surface of the planoconcave negative lens L1, a cemented surface of the biconcave negative lens L4 and the biconvex positive lens L5, an image-side surface of the positive meniscus lens L6, and an object-side surface of the biconvex positive lens L7.

In the optical system for stereoscopic vision of the example 12, a shutter SH is disposed in the front unit GF. The shutter SH is the light beam selector.

The shutter SH shields one of a light beam passing through a first front unit GF1 and a light beam passing through a second front unit GF2. By making such arrangement, it is possible to capture a first optical image and a second optical image separately.

An optical system for stereoscopic vision of the example 13 includes in order from an object side, a front unit GF and a rear unit GR. The front unit GF includes a first front unit GF1 and a second front unit GF2. An aperture stop (a stop) S is disposed in the front unit GF.

The first front unit GF1 includes a biconcave negative lens L1, a biconvex positive lens L2, a negative meniscus lens L3 having a convex surface directed toward an image side, and a negative meniscus lens L4 having a convex surface directed toward the image side. Here, the biconvex positive lens L2 and the negative meniscus lens L3 are cemented.

The rear unit GR includes a positive meniscus lens L5 having a convex surface directed toward the object side, a biconvex positive lens L6, a biconcave negative lens L7, a biconvex positive lens L8, and a negative meniscus lens L9 having a convex surface directed toward the image side. Here, the biconvex positive lens L6 and the biconcave negative lens L7 are cemented. The biconvex positive lens L8 and the negative meniscus lens L9 are cemented.

A cover glass Cl is disposed on the object side of the biconcave negative lens L1. A cover glass C2 and a cover glass C3 are disposed on the image side of the negative meniscus lens L9.

At a time of focusing, the negative meniscus lens L4 moves. More elaborately, at the time of focusing from a far point to a near point, the negative meniscus lens L4 moves toward the image side.

An aspheric surface is provided to a total of four surfaces which are both surfaces of the biconcave negative lens L1 and both surfaces of the negative meniscus lens L4.

An optical system for stereoscopic vision of the example 14 includes in order from an object side, a front unit GF and a rear unit GR. The front unit GF includes a first front unit GF1 and a second front unit GF2. An aperture stop (a stop) S is disposed in the front unit GF.

The first front unit GF1 includes a planoconcave negative lens L1, a biconcave negative lens L2, a positive meniscus lens L3 having a convex surface directed toward the object side, a negative meniscus lens L4 having a convex surface directed toward the object side, a biconvex positive lens L5, and a positive meniscus lens L6 having a convex surface directed toward an image side. Here, the biconcave negative lens L2 and the positive meniscus lens L3 are cemented. The negative meniscus lens L4 and the biconvex positive lens L5 are cemented.

A rear unit GR includes a biconvex positive lens L7, a positive meniscus lens L8 having a convex surface directed toward the object side, a negative meniscus lens L9 having a convex surface directed toward the object side, a negative meniscus lens L10 having a convex surface directed toward the object side, a positive meniscus lens L11 having a convex surface directed toward the object side, and a biconvex positive lens L12. Here, the positive meniscus lens L8 and the negative meniscus lens L9 are cemented.

No cover glass is disposed on the object side of the planoconcave negative lens L1. A cover glass C1 and a cover glass C2 are disposed on the image side of the biconvex positive lens L12.

At a time of focusing, the positive meniscus lens L6 moves. More elaborately, at the time of focusing from a far point to a near point, the positive meniscus lens L6 moves toward the image side.

An aspheric surface is provided to a total of nine surfaces which are an image-side surface of the planoconcave negative lens L1, an image-side surface of the biconvex positive lens L5, both surfaces of the positive meniscus lens L6, both surfaces of the biconvex positive lens L7, an object-side surface of the positive meniscus lens L8, an image-side surface of the negative meniscus lens L9, and an image-side surface of the biconvex positive lens L12.

Numerical data of each example described above is shown below. In Surface data, r denotes radius of curvature of each lens surface, d denotes a distance between respective lens surfaces, nd denotes a refractive index of each lens for a d-line, vd denotes an Abbe number for each lens, and * denotes an aspherical surface.

In Various data, FP denotes at the time of focusing to a far point, and NP denotes at the time of focusing to a near point.

Moreover, a shape of an aspherical surface is defined by the following expression, where the direction of the optical axis is represented by z, the direction orthogonal to the optical axis is represented by y, a conical coefficient is represented by K, aspherical surface coefficients are represented by A4, A6, A8, A10, A12 . . . .

$$Z=(y^2/r)/[1+\{1-(1+k)(y/r)^2\}^{1/2}]+A4y^4+A6\,y^6+A8\,y^8+A10\,y^{10}+A12\,y^{12}+\ldots$$

Further, in the aspherical surface coefficients, 'e–n' (where, n is an integral number) indicates '$10^{-n}$'. Moreover, these symbols are commonly used in the following numerical data for each example.

An amount of decentering is a distance between the optical axis of the rear unit and the optical axis of the first front unit, and a distance between the optical axis of the rear unit and the optical axis of the second front unit. The unit of the amount of decentering is mm.

EXAMPLE 1

| Unit mm | | | | |
|---|---|---|---|---|
| Surface data | | | | |
| Surface no. | r | d | nd | vd |
| 1 | ∞ | 0.25 | 1.76823 | 72.24 |
| 2 | ∞ | 0.25 | | |
| 3 | ∞ | 0.40 | 1.88300 | 40.77 |

-continued

Unit mm

| | | | | |
|---|---|---|---|---|
| 4* | 1.197 | 0.68 | | |
| 5 | 2.901 | 0.89 | 1.80809 | 22.76 |
| 6 | −1.323 | 0.24 | 1.88300 | 40.77 |
| 7 | −4.585 | 0.25 | | |
| 8 | −8.168 | 0.16 | 1.92286 | 18.90 |
| 9 | 2.954 | 0.73 | 1.43875 | 94.66 |
| 10 | −1.562 | 0.32 | | |
| 11 (Stop) | ∞ | 0.32 | | |
| 12* | 3.661 | 0.81 | 1.43875 | 94.66 |
| 13 | −30.817 | 0.04 | | |
| 14 | 4.321 | 1.06 | 1.88300 | 40.77 |
| 15 | −11.682 | 0.32 | 1.85025 | 30.05 |
| 16 | 6.472 | 0.40 | | |
| 17 | −19.460 | 0.24 | 1.80610 | 40.93 |
| 18* | 2.904 | 0.40 | | |
| 19 | 10.693 | 0.20 | 1.66680 | 33.05 |
| 20 | 3.461 | 1.22 | 1.75500 | 52.33 |
| 21 | −8.186 | Variable | | |
| 22* | 14.823 | 1.30 | 1.88300 | 40.77 |
| 23* | −8.888 | Variable | | |
| 24 | ∞ | 0.40 | 1.51633 | 64.14 |
| 25 | ∞ | 0.30 | 1.50697 | 63.26 |
| 26 | ∞ | 0 | | |
| Image plane | ∞ | | | |

Aspherical surface data

4th surface k = −0.293
A4 = 3.44195e−03,    A6 = −8.86999e−04

12th surface k = 0.000
A4 = −5.33003e−04,    A6 = −9.17795e−05

18th surface k = 0.000
A4 = 3.13600e−03,    A6 = −3.57186e−04

22nd surface k = 0.000
A4 = −2.24341e−03,    A6 = −1.24521e−04

23rd surface k = 0.000
A4 = −1.60118e−04,    A6 = −2.10235e−04

Various data

| | FP | NP |
|---|---|---|
| Object distance | 57.0 | 28.0 |
| d21 | 0.48 | 0.29 |
| d23 | 0.98 | 1.17 |

Amount of decentering    0.98

EXAMPLE 2

Unit mm

Surface data

| Surface no. | r | d | nd | νd |
|---|---|---|---|---|
| 1 | ∞ | 0.25 | 1.76823 | 72.24 |
| 2 | ∞ | 0.25 | | |
| 3 | ∞ | 0.41 | 1.88300 | 40.77 |
| 4* | 1.161 | 0.62 | | |
| 5 | 2.873 | 1.07 | 1.80809 | 22.76 |
| 6 | −1.366 | 0.25 | 1.89190 | 37.13 |
| 7 | −6.751 | 0.08 | | |
| 8 | −21.486 | 0.44 | 1.92286 | 18.90 |
| 9 | 3.135 | 0.74 | 1.43875 | 94.66 |
| 10 | −1.585 | −0.08 | | |
| 11 (Stop) | ∞ | 0.66 | | |
| 12* | 3.798 | 0.66 | 1.43875 | 94.66 |
| 13 | −107.573 | 0.18 | | |
| 14 | 4.944 | 1.04 | 1.89190 | 37.13 |
| 15 | −16.472 | 0.33 | 1.80809 | 22.76 |
| 16 | 5.413 | 0.92 | | |
| 17 | −4.454 | 0.29 | 1.64250 | 58.37 |
| 18 | 3.497 | 0.21 | | |
| 19 | 4.804 | 1.07 | 1.43875 | 94.66 |
| 20 | −3.903 | Variable | | |
| 21* | 7.480 | 0.53 | 1.88300 | 40.77 |
| 22* | −15.459 | Variable | | |
| 23 | ∞ | 0.35 | 1.51633 | 64.14 |
| 24 | ∞ | 0.30 | 1.50697 | 63.26 |
| 25 | ∞ | 0 | | |
| Image plane | ∞ | | | |

Aspherical surface data

4th surface k = −0.339
A4 = −2.74523e−03,    A6 = 1.75931e−03

12th surface k = 0.000
A4 = −6.06008e−04,    A6 = 2.42850e−05

21st surface k = 0.000
A4 = −2.20652e−04,    A6 = 5.88824e−05

22nd surface k = 0.000
A4 = 3.28323e−03,    A6 = −8.07441e−05

Various data

| | FP | NP |
|---|---|---|
| Object distance | 58.0 | 29.0 |
| d20 | 0.23 | 0.08 |
| d22 | 1.75 | 1.90 |

Amount of decentering    0.99

EXAMPLE 3

Unit mm

Surface data

| Surface no. | r | d | nd | νd |
|---|---|---|---|---|
| 1 | ∞ | 0.25 | 1.76823 | 72.24 |
| 2 | ∞ | 0.25 | | |
| 3 | ∞ | 0.42 | 1.88300 | 40.77 |
| 4* | 1.173 | 0.56 | | |
| 5 | 2.840 | 1.05 | 1.80809 | 22.76 |
| 6 | −1.364 | 0.33 | 1.88300 | 40.77 |
| 7 | −4.945 | 0.08 | | |
| 8 | −10.425 | 0.60 | 1.92286 | 18.90 |
| 9 | 3.307 | 0.75 | 1.43875 | 94.66 |
| 10 | −1.645 | −0.08 | | |
| 11 (Stop) | ∞ | 0.67 | | |
| 12* | 4.899 | 0.67 | 1.43875 | 94.66 |
| 13 | 78.186 | 0.06 | | |
| 14 | 5.103 | 1.10 | 1.88300 | 40.77 |
| 15 | 27.356 | 0.42 | 1.92286 | 18.90 |
| 16 | 5.684 | 0.04 | | |

-continued

| Unit mm | | | | |
|---|---|---|---|---|
| 17 | 2.980 | 0.73 | 1.43875 | 94.66 |
| 18 | 88.050 | 0.08 | | |
| 19 | −37.443 | 0.21 | 1.43875 | 94.66 |
| 20 | 2.175 | Variable | | |
| 21* | 8.594 | 0.92 | 1.88300 | 40.77 |
| 22 | −9.298 | Variable | | |
| 23 | ∞ | 0.40 | 1.51633 | 64.14 |
| 24 | ∞ | 0.27 | 1.50697 | 63.26 |
| 25 | ∞ | 0 | | |
| Image plane | ∞ | | | |

Aspherical surface data

4th surface k = −0.454
A4 = 7.89111e−03
12th surface k = 0.000
A4 = −6.62453e−04
21st surface k = 0.000
A4 = −3.44876e−03

Various data

| | FP | NP |
|---|---|---|
| Object distance | 59.0 | 25.0 |
| d20 | 1.30 | 1.11 |
| d22 | 1.41 | 1.60 |

| Amount of decentering | 1.00 |
|---|---|

EXAMPLE 4

| Unit mm | | | | |
|---|---|---|---|---|
| Surface data | | | | |
| Surface no. | r | d | nd | vd |
| 1 | ∞ | 0.20 | 1.88300 | 40.77 |
| 2* | 0.621 | 0.26 | | |
| 3 | −2.187 | 0.19 | 1.88300 | 40.77 |
| 4 | 0.569 | 0.34 | 1.80809 | 22.76 |
| 5 | −3.811 | 0.05 | | |
| 6 | 1.571 | 0.23 | 1.80809 | 22.76 |
| 7 | 0.910 | 0.43 | 1.43875 | 94.66 |
| 8 | −0.710 | 0.00 | | |
| 9 (Stop) | ∞ | 0.30 | | |
| 10* | 2.626 | 0.43 | 1.43875 | 94.66 |
| 11 | 6.625 | 0.03 | | |
| 12 | 2.709 | 1.02 | 1.88300 | 40.77 |
| 13 | 3.515 | 0.19 | 1.92286 | 18.90 |
| 14 | 1.936 | 0.14 | | |
| 15 | 3.230 | 0.40 | 1.43875 | 94.66 |
| 16 | −3.428 | 0.13 | | |
| 17 | 5.168 | 0.43 | 1.49700 | 81.55 |
| 18 | −27.961 | Variable | | |
| 19 | 5.555 | 0.26 | 1.88300 | 40.77 |
| 20 | −49.057 | Variable | | |
| 21 | ∞ | 0.20 | 1.51633 | 64.14 |
| 22 | ∞ | 0.15 | 1.50697 | 63.26 |
| 23 | ∞ | 0 | | |
| Image plane | ∞ | | | |

-continued

| Unit mm |
|---|

Aspherical surface data

2nd surface k = 0.765
10th surface k = 0.000
A4 = −1.30944e−02

Various data

| | FP | NP |
|---|---|---|
| Object distance | 15.0 | 7.0 |
| d18 | 0.67 | 0.42 |
| d20 | 0.29 | 0.54 |

| Amount of decentering | 0.42 |
|---|---|

EXAMPLE 5

| Unit mm | | | | |
|---|---|---|---|---|
| Surface data | | | | |
| Surface no. | r | d | nd | vd |
| 1 | ∞ | 0.20 | 1.88300 | 40.77 |
| 2 | 0.620 | 0.26 | | |
| 3 | −2.442 | 0.19 | 1.88300 | 40.77 |
| 4 | 0.542 | 0.33 | 1.80809 | 22.76 |
| 5 | −3.706 | 0.04 | | |
| 6 | 1.628 | 0.28 | 1.80809 | 22.76 |
| 7 | 0.899 | 0.42 | 1.43875 | 94.66 |
| 8 | −0.696 | 0.00 | | |
| 9 (Stop) | ∞ | Variable | | |
| 10* | 2.453 | 0.34 | 1.49700 | 81.55 |
| 11 | 6.137 | Variable | | |
| 12 | 2.842 | 0.27 | 1.88300 | 40.77 |
| 13 | 5.248 | 0.08 | | |
| 14 | 5.239 | 0.49 | 1.88300 | 40.77 |
| 15 | 3.218 | 0.21 | 1.92286 | 18.90 |
| 16 | 1.929 | 0.23 | | |
| 17 | 3.591 | 0.39 | 1.43875 | 94.66 |
| 18 | −7.211 | 0.04 | | |
| 19 | 1.858 | 0.51 | 1.43875 | 94.66 |
| 20 | 10.742 | 0.49 | | |
| 21* | 4.236 | 0.54 | 1.88300 | 40.77 |
| 22 | 7.226 | 0.31 | | |
| 23 | ∞ | 0.17 | 1.51633 | 64.14 |
| 24 | ∞ | 0.17 | 1.50697 | 63.26 |
| 25 | ∞ | 0 | | |
| Image plane | ∞ | | | |

Aspherical surface data

2nd surface k = 0.667
10th surface k = 0.000
A4 = −4.63216e−03
21st surface k = 0.000
A4 = −1.60872e−02

-continued

Unit mm

Various data

| | FP | NP |
|---|---|---|
| Object distance | 15.3 | 5.0 |
| d9 | 1.12 | 0.07 |
| d11 | 0.03 | 1.08 |

| Amount of decentering | 0.43 |
|---|---|

EXAMPLE 6

Unit mm

Surface data

| Surface no. | r | d | nd | vd |
|---|---|---|---|---|
| 1 | ∞ | 0.25 | 1.76823 | 72.24 |
| 2 | ∞ | 0.25 | | |
| 3 | ∞ | 0.40 | 1.88300 | 40.77 |
| 4* | 1.140 | 0.55 | | |
| 5 | 2.695 | 0.94 | 1.80809 | 22.76 |
| 6 | −1.369 | 0.25 | 1.88300 | 40.77 |
| 7 | −5.055 | 0.08 | | |
| 8 | −11.962 | 0.67 | 1.92286 | 18.90 |
| 9 | 3.053 | 0.74 | 1.43875 | 94.66 |
| 10 | −1.599 | −0.16 | | |
| 11 (Stop) | ∞ | 0.74 | | |
| 12* | 4.662 | 0.66 | 1.43875 | 94.66 |
| 13 | 72.593 | 0.07 | | |
| 14 | 5.007 | 1.15 | 1.88300 | 40.77 |
| 15 | 23.124 | 0.41 | 1.92286 | 18.90 |
| 16 | 5.369 | 0.04 | | |
| 17 | 3.568 | 0.65 | 1.43875 | 94.66 |
| 18 | −70.565 | Variable | | |
| 19 | −21.214 | 0.25 | 1.59522 | 67.74 |
| 20 | 2.589 | Variable | | |
| 21* | 6.280 | 0.71 | 1.88300 | 40.77 |
| 22 | −7.664 | 1.63 | | |
| 23 | ∞ | 0.33 | 1.51633 | 64.14 |
| 24 | ∞ | 0.33 | 1.50697 | 63.26 |
| 25 | ∞ | 0 | | |
| Image plane | ∞ | | | |

Aspherical surface data

4th surface k = −0.484
A4 = 1.12556e−02

12th surface k = 0.000
A4 = −1.01916e−03

21st surface k = 0.000
A4 = −2.91406e−03

Various data

| | FP | NP |
|---|---|---|
| Object distance | 58.0 | 33.0 |
| d18 | 0.25 | 0.31 |
| d20 | 1.09 | 1.03 |

| Amount of decentering | 1.00 |
|---|---|

EXAMPLE 7

Unit mm

Surface data

| Surface no. | r | d | nd | vd |
|---|---|---|---|---|
| 1 | ∞ | 0.25 | 1.76823 | 72.24 |
| 2 | ∞ | 0.25 | | |
| 3 | ∞ | 0.41 | 1.88300 | 40.77 |
| 4* | 1.053 | 0.62 | | |
| 5 | 2.557 | 1.06 | 1.80809 | 22.76 |
| 6 | −1.268 | 0.24 | 1.89190 | 37.13 |
| 7 | −7.864 | 0.08 | | |
| 8 | 144.485 | 0.53 | 1.92286 | 18.90 |
| 9 | 2.471 | 0.81 | 1.43875 | 94.66 |
| 10 | −1.529 | −0.08 | | |
| 11 (Stop) | ∞ | 0.65 | | |
| 12* | 16.458 | 0.65 | 1.43875 | 94.66 |
| 13 | −9.822 | Variable | | |
| 14 | 5.640 | 0.49 | 1.89190 | 37.13 |
| 15 | −25.417 | 0.24 | 1.80809 | 22.76 |
| 16 | 6.854 | Variable | | |
| 17 | 14.908 | 0.28 | 1.64250 | 58.37 |
| 18 | 5.406 | 0.43 | | |
| 19 | −48.644 | 0.65 | 1.43875 | 94.66 |
| 20 | −3.852 | 0.21 | | |
| 21* | 9.380 | 0.49 | 1.88300 | 40.77 |
| 22 | −324.542 | 1.83 | | |
| 23 | ∞ | 0.35 | 1.51633 | 64.14 |
| 24 | ∞ | 0.30 | 1.50697 | 63.26 |
| 25 | ∞ | 0 | | |
| Image plane | ∞ | | | |

Aspherical surface data

4th surface k = −0.440
A4 = 2.16655e−03

12th surface k = 0.000
A4 = −1.62381e−03

21st surface k = 0.000
A4 = −1.86843e−03

Various data

| | FP | NP |
|---|---|---|
| Object distance | 60.0 | 24.0 |
| d13 | 0.46 | 0.04 |
| d16 | 2.28 | 2.70 |

| Amount of decentering | 0.98 |
|---|---|

EXAMPLE 8

Unit mm

Surface data

| Surface no. | r | d | nd | vd |
|---|---|---|---|---|
| 1 | ∞ | 0.25 | 1.76823 | 72.24 |
| 2 | ∞ | 0.25 | | |
| 3 | ∞ | 0.41 | 1.88300 | 40.77 |
| 4* | 1.213 | 0.71 | | |
| 5 | 2.984 | 0.91 | 1.80809 | 22.76 |
| 6 | −1.360 | 0.25 | 1.88300 | 40.77 |
| 7 | −4.647 | 0.24 | | |

-continued

Unit mm

| | | | | |
|---|---|---|---|---|
| 8 | −8.487 | 0.17 | 1.92286 | 18.90 |
| 9 | 2.992 | 0.74 | 1.43875 | 94.66 |
| 10 | −1.587 | 0.33 | | |
| 11 (Stop) | ∞ | 0.33 | | |
| 12* | 3.780 | 0.83 | 1.43875 | 94.66 |
| 13 | −26.874 | 0.04 | | |
| 14 | 4.427 | 1.08 | 1.88300 | 40.77 |
| 15 | −11.933 | 0.33 | 1.85025 | 30.05 |
| 16 | 6.567 | 0.42 | | |
| 17 | −16.045 | 0.25 | 1.80610 | 40.93 |
| 18* | 3.060 | Variable | | |
| 19 | 10.661 | 0.21 | 1.66680 | 33.05 |
| 20 | 3.461 | 1.24 | 1.75500 | 52.33 |
| 21 | −8.244 | Variable | | |
| 22* | 16.104 | 1.18 | 1.88300 | 40.77 |
| 23* | −8.813 | 1.14 | | |
| 24 | ∞ | 0.35 | 1.51633 | 64.14 |
| 25 | ∞ | 0.30 | 1.51009 | 63.46 |
| 26 | ∞ | 0 | | |
| Image plane | ∞ | | | |

Aspherical surface data

4th surface k = −0.282
A4 = 2.22837e−03,    A6 = 1.05849e−03
12th surface k = 0.000
A4 = −4.15106e−04,    A6 = −8.56740e−05
18th surface k = 0.000
A4 = 2.82331e−03,    A6 = −4.15369e−04
22nd surface k = 0.000
A4 = −2.49480e−03,    A6 = −1.71939e−04
23rd surface k = 0.000
A4 = 1.90765e−04,    A6 = −1.58023e−04

Various data

| | FP | NP |
|---|---|---|
| Object distance | 53.0 | 32.0 |
| d18 | 0.59 | 0.44 |
| d21 | 0.31 | 0.46 |
| Amount of decentering | 1.00 | |

EXAMPLE 9

Unit mm

Surface data

| Surface no. | r | d | nd | vd |
|---|---|---|---|---|
| 1 | ∞ | 0.25 | 1.76823 | 72.24 |
| 2 | ∞ | 0.20 | | |
| 3 | ∞ | 0.38 | 1.88300 | 40.77 |
| 4* | 1.232 | 0.45 | | |
| 5 | 2.126 | 1.37 | 1.80809 | 22.76 |
| 6 | −1.283 | 0.23 | 1.89190 | 37.13 |
| 7 | −8.122 | 0.09 | | |
| 8 | −4.180 | 0.19 | 1.92286 | 18.90 |
| 9 | 4.581 | 0.73 | 1.43875 | 94.66 |
| 10 | −1.725 | Variable | | |
| 11 | −16.894 | 0.38 | 1.43875 | 94.66 |

-continued

Unit mm

| | | | | |
|---|---|---|---|---|
| 12* | −3.994 | Variable | | |
| 13 (Stop) | ∞ | 0.00 | | |
| 14* | 3.138 | 0.76 | 1.43875 | 94.66 |
| 15 | −27.271 | 0.04 | | |
| 16 | 4.663 | 0.76 | 1.88300 | 40.77 |
| 17 | −45.015 | 0.30 | 1.84666 | 23.78 |
| 18 | 5.644 | 0.68 | | |
| 19 | −11.783 | 0.27 | 1.64250 | 58.37 |
| 20 | 2.635 | 0.42 | | |
| 21 | 7.906 | 0.76 | 1.43875 | 94.66 |
| 22 | −5.249 | Variable | | |
| 23 | 5.327 | 0.76 | 1.88300 | 40.77 |
| 24* | 59.414 | Variable | | |
| 25 | ∞ | 0.30 | 1.51633 | 64.14 |
| 26 | ∞ | 0.30 | 1.50697 | 63.26 |
| 27 | ∞ | 0 | | |
| Image plane | ∞ | | | |

Aspherical surface data

4th surface k = −0.560
A4 = 1.45910e−02
12th surface k = 0.000
A4 = −1.68170e−03
14th surface k = 0.000
A4 = −2.31984e−03,    A6 = −1.46364e−04
24th surface k = 0.000
A4 = −2.33049e−04

Various data

| | FP | NP |
|---|---|---|
| Object distance | 55.0 | 25.0 |
| d10 | 0.43 | 0.83 |
| d12 | 0.48 | 0.08 |
| d22 | 0.23 | 0.15 |
| d24 | 1.54 | 1.62 |
| Amount of decentering | 1.10 | |

EXAMPLE 10

Unit mm

Surface data

| Surface no. | r | d | nd | vd |
|---|---|---|---|---|
| 1 | ∞ | 0.28 | 1.76823 | 72.24 |
| 2 | ∞ | 0.28 | | |
| 3 | ∞ | 0.46 | 1.88300 | 40.77 |
| 4* | 1.539 | 0.54 | | |
| 5 | 2.650 | 1.36 | 1.80809 | 22.76 |
| 6 | −1.478 | 0.28 | 1.89190 | 37.13 |
| 7 | −9.823 | 0.18 | | |
| 8 | −5.116 | 0.23 | 1.92286 | 18.90 |
| 9* | 5.598 | 0.86 | 1.43875 | 94.66 |
| 10 | −2.101 | Variable | | |
| 11 | −26.150 | 0.46 | 1.43875 | 94.66 |
| 12* | −4.852 | Variable | | |
| 13 (Stop) | ∞ | 0.00 | | |
| 14* | 3.841 | 0.83 | 1.43875 | 94.66 |
| 15 | −108.280 | 0.05 | | |
| 16 | 5.653 | 1.04 | 1.88300 | 40.77 |

-continued

Unit mm

| | | | | |
|---|---|---|---|---|
| 17 | −19.896 | 0.37 | 1.84666 | 23.78 |
| 18 | 6.959 | 0.83 | | |
| 19 | −11.383 | 0.32 | 1.64250 | 58.37 |
| 20 | 3.397 | 0.51 | | |
| 21 | 11.317 | 0.92 | 1.43875 | 94.66 |
| 22 | −5.214 | 0.05 | | |
| 23 | 4.887 | 0.92 | 1.88300 | 40.77 |
| 24 | 19.043 | 1.90 | | |
| 25 | ∞ | 0.40 | 1.51633 | 64.14 |
| 26 | ∞ | 0.35 | 1.50697 | 63.26 |
| 27 | ∞ | 0 | | |
| Image plane | ∞ | | | |

Aspherical surface data

4th surface $k = -0.496$
$A4 = 8.31497e-03$
9th surface $k = 0.000$
$A4 = -5.89735e-03$
12th surface $k = 0.000$
$A4 = -1.76600e-04$
14th surface $k = 0.000$
$A4 = -1.20112e-03$, $A6 = -2.81130e-05$ Various data

| | FP | NP |
|---|---|---|
| Object distance | 65.0 | 30.0 |
| d10 | 0.09 | 0.84 |
| d12 | 0.84 | 0.09 |
| Amount of decentering | | 1.10 |

EXAMPLE 11

Unit mm

Surface data

| Surface no. | r | d | nd | vd |
|---|---|---|---|---|
| 1 | ∞ | 0.27 | 1.76823 | 72.24 |
| 2 | ∞ | 0.27 | | |
| 3 | ∞ | 0.46 | 1.88300 | 40.77 |
| 4* | 1.531 | 0.54 | | |
| 5 | 2.536 | 1.62 | 1.80809 | 22.76 |
| 6 | −1.414 | 0.27 | 1.89190 | 37.13 |
| 7 | −9.585 | 0.15 | | |
| 8 | −4.983 | 0.23 | 1.92286 | 18.90 |
| 9* | 5.772 | 0.81 | 1.43875 | 94.66 |
| 10 | −2.116 | 0.05 | | |
| 11 (Stop) | ∞ | Variable | | |
| 12 | −25.897 | 0.46 | 1.43875 | 94.66 |
| 13* | −4.860 | Variable | | |
| 14* | 4.058 | 1.28 | 1.43875 | 94.66 |
| 15 | −45.636 | 0.05 | | |
| 16 | 5.783 | 0.97 | 1.88300 | 40.77 |
| 17 | −28.155 | 0.37 | 1.84666 | 23.78 |
| 18 | 6.846 | 0.82 | | |
| 19 | −8.926 | 0.32 | 1.64250 | 58.37 |
| 20 | 3.855 | 0.59 | | |
| 21 | 9.614 | 0.91 | 1.43875 | 94.66 |
| 22 | −5.528 | 0.05 | | |
| 23 | 4.704 | 0.91 | 1.88300 | 40.77 |

-continued

Unit mm

| | | | | |
|---|---|---|---|---|
| 24 | 20.245 | 1.85 | | |
| 25 | ∞ | 0.40 | 1.51633 | 64.14 |
| 26 | ∞ | 0.35 | 1.50697 | 63.26 |
| 27 | ∞ | 0 | | |
| Image plane | ∞ | | | |

Aspherical surface data

4th surface $k = -0.489$
$A4 = 4.63651e-03$
9th surface $k = 0.000$
$A4 = -2.87503e-03$
13th surface $k = 0.000$
$A4 = -6.76425e-05$
14th surface $k = 0.000$
$A4 = -9.30817e-04$, $A6 = -2.57386e-05$ Various data

| | FP | NP |
|---|---|---|
| Object distance | 64.0 | 29.0 |
| d11 | 0.19 | 0.98 |
| d13 | 0.88 | 0.09 |
| Amount of decentering | | 1.10 |

EXAMPLE 12

Unit mm

Surface data

| Surface no. | r | d | nd | vd |
|---|---|---|---|---|
| 1 | ∞ | 0.28 | 1.76823 | 72.24 |
| 2 | ∞ | 0.28 | | |
| 3 | ∞ | 0.46 | 1.88300 | 40.77 |
| 4* | 1.559 | 0.54 | | |
| 5 | 2.685 | 1.43 | 1.80809 | 22.76 |
| 6 | −1.494 | 0.28 | 1.89190 | 37.13 |
| 7 | −9.919 | 0.18 | | |
| 8 | −5.149 | 0.23 | 1.92286 | 18.90 |
| 9* | 5.638 | 0.86 | 1.43875 | 94.66 |
| 10 | −2.113 | Variable | | |
| 11 | −25.487 | 0.46 | 1.43875 | 94.66 |
| 12* | −4.921 | Variable | | |
| 13 (Stop) | ∞ | 0.00 | | |
| 14* | 3.873 | 0.84 | 1.43875 | 94.66 |
| 15 | −109.496 | 0.05 | | |
| 16 | 5.701 | 1.05 | 1.88300 | 40.77 |
| 17 | −19.988 | 0.37 | 1.84666 | 23.78 |
| 18 | 7.039 | 0.84 | | |
| 19 | −12.304 | 0.32 | 1.64250 | 58.37 |
| 20 | 3.360 | 0.51 | | |
| 21 | 10.841 | 0.93 | 1.43875 | 94.66 |
| 22 | −5.498 | 0.05 | | |
| 23 | 5.045 | 0.93 | 1.88300 | 40.77 |
| 24 | 19.422 | 1.94 | | |
| 25 | ∞ | 0.40 | | |
| 26 | ∞ | 0.35 | 1.50697 | 63.26 |
| 27 | ∞ | 0 | | |
| Image plane | ∞ | | | |

-continued

Unit mm

Aspherical surface data

4th surface k = −0.522
A4 = 8.92210e−03

9th surface k = 0.000
A4 = −5.74838e−03

12th surface k = 0.000
A4 = −2.08644e−04

14th surface k = 0.000
A4 = −1.10010e−03,   A6 = −3.46516e−05

Various data

|  | FP | NP |
|---|---|---|
| Object distance | 65.0 | 30.0 |
| d10 | 0.43 | 1.17 |
| d12 | 0.93 | 0.19 |
| Amount of decentering | 1.11 | |

EXAMPLE 13

Unit mm

Surface data

| Surface no. | r | d | nd | vd |
|---|---|---|---|---|
| 1 | ∞ | 0.55 | 1.76823 | 72.24 |
| 2 | ∞ | 0.33 | | |
| 3* | −18.428 | 0.38 | 1.88300 | 40.77 |
| 4* | 2.363 | 0.49 | | |
| 5 | 17.095 | 3.68 | 1.70000 | 48.08 |
| 6 | −1.624 | 0.33 | 2.00330 | 28.27 |
| 7 | −2.396 | 0.03 | | |
| 8 (Stop) | ∞ | Variable | | |
| 9* | −2.684 | 0.33 | 1.49700 | 81.55 |
| 10* | −3.828 | Variable | | |
| 11 | 5.641 | 1.53 | 1.74400 | 44.79 |
| 12 | 23.676 | 0.74 | | |
| 13 | 5.152 | 1.86 | 1.43875 | 94.95 |
| 14 | −18.372 | 0.01 | 1.56602 | 60.67 |
| 15 | −18.372 | 0.38 | 1.89286 | 20.36 |
| 16 | 8.204 | 0.54 | | |
| 17 | 4.365 | 2.74 | 1.43875 | 94.95 |
| 18 | −3.838 | 0.38 | 1.72047 | 34.71 |
| 19 | −326.434 | 0.06 | | |
| 20 | ∞ | 0.44 | 1.51633 | 64.14 |
| 21 | ∞ | 0.02 | 1.51187 | 64.06 |
| 22 | ∞ | 0.44 | 1.51009 | 63.64 |
| 23 | ∞ | 0 | | |
| Image plane | ∞ | | | |

Aspherical surface data

3rd surface k = 0.000
A4 = 2.43369e−02,   A6 = −1.34085e−02,   A8 = 3.94655e−03,
A10 = −4.86397e−04

4th surface k = −5.822
A4 = 9.98146e−02,   A6 = −2.60925e−02,   A8 = 8.90267e−03

9th surface k = 0.000
A4 = 5.16699e−02,   A6 = −6.21727e−03,   A8 = 8.79883e−04

10th surface k = 0.000
A4 = 4.35782e−02,   A6 = −4.69431e−03,   A8 = 4.41110e−04

Various data

|  | FP | NP |
|---|---|---|
| Object distance | 76.7 | 35.1 |
| d8 | 0.25 | 1.03 |
| d10 | 0.92 | 0.14 |
| Amount of decentering | 1.53 | |

EXAMPLE 14

Unit mm

Surface data

| Surface no. | r | d | nd | vd |
|---|---|---|---|---|
| 1 | ∞ | 0.34 | 1.88300 | 40.77 |
| 2* | 1.051 | 0.53 | | |
| 3 | −3.095 | 0.30 | 1.88300 | 40.77 |
| 4 | 1.069 | 0.44 | 1.80809 | 22.76 |
| 5 | 28.045 | 0.07 | | |
| 6 | 2.574 | 0.51 | 1.80809 | 22.76 |
| 7 | 1.917 | 0.68 | 1.49700 | 81.55 |
| 8* | −1.502 | 0.14 | | |
| 9 (Stop) | ∞ | Variable | | |
| 10* | −3.052 | 0.41 | 1.43875 | 94.66 |
| 11* | −2.091 | Variable | | |
| 12* | 3.641 | 0.96 | 1.60311 | 60.60 |
| 13* | −114.201 | 0.07 | | |
| 14* | 7.686 | 1.43 | 1.88300 | 40.77 |
| 15 | 141.743 | 0.27 | 1.92286 | 18.90 |
| 16* | 8.493 | 0.63 | | |
| 17 | 3.494 | 0.41 | 1.84666 | 23.78 |
| 18 | 1.953 | 0.41 | | |
| 19 | 4.668 | 0.99 | 1.43875 | 94.95 |
| 20 | 23.859 | 0.07 | | |
| 21 | 2.801 | 1.09 | 1.43875 | 94.95 |
| 22* | −3.870 | 0.10 | | |
| 23 | ∞ | 0.30 | 1.51633 | 64.14 |
| 24 | ∞ | 0.25 | 1.50697 | 63.26 |
| 25 | ∞ | 0 | | |
| Image plane | ∞ | | | |

Aspherical surface data

2nd surface k = 0.606
A4 = 1.28623e−02

8th surface k = 0.000
A4 = −2.91858e−03

10th surface k = 0.000
A4 = 2.02606e−03,   A6 = −3.59431e−02

11th surface k = 0.000
A4 = 8.54924e−03,   A6 = −2.38354e−02

-continued

Unit mm

12th surface k = 0.000
A4 = −4.06534e−03,    A6 = 2.93612e−04
13th surface k = 0.000
A4 = −1.75192e−03,    A6 = 3.25171e−05
14th surface k = 0.000
A4 = 2.78628e−03,    A6 = −7.16569e−04
16th surface k = 0.000
A4 = 6.35840e−03,    A6 = −9.53119e−04
22nd surface k = 0.000
A4 = 3.93027e−03

Various data

|  | FP | NP |
|---|---|---|
| Object distance | 25.0 | 11.0 |
| d9 | 0.14 | 0.94 |
| d11 | 1.08 | 0.27 |
| Amount of decentering | 0.61 | |

Next, values of conditional expressions in each example are given below. '-' (hyphen) indicates that there is no corresponding arrangement.

|  | Example1 | Example2 | Example3 |
|---|---|---|---|
| (1) De/Φ | 0.55 | 0.55 | 0.54 |
| (2) L0farfl/FLfl | 0.47 | 0.50 | 0.52 |
| (3) FLfl/TTLfl | 36.57 | 33.17 | 30.54 |
| (4) FLfla/TTLfl | −0.40 | −0.36 | −0.35 |
| (5) FLflb/TTLfl | 0.76 | 0.82 | 0.69 |
| (6) Rrflc/FLfl | −0.46 | −0.44 | −0.43 |
| (7) FLflc/FLfl | 6.65 | 2.55 | 3.85 |
| (8) FLr/TTL | 0.42 | 0.44 | 0.44 |
| (9) (Rfra + Rrra)/(Rfra − Rrra) | −0.79 | −0.93 | −1.13 |
| (10) Lr1/TTL | 0.07 | 0.07 | 0.06 |
| (11) 1 − (βfocus)$^2$ | 0.46 | 0.65 | 0.65 |
| (12) 1 − (βfocus)$^2$ × βr$^2$ | — | — | — |
| (13) FLfocus/TTL | 0.53 | 0.48 | 0.43 |

|  | Example4 | Example5 | Example6 |
|---|---|---|---|
| (1) De/Φ | 0.44 | 0.44 | 0.55 |
| (2) L0farfl/FLfl | 0.72 | 0.74 | 0.54 |
| (3) FLfl/TTLfl | 12.52 | 12.31 | 30.05 |
| (4) FLfla/TTLfl | −0.41 | −0.41 | −0.36 |
| (5) FLflb/TTLfl | — | — | 0.70 |
| (6) Rrflc/FLfl | −0.42 | −0.40 | −0.44 |
| (7) FLflc/FLfl | 0.86 | 0.86 | 3.65 |
| (8) FLr/TTL | 0.42 | 0.37 | 0.44 |
| (9) (Rfra + Rrra)/(Rfra − Rrra) | −2.31 | −2.33 | −1.14 |
| (10) Lr1/TTL | 0.07 | 0.05 | 0.06 |
| (11) 1 − (βfocus)$^2$ | 0.21 | — | — |
| (12) 1 − (βfocus)$^2$ × βr$^2$ | — | 1.00 | −0.36 |
| (13) FLfocus/TTL | 0.89 | 1.12 | −0.33 |

|  | Example7 | Example8 | Example9 |
|---|---|---|---|
| (1) De/Φ | 0.55 | 0.55 | 0.63 |
| (2) L0farfl/FLfl | 0.96 | 0.68 | 0.82 |
| (3) FLfl/TTLfl | 17.09 | 23.40 | 14.74 |
| (4) FLfla/TTLfl | −0.32 | −0.40 | −0.30 |
| (5) FLflb/TTLfl | 0.76 | 0.76 | 0.53 |
| (6) Rrflc/FLfl | −0.41 | −0.46 | −0.86 |
| (7) FLflc/FLfl | 2.08 | 6.36 | 2.54 |
| (8) FLr/TTL | 0.43 | 0.42 | 0.43 |
| (9) (Rfra + Rrra)/(Rfra − Rrra) | 0.25 | −0.75 | −0.79 |
| (10) Lr1/TTL | 0.09 | 0.07 | 0.07 |
| (11) 1 − (βfocus)$^2$ | — | 0.86 | — |
| (12) 1 − (βfocus)$^2$ × βr$^2$ | 0.83 | — | — |
| (13) FLfocus/TTL | 1.52 | 0.47 | 0.56 |

|  | Example10 | Example11 | Example12 |
|---|---|---|---|
| (1) De/Φ | 0.57 | 0.57 | 0.55 |
| (14) L0farfl/FLfarfl | 0.40 | 0.55 | 0.42 |
| (15) L0nearfl/FLnearfl | 0.43 | 0.49 | 0.43 |
| (16) FLfarfl/TTLfl' | 31.38 | 21.27 | 26.94 |
| (17) FLfla/TTL | −0.13 | −0.12 | −0.12 |
| (18) FLflb/TTL | 0.22 | 0.20 | 0.22 |
| (19) Rrflc/TTL | −0.35 | −0.33 | −0.34 |
| (20) FLflc/TTL | 0.98 | 0.93 | 0.96 |
| (21) Rrfld/FLfla | 1.21 | 1.22 | 1.20 |
| (22) FLr'/TTLr | 1.00 | 0.93 | 1.02 |
| (9') (Rfra + Rrra)/(Rfra − Rrra) | −0.93 | −0.84 | −0.93 |
| (10') Lr1/TTL | 0.06 | 0.09 | 0.06 |
| (23) (Rfrb + Rrrb)/(Rfrb − Rrrb) | −1.69 | −1.61 | −1.70 |
| (13') FLfocus/TTL | 0.98 | 0.93 | 0.96 |

|  | Example13 | Example14 |
|---|---|---|
| (1) De/Φ | 0.73 | 0.44 |
| (14) L0farfl/FLfarfl | 2.92 | 0.31 |
| (15) L0nearfl/FLnearfl | 1.56 | 0.30 |
| (16) FLfarfl/TTLfl' | 4.13 | 18.11 |
| (17) FLfla/TTL | −0.15 | −0.10 |
| (18) FLflb/TTL | 0.25 | — |
| (19) Rrflc/TTL | −0.25 | −0.18 |
| (20) FLflc/TTL | −1.28 | 1.15 |
| (21) Rrfld/FLfla | 1.02 | 1.26 |
| (22) FLr'/TTLr | 0.92 | 0.72 |
| (9') (Rfra + Rrra)/(Rfra − Rrra) | −1.63 | −0.94 |
| (10') Lr1/TTL | 0.15 | 0.09 |
| (23) (Rfrb + Rrrb)/(Rfrb − Rrrb) | −0.97 | −0.16 |
| (13') FLfocus/TTL | −1.28 | 1.15 |

Figure 73:
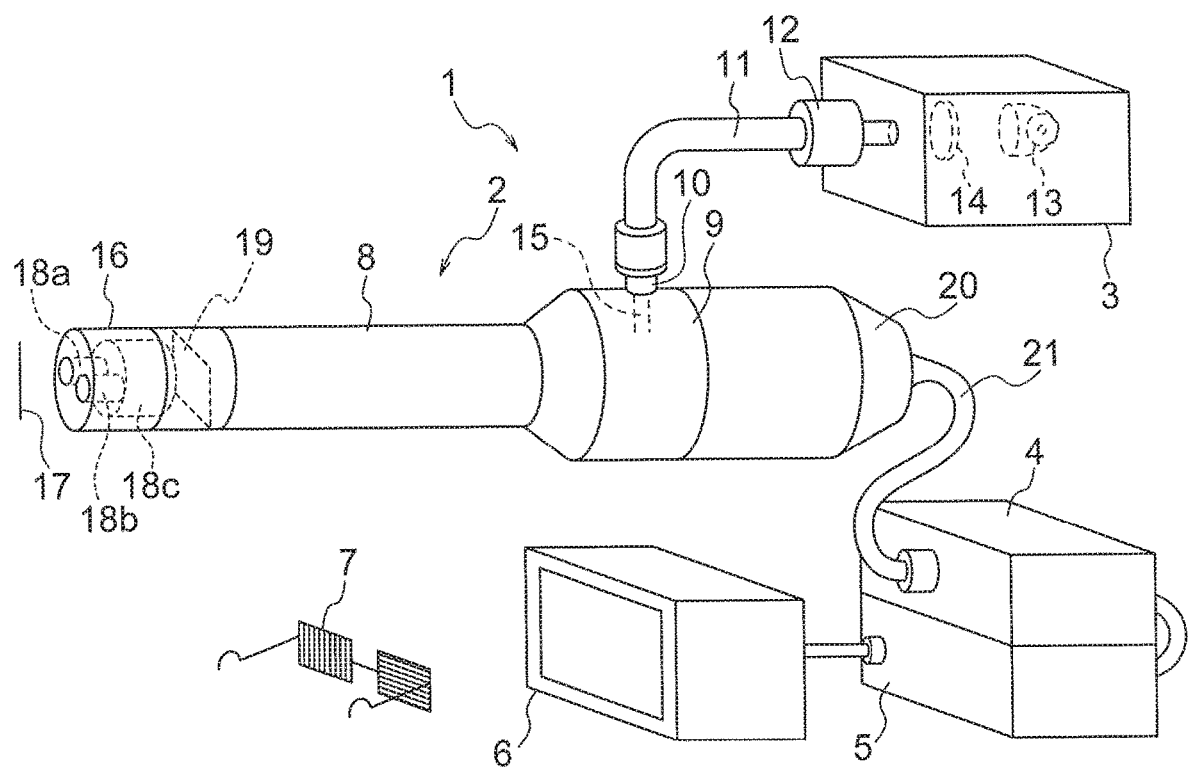
FIG. 73 is a diagram showing an image pickup apparatus of the present embodiment.

FIG. 73 is a diagram showing an image pickup apparatus of the present embodiment. The image pickup apparatus of the present embodiment is a stereoscopic-vision endoscope. A stereoscopic-vision endoscope 1 includes a body portion 2, a light-source unit 3, a camera control unit 4 (hereinafter, referred to as 'CCU 4'), a scan converter 5, a monitor 6, and shutter glasses 7.

The body portion 2 includes an insertion portion 8 and a holding portion 9. The insertion portion 8 is a portion to be inserted into a body cavity, and is formed by a hard jacket tube. The jacket tube is in the form of a circular tube, and is made of a metal such as stainless steel. In such manner, the stereoscopic-vision endoscope 1 is a rigid endoscope. The holding portion 9 is a portion to be held by an operator.

The holding portion 9 is provided with a light-guide tube 10. One end of a light-guide cable 11 is connected to the light-guide tube 10. The other end of the light-guide cable 11 is provided with a light-guide connector 12. The light-guide cable 11 is detachably connected to the holding portion 9 and the light-source unit 3.

The light-source unit 3 includes a lamp 13 and a lens 14. The lamp 13 generates illumination light such as white light. The lens 14 focuses the illumination light. The illumination light focused by the lens 14 is irradiated to an end surface of the light-guide connector 12. The illumination light irradiated to the end surface is transmitted to the body portion 2 by a light guide inside the light-guide cable 11.

The body portion 2 is provided with a light guide 15. The light guide 15 is bent inside the holding portion 9, and is passed through the insertion portion 8. The light guide 15 transmits the illumination light supplied from the light-guide cable 11 to a front-end surface which is fixed to a front-end portion 16 of the insertion portion 8. Accordingly, the illumination light is emerged frontward from the front-end surface.

Inside of the front-end portion 16, an optical system for stereoscopic vision of the present embodiment is disposed. The optical system for stereoscopic vision includes a first front unit 18a, a second front unit 18b, and a rear unit 18c.

An object 17 is illuminated by the illumination light. Light from the object 17 is incident on the first front unit 18a and the second front unit 18b. Light emerged from the first front unit 18a is incident on the rear unit 18c, and thereby a first optical image is formed at an image forming position. Light emerged from the second front unit 18b is incident on the rear unit 18c, and thereby a second optical image is formed at an image forming position.

The first optical image and the second optical image are formed same region. Therefore, when the first optical image and the second optical image are captured, one imager may be used. In the stereoscopic-vision endoscope 1, a imager 19 is disposed on the image forming position. Moreover, by disposing a light beam selector, it is possible to capture the first optical image and the second optical image separately.

One end of a signal cable 21 is connected to an output portion 20. The other end of the signal cable 21 is connected to the CCU 4. A signal which is output from the imager 19 is input to the CCU 4 via the signal cable 21.

In the CCU 4, signal processing is carried out on signals output from the imager 19. An image signal subjected to signal processing in the CCU 4 is input to the scan converter 5. In the scan converter 5, the signal output from the CCU 4 is converted to a video signal.

The video signal is input to the monitor 6. The monitor 6 displays the video signal that has been input. Two images having a parallax are displayed alternately on the monitor 6. The shutter glasses 7 have a shutter function. By using the shutter glasses 7, images displayed on the monitor 6 can be viewed stereoscopically.

According to the present disclosure, it is possible to provide an optical system for stereoscopic vision which is small-sized and in which an aberration is corrected favorably, and an image pickup apparatus using the same.

As described heretofore, the present disclosure is suitable for an optical system for stereoscopic vision which is small-sized and in which an aberration is corrected favorably, and an image pickup apparatus using the same.

What is claimed is:

1. An optical system for stereoscopic vision, comprising in order from an object side:
    a front unit, and
    a rear unit, wherein
    each of the front unit and the rear unit includes a lens component consisting of one of a single lens and a cemented lens,
    the front unit includes a first front unit and a second front unit,
    an optical axis of the first front unit, an optical axis of the second front unit, and an optical axis of the rear unit are positioned in a same plane,
    the optical axis of the rear unit is positioned between the optical axis of the first front unit and the optical axis of the second front unit, and
    the following conditional expression (1) is satisfied:

$$0.15 < De/\Phi < 0.85 \qquad (1)$$

where,
    $\Phi$ denotes an image-circle diameter at an image forming position, and
    De denotes a distance between a center of an entrance pupil in the first front unit and a center of an entrance pupil in the second front unit.

2. The optical system for stereoscopic vision according to claim 1, wherein
    the first front unit includes a front unit object-side negative lens, and
    the front unit object-side negative lens is disposed nearest to an object.

3. The optical system for stereoscopic vision according to claim 2, wherein an object-side surface of the front unit object-side negative lens is a flat surface.

4. The optical system for stereoscopic vision according to claim 2, wherein a positive lens component is disposed on an image side of the front unit object-side negative lens.

5. The optical system for stereoscopic vision according to claim 1, wherein
    the first front unit includes a front unit object-side negative lens, an object-side cemented lens, and an image-side cemented lens,
    the front unit object-side negative lens is disposed nearest to an object,
    the object-side cemented lens is disposed on an image side of the front unit object-side negative lens,
    the image-side cemented lens is disposed on the image side of the object-side cemented lens,
    the object-side cemented lens includes in order from the object side, a positive lens and a negative lens, and
    the image-side cemented lens includes in order from the object side, a negative lens and a positive lens.

6. The optical system for stereoscopic vision according to claim 1, wherein
    the first front unit includes a front unit image-side lens component, and
    the front unit image-side lens component is disposed nearest to an image, and an image-side surface thereof has a shape which is convex toward the image side.

7. The optical system for stereoscopic vision according to claim 1, wherein
    the first front unit includes a front unit image-side lens component, and
    the front unit image-side lens component is disposed nearest to an image, and has a positive refractive power.

8. The optical system for stereoscopic vision according to claim 1, wherein
    the first front unit includes a front unit image-side lens component and a first predetermined lens component,
    the front unit image-side lens component is disposed nearest to an image, and
    the first predetermined lens component is disposed on the object side of the front unit image-side lens component, and an image-side surface thereof has a shape which is convex toward the image side.

9. The optical system for stereoscopic vision according to claim 1, wherein
    the rear unit includes a rear unit object-side lens component, and the rear unit object-side lens component is disposed nearest to an object, and has a positive refractive power.

10. The optical system for stereoscopic vision according to claim 9, wherein an object-side surface of the rear unit object-side lens component has a shape which is convex toward the object side.

11. The optical system for stereoscopic vision according to claim 1, wherein
the rear unit includes a rear unit object-side lens component and a second predetermined lens component,
the rear unit object-side lens component is disposed nearest to an object, and has a positive refractive power, and
the second predetermined lens component is disposed on an image side of the rear unit object-side lens component.

12. The optical system for stereoscopic vision according to claim 1, wherein
the rear unit includes at least two positive lenses and at least one negative lens component, and
the one negative lens component is disposed between the two positive lenses.

13. The optical system for stereoscopic vision according to claim 1, wherein
the rear unit includes a rear unit image-side lens component, and
the rear unit image-side lens component is disposed nearest to an image, and has a positive refractive power.

14. The optical system for stereoscopic vision according to claim 1, wherein
the rear unit includes a rear unit image-side lens component, and
the rear unit image-side lens component is disposed nearest to an image, and has a positive refractive power, and an object-side surface thereof has a shape which is convex toward the object side.

15. The optical system for stereoscopic vision according to claim 1, wherein
the rear unit includes a focusing lens component, and
the focusing lens component moves along an optical axis at a time of focusing.

16. The optical system for stereoscopic vision according to claim 15, wherein the following conditional expression (2) is satisfied:

$$0.3 < LOfarf1/FLf1 < 2.0 \quad (2)$$

where,
LOfarf1 denotes a distance from a far point to a position of an object-side principal point of the first front unit,
FLf1 denotes a focal length of the first front unit, and
the far point is a point in a focusing range, which is positioned farthest from the optical system for stereoscopic vision.

17. The optical system for stereoscopic vision according to claim 15, wherein the following conditional expression (3) is satisfied:

$$5.0 < FLf1/TTLf1 < 100 \quad (3)$$

where,
FLf1 denotes a focal length of the first front unit, and
TTLf1 denotes a distance on the optical axis from an object-side surface of a lens disposed nearest to an object in the first front unit up to an image-side surface of a lens disposed nearest to an image in the first front unit.

18. The optical system for stereoscopic vision according to claim 15, wherein
the first front unit includes a front unit object-side negative lens,
the front unit object-side negative lens is disposed nearest to an object, and
the following conditional expression (4) is satisfied $$-0.7 < FLf1a/TTLf1 < -0.2 \quad (4)$$

where,
FLf1a denotes a focal length of the front unit object-side negative lens, and
TTLf1 denotes a distance on the optical axis from an object-side surface of a lens disposed nearest to the object in the first front unit up to an image-side surface of a lens disposed nearest to an image in the first front unit.

19. The optical system for stereoscopic vision according to claim 15, wherein
the first front unit includes a front unit object-side negative lens and a positive lens component,
the front unit object-side negative lens is disposed nearest to an object,
the positive lens component is disposed on an image side of the front unit object-side negative lens, and
the following conditional expression (5) is satisfied:

$$0.3 < FLf1b/TTLf1 < 1.2 \quad (5)$$

where,
FLf1b denotes a focal length of the positive lens component in the first front unit, and
TTLf1 denotes a distance on the optical axis from an object-side surface of a lens disposed nearest to the object in the first front unit up to an image-side surface of a lens disposed nearest to an image in the first front unit.

20. The optical system for stereoscopic vision according to claim 15, wherein
the first front unit includes a front unit image-side lens component,
the front unit image-side lens component is disposed nearest to an image, and an image-side surface thereof has a shape which is convex toward the image side, and
the following conditional expression (6) is satisfied:

$$-0.55 < Rrf1c/FLf1 < -0.25 \quad (6)$$

where,
Rrf1c denotes a radius of curvature of the image-side surface of the front unit image-side lens component, and
FLf1 denotes a focal length of the first front unit.

21. The optical system for stereoscopic vision according to claim 15, wherein
the first front unit includes a front unit image-side lens component,
the front unit image-side lens component is disposed nearest to an image, and has a positive refractive power, and
the following conditional expression (7) is satisfied:

$$0.5 < FLf1c/FLf1 < 10.0 \quad (7)$$

where,
FLf1c denotes a focal length of the front unit image-side lens component, and
FLf1 denotes a focal length of the first front unit.

22. The optical system for stereoscopic vision according to claim 15, wherein the following conditional expression (8) is satisfied:

$$0.2 < FLr/TTL < 0.7 \quad (8)$$

where,
FLr denotes a focal length of the rear unit at the time of focusing to a far point, and
TTL denotes a distance on the optical axis from an object-side surface of a lens disposed nearest to an object in the front unit up to an image plane, and
the far point is a point in a focusing range, which is positioned farthest from the optical system for stereoscopic vision.

23. The optical system for stereoscopic vision according to claim 15, wherein
the rear unit includes a rear unit object-side lens component,
the rear unit object-side lens component is disposed nearest to an object, and has a positive refractive power, and
the following conditional expression (9) is satisfied:

$$-3.5 < (Rfra+Rrra)/(Rfra-Rrra) < 0.5 \quad (9)$$

where,
Rfra denotes a radius of curvature of an object-side surface of the rear unit object-side lens component, and
Rrra denotes a radius of curvature of an image-side surface of the rear unit object-side lens component.

24. The optical system for stereoscopic vision according to claim 15, wherein
the rear unit includes a rear unit object-side lens component and a second predetermined lens component,
the rear unit object-side lens component is disposed nearest to an object, and has a positive refractive power,
the second predetermined lens component is disposed on an image side of the rear unit object-side lens component, and
the following conditional expression (10) is satisfied:

$$0.02 < Lr1/TTL < 0.2 \quad (10)$$

where,
Lr1 denotes a distance on the optical axis from an object-side surface of the rear unit object-side lens component up to an object-side surface of the second predetermined lens component, and
TTL denotes a distance on the optical axis from an object-side surface of a lens disposed nearest to the object in the front unit up to an image plane.

25. The optical system for stereoscopic vision according to claim 15, wherein the focusing lens component is disposed nearest to an image in the rear unit.

26. The optical system for stereoscopic vision according to claim 25, wherein the following conditional expression (11) is satisfied:

$$0.1 < 1-(\beta focus)^2 < 0.9 \quad (11)$$

where,
βfocus denotes a lateral magnification of the focusing lens component at the time of focusing to a far point, and
the far point is a point in the focusing range, which is positioned farthest from the optical system for stereoscopic vision.

27. The optical system for stereoscopic vision according to claim 15, wherein
the rear unit includes a rear unit image-side lens component,
the rear unit image-side lens component is disposed nearest to an image, and
the focusing lens component is disposed on the object side of the rear unit image-side lens component.

28. The optical system for stereoscopic vision according to claim 27, wherein the following conditional expression (12) is satisfied:

$$0.7 < 1-(\beta focus)^2 \times \beta r^2 < 1.0 \quad (12)$$

where,
βfocus denotes a lateral magnification of the focusing lens component at the time of focusing to a far point,
βr denotes a lateral magnification of a predetermined lens unit at the time of focusing to the farthest point,
the predetermined lens unit includes all lenses positioned on the image side of the focusing lens component, and
the farthest point is a point in the focusing range, which is positioned farthest from the optical system for stereoscopic vision.

29. The optical system for stereoscopic vision according to claim 25, wherein the following conditional expression (13) is satisfied:

$$0.2 < FLfocus/TTL < 4.0 \quad (13)$$

where,
FLfocus denotes a focal length of the focusing lens component, and
TTL denotes a distance on the optical axis from an object-side surface of a lens disposed nearest to an object in the front unit up to an image plane.

30. The optical system for stereoscopic vision according to claim 1, wherein
the first front unit includes a focusing lens component, and
the focusing lens component moves along an optical axis at the time of focusing.

31. The optical system for stereoscopic vision according to claim 30, wherein the following conditional expressions (14) and (15) are satisfied:

$$0.1 < LOfarf1/FLfarf1 < 5.0 \quad (14)$$

$$0.1 < LOnearf1/FLnearf1 < 4.0 \quad (15)$$

where,
LOfarf1 denotes a distance from a far point up to a position of an object-side principal point of the first front unit,
LOnearf1 denotes a distance from a near point up to the position of the object-side principal point of the first front unit,
FLfarf1 denotes a focal length of the first front unit at the time of focusing to the far point,
FLnearf1 denotes a focal length of the first front unit at the time of focusing to the near point,
the far point is a point in the focusing range, which is positioned farthest from the optical system for stereoscopic vision, and
the near point is a point in the focusing range, which is positioned nearest to the optical system for stereoscopic vision.

32. The optical system for stereoscopic vision according to claim 30, wherein
the first front unit includes a front unit object-side negative lens,
the front unit object-side negative lens is disposed nearest to an object, the rear unit includes a rear unit object-side lens component, the rear unit object-side lens component is disposed nearest to the object, and the following conditional expression (16) is satisfied:

$$3.0 < FLfarf1/TTLf1' < 70.0 \quad (16)$$

where,

FLfarf1 denotes a focal length of the first front unit at the time of focusing to a far point, TTLf1' denotes a distance on the optical axis from an object-side surface of the front unit object-side negative lens up to an object-side surface of the rear unit object-side lens component, and the far point is a point in the focusing range, which is positioned farthest from the optical system for stereoscopic vision.

33. The optical system for stereoscopic vision according to claim 30, wherein the first front unit includes a front unit object-side negative lens, the front unit object-side negative lens is disposed nearest to an object, and the following conditional expression (17) is satisfied:

$$-0.3 < FLf1a/TTL < -0.04 \quad (17)$$

where,

FLf1a denotes a focal length of the front unit object-side negative lens, and

TTL denotes a distance on the optical axis from an object-side surface of a lens disposed nearest to the object in the front unit up to an image plane.

34. The optical system for stereoscopic vision according to claim 30, wherein the first front unit includes a front unit object-side negative lens and a positive lens component, the front unit object-side negative lens is disposed nearest to an object, the positive lens component is disposed on an image side of the front unit object-side negative lens, and the following conditional expression (18) is satisfied:

$$0.1 < FLf1b/TTL < 0.4 \quad (18)$$

where,

FLf1b denotes a focal length of the positive lens component in the first front unit, and TTL denotes a distance on the optical axis from an object-side surface of a lens disposed nearest to the object in the front unit up to an image plane.

35. The optical system for stereoscopic vision according to claim 30, wherein the first front unit includes a front unit object-side negative lens, an object-side cemented lens, and an image-side cemented lens, the front unit object-side negative lens is disposed nearest to an object, the object-side cemented lens is disposed on the image side of the front unit object-side negative lens, and the image-side cemented lens is disposed on the image side of the object-side cemented lens, the object-side cemented lens includes in order from the object side, a positive lens and a negative lens, the image-side cemented lens includes in order from the object side, a negative lens and a positive lens, and the focusing lens component is disposed on the image side of the image-side cemented lens.

36. The optical system for stereoscopic vision according to claim 30, wherein the first front unit includes a front unit image-side lens component, the front unit image-side lens component is disposed nearest to an image, and an image-side surface thereof has a shape which is convex toward the image side, and the following conditional expression (19) is satisfied:

$$-0.5 < Rrf1c/TTL < -0.1 \quad (19)$$

where,

Rrf1c denotes a radius of curvature of the image-side surface of the front unit image-side lens component, and TTL denotes a distance on the optical axis from an object-side surface of a lens disposed nearest to an object in the front unit up to an image plane.

37. The optical system for stereoscopic vision according to claim 30, wherein the first front unit includes a front unit image-side lens component, the front unit image-side lens component is disposed nearest to an image, and an image-side surface thereof has a shape which is convex toward the image side, and the following conditional expression (20) is satisfied:

$$-2.0 < FLf1c/TTL < 2.0 \quad (20)$$

where,

FLf1c denotes a focal length of the front unit image-side lens component, and

TTL denotes a distance on the optical axis from an object-side surface of a lens disposed nearest to an object in the front unit up to an image plane.

38. The optical system for stereoscopic vision according to claim 30, wherein the first front unit includes a front unit object-side negative lens, a front unit image-side lens component, and a first predetermined lens component, the front unit object-side negative lens is disposed nearest to an object, the front unit image-side lens component is disposed nearest to an image, the first predetermined lens component is disposed on the object side of the front unit image-side lens component, and the following conditional expression (21) is satisfied:

$$0.5 < Rrf1d/FLf1a < 2.0 \quad (21)$$

where,

Rrf1d denotes a radius of curvature of an image-side surface of the first predetermined lens component, and FLf1a denotes a focal length of the front unit object-side negative lens.

39. The optical system for stereoscopic vision according to claim 30, wherein the following conditional expression (22) is satisfied:

$$0.3 < FLr'/TTLr < 2.0 \quad (22)$$

where,

FLr' denotes a focal length of the rear unit, and

TTLr denotes a distance on the optical axis from an object-side surface of a lens disposed nearest to an object in the rear unit up to an image-side surface of a lens disposed nearest to an image in the rear unit.

40. The optical system for stereoscopic vision according to claim 30, wherein
the rear unit includes a rear unit object-side lens component,
the rear unit object-side lens component is disposed nearest to an object, and an object-side surface thereof is a convex surface, and
the following conditional expression (9') is satisfied:

$$-2.5 < (Rfra+Rrra)/(Rfra-Rrra) < -0.2 \qquad (9')$$

where,
Rfra denotes a radius of curvature of the object-side surface of the rear unit object-side lens component, and
Rrra denotes a radius of curvature of an image-side surface of the rear unit object-side lens component.

41. Optical system for stereoscopic vision according to claim 30, wherein
the rear unit includes a rear unit object-side lens component and a second predetermined lens component,
the rear unit object-side lens component is disposed nearest to an object, and has a positive refractive power,
the second predetermined lens component is disposed on the image side of the rear unit object-side lens component, and
the following conditional expression (10') is satisfied:

$$0.02 < Lr1/TTL < 0.3 \qquad (10')$$

where,
Lr1 denotes a distance on the optical axis from an object-side surface of the rear unit object-side lens component up to an object-side surface of the second predetermined lens component, and
TTL denotes a distance on the optical axis from an object-side surface of a lens disposed nearest to the object in the front unit up to an image plane.

42. The optical system for stereoscopic vision according to claim 30, wherein
the rear unit includes a rear unit image-side lens component,
the rear unit image-side lens component is disposed nearest to an image, and
the following conditional expression (23) is satisfied:

$$-2.5 < (Rfrb+Rrrb)/(Rfrb-Rrrb) < -0.1 \qquad (23)$$

where,
Rfrb denotes a radius of curvature of an object-side surface of the rear unit image-side lens component, and
Rrrb denotes a radius of curvature of an image-side surface of the rear unit image-side lens component.

43. The optical system for stereoscopic vision according to claim 30, wherein the focusing lens component is disposed nearest to an image in the front unit.

44. The optical system for stereoscopic vision according to claim 30, wherein the following conditional expression (13') is satisfied:

$$-2.0 < FLfocus/TTL < 2.0 \qquad (13')$$

where,
FLfocus denotes a focal length of the focusing lens component, and
TTL denotes a distance on the optical axis from an object-side surface of a lens disposed nearest to an object in the front unit up to an image plane.

45. The optical system for stereoscopic vision according to claim 30, wherein
the second front unit includes a focusing lens component, and
the focusing lens component in the first front unit and the focusing lens component in the second front unit move together.

46. The optical system for stereoscopic vision according to claim 30, wherein
the second front unit includes a focusing lens component, and
the focusing lens component in the first front unit and the focusing lens component in the second front unit are integrated.

47. The optical system for stereoscopic vision according to claim 1, wherein the first front unit and the second front unit are same optical systems.

48. The optical system for stereoscopic vision according to claim 1, wherein
a light beam selector is disposed on the object side of the rear unit,
the light beam selector shields one of a light beam that passes through the first front unit and a light beam that passes through the second front unit.

49. The optical system for stereoscopic vision according to claim 48, wherein
each of the first front unit and the second front unit includes an aperture stop,
the light-beam selector includes a light shielding portion,
at a first position, the light shielding portion is positioned in an optical path of the first front unit, and
at a second position, the light shielding portion is positioned in an optical path of the second front unit.

50. An image pickup apparatus, comprising:
an optical system; and
an imager which has an image pickup surface, and which converts an image formed on the image pickup surface by the optical system to an electric signal, wherein
the optical system is an optical system for stereoscopic vision according to claim 1.

* * * * *